United States Patent
Halby et al.

(10) Patent No.: US 9,951,044 B2
(45) Date of Patent: Apr. 24, 2018

(54) QUINAZOLINE DERIVATIVES AND THEIR USE AS DNA METHYLTRANSFERASE INHIBITORS

(71) Applicants: PIERRE FABRE MEDICAMENT, Boulogne-billancourt (FR); CENTRE NATIONAL DE LA RECHERCHE SCIENTIFIQUE (CNRS), Paris (FR)

(72) Inventors: Ludovic Halby, Toulouse (FR); Paola Barbara Arimondo, Toulouse (FR)

(73) Assignees: PIERRE FABRE MEDICAMENT, Boulogne-Billancourt (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/023,209

(22) PCT Filed: Sep. 19, 2014

(86) PCT No.: PCT/EP2014/070011
§ 371 (c)(1),
(2) Date: Mar. 18, 2016

(87) PCT Pub. No.: WO2015/040169
PCT Pub. Date: Mar. 26, 2015

(65) Prior Publication Data
US 2016/0229834 A1    Aug. 11, 2016

(30) Foreign Application Priority Data
Sep. 19, 2013   (EP) .................................... 13306281

(51) Int. Cl.
C07D 401/12   (2006.01)
C07D 401/14   (2006.01)
A61K 31/517   (2006.01)

(52) U.S. Cl.
CPC .......... *C07D 401/12* (2013.01); *A61K 31/517* (2013.01); *C07D 401/14* (2013.01)

(58) Field of Classification Search
CPC ... A61K 31/517; C07D 401/12; C07D 401/14
See application file for complete search history.

(56) References Cited

FOREIGN PATENT DOCUMENTS

| CN | 101857617 A | 10/2010 |
| CN | 101857618 A | 10/2010 |
| WO | WO 2004/094410 A1 | 11/2004 |
| WO | WO 2005/051923 A1 | 6/2005 |
| WO | WO 2006/078752 A2 | 7/2006 |
| WO | WO 2009/049132 A1 | 4/2009 |

OTHER PUBLICATIONS

Fang et al. (Shanghai Institute of Pharmaceutical Industry, 1998, 19, 9, 396-400).*
Block et al. (Drug Design and Discovery (1992), 9(2), 167-76).*
International Search Report (PCT/ISA/210) issued in PCT/EP2014/070011, dated Dec. 23, 2014.
Written Opinion (PCT/ISA/237) issued in PCT/EP2014/070011, dated Dec. 23, 2014.
Baylin et al., "A Decade of Exploring the Cancer Epigenome—Biological and Translational Implications," Nature Reviews Cancer, vol. 11, Oct. 2011, pp. 726-734.
Berger et al., "An Operational Definition of Epigenetics," Genes & Development, vol. 23, 2009, pp. 781-783 (4 pages total).
Ceccaldi et al., "C5-DNA Methyltransferase Inhibitors: From Screening to Effects on Zebrafish Embryo Development," ChemBioChem, vol. 12, 2011 (Published online Jun. 1, 2011), pp. 1337-1345.
Esteller, "Epigenetics in Cancer," N Engl J Med, vol. 358, No. 11, Mar. 13, 2008, pp. 1148-1159.
Fahy et al., "DNA Methyltransferase Inhibitors in Cancer: A Chemical and Therapeutic Patent Overview and Selected Clinical Studies," Expert Opin. Ther. Patents, vol. 22, No. 12, 2012, pp. 1427-1442.
Gros et al., "Development of a Universal Radioactive DNA Methyltransferase Inhibition Test for High-throughput Screening and Mechanistic Studies," Nucleic Acids Research, vol. 41, No. 19, 2013 (Published online Aug. 25, 2013), pp. 1-12.
Gros et al., "DNA Methylation Inhibitors in Cancer: Recent and Future Approaches," Biochimie, vol. 94, 2012 (Available online Aug. 11, 2012), pp. 2280-2296.
Halby et al., "Rapid Synthesis of New DNMT Inhibitors Derivatives of Procainamide," ChemBioChem vol. 13, 2012 (Published online Dec. 14, 2011), pp. 157-165.
Jurkowska et al., "Structure and Function of Mammalian DNA Methyltransferases," ChemBioChem, vol. 12, 2011 (Published online Nov. 29, 2010), pp. 206-222.
Kelly et al., "Epigenetic Modifications as Therapeutic Targets," Nat Biotechnol, vol. 28, No. 10, Oct. 2010, pp. 1-22.
Sharma et al., "Epigenetics in Cancer," Carcinogenesis, vol. 31, No. 1, 2010 (Advance Access Publiciation Sep. 13, 2009), pp. 27-36.

* cited by examiner

*Primary Examiner* — Umamaheswari Ramachandran
(74) *Attorney, Agent, or Firm* — Birch, Stewart, Kolasch & Birch, LLP

(57) ABSTRACT

The present invention relates to compounds of the following formula (I): and pharmaceutically acceptable salts and solvates thereof, their methods of preparation, their use as a drug, notably in the treatment of cancer, and pharmaceutical compositions containing such compounds.

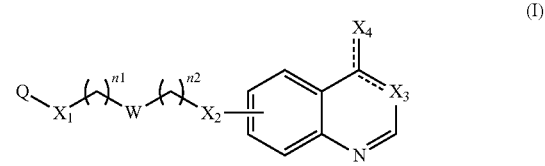

16 Claims, No Drawings

QUINAZOLINE DERIVATIVES AND THEIR USE AS DNA METHYLTRANSFERASE INHIBITORS

The present invention relates to quinazoline derivatives useful as DNA methyltransferase (DNMT) inhibitors, notably in the treatment of cancer.

Gene expression is known to be controlled by epigenetic modifications. Methylation of deoxycytidines (dC) in the DNA was shown to play a key role in epigenetic regulation in mammals (Berger et al. *Genes Dev.* 2009, 23, 781; Kelly et al. *Biotechnol.* 2010, 28, 1069). It is the most stable epigenetic mark and occurs at CpG sites, which are regrouped in island and essentially located in promoters, repeated sequences and CpG island shores (Gros et al. *Biochimie* 2012, 94, 2280). Hypermethylation of promoters' CpG islands induces gene silencing while hypomethylation induces gene expression (Sharma et al. *Carcinogenesis* 2010, 31, 27; Esteller *N. Engl. J. Med.* 2008, 358, 1148).

The enzymes responsible for DNA methylation are DNA methyltransferases (DNMTs). Two families of catalytically-active DNMTs have been identified: DNMT1, responsible for DNA methylation maintenance during replication, and DNMT3A and 3B, responsible for de novo DNA methylation. DNMTs add a methyl group on the carbon-5 position of the deoxycytosine at the CpG site in the DNA by using S-adenosyl-L-methionine (AdoMet) as methyl donor (Jurkowska et al. *ChemBioChem* 2011, 12, 206).

Alteration of DNA methylation patterns lead to various diseases such as cancer (Baylin and Jones *Nat. Rev. Cancer* 2011, 11, 726). Cancerous cells often present aberrant DNA methylation, in particular a specific hypermethylation of tumour suppressor genes is observed. Restoring their expression by specific inhibition of DNA methylation represents an attractive therapeutic strategy (Kelly et al. *Biotechnol.* 2010, 28, 1069; Fahy et al. *Expert Opin. Ther. Pat.* 2012, 22, 1427).

DNMT inhibitors can be divided into two families: nucleoside analogues and non-nucleosides. The first are the most active ones. Two of them were FDA approved: 5-azacytidine (Vidaza®) and 5-azadeoxycytidine (Dacogene®) (Gros et al. *Biochimie* 2012, 94, 2280). Despite their high efficiency, their poor bioavailability, their instability in physiologic media and their little selectivity restrict their use (Fahy et al. *Expert Opin. Ther. Pat.* 2012, 22, 1427). Non-nucleoside analogues present various structures and mechanisms of action. Many of them were shown to target the catalytic site but suffer from high toxicity, lack of specificity and weak activity.

There exists thus a need for novel DNMT inhibitors.

The inventors of the present invention have thus discovered that quinazoline derivatives can be used as DNA methyltransferase (DNMT) inhibitors.

The present invention concerns thus a compound of the following formula (I):

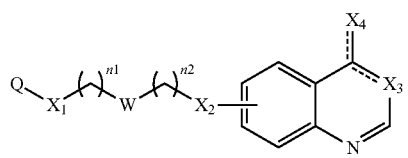

(I)

or a pharmaceutically acceptable salt or solvate thereof, wherein:

===== represents a single bond or a double bond on the condition that the two bonds ===== do not represent a double bond at the same time, n1 and n2 represent, independently of each other, an integer comprised between 0 and 8, notably between 1 and 8, Q represents an optionally substituted aryl or an optionally substituted heterocycle, W represents a bond, $NR_0$, a piperidinediyl, a piperazinediyl or a pyrrolidinediyl, $X_1$ represents O or $NR_1$, $X_2$ represents O or $NR_2$, $X_3$ represents:
  N when ===== $X_3$ represents a double bond =$X_3$, and
  $NR_3$ when ===== $X_3$ represents a single bond —$X_3$, $X_4$ represents:
  O or $NR_4$ when ===== $X_4$ represents a double bond =$X_4$, and
  —$OR_4$ or $NR_4R_5$ when ===== $X_4$ represents a single bond —$X_4$, —$R_0$ represents H; CHO; $CO_2$—(($C_1$-$C_6$)alkyl); or a ($C_1$-$C_6$)alkyl optionally substituted with CHO, $CO_2H$ or $CO_2$—(($C_1$-$C_6$)alkyl), $R_1$ and $R_2$ represent, independently of each other, H or a ($C_1$-$C_6$)alkyl, $R_3$ and $R_4$ represent, independently of each other, H, ($C_1$-$C_6$)alkyl, aryl, heterocycle, —(($C_1$-$C_6$)alkyl)-$X_5$-aryl or —(($C_1$-$C_6$)alkyl)-$X_5$-heterocycle, with $X_5$ representing a bond, O or $NR_6$ and each aryl or heterocycle moiety being optionally substituted, and $R_5$ and $R_6$ represent, independently of each other, H or a ($C_1$-$C_6$)alkyl.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "($C_1$-$C_6$)alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "($C_2$-$C_6$)alkenyl", as used in the present invention, refers to a straight or branched unsaturated hydrocarbon chain containing from 2 to 6 carbon atoms and comprising at least one double bond, notably one double bond, including, but not limited to, ethenyl, propenyl, butenyl, pentenyl, hexenyl and the like. It can be in particular an allyl group.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group. Advantageously, it will be a phenyl group.

The term "aryl-($C_1$-$C_6$)alkyl", as used in the present invention, refers to an aryl group as defined above bound to the molecule via a ($C_1$-$C_6$)alkyl group as defined above. In particular, the aryl-($C_1$-$C_6$)alkyl group is a benzyl group.

The term "($C_1$-$C_6$)alkyl-aryl", as used in the present invention, refers to a ($C_1$-$C_6$)alkyl group as defined above bound to the molecule via an aryl group as defined above. In particular, it can be a tolyl group (-$PhCH_3$).

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). The ring(s) of the heterocycle has/have advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc.

The term "heterocycle-($C_1$-$C_6$)alkyl", as used in the present invention, refers to a heterocycle group as defined above bound to the molecule via a ($C_1$-$C_6$)alkyl group as defined above.

The term "heteroaryl" as used in the present invention refers to an aromatic heterocycle as defined above.

According to a particular embodiment, the heteroaryl is an aromatic hydrocarbon monocycle or bicycle (i.e. comprising fused rings), each cycle having 5 or 6 members, notably 6 members, and 1 to 4, notably 1 or 2, carbon atoms having each been replaced with a nitrogen or oxygen atom, notably a nitrogen atom.

A heteroaryl can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc.

The term "heteroaryl-($C_1$-$C_6$)alkyl", as used in the present invention, refers to a heteroaryl group as defined above bound to the molecule via a ($C_1$-$C_6$)alkyl group as defined above.

The term "piperidinediyl", as used in the present invention, refers to a divalent piperidine moiety. It can be in particular

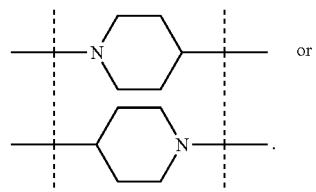

The term "piperazinediyl", as used in the present invention, refers to a divalent piperazine moiety. It can be in particular

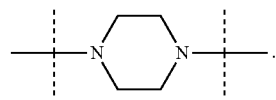

The term "pyrrolidinediyl", as used in the present invention, refers to a divalent pyrrolidine moiety. It can be in particular

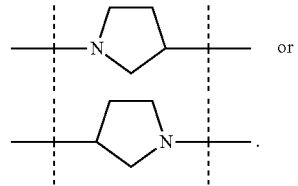

An "optionally substituted" radical, as used in the present invention, refers to a radical optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-($C_1$-$C_6$)alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$,
with $R_{11}$ to $R_{40}$ and $R_{50}$ to $R_{61}$ representing, independently of one another, H or ($C_1$-$C_6$)alkyl.

An "optionally substituted" radical can be in particular a radical optionally substituted with one or several groups selected from halogen; oxo (=O); $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; ($C_1$-$C_6$)alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; and aryl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$, with $R_{11}$ to $R_{40}$ as defined previously.

The term "halogen", as used in the present invention, refers to a fluorine, bromine, chlorine or iodine atom.

According to a particular embodiment of the present invention, the compound of the present invention is a compound of the following formula (I-1):

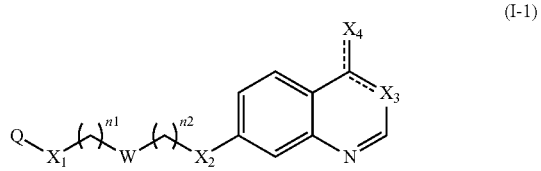
(I-1)

or a pharmaceutically acceptable salt or solvate thereof.

The formula (I) of the present invention comprises two bonds ═══ . According to a particular embodiment, one of them is a single bond and the other is a double bond. Thus the compound of the present invention can correspond to a compound of the following formulas (Ia) and (Ib), preferably of the following formulas (I-1a) and (I-1b):

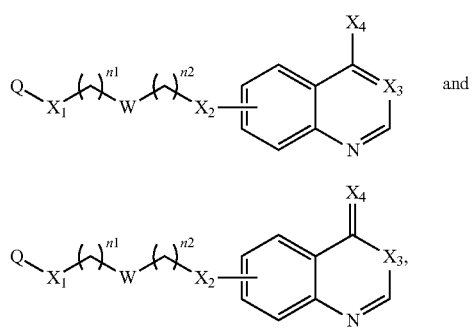
(Ia) and (Ib)

preferably

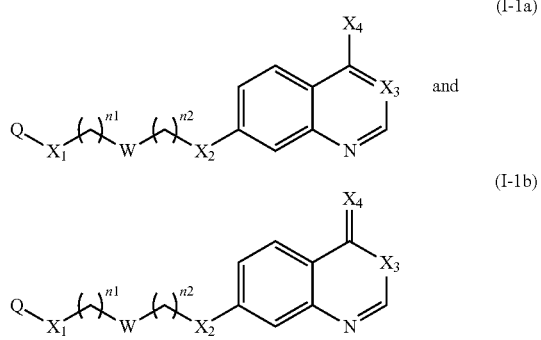
(I-1a) and (I-1b)

or a pharmaceutically acceptable salt or solvate thereof.

In particular, n1 can represent 0, 1, 2, 3 or 4, notably 1, 2, 3, or 4.

In particular, n2 can represent 0, 1, 2, 3 or 4, notably 1, 2, 3, or 4, such as 2 or 3.

$X_1$ represents advantageously NH or O, in particular NH.

$X_2$ represents advantageously NH or O, in particular O.

According to a particular embodiment, $X_1$ represents $NR_1$ and $X_2$ represents O, notably $X_1$ represents NH and $X_2$ represents O.

According to a first embodiment, W represents a bond, $NR_0$, a piperidinediyl or a piperazinediyl. Advantageously, W represents $NR_0$, a piperidinediyl or a piperazinediyl, notably $NR_0$ or a piperidinediyl.

According to a second embodiment, W represents a bond, $NR_0$, a piperidinediyl, a piperazinediyl or a pyrrolidinediyl. Advantageously, W represents $NR_0$, a piperidinediyl, a piperazinediyl or a pyrrolidinediyl, notably $NR_0$, a piperidinediyl or a pyrrolidinediyl.

In these two embodiments, the piperidinediyl group can be

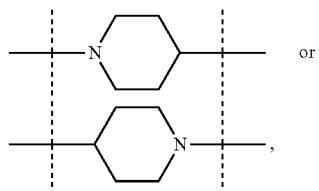

and in particular is

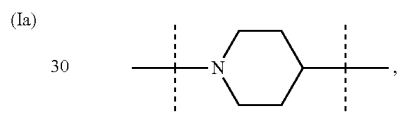

the nitrogen atom being linked to $(CH_2)_{n1}$. The piperazinediyl group is in particular

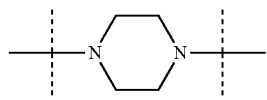

The pyrrolidinediyl group can be

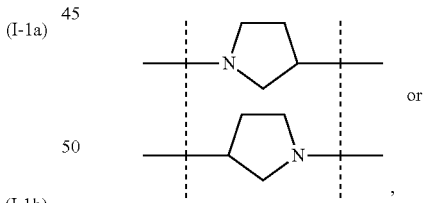

and in particular is

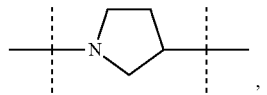

the nitrogen atom being linked to $(CH_2)_{n1}$.

$R_0$ represents notably H; CHO; or a $(C_1-C_6)$alkyl optionally substituted with $CO_2H$ or $CO_2-((C_1-C_6)alkyl)$ (e.g. $CO_2Me$). According to a first particular embodiment, $R_0$ represents H. According to a second particular embodiment, $R_0$ represents CHO or $CO_2-((C_1-C_6)alkyl)$, such as CHO.

According to a third particular embodiment, $R_0$ represents a $(C_1\text{-}C_6)$alkyl optionally substituted with CHO, $CO_2H$ or $CO_2\text{—}((C_1\text{-}C_6)$alkyl), notably with $CO_2H$ or $CO_2\text{—}((C_1\text{-}C_6)$alkyl) (e.g. $CO_2Me$).

Q represents notably an aryl or heterocycle, notably a heterocycle, optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1\text{-}C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1\text{-}C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$ to $R_{40}$ and $R_{50}$ to $R_{61}$ representing, independently of one another, H or $(C_1\text{-}C_6)$alkyl.

Q represents notably an aryl or heterocycle, notably a heterocycle, optionally substituted with one or several groups selected from halogen; oxo (=O); $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1\text{-}C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; and aryl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$,
with $R_{11}$ to $R_{40}$ representing, independently of one another, H or $(C_1\text{-}C_6)$alkyl.

Q represents in particular an aryl or heterocycle, notably a heterocycle, optionally substituted with one or several groups selected from halogen; oxo (=O); $(C_1\text{-}C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; and aryl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$.

Q can also represent an aryl or heterocycle, notably a heterocycle, optionally substituted with one or several groups selected from halogen; oxo (=O); $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; and $(C_1\text{-}C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$.

Q can represent in particular an aryl or heterocycle, notably a heterocycle, optionally substituted with one or several groups selected from halogen; oxo (=O); $OR_{11}$; $NR_{12}R_{13}$; and $(C_1\text{-}C_6)$alkyl optionally substituted with one or several groups selected from halogen, $OR_{21}$ and $NR_{22}R_{23}$.

Q represents particularly an aryl or heterocycle, notably a heterocycle, optionally substituted with one or several groups selected from halogen; oxo (=O); and $(C_1\text{-}C_6)$alkyl optionally substituted with one or several groups selected from halogen, $OR_{21}$ and $NR_{22}R_{23}$.

In the definitions of Q above, the aryl is preferably a phenyl or a naphtyl, in particular a phenyl.

In the definitions of Q above, the heterocycle is notably a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom. The heterocycle can be notably chosen among pyrrole, imidazole, pyrazole, triazoles, indole, benzimidazole, indazole, pyridine, pyrimidine, pyridazine, pyrazine, triazine, quinoline, isoquinoline, quinoxaline, quinazoline, piperidine, piperazine, triazinane, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines and tetrahydrotriazines. In particular, the heterocycle can be chosen among pyridine, pyrimidine, pyridazine, pyrazine, quinoline, isoquinoline, quinoxaline, quinazoline, piperidine, piperazine, dihydropyridines, dihydropyrimidines (notably 1,2-dihydropyrimidine), dihydropyridazines, dihydropyrazines, tetrahydropyridines, tetrahydropyrimidines, tetrahydropyridazines and tetrahydropyrazines. More particularly, the heterocycle can be chosen among quinoline, quinazoline, pyridine, pyrimidine and dihydropyrimidines (notably 1,2-dihydropyrimidine). Notably, the heterocycle can be chosen among quinoline, pyridine and dihydropyrimidines (notably 1,2-dihydropyrimidine).

In the definitions of Q above, the heterocycle is preferably an heteroaryl, such as an aromatic hydrocarbon monocycle or bicycle (i.e. comprising fused rings), each cycle having 5 or 6 members, notably 6 members, and 1 to 4, notably 1 or 2, carbon atoms having each been replaced with a nitrogen or oxygen atom, notably a nitrogen atom. Preferably, the heretoaryl is an aromatic hydrocarbon monocycle or bicycle (i.e. comprising fused rings), each cycle having 6 members, and 1 or 2 carbon atoms having each been replaced with a heteroatom chosen among nitrogen and oxygen atoms, at least one heteroatom being a nitrogen atom and preferably all the heteroatoms being a nitrogen atom when two heteroatoms are present. The heteroaryl can be notably chosen among thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline and quinazoline. In particular, the heteroaryl can be chosen among pyridine, pyrimidine, pyridazine, pyrazine, quinoline, isoquinoline, quinoxaline, and quinazoline. Notably, the heteroaryl can be chosen among quinoline, quinazoline, pyridine and pyrimidine. In particular, it is quinoline or pyridine.

According to a preferred embodiment, Q represents a cycle of the following formula:

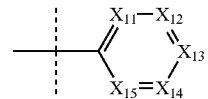

wherein:
$X_{11}$ represents N or $CR_{41}$,
$X_{12}$ represents N or $CR_{42}$,
$X_{13}$ represents N or C—$NR_{43a}R_{43b}$,
$X_{14}$ represents N or $CR_{44}$,
$X_{15}$ represents N or $CR_{45}$,
$R_{43a}$ and $R_{43b}$ each represent, independently of each other, H or $(C_1\text{-}C_6)$alkyl, and in particular H,
$R_{41}$, $R_{42}$, $R_{44}$ and $R_{45}$ each represent, independently of each other, hydrogen; halogen; $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1\text{-}C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; or aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, or in the case of $R_{44}$ and $R_{45}$, $R_{44}$ and $R_{45}$ form together a chain of the following formula:

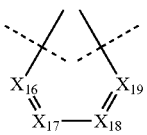

wherein:
$X_{16}$ represents N or $CR_{46}$,
$X_{17}$ represents N or $CR_{47}$,
$X_{18}$ represents N or $CR_{48}$,
$X_{19}$ represents N or $CR_{49}$, and
$R_{46}$, $R_{47}$, $R_{48}$ and $R_{49}$ each represent, independently of one another, hydrogen; halogen; $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; or aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, on the proviso that no more than three, notably two, and preferably one, of $X_{11}$, $X_{12}$, $X_{14}$, $X_{15}$, $X_{16}$, $X_{17}$, $X_{18}$ and $X_{19}$ represent N.

In particular, none of $X_{11}$, $X_{12}$, $X_{14}$, $X_{15}$, $X_{16}$, $X_{17}$, $X_{18}$ and $X_{19}$ represents N.

Advantageously, $R_{41}$, $R_{42}$, $R_{44}$ and $R_{45}$ each represent, independently of each other, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$, or in the case of $R_{44}$ and $R_{45}$, $R_{44}$ and $R_{45}$ form together a chain of the following formula:

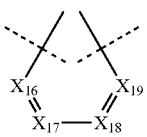

with $R_{46}$, $R_{47}$, $R_{48}$ and $R_{49}$ each representing, independently of one another, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$.

In particular, $R_{41}$, $R_{42}$, $R_{44}$ and $R_{45}$ each represent, independently of each other, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; or $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$, or in the case of $R_{44}$ and $R_{45}$, $R_{44}$ and $R_{45}$ form together a chain of the following formula:

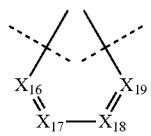

with $R_{46}$, $R_{47}$, $R_{48}$ and $R_{49}$ each representing, independently of one another, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; or $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$.

Notably, $R_{41}$, $R_{42}$, $R_{44}$ and $R_{45}$ each represent, independently of each other, hydrogen; halogen; $OR_{11}$; $NR_{12}R_{13}$; or $(C_1-C_6)$alkyl optionally substituted with one or several groups selected from halogen, $OR_{21}$, and $NR_{22}R_{23}$, or in the case of $R_{44}$ and $R_{45}$, $R_{44}$ and $R_{45}$ form together a chain of the following formula:

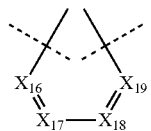

with $R_{46}$, $R_{47}$, $R_{48}$ and $R_{49}$ each representing, independently of one another, hydrogen; halogen; $OR_{11}$; $NR_{12}R_{13}$; or $(C_1-C_6)$alkyl optionally substituted with one or several groups selected from halogen, $OR_{21}$, and $NR_{22}R_{23}$.

In particular, $R_{41}$, $R_{42}$, $R_{44}$ and $R_{45}$ each represent, independently of each other, hydrogen; halogen; $OR_{11}$; or $NR_{12}R_{13}$; and notably hydrogen, or in the case of $R_{44}$ and $R_{45}$, $R_{44}$ and $R_{45}$ form together a chain of the following formula:

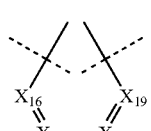

with $R_{46}$, $R_{47}$, $R_{48}$ and $R_{49}$ each representing, independently of one another, hydrogen; halogen; $OR_{11}$; or $NR_{12}R_{13}$.

According to a most preferred embodiment, Q represents one of the following cycles:

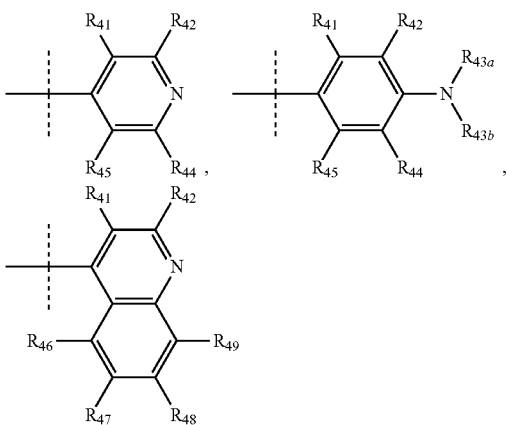

with $R_{43a}$ and $R_{43b}$ as defined above and in particular representing H, and with $R_{41}$, $R_{42}$ and $R_{44}$ to $R_{49}$ as defined above, and in particular with $R_{41}$, $R_{42}$ and $R_{44}$ to $R_{49}$ each representing, independently of one another, hydrogen; halogen; $OR_{11}$; or $NR_{12}R_{13}$.

In particular, Q represents one of the following cycles:

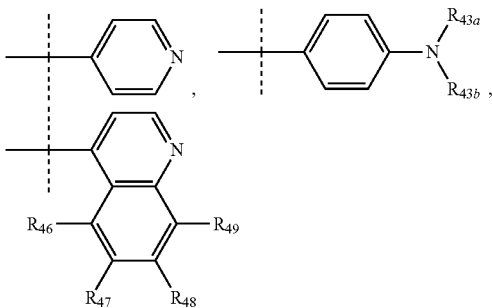

with $R_{43a}$ and $R_{43b}$ as defined above and in particular representing H, and with $R_{46}$ to $R_{49}$ each representing, independently of one another, hydrogen; halogen; $OR_{11}$; or $NR_{12}R_{13}$.

Q can be for example one of the following cycles:

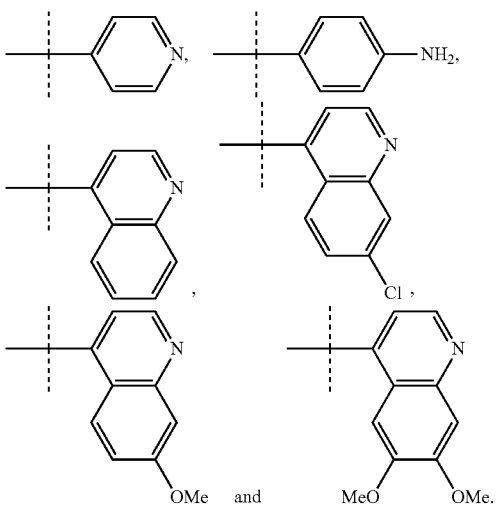

According to a particular embodiment, $X_3$ represents:
N when ═══ $X_3$ represents a double bond ═$X_3$, and
$NR_3$ when ═══ $X_3$ represents a single bond —$X_3$, According to another particular embodiment, $X_4$ represents:
O when ═══ $X_4$ represents a double bond ═$X_4$, and
$NR_4R_5$ when ═══ $X_4$ represents a single bond —$X_4$, The compound of the present invention can correspond in particular to a compound of the following formulas (Ic) and (Id), preferably of the following formulas (I-1c) and (I-1d):

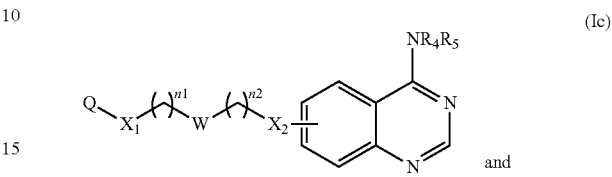

(Ic)

and

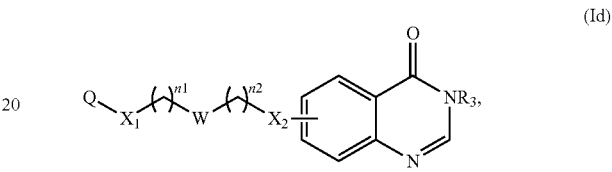

(Id)

preferably

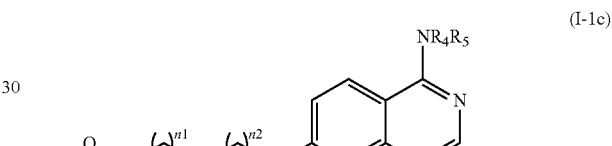

(I-1c)

and

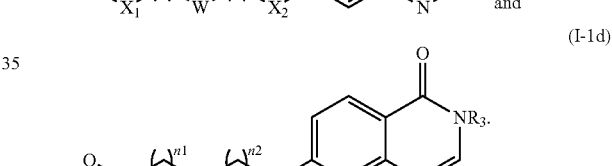

(I-1d)

or a pharmaceutically acceptable salt or solvate thereof.

More particularly, $R_3$ and $R_4$ will represent, independently of each other, H, $(C_1-C_6)$alkyl, aryl, heterocycle, —$((C_1-C_6)$alkyl$)$-$X_5$-aryl or —$((C_1-C_6)$alkyl$)$-$X_5$-heterocycle, each aryl or heterocycle moiety being optionally substituted with one or several groups selected from halogen; oxo (═O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{30}C(O)R_{40}$, $S(O)R_{58}$, $S(O)_2R_{59}$, and $S(O)_2NR_{60}R_{61}$, with $R_{11}$ to $R_{40}$ and $R_{50}$ to $R_{61}$ representing, independently of one another, H or $(C_1-C_6)$alkyl.

$R_3$ and $R_4$ represent notably, independently of each other, H, $(C_1-C_6)$alkyl, aryl, heterocycle, —$((C_1-C_6)$alkyl$)$-$X_5$-aryl or —$((C_1-C_6)$alkyl$)$-$X_5$-heterocycle, each aryl or heterocycle moiety being optionally substituted with one or several groups selected from halogen; oxo (═O); $NO_2$; $OR_{11}$; $NR_{12}R_{13}$; $C(O)R_{14}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, C(O)R$_{24}$, S(O)R$_{54}$, S(O)$_2$R$_{55}$, and S(O)$_2$NR$_{56}$R$_{57}$; and aryl or aryl-(C$_1$-C$_6$)alkyl optionally substituted with one or several groups selected from halogen, OR$_{31}$, NR$_{32}$R$_{33}$, C(O)R$_{34}$, S(O)R$_{58}$, S(O)$_2$R$_{59}$, and S(O)$_2$NR$_{60}$R$_{61}$.

R$_3$ and R$_4$ represent notably, independently of each other, H, (C$_1$-C$_6$)alkyl, aryl, heterocycle, —((C$_1$-C$_6$)alkyl)-X$_5$-aryl or —((C$_1$-C$_6$)alkyl)-X$_5$-heterocycle, each aryl or heterocycle moiety being optionally substituted with one or several groups selected from halogen; oxo (=O); NO$_2$; OR$_{11}$; NR$_{12}$R$_{13}$; C(O)R$_{14}$; S(O)R$_{50}$; S(O)$_2$R$_{51}$; S(O)$_2$NR$_{52}$R$_{53}$; (C$_1$-C$_6$)alkyl optionally substituted with one or several groups selected from halogen, OR$_{21}$, and NR$_{22}$R$_{23}$; and aryl or aryl-(C$_1$-C$_6$)alkyl optionally substituted with one or several groups selected from halogen, OR$_{31}$, and NR$_{32}$R$_{33}$.

R$_3$ and R$_4$ represent notably, independently of each other, H, (C$_1$-C$_6$)alkyl, aryl, heterocycle, —((C$_1$-C$_6$)alkyl)-X$_5$-aryl or —((C$_1$-C$_6$)alkyl)-X$_5$-heterocycle, each aryl or heterocycle moiety being optionally substituted with one or several groups selected from halogen; oxo (=O); NO$_2$; OR$_{11}$; NR$_{12}$R$_{13}$; C(O)R$_{14}$; S(O)$_2$NR$_{52}$R$_{53}$; (C$_1$-C$_6$)alkyl optionally substituted with one or several groups selected from halogen, OR$_{21}$, NR$_{22}$R$_{23}$, C(O)R$_{24}$, and S(O)$_2$NR$_{56}$R$_{57}$; and aryl or aryl-(C$_1$-C$_6$)alkyl optionally substituted with one or several groups selected from halogen, OR$_{31}$, NR$_{32}$R$_{33}$, C(O)R$_{34}$, and S(O)$_2$NR$_{60}$R$_{61}$.

R$_3$ and R$_4$ represent notably, independently of each other, H, (C$_1$-C$_6$)alkyl, aryl, heterocycle, —((C$_1$-C$_6$)alkyl)-X$_5$-aryl or —((C$_1$-C$_6$)alkyl)-X$_5$-heterocycle, each aryl or heterocycle moiety being optionally substituted with one or several groups selected from halogen; oxo (=O); NO$_2$; OR$_{11}$; NR$_{12}$R$_{13}$; C(O)R$_{14}$; S(O)$_2$NR$_{52}$R$_{53}$; (C$_1$-C$_6$)alkyl optionally substituted with one or several groups selected from halogen, OR$_{21}$, and NR$_{22}$R$_{23}$; and aryl or aryl-(C$_1$-C$_6$)alkyl optionally substituted with one or several groups selected from halogen, OR$_{31}$, and NR$_{32}$R$_{33}$.

R$_3$ and R$_4$ represent notably, independently of each other, H, (C$_1$-C$_6$)alkyl, aryl, heterocycle, —((C$_1$-C$_6$)alkyl)-X$_5$-aryl or —((C$_1$-C$_6$)alkyl)-X$_5$-heterocycle, each aryl or heterocycle moiety being optionally substituted with one or several groups selected from halogen; oxo (=O); NO$_2$; OR$_{11}$; NR$_{12}$R$_{13}$; C(O)R$_{14}$; S(O)$_2$NR$_{52}$R$_{53}$; (C$_1$-C$_6$)alkyl; aryl; and aryl-(C$_1$-C$_6$)alkyl.

R$_3$ and R$_4$ represent notably, independently of each other, H, (C$_1$-C$_6$)alkyl, aryl, heterocycle, —((C$_1$-C$_6$)alkyl)-X$_5$-aryl or —((C$_1$-C$_6$)alkyl)-X$_5$-heterocycle, each aryl or heterocycle moiety being optionally substituted with one or several groups selected from halogen; oxo (=O); OR$_{11}$; NR$_{12}$R$_{13}$; C(O)R$_{14}$; CO$_2$R$_{15}$; OC(O)R$_{16}$; C(O)NR$_{17}$R$_{18}$; NR$_{19}$C(O)R$_{20}$; (C$_1$-C$_6$)alkyl optionally substituted with one or several groups selected from halogen, OR$_{21}$, NR$_{22}$R$_{23}$, C(O)R$_{24}$, CO$_2$R$_{25}$, OC(O)R$_{26}$, C(O)NR$_{27}$R$_{28}$, and NR$_{29}$C(O)R$_{30}$; and aryl optionally substituted with one or several groups selected from halogen, OR$_{31}$, NR$_{32}$R$_{33}$, C(O)R$_{34}$, CO$_2$R$_{35}$, OC(O)R$_{36}$, C(O)NR$_{37}$R$_{38}$, and NR$_{39}$C(O)R$_{40}$.

R$_3$ and R$_4$ represent notably, independently of each other, H, (C$_1$-C$_6$)alkyl, aryl, heterocycle, —((C$_1$-C$_6$)alkyl)-X$_5$-aryl or —((C$_1$-C$_6$)alkyl)-X$_5$-heterocycle, each aryl or heterocycle moiety being optionally substituted with one or several groups selected from halogen; OR$_{11}$; NR$_{12}$R$_{13}$; (C$_1$-C$_6$)alkyl optionally substituted with one or several groups selected from halogen, OR$_{21}$ and NR$_{22}$R$_{23}$; and aryl optionally substituted with one or several groups selected from halogen, OR$_{31}$ and NR$_{32}$R$_{33}$.

R$_3$ and R$_4$ represent notably, independently of each other, H, (C$_1$-C$_6$)alkyl, aryl, heterocycle, aryl-(C$_1$-C$_6$)alkyl, heterocycle-(C$_1$-C$_6$)alkyl, —((C$_1$-C$_6$)alkyl)-NH-aryl or —((C$_1$-C$_6$)alkyl)-NH-heterocycle, each aryl or heterocycle moiety being optionally substituted with one or several groups selected from halogen; OR$_{11}$; NR$_{12}$R$_{13}$; (C$_1$-C$_6$)alkyl optionally substituted with one or several groups selected from halogen, OR$_{21}$ and NR$_{22}$R$_{23}$; and aryl optionally substituted with one or several groups selected from halogen, OR$_{31}$ and NR$_{32}$R$_{33}$.

In the definitions of R$_3$ and R$_4$ above, the aryl preferably is a phenyl or a naphtyl, in particular a phenyl.

In the definitions of R$_3$ and R$_4$ above, the heterocycle is notably a saturated, unsaturated or aromatic (notably aromatic) hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom. The heterocycle can be a heteroaryl. The heterocycle can be notably chosen among pyrrole, imidazole, pyrazole, triazoles, indole, benzimidazole, indazole, pyridine, pyrimidine, pyridazine, pyrazine, triazine, quinoline, isoquinoline, quinoxaline, quinazoline, piperidine, piperazine, triazinane, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines and tetrahydrotriazines. According to a first embodiment, the heterocycle is chosen among pyrrole, imidazole, pyrazole, triazoles, indole, benzimidazole, indazole, pyridine, pyrimidine, pyridazine, pyrazine, triazine, quinoline, isoquinoline, quinoxaline and quinazoline; notably chosen among pyridine, pyrimidine, pyridazine, pyrazine, triazine, quinoline, isoquinoline, quinoxaline and quinazoline. According to a second embodiment, the heterocycle is chosen among piperidine, piperazine, triazinane or pyrrolidine; and in particular is piperidine.

In the definitions of R$_3$ and R$_4$ above, X$_5$ represents in particular a bond or NR$_6$, notably a bond or NH.

According to a preferred embodiment, R$_5$ represents H.

According to a particular embodiment, the compounds according to the present invention are compounds of formula (I-1c) or (I-id), or a pharmaceutically acceptable salt or solvate thereof, wherein:

n1 and n2 represent, independently of each other, 1, 2, 3 or 4,

Q represents an aryl or heteroaryl optionally substituted with one or several groups selected from halogen; oxo (=O); OR$_{11}$; NR$_{12}$R$_{13}$; and (C$_1$-C$_6$)alkyl optionally substituted with one or several groups selected from halogen, OR$_{21}$ and NR$_{22}$R$_{23}$.

W represents a bond, NR$_0$,

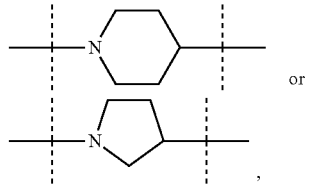

or the nitrogen atom being linked to (CH$_2$)$_{n1}$; notably NR$_0$,

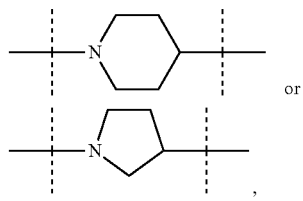

or

, the nitrogen atom being linked to $(CH_2)_{n1}$,
$X_1$ represents NH,
$X_2$ represents O,
$R_0$ represents H; CHO; or a $(C_1-C_6)$alkyl optionally substituted with $CO_2H$ or $CO_2$—$((C_1-C_6)$alkyl),
$R_3$ and $R_4$ represent, independently of each other, H, $(C_1-C_6)$alkyl, aryl heterocycle, aryl-$(C_1-C_6)$alkyl, heterocycle-$(C_1-C_6)$alkyl, —$((C_1-C_6)$alkyl)-NH-aryl or —$((C_1-C_6)$alkyl)-NH-heterocycle, notably, H, $(C_1-C_6)$ alkyl, heterocycle, aryl-$(C_1-C_6)$alkyl, or —$((C_1-C_6)$ alkyl)-NH-aryl,
each aryl or heterocycle moiety being optionally substituted with one or several groups selected from halogen; oxo (=O); $NO_2$; $OR_{11}$; $NR_{12}R_{13}$; $C(O)R_{14}$; $S(O)_2$ $NR_{52}R_{53}$; $(C_1-C_6)$alkyl optionally substituted with one or several groups selected from halogen, $OR_{21}$, and $NR_{22}R_{23}$; and aryl or aryl-$(C_1-C_6)$alkyl optionally substituted with one or several groups selected from halogen, $OR_{31}$, and $NR_{32}R_{33}$, and
$R_5$ represents H,
wherein:
the aryl is phenyl,
the heterocycle is a saturated hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom; such as piperidine, piperazine, triazinane or pyrrolidine; and in particular piperidine, and
the heteroaryl is an aromatic hydrocarbon monocycle or bicycle (comprising fused rings), each cycle having 5 or 6 members and 1 to 4, notably 1 or 2, carbon atoms having each been replaced with a nitrogen or oxygen atom, notably a nitrogen atom; such as pyridine, pyrimidine, pyridazine, pyrazine, triazine, quinoline, isoquinoline, quinoxaline or quinazoline; in particular pyridine or quinoline.

According to another particular embodiment, the compounds according to the present invention are compounds of formula (I-1c) or (I-1d), or a pharmaceutically acceptable salt or solvate thereof,
wherein:
n1 and n2 represent, independently of each other, 1, 2, 3 or 4,
Q represents an aryl or heterocycle, notably a heterocycle, optionally substituted with one or several groups selected from halogen; oxo (=O); and $(C_1-C_6)$alkyl optionally substituted with one or several groups selected from halogen, $OR_{21}$ and $NR_{22}R_{23}$.
W represents a bond, $NR_0$ or

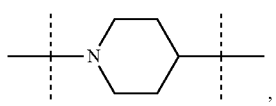

the nitrogen atom being linked to $(CH_2)_{n1}$; notably $NR_0$ or

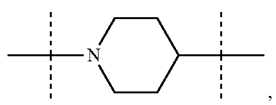

the nitrogen atom being linked to $(CH_2)_{n1}$,
$X_1$ represents NH,
$X_2$ represents O,
$R_0$ represents H; CHO; or a $(C_1-C_6)$alkyl optionally substituted with $CO_2H$ or $CO_2$—$((C_1-C_6)$alkyl),
$R_3$ and $R_4$ represent, independently of each other, H, $(C_1-C_6)$alkyl, aryl, heteroaryl, aryl-$(C_1-C_6)$alkyl, heteroaryl-$(C_1-C_6)$alkyl, —$((C_1-C_6)$alkyl)-NH-aryl or —$((C_1-C_6)$alkyl)-NH-heteroaryl,
each aryl or heteroaryl moiety being optionally substituted with one or several groups selected from halogen; $OR_{11}$; $NR_{12}R_{13}$; $(C_1-C_6)$alkyl optionally substituted with one or several groups selected from halogen, $OR_{21}$ and $NR_{22}R_{23}$; and aryl optionally substituted with one or several groups selected from halogen, $OR_{31}$ and $NR_{32}R_{33}$, and
$R_5$ represents H,
wherein:
the aryl is phenyl,
the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom; such as pyridine, pyrimidine, pyridazine, pyrazine, quinoline, isoquinoline, quinoxaline, quinazoline, piperidine, piperazine, dihydropyridines, dihydropyrimidines, dihydropyridazines, dihydropyrazines, tetrahydropyridines, tetrahydropyrimidines, tetrahydropyridazines or tetrahydropyrazines; in particular quinoline, pyridine or dihydropyrimidines (notably 1,2-dihydropyrimidine), and
the heteroaryl is an aromatic hydrocarbon monocycle or bicycle (comprising fused rings), each cycle having 5 or 6 members and 1 to 4, notably 1 or 2, carbon atoms having each been replaced with a nitrogen or oxygen atom, notably a nitrogen atom; such as pyridine, pyrimidine, pyridazine, pyrazine, triazine, quinoline, isoquinoline, quinoxaline or quinazoline; in particular quinoline or pyrimidine.

The compounds of the present invention may be selected from compounds A to U described in the experimental part below and the pharmaceutically acceptable salts and solvates thereof.

The compounds of the present invention can also be selected from compounds AA to AS described in the experimental part below and the pharmaceutically acceptable salts and solvates thereof.

The present invention relates also to a compound of formula (I) such as defined above, for use as a drug, notably intended for the treatment of cancer.

The present invention also relates to the use of a compound of formula (I) such as defined above, for the manufacture of a drug, notably intended for the treatment of cancer.

The present invention also relates to a method for the treatment of cancer comprising the administration to a person in need thereof of an effective dose of a compound of formula (I) such as defined above.

The cancer may be more particularly in this case colon cancer, breast cancer, kidney cancer, liver cancer, pancreatic cancer, prostate cancer, glioblastoma, non-small cell lung cancer, neuroblastoma, inflammatory myofibroblastic tumor, leukemia (acute myeloid leukemia, myelodysplastic syndrome, chronic myelomonocytic leukemia), melanoma, diffuse B-cell lymphoma or anaplastic large-cell lymphoma.

The present invention relates also to a compound of formula (I) such as defined above, for use as a DNA methylation inhibitor, in particular as a DNMT inhibitor.

According to the invention, the expression "DNA methylation inhibitor" and "DNMT inhibitor" refers to molecules that are able to reduce or inhibit the DNA methylation and the DNA methyltransferase activity respectively. Preferentially, the use of a DNMT inhibitor according to the invention makes it possible to suppress the activity of said DNMT.

The present invention also relates to a pharmaceutical composition comprising at least one compound of formula (I) such as defined above, and at least one pharmaceutically acceptable excipient.

The pharmaceutical compositions according to the invention may be formulated notably for oral administration or for injection, wherein said compositions are intended for mammals, including humans.

The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

The pharmaceutical compositions according to the invention may further comprise at least one other active ingredient, such as an anticancer agent.

The present invention relates also to a pharmaceutical composition comprising:
(i) at least one compound of formula (I) such as defined above, and
(ii) at least one other active ingredient, such as an anticancer agent, as a combination product for simultaneous, separate or sequential use.

The present invention also relates to a pharmaceutical composition such as defined above for use as a drug, notably intended for the treatment of cancer.

The present invention also relates to methods for the preparation of the compounds of formula (I) according to the invention.

A first method is a method to prepare a compound of formula (I) or a pharmaceutically acceptable salt or solvate thereof, in which $W=NR_0$ with $R_0 \neq H$, comprising:
(a) reacting a compound of formula (I) in which $W=NH$ with:
a compound of formula $R_0$-LG where $R_0$ represents a $(C_1\text{-}C_6)$alkyl optionally substituted with CHO, $CO_2H$ or $CO_2$—$((C_1\text{-}C_6)$alkyl) and LG represents a leaving group to give a compound of formula (I) in which $W=NR_0$ with $R_0$ representing a $(C_1\text{-}C_6)$alkyl optionally substituted with CHO, $CO_2H$ or $CO_2$—$((C_1\text{-}C_6)$alkyl),
dimethylformamide (DMF) to give a compound of formula (I) in which $W=NR_0$ with $R_0=CHO$, or
a compound of formula $R_0$-$A_1$ where $R_0$ represents $CO_2$—$((C_1\text{-}C_6)$alkyl) and $A_1$ represents a $(C_1\text{-}C_6)$ alkoxy group or a halogen atom (such as Cl or Br) to give a compound of formula (I) in which $W=NR_0$ with $R_0$ representing $CO_2$—$((C_1\text{-}C_6)$alkyl), and
(b) optionally salifying or solvating the compound obtained in step (a) to give a pharmaceutically acceptable salt or solvate of a compound of formula (I) in which $W=NR_0$ with $R_0$ as defined above.

Step (a):
When $R_0$ Represents a $(C_1\text{-}C_6)$Alkyl Optionally Substituted with CHO, $CO_2H$ or $CO_2$—$((C_1\text{-}C_6)$Alkyl):

The term "leaving group", as used in the present invention, refers to a chemical group which can be easily replaced with a nucleophile during a nucleophile substitution reaction, the nucleophile being in the case of step (a) a secondary amine, i.e. a molecule carrying a group NH. Such a leaving group can be in particular a halogen atom or a sulfonate. The sulfonate is in particular a group —$OSO_2$—$R_7$ with $R_7$ representing a $(C_1\text{-}C_6)$alkyl, aryl, aryl-$(C_1\text{-}C_6)$-alkyl or $(C_1\text{-}C_6)$-alkyl-aryl group. The sulfonate can be in particular a mesylate ($CH_3$—$S(O_2)O$—), a triflate ($CF_3$—$S(O)_2O$—) or a tosylate (p-Me-$C_6H_4$—$S(O)_2O$—).

The LG group can be in particular a halogen atom such as a bromine.

Step (a) is advantageously carried out in the presence of a base such as triethylamine.

When $R_0$ represents a substituted $(C_1\text{-}C_6)$alkyl group, the $(C_1\text{-}C_6)$alkyl group will be advantageously substituted with a $CO_2$—$((C_1\text{-}C_6)$alkyl) group. This group can then be hydrolysed, notably in the presence of NaOH or KOH, to give a $CO_2H$ group ($R_0$ represents then a $(C_1\text{-}C_6)$alkyl substituted with $CO_2H$). A reduction step in conditions well known to the one skilled in the art allows obtaining a CHO group ($R_0$ represents then a $(C_1\text{-}C_6)$alkyl substituted with CHO).

When $R_0$ Represents CHO:
The reaction is advantageously performed using DMF as solvent, notably in the presence of a base such as triethylamine.

When $R_0$ Represents $CO_2$—$((C_1\text{-}C_6)$Alkyl):
This reaction can be carried out in conditions to prepare carbamates well known to the one skilled in the art.

Step (b):
The salification or solvatation step can be carried out by methods well known to the one skilled in the art, in particular by reaction of the compound of formula (I) obtained in step (a) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (a).

Thus steps (a) and (b) can be carried out in a single step, without isolating intermediate compounds.

A second method is a method to prepare a compound of formula (I) or a pharmaceutically acceptable salt or solvate thereof, in which W represents $NR_0$,

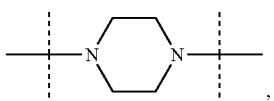

-continued

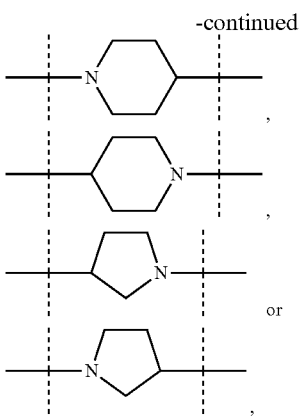

comprising:
(1) reacting a compound of the following formula (II):

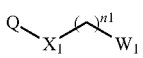
(II)

in which Q, $X_1$ and n1 are as defined above and $W_1$ represents $LG_1$, $NHR_8$,

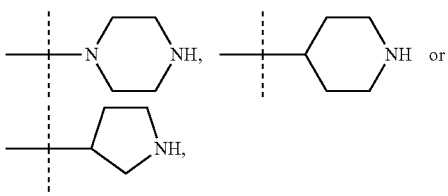

with a compound of the following formula (III):

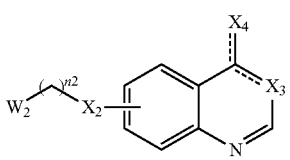
(III)

in which $X_2$, $X_3$, $X_4$ and n2 are as defined above and $W_2$ represents $LG_2$, $NHR_8$,

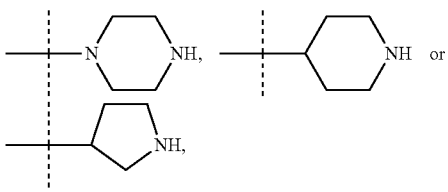

wherein $LG_1$ and $LG_2$ represent, independently of each other, a leaving group and $R_8$ represents $R_0$ or a N-protecting group, on the condition that:
when $W_1$ represents $LG_1$, then $W_2$ represents $NHR_8$,

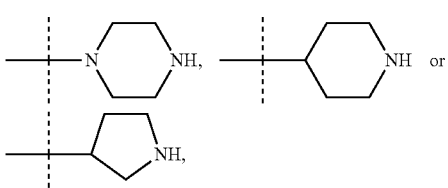

and when $W_1$ represents $NHR_8$,

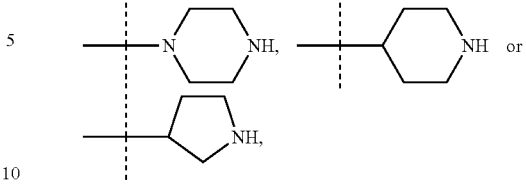

then $W_2$ represents $LG_2$,
and, when $W_1$ or $W_2$ represents $NHR_8$ with $R_8$ representing a N-protecting group, deprotecting the nitrogen atom bearing the N-protecting group, to give a compound of formula (I) as defined above, and
(2) optionally salifying or solvating the compound obtained in step (1) to give a pharmaceutically acceptable salt or solvate of a compound of formula (I) as defined above.

Step (1):

The $LG_1$ and $LG_2$ groups can be in particular a halogen atom such as a bromine or chlorine.

The reaction between the compounds of formula (II) and (III) can be carried out in the presence of a base, such as $K_2CO_3$. A catalytic amount of KI can also be added to the reaction medium.

$R_8$ can represent in particular H or a N-protecting group, notably a N-protecting group. When $W_1$ or $W_2$ represents $NHR_8$ with $R_8$ representing H or a N-protecting group, it is possible to prepare compounds of formula (I) with W=NH.

The term "protecting group", as used in the present invention, refers to a chemical group which selectively blocks a reactive site in a multifunctional compound so as to allow selectively performing a chemical reaction on another unprotected reactive site.

The term "N-protecting group", as used in the present invention, refers to those groups intended to protect an amine function (notably a primary amine function) against undesirable reactions (such as a disubstitution of the primary amine function) during synthetic procedures. Commonly used N-protecting groups are disclosed in Greene, "Protective Groups In Organic Synthesis," (John Wiley & Sons, New York (1981)). An amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular, N-protecting groups include formyl; benzyl (Bn); —CO—$R_9$ such as acetyl (Ac), pivaloyl (Piv or Pv) or benzoyl (Bz); —$CO_2$—$R_9$ such as tbutyloxycarbonyl (Boc), trichloroethoxycarbonyl (TROC), allyloxycarbonyl (Alloc) or benzyloxycarbonyl (Cbz or Z); —$SO_2$—$R_9$ such as phenylsulfonyl or 2-nitrobenzenesulfonyl (Nos or Ns); and the like, with $R_9$ representing a ($C_1$-$C_6$)alkyl optionally substituted with one or several halogen atoms such as F or Cl; a ($C_2$-$C_6$)alkenyl such as an allyl; an aryl, such as a phenyl, optionally substituted with $NO_2$; or an aryl-($C_1$-$C_6$)alkyl such as a benzyl.

The step of deprotecting the nitrogen atom bearing the N-protecting group can be carried out by methods well known to the one skilled in the art, notably as disclosed in Greene, "Protective Groups In Organic Synthesis," (John Wiley & Sons, New York (1981)).

The N-protecting group will be in particular 2-nitrobenzenesulfonyl (Nos or Ns). It can be deprotected in the presence of thiophenol.

The compounds of formulas (II) and (III) are either commercially available or prepared by methods well known to the one skilled in the art, notably as illustrated in the examples below.

In particular, the compound of formula (II) can be prepared by reacting a compound of formula Q-Hal with a compound of formula $HX_1$—$(CH_2)_{n1}$—$W_3$ where:
Q, $X_1$ and n1 are as defined above,
Hal represents a halogen atom such as Cl or Br, and
$W_3$ represents a group $W_1$, optionally in a protected form ($W_3$ can represent notably OH).

This reaction can be performed optionally in the presence of a base.

Further steps of protection(s), deprotection(s) and/or functionalization(s) well known to the one skilled in the art can be carried out, in particular a deprotection step of the $W_3$ group can be carried out to introduce the $W_1$ function on the molecule.

When the compound of formula (III) is a compound of the following formula (IIIc):

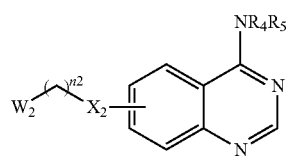

(IIIc)

with $W_2$, $X_2$, $R_4$, $R_5$ and n2 as defined above,
this compound can be prepared by reacting a compound of the following formula (IV):

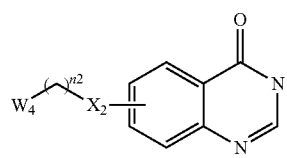

(IV)

with $X_2$ and n2 as defined above and $W_4$ representing a group $W_2$, optionally in a protected form,
with an amine of formula $R_4R_5NH$ with $R_4$ and $R_5$ as defined above.

This reaction can be performed in the presence of a base such as $K_2CO_3$ or triethylamine.

The carbonyl function of the compound of formula (IV) can be activated in the form of a triazole, notably by reaction with $POCl_3$ and triazole (more particularly 1,2,3-triazole) preferably in the presence of a base such as triethylamine.

Thus the compound of formula (IIIc) can be prepared by:
activating the compound of formula (IV) in the form of a triazole of the following formula (V):

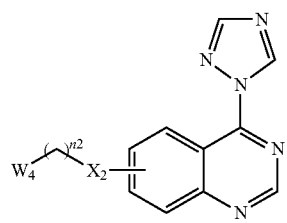

(V)

with $W_4$, $X_2$ and n2 as defined above, and
reacting the triazole of formula (V) with the amine of formula $R_4R_5NH$.

Further steps of protection(s), deprotection(s) and/or functionalization(s) well known to the one skilled in the art can be carried out, in particular a deprotection step of the $W_4$ group can be carried out to introduce the $W_2$ function on the molecule.

When the compound of formula (III) is a compound of the following formula (IIId):

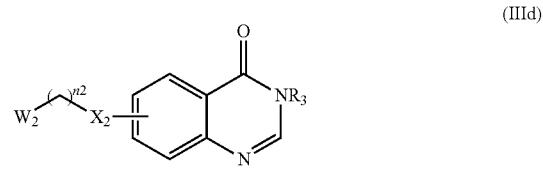

(IIId)

with $W_2$, $X_2$, $R_3$ and n2 as defined above, and $R_3 \neq H$,
this compound can be prepared by reacting a compound of formula (IV) as defined above with a compound of formula $R_3$-$LG_3$ with $R_3$ as defined above and $LG_3$ representing a leaving group, such as a halogen atom (e.g. Cl or Br).

This reaction can be carried out in the presence of a base, such as $K_2CO_3$. A catalytic amount of KI can also be added to the reaction medium.

Further steps of protection(s), deprotection(s) and/or functionalization(s) well known to the one skilled in the art can be carried out, in particular a deprotection step of the $W_4$ group can be carried out to introduce the $W_2$ function on the molecule.

The compound of formula (IV) can be prepared by reacting a compound of the following formula (VI):

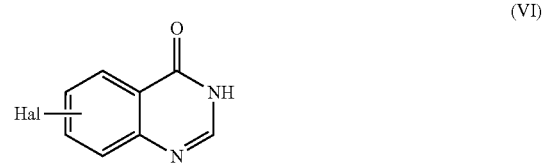

(VI)

where Hal represents a halogen atom such as F,
with a compound of formula $W_4$—$(CH_2)_{n2}$—$X_2H$ where $W_4$, $X_2$ and n2 are as defined above.

This reaction can be carried out in the presence of a base such as NaH.

Step (2):

The salification or solvatation step can be carried out by methods well known to the one skilled in the art, in particular by reaction of the compound of formula (I) obtained in step (1) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (1).

Thus steps (1) and (2) can be carried out in a single step, without isolating intermediate compounds.

A third method is a method to prepare a compound of formula (I) or a pharmaceutically acceptable salt or solvate thereof, comprising:
(A) reacting a compound of the following formula (VII):

$Q$-$X_6$     (VII)

in which Q is as defined above and $X_6$ represents a halogen atom (e.g. Cl or Br) or —$X_1$—$(CH_2)_{n1}$—$W$—$(CH_2)_{n2}$—$X_2H$ with W, $X_1$, $X_2$, n1 and n2 as defined above, with a compound of the following formula (VIII):

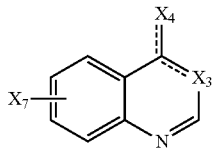

(VIII)

in which $X_3$ and $X_4$ are as defined above and $X_7$ represents a halogen atom (e.g. F) or $-X_2-(CH_2)_{n2}-W-(CH_2)_{n1}-X_1H$ with W, $X_1$, $X_2$, n1 and n2 as defined above, on the condition that:
when $X_6$ represents a halogen atom, then $X_7$ represents $-X_2-(CH_2)_{n2}-W-(CH_2)_{n1}-X_1H$, and
when $X_6$ represents $-X_1-(CH_2)_{n1}-W-(CH_2)_{n2}-X_2H$, then $X_7$ represents a halogen atom,
to give a compound of formula (I), and
(B) optionally salifying or solvating the compound obtained in step (A) to give a pharmaceutically acceptable salt or solvate of a compound of formula (I) as defined above.

Step (A):

The reaction between the compounds of formula (VII) and (VIII) can be carried out in the presence of a base, such as $K_2CO_3$. A catalytic amount of KI can also be added to the reaction medium.

The compounds of formulas (VII) and (VIII) are either commercially available or prepared by methods well known to the one skilled in the art, notably as illustrated in the examples below.

In particular, the compound of formula (VII), when $X_6$ represents $-X_1-(CH_2)_{n1}-W-(CH_2)_{n2}-X_2H$, can be prepared by reacting a compound of formula Q-Hal with a compound of formula $HX_1-(CH_2)_{n1}-W-(CH_2)_{n2}-X_8$ where:
Q, $X_1$, W, n1 and n2 are as defined above,
Hal represents a halogen atom such as Cl or Br, and
$X_8$ represents a group $X_2H$, optionally in a protected form.

This reaction can be performed optionally in the presence of a base.

Further steps of protection(s), deprotection(s) and/or functionalization(s) well known to the one skilled in the art can be carried out, in particular a deprotection step of the $X_8$ group can be carried out to introduce the $X_2H$ function on the molecule.

When the compound of formula (VIII) is a compound of the following formula (VIIIc):

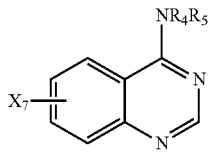

(VIIIc)

with $X_7$, $R_4$ and $R_5$ as defined above,
this compound can be prepared by reacting a compound of the following formula (IX):

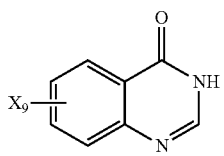

(IX)

with $X_9$ representing a group $X_7$, optionally in a protected form,
with an amine of formula $R_4R_5NH$ with $R_4$ and $R_5$ as defined above.

This reaction can be performed in the presence of a base such as $K_2CO_3$ or triethylamine.

The carbonyl function of the compound of formula (IX) can be activated in the form of a triazole, notably by reaction with $POCl_3$ and triazole (more particularly 1,2,3-triazole) preferably in the presence of a base such as triethylamine.

Thus the compound of formula (VIIIc) can be prepared by:
activating the compound of formula (IX) in the form of a triazole of the following formula (X):

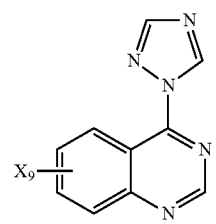

(X)

with $X_9$ as defined above, and
reacting the triazole of formula (X) with the amine of formula $R_4R_5NH$.

Further steps of protection(s), deprotection(s) and/or functionalization(s) well known to the one skilled in the art can be carried out, in particular a deprotection step of the $X_9$ group can be carried out to introduce the $X_7$ group on the molecule.

When the compound of formula (VIII) is a compound of the following formula (VIIId):

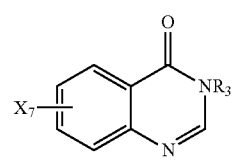

(VIIId)

with $X_7$ and $R_3$ as defined above, and $R_3 \neq H$,
this compound can be prepared by reacting a compound of formula (IX) as defined above with a compound of formula $R_3$-$LG_3$ with $R_3$ as defined above and $LG_3$ representing a leaving group, such as a halogen atom (e.g. Cl or Br).

This reaction can be carried out in the presence of a base, such as $K_2CO_3$. A catalytic amount of KI can also be added to the reaction medium.

Further steps of protection(s), deprotection(s) and/or functionalization(s) well known to the one skilled in the art can be carried out, in particular a deprotection step of the $X_9$ group can be carried out to introduce the $X_7$ group on the molecule.

The compound of formula (IX), when $X_9$ represents $-X_2-(CH_2)_{n2}-W-(CH_2)_{n1}-X_{10}$ where $X_{10}$ represents $X_1H$ optionally in a protected form, can be prepared by reacting a compound of the formula (VI) with a compound of formula $HX_2-(CH_2)_{n2}-W-(CH_2)_{n1}-X_{10}$ where W, $X_2$, $X_{10}$, n1 and n2 are as defined above.

This reaction can be carried out in the presence of a base such as NaH.

Step (B):

The salification or solvatation step can be carried out by methods well known to the one skilled in the art, in particular by reaction of the compound of formula (I) obtained in step (A) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (A).

Thus steps (A) and (B) can be carried out in a single step, without isolating intermediate compounds.

Further steps of protection(s), deprotection(s) and/or functionalization(s) well known to the one skilled in the art can be carried out to obtained the compounds of formula (I).

The compound according to the present invention obtained by one of the methods described above can be separated from the reaction medium by methods well known to the one skilled in the art, such as by extraction, evaporation of the solvent or by precipitation or crystallisation (followed by filtration).

This compound can also be purified if necessary by methods well known to the one skilled in the art, such as by recrystallisation, by distillation, by chromatography on a column of silica gel or by high performance liquid chromatography (HPLC).

The examples which follow illustrate the invention without limiting its scope in any way.

EXAMPLES

The following abbreviations have been used in the following examples.

a.a.: Amino acid
AdoMet: S-Adenosyl-L-methionine
BSA: N,O-Bis(trimethylsilyl)acetamide
DCM: Dichloromethane
DiPEA: N,N-Diisopropylethylamine
DMAP: 4-Dimethylaminopyridine
DMF: Dimethylformamide
DMSO: Dimethylsulfoxide
EDTA: Ethylenediaminetetraacetic acid
ESI: Electrospray ionisation
HEPES: 4-(2-Hydroxyethyl)-1-piperazineethanesulfonic acid
HPLC: High Performance Liquid Chromatography
HRMS: High Resolution Mass Spectrometry
NMR: Nuclear Magnetic Resonance
Nos: 2-Nitrobenzenesulfonyl
PBS: Phosphate buffered saline
PBST: Phosphate buffered saline+Tween-20
RT: Room temperature
SAH: S-Adenosyl-L-homocysteine
SAM: S-Adenosyl-L-methionine
TEA: Triethylamine
TFA: Trifluoroacetic acid
TLC: Thin Layer Chromatography
Tris: Tris(hydroxymethyl)aminomethane

I. Synthesis of the Compounds According to the Invention

Example 1: Compound F

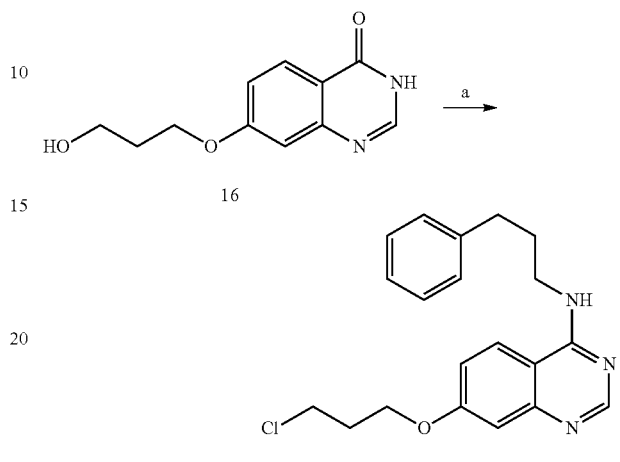

a) i) SOCl$_2$, 110° C., 1 h. ii) Phenylpropylamine, DMF, K$_2$CO$_3$, RT, 2 h, 85%.

4-(3-phenylpropylamino)-7-(2-chloroethoxy)quinazoline (17)

A solution of 16 (440 mg; 2.01 mmol) in thionylchloride (10 mL) and a catalytic amount of DMF was boiled for 30 min. The solvent was removed and the crude product was dissolved in a solution of phenylpropylamine (570 μL; 4.0 mmol) in DMF and the mixture was stirred at room temperature for 2 h. The mixture was diluted with ethylacetate and the organic phase was washed with a saturated solution of Na$_2$CO$_3$, brine and dried over magnesium sulfate. The solvent was removed and the residue was purified by silica gel flash chromatography using a linear gradient of ethylacetate (0→100% ethylacetate) in cyclohexane to obtain 17 as a pale brown solid (607 mg; 1.70 mmol; yield 85%).

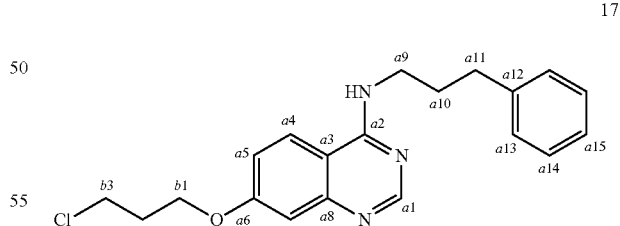

$^1$H NMR (500 MHz, CDCl$_3$) δ 8.58 (s, 2H, Ha1), 7.35-7.13 (m, 7H, Ha7, Ha15, Ha13 and Ha14), 6.99 (dd, J=2.4, 9.0 Hz, 1H, Ha5), 5.53 (brs, 1H, HNH), 4.22 (t, J=6.0 Hz, 2H, Hb1), 3.76 (t, J=6.0 Hz, 2H, Hb3), 3.70 (q, J=7.2 Hz, 2H, Ha9), 2.79 (t, J=7.2 Hz, 2H, Ha11), 2.28 (quint, J=6.1 Hz, 2H, Ha10), 2.07 (quint, J=7.0 Hz, 2H, Hb2).

$^{13}$C NMR (125 MHz, CDCl$_3$) δ 162.0 (Ca6), 159.1 (Ca2), 156.1 (Ca1), 151.7 (Ca8), 141.7 (Ca12), 128.8 (Ca13), 128.6 (Ca14), 126.3 (Ca15), 122.0 (Ca4), 117.8 (Ca5), 109.3

(Ca3), 108.1 (Ca7), 64.7 (Cb1), 41.4 (Cb3), 41.3 (Ca9), 33.8 (Ca11), 32.1 (Cb2), 30.8 (Ca10).

HRMS-ESI (m/z) calculated for $C_{20}H_{23}N_3ClO$ [M+H]$^+$: 356.1524. Found: 356.1527.

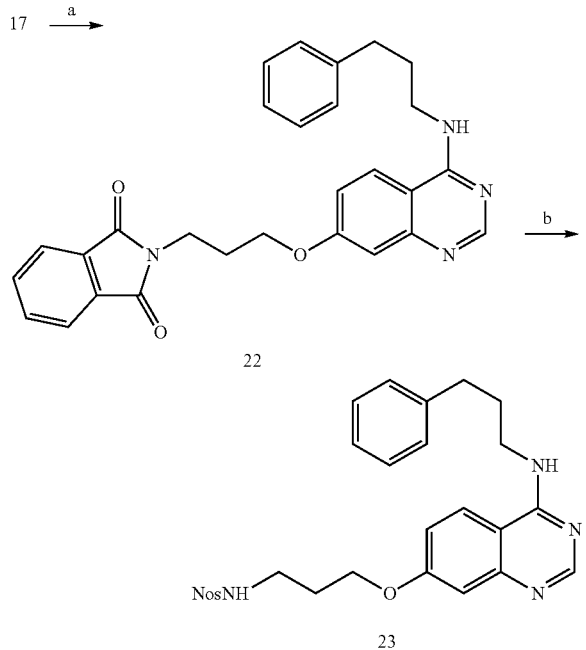

a) phthalimide potassium salt, DMF, 90° C., 3 h, 98%. b) i) CH$_3$NHNH$_2$, ethanol, RT, 18 h, 82%. ii) NosCl, TEA, DMF, RT, 6 h, 96%

7-((3-phthalimido)propyloxy)-4-((3-phenylpropyl)amino)quinazoline (22)

To a solution of 17 (50 mg; 141 μmol) in DMF (1 mL) was added phthalimide potassiums salt and the mixture was heated at 90° C. for 6 h. The mixture was diluted with ethylacetate and the organic phase was washed with a saturated solution of Na$_2$CO$_3$, brine and dried over magnesium sulfate. The solvent was removed and the residue was purified by silica gel flash chromatography using a linear gradient of ethylacetate (0→100% ethylacetate) in cyclohexane to obtain 22 as a pale yellow solid (63 mg; 138 μmol; yield 98%).

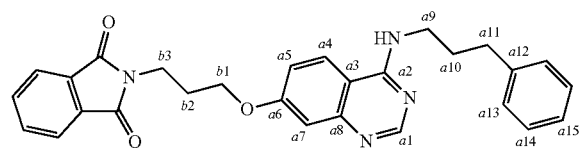

$^1$H NMR (500 MHz; CDCl$_3$) δ 8.58 (s, 1H, Ha1), 7.86 (m, 2H, Hphtha), 7.74 (m, 4H, Hphtha), 7.35-7.25 (m, 6H, Ha4 and Ha13 and Ha14 and Ha15), 7.10 (d, J=2.5 Hz, 1H, Ha7), 6.92 (dd, J=2.5, 9.0 Hz, 1H, Ha5), 5.47 (brt, J=5.1 Hz, 1H, HNH), 4.15 (t, J=6.3 Hz, 2H, Hb1), 3.96 (t, J=7.0 Hz, 2H, Hb3), 3.72 (q, J=6.7 Hz, 2H, Ha9), 2.82 (q, J=7.3 Hz, 2H, Ha11), 2.26 (quint, J=6.3 Hz, 2H, Hb2), 2.10 (quint, H=7.3 Hz, 2H, Ha10).

$^{13}$C NMR (125 MHz, CDCl$_3$) δ 168.3 (Cphtha), 162.0 (Ca6), 159.0 (Ca2), 157.8 (Ca1), 151.3 (Ca8), 141.5 (Ca12), 134.0 (Cphtha), 132.1 (Cphtha), 128.7 (Ca13), 128.4 (Ca14), 126.1 (Ca15), 123.3 (Cphtha), 121.8 (Ca4), 117.9 (Ca5), 109.0 (Ca3), 107.6 (Ca7), 65.7 (Cb1), 41.1 (Ca9), 35.3 (Cb3), 33.7 (Ca11), 30.7 (Ca10), 28.0 (Cb2).

HRMS-ESI (m/z) calculated for $C_{28}H_{27}N_4O_3$ [M+H]$^+$: 467.2078. Found: 467.2078.

7-((2-nitrobenzenesulfonamido)propyloxy)-4-((3-phenylpropyl)amino)quinazoline (23)

To a solution of 22 (60 mg; 129 μmol) in ethanol (2 mL), was added N-methylhydrazine (2004). After stirring at room temperature for 12 h, the solvent was removed and the residue was co-evaporated with toluene until the N-methylhydrazine was completely eliminated. To the crude product was added a solution of 2-nitrobenzene sulfonyl chloride (71 mg; 322 mmol) and TEA (54 μL; 387 μmol). The mixture was stirred at room temperature for 3 h, then was diluted with ethylacetate. The organic phase was washed with saturated Na$_2$CO$_3$, with brine and dried over magnesium sulfate. The solvent was removed and the residue was purified by silica gel flash chromatography using a linear gradient of methanol (0→10% MeOH) in dichloromethane to obtain 23 as a pale yellow solid (61 mg; 117 μmol; yield 91%).

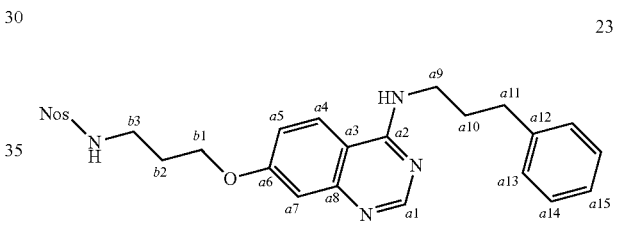

$^1$H NMR (500 MHz; CDCl$_3$) δ 8.59 (s, 1H, Ha1), 8.15 (m, 1H, HNos), 7.83 (m, 1H, HNos), 7.69 (m, 2H, HNos), 7.37-7.30 (m, 3H, Ha4 and Ha13), 7.22-7.15 (m, 3H, Ha14 and Ha15), 7.10-7.05 (m, 2H, Ha7 and Ha5), 5.84 (brt, J=5.3 Hz, 1H, HNH), 5.51 (brt, J=5.4 Hz, 1H, HNH), 4.13 (t, J=3.4 Hz, 2H, Hb1), 3.73 (q, J=6.3 Hz, 2H, Ha9), 3.42 (q, J=6.5 Hz, Hb3), 2.82 (q, J=6.8 Hz, 2H, Ha11), 2.17-2.07 (m, 4H, Ha10 and Hb2).

$^{13}$C NMR (125 MHz, CDCl$_3$) δ 161.5 (Ca6), 159.0 (Ca2), 155.9 (Ca1), 151.3 (Ca8), 148.0 (CNos), 141.5 (Ca12), 133.6 (CNos), 133.5 (CNos), 132.8 (CNos), 130.9 (CNos), 128.7 (Ca13), 128.4 (Ca14), 126.2 (Ca15), 125.4 (CNos), 122.0 (Ca4), 117.9 (Ca5), 109.2 (Ca3), 107.6 (Ca7), 66.1 (Cb1), 41.8 (Cb3), 41.2 (Ca9), 33.7 (Ca11), 30.7 (Ca10), 28.9 (Cb2).

HRMS-ESI (m/z) calculated for $C_{29}H_{37}N_8O_4$ [M+H]$^+$: 522.1806. Found: 522.1801.

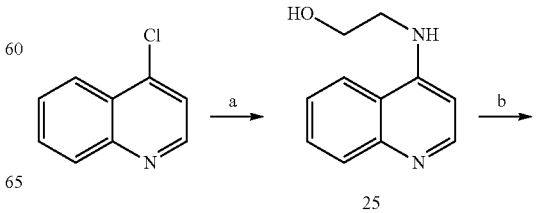

-continued

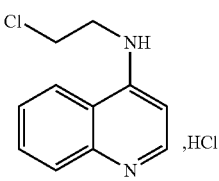

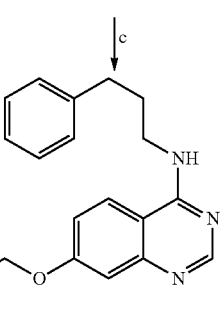

Compound F a) Ethanolamine, 125° C., 4 h, quantitative yield. b) SOCl₂, DMF cat., Flash boiling, quantitative yield. c) i) 23, K₂CO₃, KI, DMF, 90° C., 12 h, 74%. ii) PhSH, K₂CO₃, DMF, RT, 24 h, 91%.

4-((2-Hydroxyethyl)amino)quinoline (25)

A mixture of 4-chloroquinoline (360 mg; 2.21 mmol) in ethanolamine (1.5 mL; 22 mmol) was stirred at 110° C. for 3 h. The solvent was removed and the residue was purified by silica gel flash chromatography using a linear gradient of methanol (0→10% MeOH) in dichloromethane to afford 25 as a white powder (414 mg; 2.20 mmol; quantitative yield).

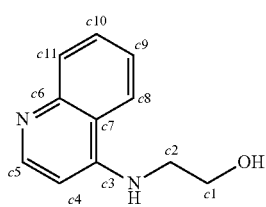

$^1$H NMR (500 MHz; CDCl$_3$) δ 8.38 (d, J=5.4 Hz, 1H, Hc5), 8.19 (dd, J=0.9, 8.3 Hz, 1H, Hc8), 7.77 (dd, J=0.9, 8.3 Hz, 1H, Hc11), 7.59 (ddd, J=1.3, 6.7, 8.3 Hz, 1H, Hc10), 7.40 (ddd, J=1.3, 6.7, 8.3 Hz, 1H, Hc9), 7.07 (brt, J=5.2 Hz, 1H, HOH), 6.46 (d, J=5.4 Hz, 1H, Hc4), 4.83 (brt, J=5.5 Hz, 1H, HNHc), 3.66 (q, J=6.0 Hz, 2H, Hc1), 3.35 (q, J=5.4 Hz, 2H, Hc2).

$^{13}$C NMR (125 MHz, CDCl$_3$) δ 151.1 (Cc5), 150.5 (Cc3), 148.8 (Cc6), 129.5 (Cc8), 129.1 (Cc10), 124.2 (Cc9), 122.1 (Cc11), 119.3 (Cc7), 98.6 (Cc4), 59.3 (Cc1), 45.5 (Cc2).

HRMS-ESI (m/z) calculated for C$_{11}$H$_{13}$N$_2$O [M+H]$^+$: 189.1022. found: 189.1031.

4-((2-chloroethyl)amino)quinoline chlorhydrate (26)

25 (360 mg; 1.92 mmol) was solubilized in thionyl chloride (3 ml). The mixture was flash boiled and the solvent was removed. Toluene was added to remove the residual thionyl chloride by co-evaporation. The residue was triturated in dichloromethane and the solid was filtrated to afford 26 as a white solid (360 mg; 1.75 mmol; 91%).

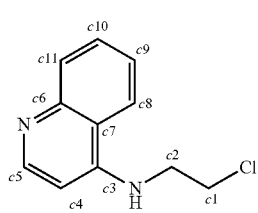

$^1$H NMR (500 MHz; CDCl$_3$) δ 8.59 (d, J=5.2 Hz, 1H, Hc5), 8.00 (dd, J=0.7, 8.3 Hz, 1H, Hc8), 7.79 (d, J=8.3 Hz, 1H, Hc11), 7.65 (ddd, J=1.3, 7.9, 8.3 Hz, 1H, Hc10), 7.45 (ddd, J=1.3, 7.0, 8.3 Hz, 1H, Hc9), 6.43 (d, J=5.3 Hz, 1H, Hc4), 5.51 (brs, 1H, HNHc), 3.84 (t, J=5.8 Hz, 2H, Hc1), 3.70 (q, J=5.8 Hz, 2H, Hc1).

$^{13}$C NMR (125 MHz, CDCl$_3$) δ 151.0 (Cc5), 148.9 (Cc3), 148.5 (Cc6), 130.0 (Cc8), 129.2 (Cc10), 125.0 (Cc9), 119.3 (Cc11), 118.9 (Cc7), 99.0 (Cc4), 44.4 (Cc2), 42.6 (Cc1).

HRMS-ESI (m/z) calculated for C$_{11}$H$_{13}$N$_2$Cl [M+H]$^+$: 207.0684. found: 207.0678.

7-(3-((2-(quinolin-4-ylamino)ethyl)amino)propyloxy)-4-((3-phenylpropyl)amino)quinazoline (Compound F)

To a solution of 23 (50 mg; 96 μmol), K$_2$CO$_3$ (22 mg; 0.160 mmol) and a catalytic amount of KI in DMF (1 mL) was added 26 (40 mg; 288 μmol). The mixture was stirred at 65° C. overnight then thiophenol (24 μL; 240 mmol) was added. The mixture was stirred for a day then diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.2% of TEA (0→80% CH$_3$CN) to afford Compound F as a white powder (32 mg; 0.64 mmol, 67%).

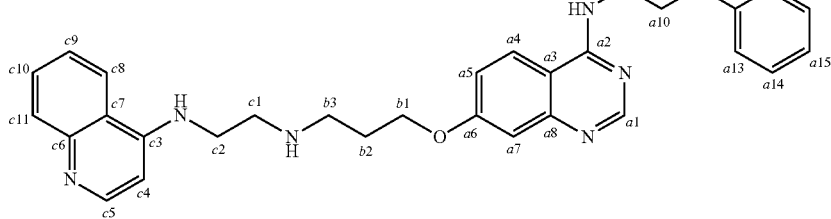

¹H NMR (DMSO+MeOD) δ 8.39 (m, 2H, Ha1 and Hc5), 8.19-8.07 (m, 3H, Hc8, HNH and Ha4), 7.76 (dd, J=0.9, 8.4 Hz, 1H, He11), 7.58 (ddd, J=1.3, 6.7, 8.2 Hz, 1H, Hc10), 7.39 (ddd, J=1.3, 6.7, 8.2 Hz, 1H, Hc9), 7.43-7.20 (m, 4H, Ha13 and Ha14), 7.17 (brt, J=7.1 Hz, Ha15), 7.12-7.04 (m, 3H, Ha7, HNH and Ha5), 6.47 (d, J=5.7 Hz, 1H, Hc4), 4.17 (t, J=6.2 Hz, 2H, Hb1), 3.52 (q, J=6.9 Hz, 2H, Ha9), 3.35 (m, 2H, Hc2), 2.84 (t, J=6.6 Hz, 2H, Hc1), 2.73 (t, J=6.5 Hz, 2H, Hb3), 2.67 (t, J=7.4 Hz, 2H, Ha11), 2.00-1.83 (m, 4H, Ha10 and Hb2).
¹³C NMR (DMSO+MeOD) δ 162.1 (Ca6), 159.5 (Ca2), 156.1 (Ca1), 151.8 (Ca8), 151.1 (Cc5), 150.4 (Cc3), 148.7 (Cc6), 142.2 (Ca12), 129.5 (Cc11), 129.1 (Cc10), 128.8 (Ca13), 128.7 (Ca14), 126.2 (Ca15), 124.7 (Ca4), 124.2 (Cc9), 122.0 (Cc8), 119.3 (Cc7), 117.1 (Ca5), 109.5 (Ca3), 107.8 (Ca7), 98.6 (Cc4), 66.9 (Cb1), 48 (Cc1), 46 (Cb3), 43 (Cc2), 40.6 (Ca9), 33.1 (Ca11), 30.8 (Ca10), 29.8 (Cb2).
HRMS-ESI (m/z) calculated for $C_{31}H_{35}N_6O$ [M+H]⁺: 507.2667. found: 507.2666.
Example 2: Compounds A, B, C, D, E, T and U
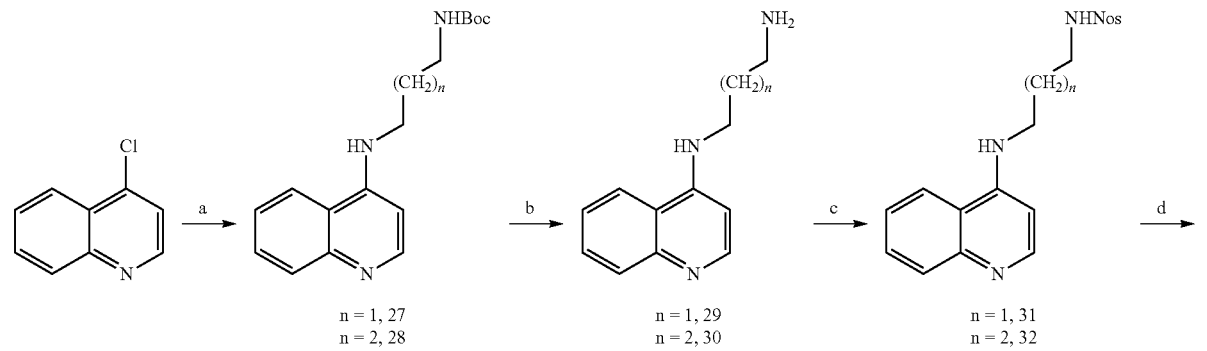
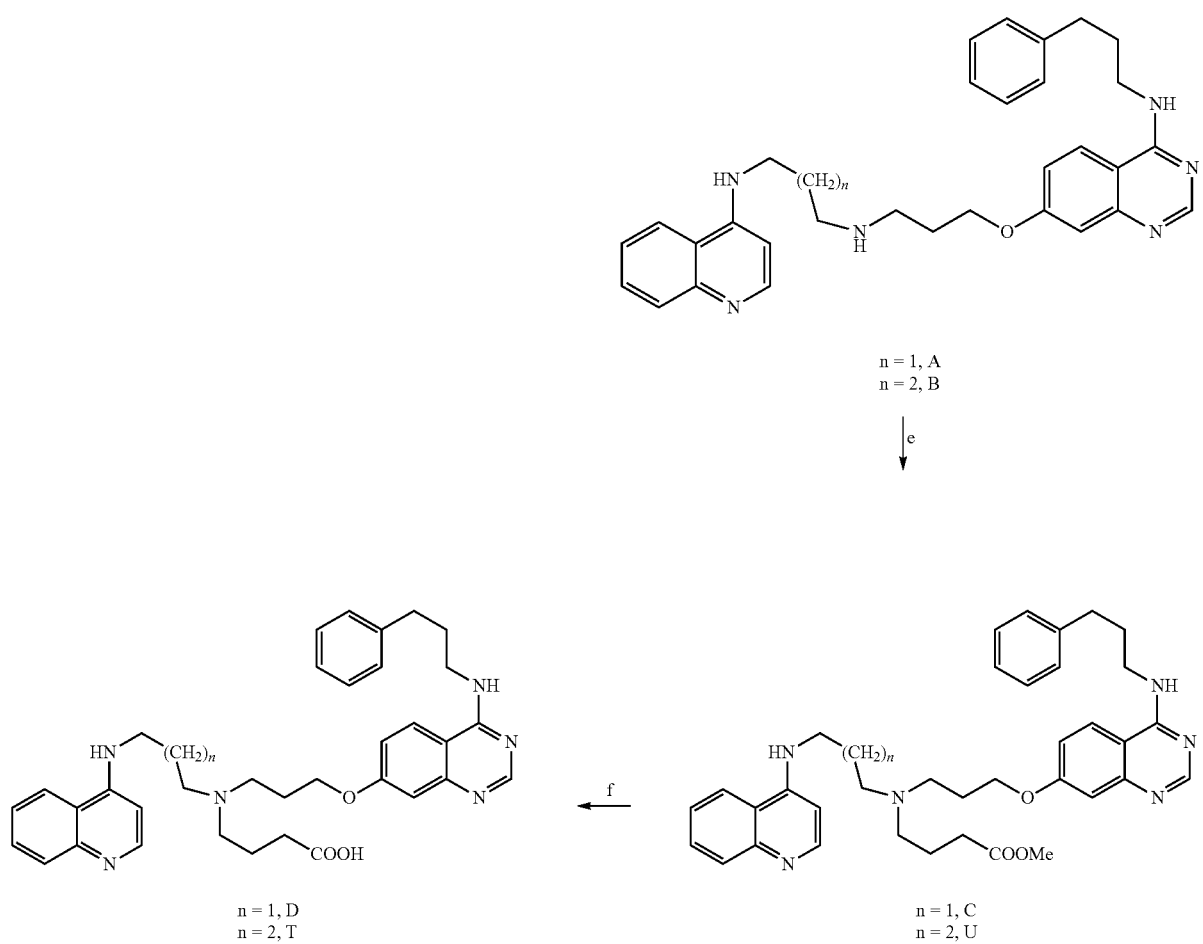

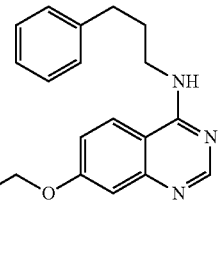

E a) 3-Bocaminopropylamine or 4-Bocaminobutylamine, DMF, 125° C., 4 h, 78% for n = 1 and 73% for n = 2. b) TFA, 91% for n = 1 and 84% for n = 2. c) NosCl, TEA, DMAP cat., DMF, RT, 6 h, 66% for n = 1 and 71% for n = 2. d) i) 17, $K_2CO_3$, KI cat., DMF, RT, 80° C., 6 h, 71% for n = 1 and 75% for n = 2. ii) PhSH, $K_2CO_3$, MeCN, RT, 24 h, 85% for n = 1 and 75% for n = 2. e) TFA, water, RT, 1 h. or e) i) 4-Bromobutanoic acid methyl ester, TEA, DMF, 90° C., 12 h, 44% for n = 1 and 45% for n =2. f) 0.5N NaOH, dioxane, 18 h, 78% for n = 1 and 79% for n = 2.

4-((2-Bocaminopropyl)amino)quinoline (27)

4-((2-Bocaminobutyl)amino)quinoline (28)

A solution of N-bocaminopropane amine (2.06 g, 11.84 mmol) or N-bocaminobutane amine (2.25 g, 12 mmol), 4-chloroquinoline (1.525 g, 9.32 mmol) and DiPEA (1.8 mL, 10.3 mmol) in 12 mL of n-pentanol was stirred at reflux for 6 hours. The solvent was removed and the residue was diluted in DCM. The organic layer was washed with NaOH 2M (2×) and the aqueous phase was extracted with DCM (3×). The organics layers are collected and combined, dried over $Na_2SO_4$ and the solvent was removed. The residue was purified by recrystallization in toluene. 27 was obtained as a brown solid (2.02 g, 6.69 mmol; 72%) and 28 was obtained as a pale brown solid (2.35 g; 7.44 mmol; 62%).

27

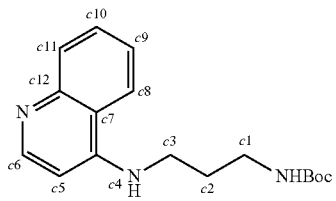

$^1$H NMR (500 MHz; DMSO) δ 8.37 (d, J=5.5 Hz, 1H, Hc6), 8.19 (d, J=8.6 Hz, 1H, Hc8), 7.77 (d, J=8.39 Hz, 1H, Hc11), 7.60 (dd, J=1.2, 6.9 Hz, 1H, Hc10), 7.56 (dd, J=1.2, 6.9 Hz, 1H, Hc9), 7.17 (t, J=4.9 Hz, 1H, HNHBoc), 6.98 (t, J=5.4 Hz, 1H, HNH), 6.43 (d, J=5.4 Hz, 1H, Hc5), 3.31 (q, J=6.3 Hz, 2H, Hc3), 3.09 (q, J=6.3 Hz, 2H, Hc1), 1.81 (quint, J=7.1 Hz, 2H, Hc2), 1.38 (s, 9H, HBoc).
$^{13}$C NMR (125 MHz, CDCl$_3$) δ 156.1 (CBoc), 151.1 (Cc6), 150.2 (Cc4), 148.7 (Cc12), 129.5 (Cc10), 129.1 (Cc11), 124.2 (CC9), 122.0 (Cc8), 119.2 (Cc7), 98.5 (Cc5), 78.0 (CcBoc), 40.4 (Cc3), 38.2 (Cc1), 28.7 (CcBoc), 28.6 (Cc2).
HRMS-ESI (m/z) calculated for $C_{17}H_{23}N_3O_2$ [M+H]+: 302.1863. Found: 302.1865.

28

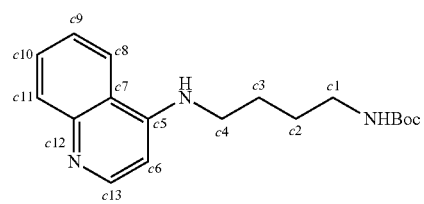

$^1$H NMR (500 MHz, DMSO) δ 8.37 (d, J=5.4 Hz, 1H, Hc13), 8.22 (d, J=8.3, 1H, Hc8), 7.77 (d, J=8.3 Hz, 1H, Hc11), 7.59 (m, 1H, Hc10), 7.40 (ddd, J=1.1, 6.9, 8.9 Hz, 1H, Hc9), 7.15 (brt, J=5.2 Hz, 1H, HNH), 6.86 (brt, J=5.6 Hz, 1H, HNH), 6.43 (d, J=5.6 Hz, 1H, Hc6), 3.27 (q, J=5.6 Hz, 2H, Hc4), 2.98 (q, J=6.3 Hz, 2H, Hc1), 1.64 (quint, J=7.0 Hz, 2H, Hc3), 1.51 (quint, J=7.0 Hz, 2H, Hc2), 1.37 (s, 9H, HBoc).
$^{13}$C NMR (125 MHz, CDCl$_3$) δ 156.1 (CBoc), 151.1 (Cc6), 150.2 (Cc4), 148.7 (Cc12), 129.5 (Cc10), 129.1 (Cc11), 124.2 (CC9), 122.0 (Cc8), 119.2 (Cc7), 98.5 (Cc5), 78.0 (CcBoc), 40.4 (Cc3), 38.2 (Cc1), 28.7 (CcBoc), 28.6 (Cc2).
HRMS-ESI (m/z) calculated for $C_{18}H_{26}N_3O_2$ [M+H]+: 316.2020. Found: 316.2018.

4-((2-aminoethyl)amino)quinoline (29)

4-((2-aminobutyl)amino)quinoline (30)

A solution of 27 (1 g; 3.32 mmol) or 28 (1.1 g; 3.48 mmol) in 10 mL of trifluoroacetic acid was stirred 1 hour at room temperature. The reaction mixture was diluted in toluene and the solvents were removed. The residue was diluted in water, basified to pH=14 with NaOH 30% and extracted with DCM. The organic layer was dried and the solvent was removed.

29 was obtained as a yellow oil (638 mg; 3.17 mmol; 96%) and 30 was obtained as a yellow oil (710 mg; 3.30 mmol; 95%).

29

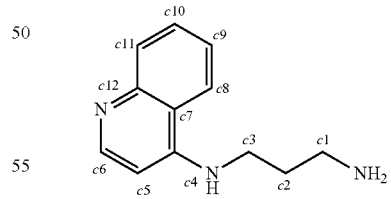

$^1$H NMR (500 MHz; DMSO) δ 8.38 (d, J=4.9 Hz, 1H, Hc6), 8.17 (d, J=8.7 Hz, 1H, Hc8), 7.76 (d, J=8.3 Hz, 1H, Hc11), 7.60 (m, 1H, Hc10), 7.40 (m, 1H, Hc9), 7.25 (brs, 1H, FINE), 6.71 (brs, 2H, HNH2), 6.44 (d, J=5.9 Hz, 1H, Hc5), 3.32 (m, 2H, Hc3), 2.71 (m, 2H, Hc1), 1.76 (m, 2H, Hc2).
$^{13}$C NMR (125 MHz, DMSO) δ 151.7 (Cc6), 150.9 (Cc4), 149.2 (Cc12), 130.0 (Cc10), 129.6 (Cc11), 124.7 (CC9), 122.6 (Cc8), 119.8 (Cc7), 99.0 (Cc5), 41.6 (Cc3), 39.0 (Cc1), 29.4 (Cc2).

HRMS-ESI (m/z) calculated for $C_{12}H_{16}N_3$ [M+H]$^+$: 202.1339. Found: 202.1343.

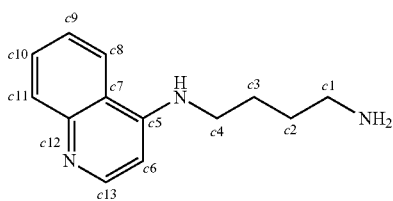

$^1$H NMR (500 MHz; DMSO) δ 8.37 (d, J=5.2 Hz, 1H, Hc13), 8.22 (d, J=8.2 Hz, 1H, Hc8), 7.76 (d, J=8.4 Hz, 1H, Hc11), 7.59 (m, 1H, Hc10), 7.40 (m, 1H, Hc9), 7.25 (brt, J=5.2 Hz, 1H, HNH), 6.44 (d, J=5.4 Hz, 1H, Hc6), 3.34 (m, 2H, Hc4), 3.18 (m, 2H, Hc1), 1.72 (m, 2H, Hc3), 1.64 (m, 2H, Hc2).

$^{13}$C NMR (125 MHz, DMSO) δ 151.2 (Cc13), 150.4 (Cc5), 148.8 (Cc12), 129.4 (Cc10), 129.1 (Cc11), 124.1 (CC9), 122.1 (Cc8), 119.3 (Cc7), 98.6 (Cc6), 50.7 (Cc4), 42.7 (Cc1), 28.5 (Cc3), 26.4 (Cc2).

HRMS-ESI (m/z) calculated for $C_{13}H_{18}N_3$ [M+H]$^+$: 216.1495. Found: 216.1493.

4-((2-(2-nitrobenzenesulfonamido)propyl)amino) quinoline (31)

4-((2-(2-nitrobenzenesulfonamido)butyl)amino)qui- noline (32)

To a solution of 29 (170 mg; 0.85 mmol) or 30 (182 mg; 0.85 mmol), triethylamine (378 μL; 2.72 mmol) and DMAP in catalytic amount in 4 mL of DMF was added 2-nosyl chloride (207 mg; 0.94 mmol). The reaction was stirred at room temperature overnight. The solvent was removed.

The residue containing crude product of 31 was suspended in DCM and one piece of methanol was added until the suspension was diluted. After 30 min at room temperature, 31 crystallized and it was filtrated and washed with DCM to give a yellow powder (225 mg; 0.58 mmol; 68%).

The residue containing crude product of 32 was purified by silica gel flash chromatography using a linear gradient of dicholomethane/methanol (0 to 10%) to give 32 (108 mg; 0.27 mmol; 32%) as a yellow oil.

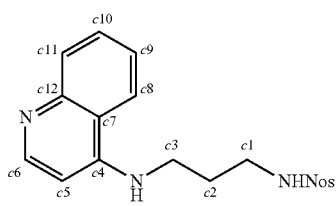

$^1$H NMR (500 MHz; CDCl$_3$) δ 8.49 (d, J=5.4 Hz, 1H, Hc6), 8.08 (dd, J=1.7, 7.7 Hz, 1H, HNos), 7.97 (dd, J=1.0, 8.7 Hz, 1H, Hc8), 7.83-7.78 (m, 2H, Hc11 and HNos), 7.69-7.59 (m, 3H, Hc10 and HNos), 7.45 (ddd, J=1.4, 7.0 Hz, 1H, Hc9), 6.37 (d, J=5.4 Hz, 1H, Hc5), 5.64 (brs, 1H, HNH), 3.29 (brt, J=6.1 Hz, 2H, Hc3), 3.09 (q, J=6.1 Hz, 2H, Hc1), 1.99 (quint, J=6.2 Hz, 2H, Hc2).

$^{13}$C NMR (125 MHz, CDCl$_3$) δ 150.6 (Cc6), 149.5 (Cc4), 148.1 (Cc12), 148.0 (CNos), 133.7 (CNos), 133.3 (CNos), 132.8 (CNos), 130.9 (CNos), 129.5 (Cc10), 129.3 (Cc11), 125.4 (CNos), 124.9 (CC9), 119.5 (Cc8), 118.8 (Cc7), 98.5 (Cc5), 78.0 (CcBoc), 40.9 (Cc3), 39.4 (Cc1), 28.1 (Cc2).

HRMS-ESI (m/z) calculated for $C_{18}H_{19}N_4O_4S$ [M+H]$^+$: 387.1122. Found: 387.1130.

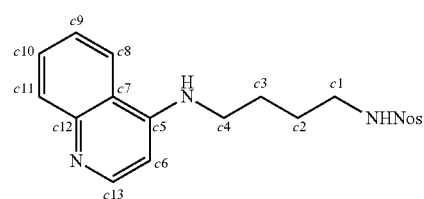

$^1$H NMR (500 MHz; CDCl$_3$) δ 8.52 (d, J=5.4 Hz, 1H, Hc13), 8.08 (m, 1H, HNos), 7.99 (dd, J=1.0, 8.7 Hz, 1H, Hc8), 7.80-7.75 (m, 2H, Hc11 and HNos), 7.69-7.61 (m, 3H, Hc10 and HNos), 7.45 (ddd, J=1.4, 7.1 Hz, 1H, Hc9), 6.37 (d, J=5.5 Hz, 1H, Hc6), 5.26 (brs, 1H, HNH), 3.34 (m, 2H, Hc4), 3.21 (t, J=6.7 Hz 2H, Hc1), 1.83 (m, 2H, Hc2), 1.73 (m, 2H, Hc3).

$^{13}$C NMR (125 MHz, CDCl$_3$) δ 150.6 (Cc13), 149.7 (Cc5), 148.0 (CNos), 147.9 (Cc12), 133.6 (CNos), 133.5 (CNos), 132.8 (CNos), 130.9 (CNos), 129.5 (Cc10), 129.3 (Cc11), 125.3 (CNos), 124.8 (CC9), 119.5 (Cc8), 118.6 (Cc7), 98.6 (Cc6), 43.4 (Cc4), 42.6 (Cc1), 27.3 (Cc3), 25.7 (Cc2).

HRMS-ESI (m/z) calculated for $C_{19}H_{21}N_4O_4S$ [M+H]$^+$: 401.1284. Found: 401.1280.

7-(3-((2-(quinolin-4-ylamino)propyl)amino)propy- loxy)-4-((3-phenylpropyl)amino)quinazoline (Compound A)

7-(3-((2-(quinolin-4-ylamino)butyl)amino)propy- loxy)-4-((3-phenylpropyl)amino)quinazoline (Compound B)

To a solution of 17 (30 mg; 85 μmol) in DMF (1 mL) was added K$_2$CO$_3$ (35 mg; 253 μmol), a catalytic amount of KI and 31 or 32 (128 μmol). The mixture was heated at 90° C. for 6 h then thiophenol (32 μL; 320 mmol) was added. The mixture was stirred at room temperature overnight then diluted with ethyl acetate. The organic phase was washed with a solution of saturated Na$_2$CO$_3$ and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.2% of TEA (0→80% CH$_3$CN) to afford Compound A as a white powder (26 mg; 51 μmol; 60%) or Compound B as a white powder (25 mg; 0.48 mmol; 56%).

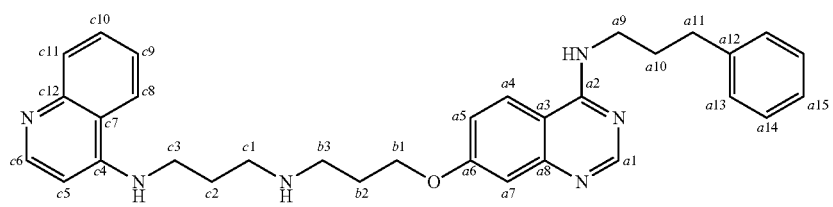

A

¹H NMR (CDCl₃) δ 8.58 (s, 1H, Ha1), 8.48 (d, J=5.5 Hz, 1H, Hc6), 7.96 (d, J=8.4, 1H, Hc8), 7.85 (d, J=8.4 Hz, 1H, Ha4), 7.64 (brs, 1H, HNH), 7.58 (ddd, J=1.3, 6.8, 8.2 Hz, 1H, Hc10), 7.43-7.20 (m, 8H, Hc9, Ha15, Ha5, Hc11, Ha13 and Ha14), 7.14 (d, J=2.6 Hz, 1H, Ha7), 6.34 (d, J=5.7 Hz, 1H, Hc5), 5.72 (brt, J=5.2 Hz, 1H, HNH), 4.19 (t, J=6.0 Hz, 2H, Hb1), 3.71 (q, J=7.0 Hz, 2H, Ha9), 3.45 (t, J=6.0 Hz, 2H, Hc3), 3.00-2.92 (m, 4H, Hc1 and Hb3), 2.80 (t, J=7.4 Hz, 2H, Ha11), 2.21-2.00 (m, 4H, Ha10 and Hb2), 1.98 (quint, J=6.0 Hz, 2H, Hc2).

¹³C NMR (CDCl₃) δ 161.8 (Ca6), 159.0 (Ca2), 156.0 (Ca1), 151.4 (Ca8), 151.1 (Cc4), 149.8 (Cc6), 146.9 (Cc12), 141.5 (Ca12), 135.0 (Cc11), 129.4 (Cc10), 128.6 (Ca13), 128.4 (Ca14), 126.1 (Ca15), 124.6 (Ca4), 122.1 (Cc9), 120.4 (Cc8), 118.8 (Cc7), 117.5 (Ca5), 109.2 (Ca3), 107.8 (Ca7), 97.9 (Cc5), 66.6 (Cb1), 49.2 (Cc1), 47.3 (Cb3), 43.6 (Cc3), 41.1 (Ca9), 33.6 (Ca11), 30.6 (Ca10), 29.3 (Cb2) 27.4 (Cc2).

HRMS-ESI (m/z) calculated for $C_{32}H_{37}N_6O$ [M+H]+: 521.3023. Found: 521.3022.

¹³C NMR (CDCl₃) δ 162.0 (Ca6), 159.0 (Ca2), 155.9 (Ca1), 151.4 (Ca8), 150.4 (Cc5), 150.1 (Cc13), 147.3 (Cc12), 141.5 (Ca12), 134.9 (Cc11), 129.3 (Cc10), 128.6 (Ca13), 128.4 (Ca14), 126.1 (Ca15), 124.7 (Ca4), 122.1 (Cc9), 119.9 (Cc8), 118.6 (Cc7), 117.6 (Ca5), 109.1 (Ca3), 107.7 (Ca7), 98.5 (Cc6), 66.5 (Cb1), 49.1 (Cc1), 46.8 (Cb3), 43.1 (Cc4), 41.1 (Ca9), 33.6 (Ca11), 30.7 (Ca10), 29.1 (Cb2), 27.4 (Cc2), 26.3 (Cc3).

HRMS-ESI (m/z) calculated for $C_{33}H_{38}N_6O$ [M+H]+: 535.3180. Found: 535.3172.

Methyl 4-((3-((4-((3-phenylpropyl)amino)quinazolin-7-yl)oxy)propyl) (3-(quinolin-4-ylamino)propyl) amino)butanoate (Compound U)

Methyl 4-((3-((4-((3-phenylpropyl)amino)quinazolin-7-yl)oxy)propyl) (4-(quinolin-4-ylamino)butyl) amino)butanoate (Compound C)

To a solution of Compound A (30 mg; 59 μmol) or Compound B (26 mg; 49 μmol), K₂CO₃ (25 mg; 181 μmol),

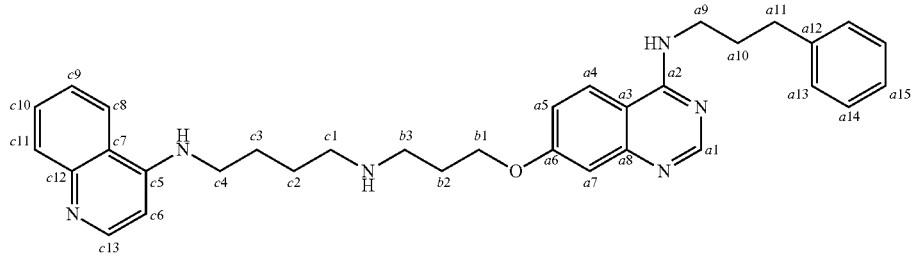

B

¹H NMR (CDCl₃) δ 8.54 (s, 1H, Ha1), 8.46 (d, J=5.7 Hz, 1H, Hc13), 7.94 (d, J=8.3, 1H, Hc8), 7.81 (d, J=8.3 Hz, 1H, Ha4), 7.58 (ddd, J=1.1, 6.9, 8.3 Hz, 1H, Hc10), 7.37 (ddd, J=1.1, 6.9, 8.3 Hz, 1H, Hc9), 7.33-7.17 (m, 6H, Ha15, Hc11, Ha13 and Ha14), 7.10 (d, J=2.5 Hz, 1H, Ha7), 6.90 (dd, J=2.3, 9.1 Hz, 1H, Ha5), 6.35 (d, J=5.6 Hz, 1H, Hc6), 6.00 (brs, 1H, HNH), 5.67 (brt, J=4.9 Hz, 2H, HNH), 4.14 (t, J=6.0 Hz, 2H, Hb1), 3.67 (q, J=6.5 Hz, 2H, Ha9), 3.31 (t, J=6.3 Hz, 2H, Hc4), 2.87 (t, J=6.4 Hz, 2H, Ha11), 2.80-2.72 (m, 4H, Hc1 and Hb3), 2.11-2.01 (m, 4H, Ha10 and Hb2), 1.85 (quint, J=7.2 Hz, 2H, Hc2 or Hc3), 1.71 (quint, J=7.2 Hz, 2H, Hc2 or Hc3).

methyl 4-bromobutyrate (10 μL; 87 μmol) and a catalytic amount of KI was added. The mixture was stirred at 90° C. overnight then diluted with ethylacetate. The organic phase was washed with a saturated solution of NaHCO₃ and brine. The organic phase was dried over Na₂SO₄ and the solvent was removed. The residue was purified by silica gel flash chromatography using a linear gradient of methanol (0→10% MeOH) in dichloromethane.

Compound U (Methyl ester of Compound D) was obtained as a white amorphous solid (16 mg; 26 μmol; 44%) and Compound C (Methyl ester of Compound T) was obtained as a white amorphous solid (14 mg; 26 μmol; 45%).

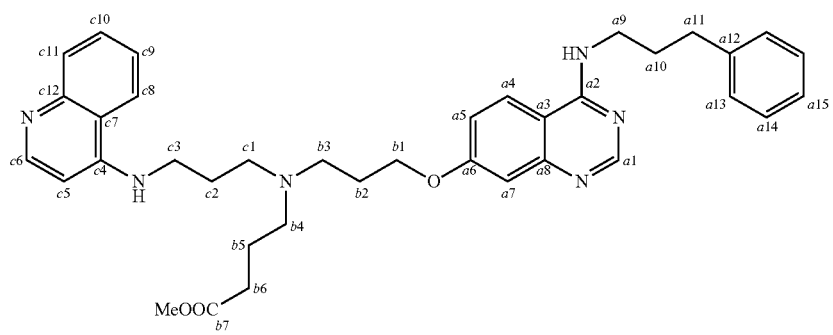

¹H NMR (CDCl₃) δ 8.52 (s, 1H, Ha1), 8.40 (d, J=6.0 Hz, 1H, Hc6), 7.96 (d, J=8.4, 1H, Hc8), 7.79 (d, J=8.4 Hz, 1H, Ha4), 7.56 (ddd, J=1.0, 6.0, 8.4 Hz, 1H, Hc10), 7.43-7.20 (m, 8H, Hc9, Ha15, HNH, Hc11, Ha13 and Ha14), 7.10-7.02 (m, 2H, Ha7 and HNH), 7.14 (dd, J=2.6, 9.0 Hz, 1H, Ha5), 6.31 (d, J=5.7 Hz, 1H, Hc5), 5.92 (m, 1H, HNH), 4.06 (t, J=6.0 Hz, 2H, Hb1), 3.67 (q, J=6.3 Hz, 2H, Ha9), 3.62 (s, 3H, HMe), 3.37 (q, J=6.0 Hz, 2H, Hc3), 2.76 (t, J=7.4 Hz, 2H, Hb3), 2.71 (t, J=7.2 Hz, 2H, Hb4), 2.65 (t, J=6.0 Hz, 2H, Hc1), 2.55 (t, J=7.2 Hz, 2H, Hb6), 2.35 (t, J=7.4 Hz, 2H, Ha11), 2.06 (quint, J=7.4 Hz, 2H, Ha10), 2.01-1.80 (m, 6H, Hb5, Hb2 and Hc2).

¹³C NMR (CDCl₃) δ 173.9 (Cb7), 161.9 (Ca6), 159.1 (Ca2), 155.9 (Ca1), 151.3 (Ca8), 151.2 (Cc4), 148.7 (Cc6), 145.9 (Cc12), 141.6 (Ca12), 129.8 (Cc11), 128.6 (Ca13), 128.4 (Ca14), 127.7 (Cc10), 126.0 (Ca15), 124.9 (Ca4), 122.4 (Cc9), 120.2 (Cc8), 118.4 (Cc7), 117.2 (Ca5), 109.1 (Ca3), 107.8 (Ca7), 98.0 (Cc5), 66.0 (Cb1), 53.5 (Cc1), 52.8 (Cb3), 51.6 (CMe), 50.5 (Cb4), 43.0 (Cc3), 41.1 (Ca9), 33.6 (Ca11), 31.7 (Cb6), 30.7 (Ca10), 26.5 (Cb2) 25.4 (Cc2), 22.0 (Cb5).

HRMS-ESI (m/z) calculated for $C_{37}H_{45}N_6O_3$ [M+H]+: 621.3548. Found: 621.3560.

¹H NMR (CDCl₃) δ 8.50 (s, 1H, Ha1), 8.47 (d, J=5.4 Hz, 1H, Hc13), 7.94 (d, J=7.4, 1H, Hc8), 7.69 (d, J=8.3 Hz, 1H, Ha4), 7.56 (t, J=7.4 Hz, 1H, Hc10), 7.34 (t, J=7.4 Hz, 1H, Hc9), 7.30-7.22 (m, 3H, Ha13 and Hc11) 7.21-7.12 (m, 3H, Ha15 and Ha14), 7.11 (d, J=2.5 Hz, 1H, Ha7), 6.90 (dd, J=2.5, 8.9 Hz, 1H, Ha5), 6.31 (d, J=5.3 Hz, 1H, Hc6), 5.65 (m, 1H, HNH), 5.30 (m, 1H, HNH), 4.10 (t, J=6.1 Hz, 2H, Hb1), 3.67-3.60 (m, 5H, Ha9 and HMe), 3.19 (q, J=7.0 Hz, 2H, Hc4), 2.75 (t, J=7.4 Hz, 2H, Hc1), 2.59 (t, J=6.6 Hz, 2H, Hb6), 2.55 (m, 4H, Hb4 and Hb3), 2.32 (t, J=7.4 Hz, 2H, Ha11), 2.03 (quint, J=7.4 Hz, 2H, Ha10), 1.91 (quint, J=6.3 Hz, 2H, Hb5), 1.80-1.68 (m, 4H, Hb2 and Hc2), 1.56 (quint, J=7.3 Hz, 2H, Hc3).

¹³C NMR (CDCl₃) δ 174.1 (Cb7), 162.2 (Ca6), 159.0 (Ca2), 155.9 (Ca1), 151.4 (Cc5), 150.5 (Cc13), 149.7 (Ca8), 147.9 (Cc12), 141.6 (Ca12), 129.3 (Cc11), 129.1 (Cc10), 128.6 (Ca13), 128.4 (Ca14), 126.0 (Ca15), 124.5 (Ca4), 122.1 (Cc9), 119.6 (Cc8), 118.6 (Cc7), 117.6 (Ca5), 109.0 (Ca3), 107.6 (Ca7), 98.5 (Cc6), 65.9 (Cb1), 53.1 (Cb3), 51.5 (CMe), 49.9 (Cb4), 43.2 (Cc4), 41.1 (Ca9), 33.6 (Ca11), 31.7 (Cb6), 30.7 (Ca10), 26.8 (Cc3), 26.6 (Cb2), 25.2 (Cc2), 22.4 (Cb5).

HRMS-ESI (m/z) calculated for $C_{38}H_{47}N_6O_3$ [M+H]+: 635.3704. Found: 635.3709.

N-(3-((4-((3-phenylpropyl)amino)quinazolin-7-yl)oxy)propyl)-N-(3-(quinolin-4-ylamino)propyl)formamide (Compound E)

Compound E is a by-product isolated from the synthesis of Compound U and was obtained as a white amorphous solid (8 mg; 15 μmol; 25%).

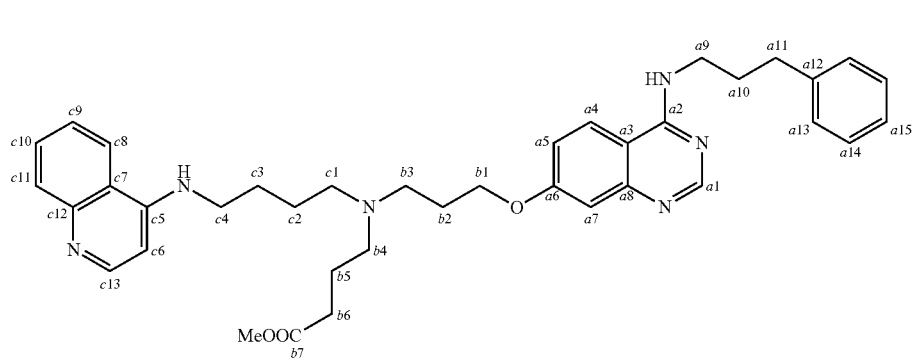

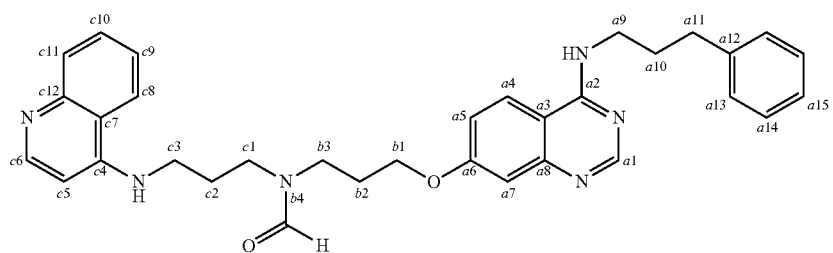

E

¹H NMR (DMSO) δ 8.42-8.35 (m, 2H, Ha1 and Hc6), 8.24-8.10 (m, 3H, Hc8, Ha4 and HNH), 8.08 (d, J=8.9 Hz, 1H, Hb4), 7.78 (d, J=8.5 Hz, Hc11), 7.63-7.58 (m, 1H, Hc10), 7.44-7.39 (m, 1H, Hc9), 7.32-7.22 (m, 4H, Ha13 and Ha14), 7.21-7.11 (m, 2H, Ha15 and HNH), 7.10-7.02 (m, 2H, Ha5 and Ha7), 6.45 (t, J=5.0 Hz, 1H, Hc5), 4.09 (m, 2H, Hb1), 3.57-3.31 (m, 6H, Hc3, Hc1 and Hb3), 3.30-3.22 (m, 1H, Ha9a), 2.71 (t, J=7.4 Hz, 2H, Ha11), 2.05-1.87 (m, 6H, Hc2, Ha10 and Hb2).

¹³C NMR (DMSO) δ 163.5-163.4 (Cb4), 161.9-161.8 (Ca6), 159.5 (Ca2), 156.1 (Ca1), 151.8 (Ca8), 151.2 (Cc6), 150.3-150.2 (Cc4), 148.8-148.7 (Cc12), 142.2 (Ca12), 129.5-129.4 (Cc11), 129.1 (Cc10), 128.8 (Ca13), 128.7 (Ca14), 126.2 (Ca15), 124.8-124-7 (Ca4), 124.2-124.2 (Cc9), 122.2-122.0 (Cc8), 119.3 (Cc7), 117.2-117.1 (Ca5), 109.7-109.6 (Ca3), 107.9-107.8 (Ca7), 98.7-98.6 (Cc5), 66.1-65.4 (Cb1), 46.1 (Cc1), 45.9 (Cb3), 40.5 (Cc3), 39.1 (Ca9), 33.1 (Ca11), 30.8 (Ca10), 27.9-27.3 (Cb2), 27.1-26.3 (Cc2).

HRMS-ESI (m/z) calculated for $C_{33}H_{37}N_6O_2$ [M+H]+: 549.2973. Found: 549.2972.

4-((3-((4-((3-phenylpropyl)amino)quinazolin-7-yl)oxy)propyl)(3-(quinolin-4-ylamino)propyl)amino)butanoic acid (Compound D)

4-((3-((4-((3-phenylpropyl)amino)quinazolin-7-yl)oxy)propyl)(4-(quinolin-4-ylamino)butyl)amino)butanoic acid (Compound T)

To a solution of Compound U (16 mg; 26 μmol) or Compound C (14 mg; 22 μmol) in dioxane (0.5 mL) was added a 0.5N solution of NaOH (0.5 mL). The mixture was stirred at room temperature for 6 h then was neutralized using a 0.5N HCl solution (0.5 mL). The solvent was removed and the residue was triturated in methanol. The mixture was filtrated and the filtrate was purified by reversed phase HPLC using a linear acetonitrile gradient (0→80% CH₃CN).

Compound D was obtained as pale yellow viscous oil (12 mg; 20 μmol; 78%) and Compound T was obtained as pale yellow viscous oil (11 mg; 17 μmol; 79%).

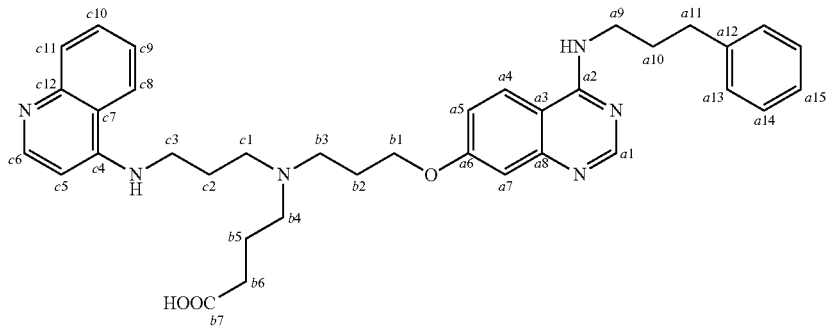

D

¹H NMR (DMSO+MeOD) δ 8.38 (s, 1H, Ha1), 8.33 (d, J=5.3 Hz, 1H, Hc6), 8.1 (d, J=7.7 Hz, 1H, Hc8), 8.13 (d, J=8.9 Hz, 1H, Ha4), 8.09 (t, J=5.3 Hz, 1H, HNH), 7.76 (dd, J=0.8, 8.3 Hz, 1H, Hc11), 7.58 (ddd, J=1.0, 6.0, 8.4 Hz, 1H, Hc10), 7.39 (ddd, J=1.0, 6.0, 8.4 Hz, 1H, Hc9), 7.32-7.21 (m, 4H, Ha13 and Ha14), 7.22-7.12 (m, 2H, Ha15, HNH), 7.10-7.02 (m, 2H, Ha7 and Ha5), 6.37 (d, J=5.7 Hz, 1H, Hc5), 4.12 (t, J=6.1 Hz, 2H, Hb1), 3.53 (q, J=6.3 Hz, 2H, Ha9), 3.27 (q, J=5.6 Hz, 2H, Hc3), 2.67 (t, J=7.5 Hz, 2H, Hc1), 2.60 (t, J=6.7 Hz, 2H, Hb4), 2.56 (t, J=6.7 Hz, 2H, Hb3), 2.46 (t, J=6.7 Hz, 2H, Hb6), 2.22 (t, J=7.1 Hz, 2H, Ha11), 1.99-1.86 (m, 4H, Hb2 and Ha10), 1.81 (quint, J=7.4 Hz, 2H, Hb5), 1.65 (quint, J=7.4 Hz, 2H, Hc2).

¹³C NMR (DMSO+MeOD) δ 175.1 (Cb7), 162.1 (Ca6), 159.5 (Ca2), 156.0 (Ca1), 151.8 (Ca8), 151.0 (Cc6), 150.4 (Cc4), 148.6 (Cc12), 142.2 (Ca12), 129.3 (Cc11), 129.1 (Cc10), 128.8 (Ca13), 128.7 (Ca14), 126.1 (Ca15), 124.7 (Ca4), 124.2 (Cc8), 122.1 (Cc9), 119.3 (Cc7), 117.1 (Ca5), 109.5 (Ca3), 107.8 (Ca7), 98.5 (Cc5), 66.4 (Cb1), 53.4 (Cc1), 51.8 (Cb3), 50.2 (Cb4), 41.2 (Ca9), 40.6 (Cc3), 33.1 (Ca11), 32.6 (Cb6), 30.8 (Ca10), 26.7 (Cb2), 25.8 (Cc2), 22.6 (Cb5).

HRMS-ESI (m/z) calculated for $C_{36}H_{43}N_6O_3$ [M+H]+: 607.3391. Found: 607.3391.

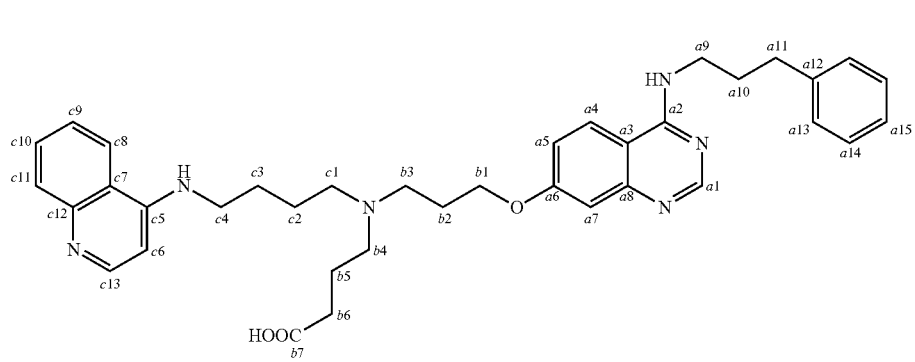

¹H NMR (DMSO+MeOD) δ 8.37 (s, 1H, Ha1), 8.33 (d, J=5.5 Hz, 1H, Hc13), 8.19 (d, J=7.9 Hz, 1H, Hc8), 8.13 (d, J=8.9 Hz, 1H, Ha4), 8.09 (t, J=5.3 Hz, 1H, HNH), 7.75 (dd, J=0.9, 8.4 Hz, 1H, Hc11), 7.57 (ddd, J=1.2, 6.7, 8.2 Hz, 1H, Hc10), 7.38 (ddd, J=1.2, 6.7, 8.2 Hz, 1H, Hc9), 7.29-7.20 (m, 4H, Ha13 and Ha14), 7.19-7.11 (m, 2H, Ha15, HNH), 7.09 (dd, J=2.5, 9.0 Hz, 1H, Ha5), 7.03 (d, J=2.5 Hz, 1H, Ha7), 6.35 (d, J=5.3 Hz, 1H, Hc5), 4.11 (t, J=6.1 Hz, 2H, Hb1), 3.52 (q, J=7.0 Hz, 2H, Ha9), 3.19 (m, 2H, Hc4), 2.67 (t, J=7.5 Hz, 2H, Hc1), 2.56 (t, J=6.7 Hz, 2H, Hb6), 2.48-2.39 (m, 4H, Hb4 and Hb3), 2.22 (t, J=7.1 Hz, 2H, Ha11), 1.91 (quint, J=7.4 Hz, 2H, Ha10), 1.86 (quint, J=6.3 Hz, 2H, Hb5), 1.71-1.58 (m, 4H, Hb2 and Hc2), 1.51 (quint, J=7.6 Hz, 2H, Hc3).

¹³C NMR (DMSO+MeOD) δ 175.2 (Cb7), 162.0 (Ca6), 159.5 (Ca2), 156.0 (Ca1), 151.7 (Cc5), 151.0 (Cc13), 150.4 (Ca8), 148.6 (Cc12), 142.2 (Ca12), 129.3 (Cc11), 129.1 (Cc10), 128.8 (Ca13), 128.7 (Ca14), 126.1 (Ca15), 124.7 (Ca4), 124.1 (Cc8), 122.2 (Cc9), 119.2 (Cc7), 117.2 (Ca5), 109.5 (Ca3), 107.8 (Ca7), 98.5 (Cc6), 65.4 (Cb1), 53.6 (Cc1), 53.4 (Cb3), 50.1 (CMe), 46.0 (Cb4), 42.8 (Cc4), 40.5 (Ca9), 33.2 (Ca11), 32.7 (Cb6), 30.8 (Ca10), 26.7 (Cc3), 26.1 (Cb2), 24.7 (Cc2), 22.6 (Cb5).

HRMS-ESI (m/z) calculated for $C_{37}H_{45}N_6O_3$ [M+H]+: 621.3548. Found: 621.3545.

Example 3: Compound G

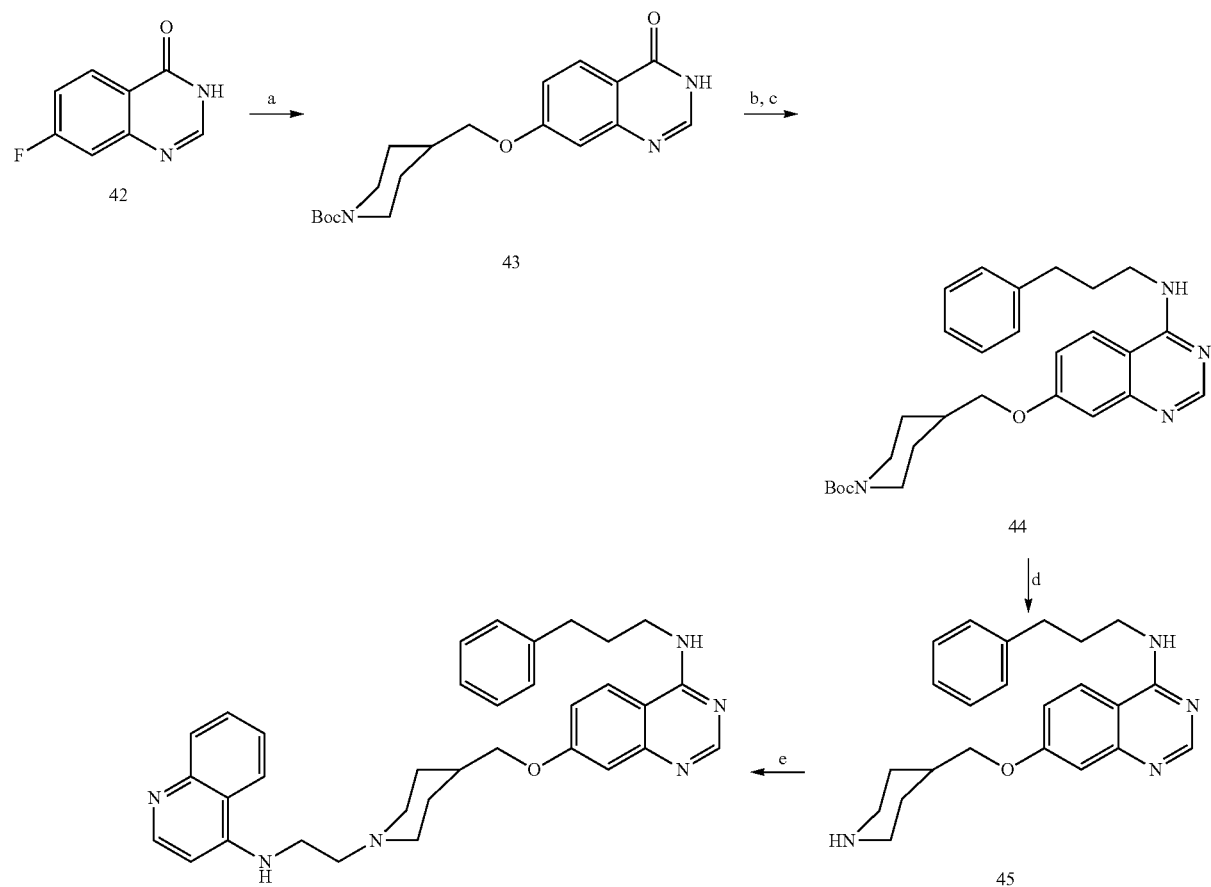

Compound G a) N-Boc-piperidine-4-methanol, NaH, DMF, 110° C., 3 h, 67%. b) POCl₃, triazole, TEA, MeCN, RT, 18 h. c) 3-Phenylpropylamine, TEA, DMF, RT, 2 h, 80% over two steps. d) TFA, RT, 1 h, 96%. e) 26, $K_2CO_3$, KI, DMF, 65° C., 12 h, 62%.

7-O—((N-Boc)piperidin-4-ylmethoxy)quinazolinone (43)

To a mixture of (N-Boc)piperidin-4-ylmethanol (1.12 g; 5.2 mmol) in DMF (2 mL) at 0° C. under argon was added sodium hydride (125 mg, 5.2 mmol). The mixture was stirred for 15 min at 0° C. then 42 (162 mg; 1 mmol) was added portion wise. The mixture was stirred at 0° C. for 10 min then at room temperature for 10 min, at 60° C. for 15 min and finally at 110° C. for 2 h. The reaction mixture was diluted with ethylacetate and washed with water and brine. The organic phase was dried over magnesium sulfate and the solvent was removed. The crude product was purified by silica gel flash chromatography using a linear gradient of ethylacetate (0→100% AcOEt) in cyclohexane to afford 43 as a white powder (241 mg; 0.67 μmol; 67%).

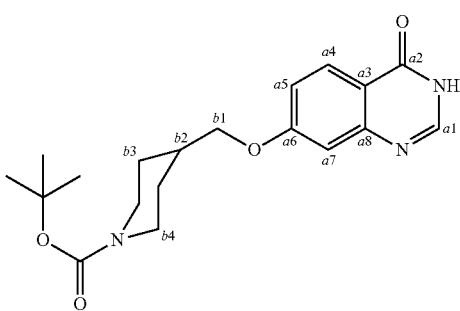

43

$^1$H NMR (500 MHz; CDCl$_3$) δ 11.50 (s, 1H, HNH), 8.19 (d, 1H, J=8.9, Ha4), 8.7 (s, 1H, Ha1), 7.12-7.07 (m, 2H, Ha7 and Ha5), 4.18 (sb, 2H, Hb4), 3.94 (d, J=6.8, 2H, Hb1), 2.76 (m, 2H, Hb4), 2.03 (m, 1H, Hb2), 1.84 (m, 2H, Hb3), 1.47 (s, 9H, HBoc), 1.38-1.11 (m, 2H, Hb3).

$^{13}$C NMR (125 MHz, CDCl$_3$) δ 164.6 (Ca6), 162.3 (Ca2), 155.2 (CBoc), 151.5 (Ca8), 144.3 (Ca1), 128.3 (Ca4), 118.0 (Ca5), 116.3 (Ca3), 109.4 (Ca7), 79.9 (CBoc), 73.0 (Cb1), 47.0 (Cb4), 36.3 (Cb2), 29.1 (Cb3), 28.8 (CBoc).

HRMS-ESI (m/z) calculated for C$_{19}$H$_{26}$N$_3$O$_4$[M+H]$^+$: 360.1918. found: 360.1911.

4-((3-phenylpropyl)amino)-7-(O—((N-Boc)piperidin-4-ylmethoxy))quinazoline (44)

To a solution of triazole (280 mg; 4 mmol) and POCl$_3$ (120 μl; 1.32 mmol) in 3 mL of acetonitrile at 0° C. was added TEA (5604) dropwise. The reaction mixture was stirred at 0° C. for 40 min then 30 min at room temperature. 43 (215 mg; 0.6 mmol) was added and the mixture was vigorously stirred at room temperature overnight. The reaction was followed by TLC using ethyl acetate as eluent. The mixture was refluxed for 1 h to reach completion. After complete consumption of the starting material, the solvent was removed and the residue was taken off with ethylacetate and washed with water and brine, and dried over sodium sulfate. The solvent was removed and the residue was solubilized in DMF (2 mL). Phenylpropylamine (130 μL; 1.0 mmol) and TEA (167 μL; 1.2 mmol) were added and the mixture was stirred for 3 h at room temperature. The mixture was diluted with ethyl acetate and washed with water, brine and dried over sodium sulfate. The solvent was removed and the residue was purified by silica gel flash chromatography using a linear gradient of ethyl acetate (0→100% AcOEt) in cyclohexane to afford 44 as a white powder (232 mg; 0.49 mmol; 81%).

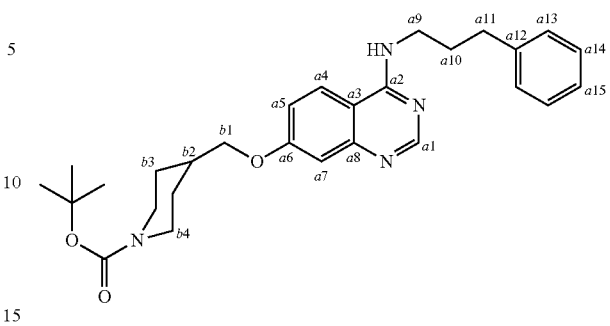

44

$^1$H NMR (500 MHz; CDCl$_3$) δ 8.57 (s, 1H, Ha1), 7.33-7.28 (m, 3H, Ha4 and Ha13), 7.25-7.20 (m, 3H, Ha15 and Ha14), 7.12 (d, J=2.6 Hz, 1H, Ha7), 7.00 (dd, J=2.6, 9.5 Hz, 1H, Ha5), 5.44 (brt, J=5.2, 1H, HNH), 4.17 (brs, 2H, Hb4eq), 3.92 (d, J=6.3 Hz, 2H, Hb1), 3.70 (q, J=7.2 Hz, 2H, Ha9), 2.79 (t, 2H, J=7.3 Hz, Ha11), 2.75 (brt, J=11.2 Hz, 2H, Hb4ax), 2.09 (quint, J=7.3 Hz, 2H, Ha10), 2.01 (m, 1H, Hb2), 1.83 (d, J=12.3 Hz, 2H, Hb3eq), 1.47 (s, 9H, HBoc), 1.31 (dq, J=4.5-12.3 Hz, 2H, Hb3ax).

$^{13}$C NMR (125 MHz; CDCl$_3$) δ 162.9 (Ca6), 159.2 (Ca2), 156.1 (Ca1), 155.0 (CBoc), 151.7 (Ca8), 141.7 (Ca12), 128.8 (Ca13), 128.6 (Ca14), 126.3 (Ca15), 122.0 (Ca4) 118.0 (Ca5), 109.1 (Ca3), 108.0 (Ca7), 79.6 (CBoc), 72.6 (Cb1), 43.7 (Cb4), 41.3 (Ca9), 36.1 (Cb2), 33.8 (Ca11), 30.9 (Ca10), 29.0 (Cb3), 28.6 (CBoc).

HRMS-ESI (m/z) calculated for C$_{19}$H$_{26}$N$_3$O$_4$[M+H]$^+$: 477.2860. found: 477.2861.

4-((3-phenylpropyl)amino)-7-O-(piperidin-4-ylmethoxy)quinazoline (45)

A mixture of 44 (220 mg; 0.46 mmol) in TFA was stirred for 1 h at room temperature. TFA was removed. The residue was diluted with dichloromethane and the organic phase was washed with saturated Na$_2$CO$_3$. The solvent was removed and 45 was obtained as pale blue foam (165 mg; 0.44 mmol; 96%).

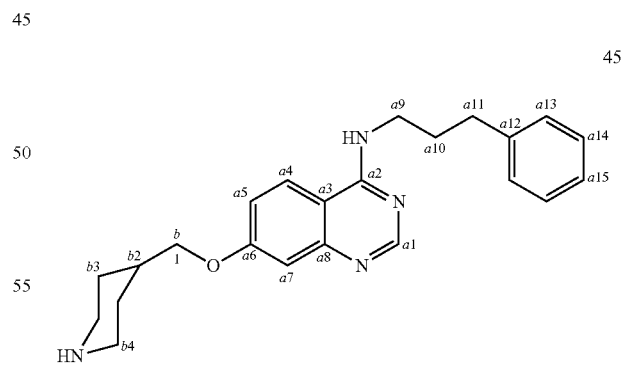

45

$^1$H NMR (DMSO) δ 9.94 (brs, 1H, HNH), 8.79 (s, 1H, Ha1), 8.4 (d, J=9.3 Hz, 1H, Ha4), 7.43-7.13 (m, 7H, Ha5, Ha7, Ha13, Ha14 and Ha15), 4.06 (d, J=6.2 Hz, 2H, Hb1), 3.70 (q, J=7.2 Hz, 2H, Ha9), 3.34 (brd, J=12.6 Hz, 2H, Hb4eq), 2.94 (brt, J=11.5 Hz, 2H, Hb4ax), 2.69 (t, J=7.3 Hz, 2H, Ha11), 2.15 (m, 1H, Hb2), 2.00 (quint, 2H, J=7.3 Hz, Ha10), 1.95 (brd, 2H, Hb3eq), 1.53 (dq, J=4.0-15.0 Hz, 2H, Hb3ax).

$^{13}$C NMR (DMSO) δ 164.5 (Ca6), 160.8 (Ca2), 152.5 (Ca1), 142.3 (Ca8), 141.7 (Ca12), 129.3 (Ca13), 129.2 (Ca14), 127.2 (Ca4), 126.7 (Ca15), 119.1 (Ca5), 107.9 (Ca3), 102.6 (Ca7), 72.9 (Cb1), 43.6 (Cb4), 42.2 (Ca9), 33.8 (Cb2), 33.4 (Ca11), 30.8 (Ca10), 26.0 (Cb3).

HRMS-ESI (m/z) calculated for $C_{19}H_{26}N_3O_4$ [M+H]$^+$: 377.2336. found: 377.2303.

4-((3-phenylpropyl)amino)-7-((1-(2-(quinolin-4-ylamino)ethyl)piperidin-4-yl)methoxy)quinazoline (Compound G)

To a solution of 45 (30 mg; 80 μmol), K$_2$CO$_3$ (22 mg; 160 μmol) and a catalytic amount of KI in DMF (1 mL) was added 26 (33 mg; 160 μmol). The mixture was stirred at 65° C. overnight then was diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.01% of TEA (0→80% CH$_3$CN) to afford Compound G as a white powder (35 mg; 64 μmol; 80%).

HRMS-ESI (m/z) calculated for $C_{19}H_{26}N_3O_4$ [M+H]$^+$: 547.3180. found: 547.3171.

Example 4: Compound O

Compound O was synthesized following the same procedure as for Compound G.

4-(3-phenethylamino)-7-((1-(2-(quinolin-4-ylamino)ethyl)piperidin-4-yl)methoxy)quinazoline (Compound O)

To a solution of 4-(2-phenethylamino)-7-(piperidin-4-yl-methoxy)quinazoline (30 mg; 0.08 mmol), K$_2$CO$_3$ (23 mg; 0.16 mmol) and a catalytic amount of KI in DMF (1.5 mL) was added 26 (40 mg; 0.16 mmol). The mixture was stirred at 65° C. for 24 hours. The solvent was removed and the residue was purified by reversed phase HPLC using a linear acetonitrile gradient with 0.01% of TEA (0→80% CH$_3$CN) to afford Compound O as a white powder (28 mg; 0.05 mmol; 64%).

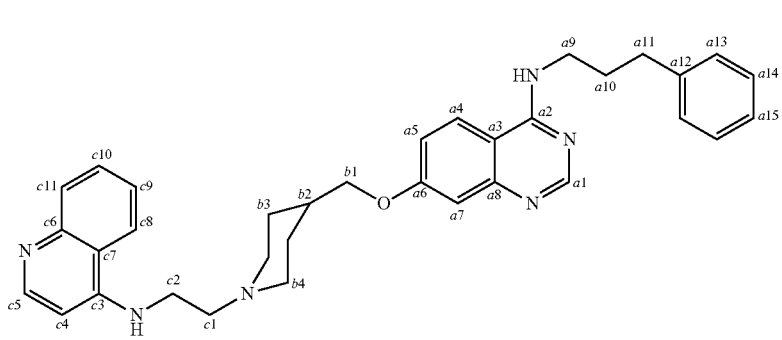

G $^1$H NMR (500 MHz; CDCl$_3$) δ 8.58 (s, 1H, Ha1), 8.56 (d, J=5.4 Hz, 1H, Hc5), 7.98 (dd, J=0.7, 8.4 Hz, 1H, Hc8), 7.76 (dd, J=0.7, 8.4 Hz, 1H, Hc11), 7.63 (ddd, J=1.2, 6.9, 8.2 Hz, 1H, Hc10), 7.46 (ddd, J=1.2, 6.9, 8.2 Hz, 1H, Hc9), 7.34-7.28 (m, 3H, Ha4 and Ha13), 7.25-7.20 (m, 3H, Ha15 and Ha14), 7.13 (d, J=2.5 Hz, 1H, Ha7), 7.00 (dd, J=2.6, 5.1 Hz, 1H, 9.1 Hz, Ha5), 6.40 (d, J=5.1 Hz, 1H, Hc4), 5.96 (brt, J=4.5 Hz, 1H, HNHc), 5.48 (brt, J=5.1 Hz, 1H, HNHa), 3.96 (d, J=6.1 Hz, 2H, Hb1), 3.70 (q, J=7.2 Hz, 2H, Ha9), 3.34 (q, J=5.2 Hz, 2H, Hc2), 3.00 (brd, J=12.0 Hz, 2H, Hb4eq), 2.75 (m, 4H, Ha11 and Hc1), 2.14 (dt, J=2.1 Hz, 2H, Hb4ax), 2.09 (quint, J=7.2 Hz, 2H, Ha10), 1.94 (m, 1H, Hb2), 1.91 (d, J=12.3 Hz, 2H, Hb3eq), 1.47 (dq, J=3.4, 12.5 Hz, 2H, Hb3ax).

$^{13}$C NMR (125 MHz, CDCl$_3$) δ 161.6 (Ca6), 158.4 (Ca2), 155.3 (Ca1), 151.0 (Ca8), 150.5 (Cc5), 149.1 (Cc3), 147.8 (Cc6), 140.9 (Ca12), 129.3 (Cc8), 128.3 (Cc10), 128.0 (Ca13), 127.8 (Ca14), 125.5 (Ca15), 124.0 (Cc9), 121.2 (Ca4), 118.8 (Cc11), 118.3 (Cc7), 117.2 (Ca5), 108.3 (Ca3), 107.2 (Ca7), 98.4 (Cc4), 72.0 (Cb1), 55.3 (Cc1), 52.3 (Cb4), 40.5 (Ca9), 38.6 (Cc2), 35.0 (Cb2), 33.0 (Ca11), 30.1 (Ca10), 28.6 (Cb3).

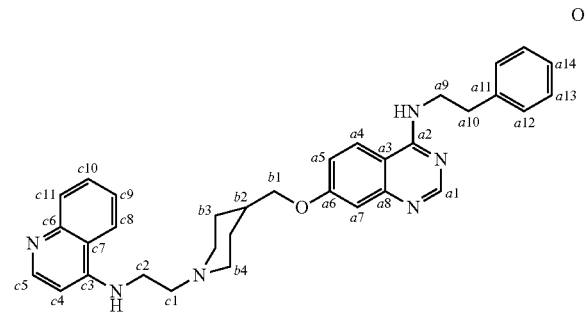 [SMILES: c1ccc(CCNc2ncnc3cc(OCC4CCN(CCNc5ccnc6ccccc56)CC4)ccc23)cc1]

O $^1$H NMR (500 MHz; CDCl$_3$) δ 8.64 (s, 1H, Ha1), 8.59 (d, J=5.6 Hz, 1H, Hc5), 8.04 (d, J=8.2 Hz, 1H, Hc8), 7.80 (d, J=0.7, 8.4 Hz, 1H, Hc11), 7.68 (ddd, J=1.3, 6.9, 8.3 Hz, 1H, Hc10), 7.51 (ddd, J=1.1, 6.7, 8.3 Hz, 1H, Hc9), 7.44 (d, J=9.28 Hz, 1H, Ha4), 7.38-7.33 (m, 2H, Ha12), 7.31-7.26 (m, 3H, Ha14 and Ha13), 7.18 (d, J=2.6 Hz, 1H, Ha7), 7.05 (dd, J=2.6, 9.0 Hz, 1H, Ha5), 6.43 (d, J=5.4 Hz, 1H, Hc4), 6.15 (brs, 1H, HNHc), 5.60 (brt, J=5.7 Hz, 1H, HNHa), 4.00 (d, J=6.2 Hz, 2H, Hb1), 3.70 (dd, J=6.7, 12.2 Hz, 2H, Ha9), 3.38 (q, J=5.2 Hz, 2H, Hc2), 3.08-3.00 (m, 4H, Hb4eq and Hc1), 2.83 (t, J=6.2 Hz, Ha10), 2.18 (dt, J=1.3, 11.6 Hz, 2H, Hb4ax), 2.09-1.89 (m, 3H, Hb2 and Hb3eq), 1.47 (dq, J=3.0-12.5 Hz, 2H, Hb3ax).

$^{13}$C NMR (125 MHz, CDCl$_3$) δ 162.2 (Ca6), 159.0 (Ca2), 156.0 (Ca1), 151.7 (Ca8), 150.3 (Cc5), 150.2 (Cc3), 147.5 (Cc6), 138.9 (Ca12), 129.4 (Cc8), 129.1 (Cc10), 128.9 (Ca12), 128.8 (Ca13), 126.6 (Ca14), 124.9 (Cc9), 121.8 (Ca4), 119.5 (Cc11), 118.7 (Cc7), 118.1 (Ca5), 109.2 (Ca3), 107.9 (Ca7), 98.8 (Cc4), 72.6 (Cb1), 55.8 (Cc1), 52.9 (Cb4), 42.1 (Ca9), 39.1 (Cc2), 35.6 (Cb2), 35.3 (Ca10), 29.2 (Cb3).

HRMS-ESI (m/z) calculated for $C_{33}H_{37}N_6O$ [M+H]$^+$: 533.3023. found: 533.3023.

Example 5: Compound P

Compound P was synthesized following the same procedure as for Compound G.

4-(3-benzylamino)-7-((1-(2-(quinolin-4-ylamino)ethyl)piperidin-4-yl)methoxy)quinazoline (Compound P)

To a solution of 4-(2-benzylamino)-7-(piperidin-4-ylmethoxy)quinazoline (30 mg; 0.086 mmol), K$_2$CO$_3$ (24 mg; 0.172 mmol) and a catalytic amount of KI in DMF (1.5 mL) was added 26 (42 mg; 0.172 mmol). The mixture was stirred at 65° C. overnight. The solvent was removed and the residue was purified by reversed phase HPLC using a linear acetonitrile gradient with 0.01% of TEA (0→80% CH$_3$CN) to afford Compound P as a white powder (30 mg; 0.058 mmol; 68%).

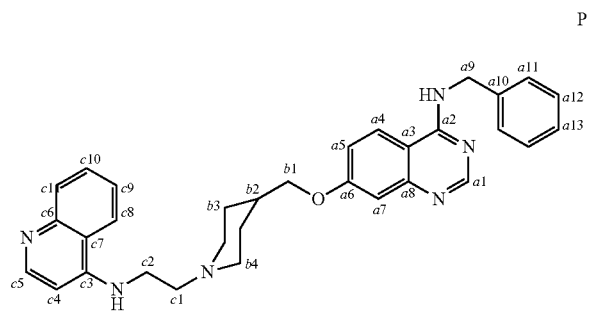 [SMILES: c1ccc(CNc2ncnc3cc(OCC4CCN(CCNc5ccnc6ccccc56)CC4)ccc23)cc1]

P $^1$H NMR (500 MHz; CDCl$_3$) δ 8.66 (s, 1H, Ha1), 8.58 (d, J=5.1 Hz, 1H, Hc5), 8.00 (dd, J=0.7, 8.5 Hz, 1H, Hc8), 7.79 (dd, J=0.7, 8.5 Hz, 1H, Hc11), 7.61 (d, J=8.9 Hz, 1H, Ha4), 7.66 (ddd, J=1.4, 6.8, 8.3 Hz, 1H, Hc10), 7.48 (ddd, J=1.4, 6.8, 8.3 Hz, 1H, Hc9), 7.45-7.32 (m, 5H, Ha11 and Ha12 and Ha13), 7.20 (d, J=2.4 Hz, 1H, Ha7), 7.08 (dd, J=2.4, 9.1 Hz, Ha5), 6.42 (d, J=5.3 Hz, 1H, Hc4), 5.96 (brt, J=4.1, 1H, HNHc), 5.87 (m, 1H, HNHa), 4.87 (d, J=5.2 Hz, Ha9), 4.00 (d, J=6.1 Hz, 2H, Hb1), 3.36 (q, J=5.2 Hz, 2H, Hc2), 3.03 (brd, J=11.7 Hz, 2H, Hb4eq), 2.81 (t, J=6.0 Hz, 2H, Ha11), 2.16 (dt, J=1.2, 11.8 Hz, 2H, Hb4ax), 2.01-1.89 (m, 3H, Hb2 and Hb3eq), 1.50 (dq, J=3.6-12.1 Hz, 2H, Hb3ax).

$^{13}$C NMR (125 MHz, CDCl$_3$) δ 162.3 (Ca6), 158.9 (Ca2), 156.0 (Ca1), 151.8 (Ca8), 151.1 (Cc5), 149.8 (Cc3), 148.3 (Cc6), 138.2 (Ca10), 129.8 (Cc8), 129.0 (Cc10), 128.8 (Ca12), 128.0 (Ca11), 127.8 (Ca13), 124.6 (Cc9), 122.0 (Ca4), 119.5 (Cc11), 118.9 (Cc7), 118.1 (Ca5), 109.0 (Ca3), 107.9 (Ca7), 99.0 (Cc4), 72.7 (Cb1), 55.9 (Cc1), 52.9 (Cb4), 45.3 (Ca9), 39.2 (Cc2), 35.7 (Cb2), 29.2 (Cb3).

HRMS-ESI (m/z) calculated for $C_{32}H_{35}N_6O$ [M+H]$^+$: 519.2867. Found: 519.2870.

Example 6: Compound H

Compound H was synthesized following the same procedure as for Compound G.

4-propylamino-7-((1-(2-(quinolin-4-ylamino)ethyl)piperidin-4-yl)methoxy)quinazoline (Compound H)

To a solution of 4-propylamino-7-O-(piperidin-4-ylmethoxy)quinazoline (10 mg; 33 µmol), K$_2$CO$_3$ (9 mg; 66 µmol) and a catalytic amount of KI in DMF (0.5 mL) was added 26 (14 mg; 67 µmol). The mixture was stirred at 65° C. overnight then was diluted with ethylacetate. The organic phase was washed with water and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.2% of TEA (0→80% CH$_3$CN) to afford Compound H as a white powder (12.0 mg; 26 µmol; 78%).

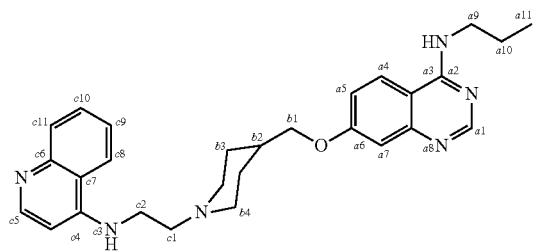

H $^1$H NMR (DMSO) δ 8.39 (d, J=5.3 Hz, 1H, Hc5), 8.37 (s, 1H, Ha1), 8.17-8.11 (m, 2H, Ha4 and Hc8), 8.07 (brt, J=5.3, 1H, HNHa), 7.77 (dd, J=1.1, 8.4 Hz, 1H, Hc11), 7.60 (ddd, J=1.3, 6.9, 8.2 Hz, 1H, Hc10), 7.41 (ddd, J=1.3, 6.9, 8.2 Hz, 1H, Hc9), 7.09 (dd, J=2.5, 9.0 Hz, 1H, Ha5), 7.04 (m, 1H, Ha7), 6.47 (d, J=5.8 Hz, 1H, Hc4), 3.96 (d, J=5.85 Hz, 2H, Hb1), 3.45 (q, J=5.8 Hz, 2H, Ha9), 3.40 (q, J=6.2 Hz, 2H, Hc2), 3.00 (brd, J=10.1 Hz, 2H, Hb4eq), 2.62 (t, J=7.1 Hz, 2H, Hc1), 2.04 (t, J=10.1 Hz, 2H, Hb4ax), 1.91 (m, 3H, Hb3eq and Hb2), 1.63 (sext, J=7.4 Hz, 2H, Ha10), 1.36 (dq, J=3.0-12.6 Hz, 2H, Hb3ax), 0.91 (t, J=7.3 Hz, 3H, Ha11).

$^{13}$C NMR (DMSO) δ 162.1 (Ca6), 159.5 (Ca2), 156.1 (Ca1), 151.8 (Ca8), 151.2 (Cc5), 150.2 (Cc3), 148.2 (Cc6), 129.5 (Cc11), 129.1 (Cc10), 124.7 (Ca4), 124.3 (Cc9), 121.9 (Cc8), 119.2 (Cc7), 117.1 (Ca5), 109.5 (Ca3), 107.9 (Ca7), 98.7 (Cc4), 72.7 (Cb1), 56.6 (Cc1), 53.5 (Cb4), 42.6 (Ca9), 40.6 (Cc2), 35.7 (Cb2), 29.0 (Cb3), 22.4 (Ca10), 11.9 (Ca11).

HRMS-ESI (m/z) calculated for $C_{28}H_{35}N_6O$ [M+H]$^+$: 471.2867. found: 471.2876.

Example 7: Compound I

Compound I was synthesized following the same procedure as for Compound G.

4-amino-7-((1-(2-(quinolin-4-ylamino)ethyl)piperidin-4-yl)methoxy)quinazoline (Compound I)

To a solution of 4-amino-7-(piperidin-4-ylmethoxy)quinazoline (10 mg; 0.039 mmol), K$_2$CO$_3$ (21 mg; 0.078 mmol) and a catalytic amount of KI in DMF (0.5 mL) was added 26 (16 mg, 0.078 mmol). The mixture was stirred at 65° C. overnight then was diluted with ethylacetate. The organic phase was washed with water and brine and dried over sodium sulfate. The solvent was removed and the residue was purified by reversed phase HPLC using a linear acetonitrile gradient with 0.01% of TEA (0→80% CH$_3$CN) to afford Compound I as a white powder (11.4 mg; 0.027 mmol; 68%).

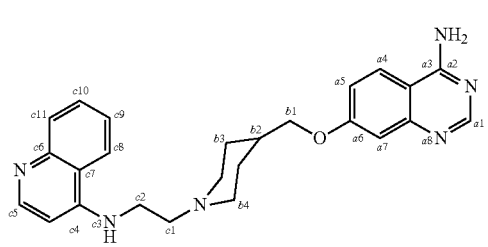

$^1$H NMR (DMSO) δ 8.39 (d, J=5.5 Hz, 1H, Hc5), 8.29 (s, 1H, Ha1), 8.15 (m, 3H, Hc8 and HNH$_2$), 8.10 (d, J=9.0, 1H, Ha4), 7.77 (dd, J=1.0 Hz, 8.4 Hz, 1H, Hc11), 7.60 (ddd, J=1.2, 6.8, 8.2 Hz, 1H, Hc10), 7.42 (ddd, J=1.2, 6.8, 8.2 Hz, 1H, Hc9), 7.08 (dd, J=2.5, 9.0 Hz, 1H, Ha5), 7.06-7.01 (m, 2H, Ha7 and HNH), 6.47 (d, J=5.3 Hz, 1H, Hc4), 3.97 (d, J=5.8 Hz, 2H, Hb1), 3.41 (q, J=6.4 Hz, 2H, Hc2), 3.00 (brd, J=11.0 Hz, 2H, Hb4eq), 2.62 (t, J=6.2 Hz, 2H, Hc1), 2.05 (t, J=11.9 Hz, 2H, Hb4ax), 1.78 (m, 3H, Hb3eq and Hb2), 1.36 (dq, J=2.5, 11.9 Hz, 2H, Hb3ax).
$^{13}$C NMR (DMSO) δ 162.4 (Ca6), 159.5 (Ca2), 156.1 (Ca1), 151.8 (Ca8), 151.2 (Cc5), 150.2 (Cc3), 148.2 (Cc6), 129.5 (Cc11), 129.1 (Cc10), 124.7 (Ca4), 124.3 (Cc9), 121.9 (Cc8), 119.2 (Cc7), 117.1 (Ca5), 109.5 (Ca3), 107.9 (Ca7), 98.7 (Cc4), 72.7 (Cb1), 56.6 (Cc1), 53.5 (Cb4), 42.6 (Ca9), 40.6 (Cc2), 35.7 (Cb2), 29.0 (Cb3), 22.4 (Ca10), 11.9 (Ca11).
HRMS-ESI (m/z) calculated for C$_{25}$H$_{29}$N$_6$O [M+H]$^+$: 429.2397. found: 429.2404.

Example 8: Compound N

Compound N was synthesized following the same procedure as for Compound G.

4-([1,1'-biphenyl]-4-ylmethylamino)-7-((1-(2-(quinolin-4-ylamino)ethyl)piperidin-4-yl)methoxy)quinazoline (Compound N)

To a solution of 4-([1,1'-biphenyl]-4-ylmethylamino)-7-((piperidin-4-yl) methoxy)quinazoline (12 mg, 28 µmol), K$_2$CO$_3$ (8 mg, 56 µmol) and a catalytic amount of KI in DMF (0.5 mL) was added 26 (14 mg, 56 µmol). The mixture was stirred at 65° C. overnight. The solvent was removed and the residue was purified by reversed phase HPLC using a linear acetonitrile gradient with 0.01% of TEA (0→80% CH$_3$CN) to afford Compound N as a white powder (5 mg, 84 µmol, 31%).

$^1$H NMR (500 MHz; CDCl$_3$) δ 8.67 (s, 1H, Ha1), 8.57 (d, J=5.3 Hz, 1H, Hc5), 8.08 (d, J=8.2 Hz, 1H, Hc8), 7.81 (dd, J=8.2 Hz, 1H, Hc11), 7.70 (ddd, J=1.2, 6.9, 8.2 Hz, 1H, Hc10), 7.46 (ddd, J=1.1, 6.8, 8.2 Hz, 1H, Hc9), 7.66-7.58 (m, 5H, Ha4 and Ha11 and Ha12), 7.56-7.43 (m, 4H, Ha11 and Ha16), 7.38 (m, 1H, Ha17), 7.20 (d, J=2.6 Hz, 1H, Ha7), 7.08 (dd, J=2.6, 9.2 Hz, 1H, Ha5), 6.43 (d, J=5.3 Hz, 1H, Hc4), 6.40 (brs, 1H, HNH), 5.93 (brt, J=5.4 Hz, 1H, HNH), 4.92 (d, J=5.3 Hz, 2H, Ha9), 4.01 (d, J=6.0 Hz, 2H, Hb1), 3.70 (q, J=7.2 Hz, 2H, Ha9), 3.41 (brq, J=4.3 Hz, 2H, Hc2), 3.00 (brd, J=11.5 Hz, 2H, Hb4eq), 2.84 (t, J=5.9 Hz, 2H, Hc1), 2.20 (dt, J=2.0, 12.0 Hz, 2H, Hb4ax), 2.05-1.91 (m, 3H, Hb2 and Hb3eq), 1.52 (dq, J=2.4, 12.5 Hz, 2H, Hb3ax).
$^{13}$C NMR (125 MHz, CDCl$_3$) δ 162.4 (Ca6), 159.0 (Ca2), 156.0 (Ca1), 151.7 (Ca8), 150.8 (Cc3), 149.2 (Cc5), 146.1 (Cc6), 140.8 (Ca14), 140.6 (Ca13), 137.3 (Ca10), 129.9 (Cc10), 128.8 (Ca16), 128.5 (Ca11), 128.1 (Cc8), 127.6 (Ca12), 127.4 (Ca17), 125.2 (Cc9), 122.0 (Ca4), 119.7 (Cc11), 118.4 (Cc7), 118.2 (Ca5), 109.0 (Ca3), 107.9 (Ca7), 98.7 (Cc4), 72.6 (Cb1), 55.7 (Cc1), 52.9 (Cb4), 45.0 (Ca9), 39.1 (Cc2), 35.6 (Cb2), 29.2 (Cb3).
HRMS-ESI(m/z) calculated for C$_{38}$H$_{39}$N$_6$O [M+H]$^+$: 595.3180. found: 595.3172.

Example 9: Compound Q

Compound Q was synthesized following the same procedure as for Compound G.

6-methyl-N$^4$-(2-((7-((1-(2-(quinolin-4-ylamino)ethyl)piperidin-4-yl)methoxy)quinazolin-4-yl)amino)ethyl)pyrimidine-2,4-diamine (Compound Q)

To a solution of 6-methyl-N4-(2-(7-(piperidin-4-ylmethoxy)quinazolin-4-ylamino)ethyl)pyrimidine-2,4-diamine (95 mg, 0.23 mmol), K$_2$CO$_3$ (64 mg, 0.46 mmol) and a catalytic amount of KI in DMF (1.5 mL) was added 26 (113 mg; 46 µmol). The mixture was stirred at 65° C. overnight. The solvent was removed and the residue was purified by reversed phase HPLC using a linear acetonitrile gradient with 0.01% of TEA (0→80% CH$_3$CN) to afford Compound Q as a white powder (46 mg; 79 µmol; 34%).

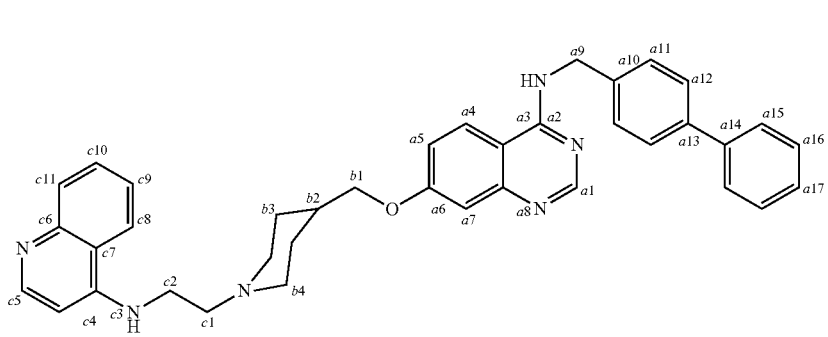

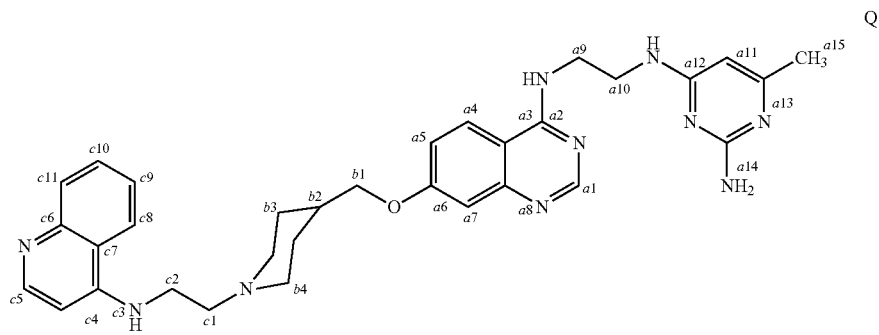 [SMILES: Cc1cc(NCCNc2ncnc3cc(OCC4CCN(CCNc5ccnc6ccccc56)CC4)ccc23)nc(N)n1]

¹H NMR (500 MHz, DMSO) δ 8.40 (m, 2H, Hc5 and Ha1), 8.20 (brt, J=8.15 Hz, 1H, HNH), 8.15 (d, J=7.9 Hz, 1H, Hc8), 8.11 (d, J=9.2 Hz, 1H, Ha4), 7.77 (dd, J=1.1, 8.5 Hz, 1H, Hc11), 7.62 (ddd, J=1.1, 7.0, 8.3 Hz, 1H, Hc10), 7.43 (ddd, J=J=1.1, 7.0, 8.3 Hz, 1H, Hc9), 7.11 (dd, J=2.5 Hz, 7.1 Hz, 1H, Ha5), 7.07 (d, J=2.5 Hz, 1H, Ha7), 7.04 (brt, 1H, HNH), 6.48 (d, J=5.2 Hz, 1H, Hc4), 5.84 (brs, 2H, HNH$_2$), 5.63 (brs, 1H, HNH), 3.98 (d, J=6.0 Hz, 2H, Hb1), 3.65 (brq, J=5.5 Hz, 2H, Ha9), 3.55-3.36 (m, 4H, Ha10 and Hc2), 3.01 (d, J=11.0 Hz, 2H, Hb4eq), 2.64 (t, J=7.0 Hz, Hc1), 2.06 (t, J=11.0 Hz, 2H, Hb4ax), 2.00 (s, 3H, Ha15), 1.86-1.76 (m, 3H, Hb2 and Hb3eq), 1.38 (dq, J=2.8-12.5 Hz, 2H, Hb3ax).

¹³C NMR (125 MHz, CDCl$_3$) δ 164.1 (Ca13), 163.3 (Ca14), 162.2 (Ca6), 159.6 (Ca2), 156.0 (Ca1), 151.8 (Ca3), 151.1 (Cc5), 150.3 (Cc7), 148.7 (Cc6), 129.4 (Cc11), 129.1 (Cc10), 124.8 (Ca4), 124.3 (Hc9), 121.9 (Cc8), 119.2 (Cc7), 117.3 (Ca5), 109.5 (Ca3), 107.9 (Ca7), 98.8 (Ca12), 98.7 (Cc4), 72.7 (Cb1), 56.6 (Cc1), 53.5 (Cb4), 41.2 (a9), 40.6 (Cc2), 39.4 (Ca10), 35.7 (Cb2), 29.0 (Cb3), 23.6 (Ca15).

HRMS-ESI (m/z) calculated for C$_{32}$H$_{39}$N$_{10}$O [M+H]$^+$: 579.3303. found: 579.3319.

Example 10: Compound K

45 $\xrightarrow{a}$

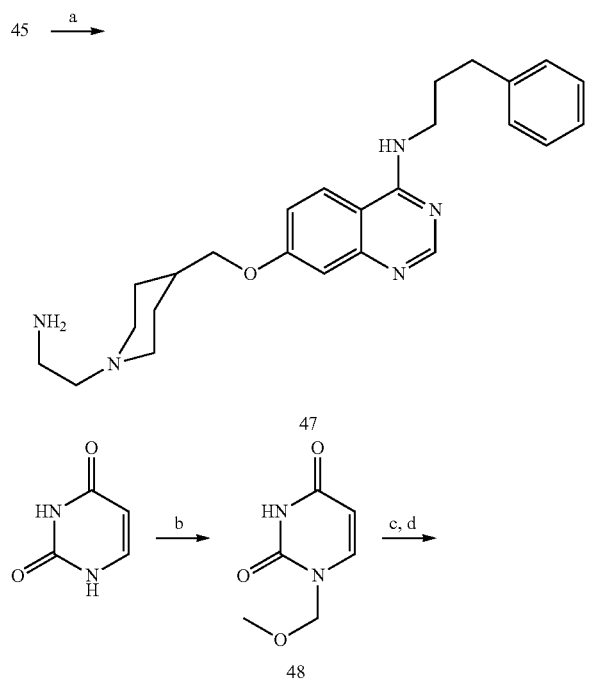

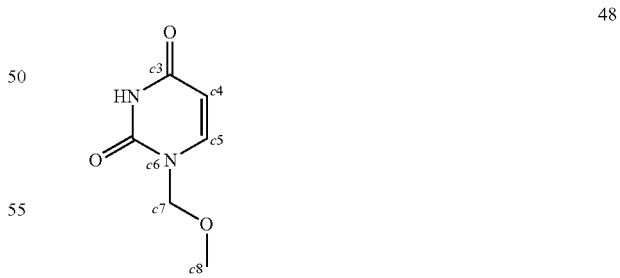

a) i) 2-(Bocamino)-ethyl bromide, TEA, DMF, 65° C., 2 h. ii) TFA, RT, 1 h. b) MOMCl, BSA, DCM, RT, 18h. C) TosCl, Me-piperidine, TEA, MeCN, 12 h, RT. d) 47, TEA, DMF, RT, 2 h, 23% over three steps from 45.

1-(methoxymethyl)uracyl (48)

To a solution of uracyl (0.88 g; 7.94 mmol) in 250 mL of dichloromethane was added N,O-bis(trimethylsilyl)acetamide (4.8 mL; 19.4 mmol). The mixture was stirred 1 hour at room temperature. To the reaction mixture was added chloromethyl methyl ether (784 µL; 10.32 mmol) and the mixture was stirred 17 hours at room temperature. The solvent was removed and the residue was purified by silica gel chromatography using the eluent cyclohexane/ethyl acetate (7/3) to give 48 (988 mg; 7.4 mmol; 93%) as a white powder.

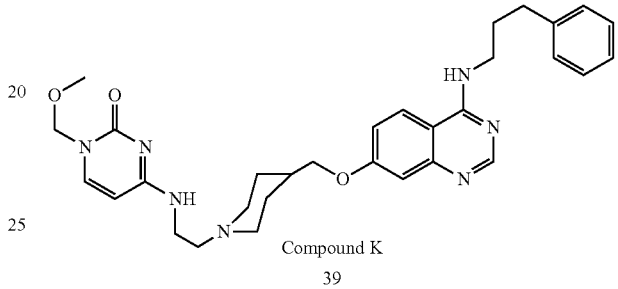

¹H NMR (500 MHz; DMSO) δ 11.32 (s, 1H, FINE), 7.70 (d, J=8.0 Hz, 1H, Hc5), 5.61 (d, J=8.0 Hz, 1H, Hc4), 5.02 (s, 2H, Hc7), 3.27 (s, 3H, Hc8).

¹³C NMR (125 MHz, CDCl$_3$) δ 164.0 (Cc3), 151.5 (Cc6), 145.4 (Cc5), 101.9 (Cc4), 78.0 (Cc7), 56.4 (C8).

HRMS-ESI (m/z) calculated for C$_6$H$_8$N$_2$NaO$_3$ [M+Na]$^+$: 179.0427. Found: 179.0416.

1-(methoxymethyl)-$N^4$-(2-(4-(((4-((3-phenylpropyl)amino)quinazolin-7-yl)oxy)methyl)piperidin-1-yl)ethyl)cytosine (Compound K)

To a solution of 45 (10 mg; 27 μmol), TEA (30 μL; 0.22 mmol), in DMF (0.2 mL) was added 2-(N-bocamino)ethyl-bromide (10 mg; 35 μmol). The mixture was stirred at room temperature for 2.5 h. The mixture was diluted with ethyl acetate. The organic phase was washed with water and brine and dried over sodium sulfate. The solvent was removed and the crude product was immediately solubilized in TFA (0.5 mL). The mixture was stirred at room temperature for 0.5 h. TFA was removed by vacuum. The residue was solubilized in ammonia 7N in methanol and the solvent was removed to afford crude 47 that was used without further purification.

To a solution of triazole (28 mg; 0.40 mmol) and $POCl_3$ (12 μl; 0.132 mmol) in 0.3 mL of acetonitrile at 0° C. was added TEA 56 μL dropwise. The reaction mixture was stirred at 0° C. for 40 min then 30 min at room temperature. 48 (10 mg; 60 μmol) was added and the mixture was vigorously stirred at room temperature overnight. The solvent was removed and 0.5 mL of a solution of previously prepared 47 was added to the residue. The reaction mixture was stirred 3 h at 35° C. The mixture was diluted with ethyl acetate. The organic phase was washed with water and brine and dried over sodium sulfate. The solvent was removed and the residue was purified by silica gel flash chromatography using a linear gradient of ammonia 1N in methanol (0→10% $MeOH/NH_3$) in dichloromethane or by reversed phase HPLC using a linear acetonitrile gradient with 0.01% of TEA (0→80% $CH_3CN$) to afford Compound K (3.5 mg; 60 μmol, 23%) as a white powder.

$^1$H NMR (500 MHz; $CDCl_3$) δ 8.57 (s, 1H, Ha1), 7.34-7.28 (m, 3H, Ha4 and Ha13), 7.28-7.20 (m, 4H, Ha15, Ha14 and Hc5), 7.11 (d, J=2.3 Hz, 1H, Ha7), 7.00 (dd, J=2.3, 8.9 Hz, 1H, Ha5), 5.79 (brt, J=4.4 Hz, 1H, HNHc), 5.67 (d, J=7.3 Hz, 1H, Hc4), 5.44 (brt, J=5.5, 1H, HNHa), 5.17 (s, 2H, Hc7), 4.85 (brt, J=5.1 Hz, 1H, HNHc), 3.92 (d, J=5.8 Hz, 2H, Hb1), 3.70 (q, J=7.0 Hz, 2H, Ha9), 3.58 (q, J=4.9 Hz, 2H, Hc2), 3.39 (s, 3H, Hc8), 2.94 (brd, J=10.6 Hz, 2H, Hb4eq), 2.79 (t, J=7.2 Hz, Ha11), 2.55 (t, J=5.7 Hz, 2H, Hc1), 2.11-2.00 (m, 4H, Ha10 and Hb4ax), 1.95-1.79 (m, 3H, Hb2 and Hb3eq), 1.46-1.35 (m, 2H, Hb3ax).

$^{13}$C NMR (125 MHz, $CDCl_3$) δ 163.6 (Cc3), 162.2 (Ca6), 159.0 (Ca2), 157.0 (Cc6), 156.0 (Ca1), 151.6 (Ca8), 142.7 (Cc5), 141.5 (Ca12), 128.6 (Ca13), 128.4 (Ca14), 126.1 (Ca15), 121.8 (Ca4), 117.9 (Ca5), 109.0 (Ca3), 107.8 (Ca7), 95.8 (Cc4), 78.8 (Cc7), 72.7 (Cb1), 56.7 (Cc8), 56.2 (Cc1), 53.0 (Cb4), 41.1 (Ca9), 37.2 (Cc2), 35.6 (Cb2), 33.7 (Ca11), 30.7 (Ca10), 29.0 (Cb3).

HRMS-ESI (m/z) calculated for $C_{31}H_{40}N_7O_3$ $[M+H]^+$: 558.3187. found: 558.3182.

Example 11: Compound J

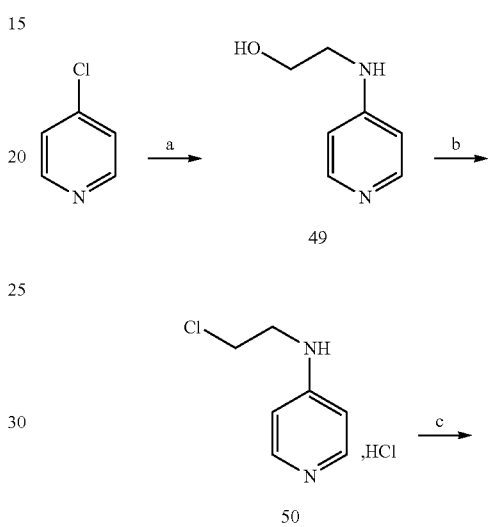

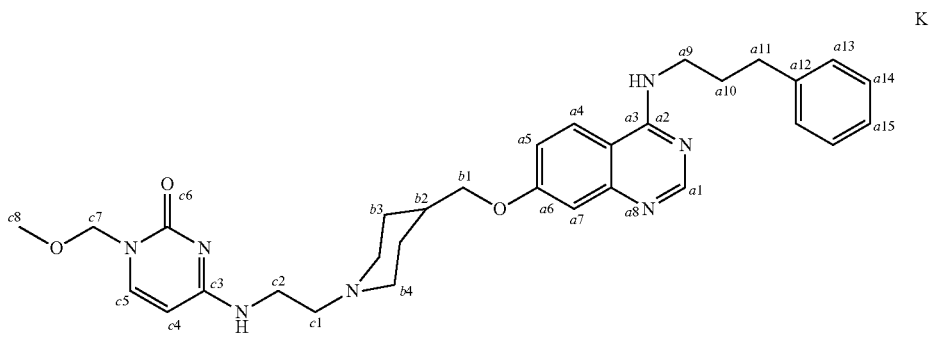 [SMILES: COCn1ccc(NCCN2CCC(COc3ccc4c(NCCCc5ccccc5)ncnc4c3)CC2)nc1=O]

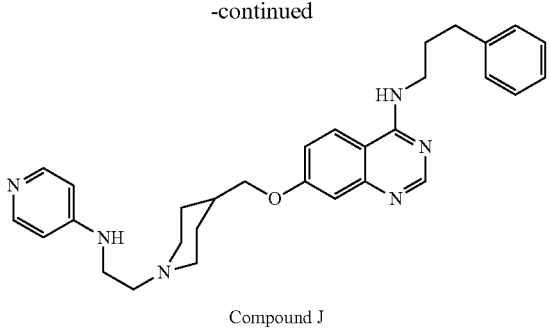

Compound J a) Ethanolamine, 125° C., 4 h, quantitative yield. b) $SOCl_2$, DMF, Flash boiling, quantitatice yield. c) 45, $K_2CO_3$, KI, DMF, 90° C., 12 h, 69%.

4-((2-Hydroxyethyl)amino)pyridine (49)

A mixture of 4-chloropyridine (500 mg; 4.41 mmol) in ethanolamine (2.6 mL; 44 mmol) was stirred at 110° C. for 3 h. The solvent was removed and the residue was purified by silica gel flash chromatography using a linear gradient of ethyl acetate (0→100% AcOEt) in cyclohexane to afford 49 as a white powder (607 mg; 4.40 mmol; quantitative yield).

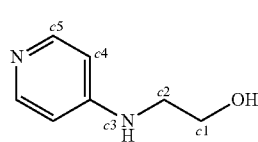

$^1$H NMR (500 MHz, DMSO) δ 8.00 (d, J=6.1 Hz, 1H, Hc5), 6.49 (m, 3H, Hc4 and HNH), 4.77 (brs, 1H, HOH), 3.53 (t, J=6.0 Hz, 2H, Hc1), 3.13 (q, J=5.9 Hz, 2H, Hc2).

$^{13}$C NMR (125 MHz, DMSO) δ : 154.1 (Cc3), 149.7 (Cc5), 107.5 (Cc4), 59.7 (Cc1), 40.6 (Cc2).

HRMS-ESI (m/z) calculated for $C_7H_{10}N_2NaO$ [M+Na]$^+$: 161.0685. found: 161.0650.

4-((2-chloroethyl)amino)quinoline chlorhydrate (50)

49 (300 mg; 1.92 mmol) was solubilized in thionyl chloride (2 ml). The mixture was flash boiled and the solvent was removed. Toluene was added to remove the residual thionyl chloride by co-evaporation. The residue was triturated in dichloromethane and the solid was filtrated to afford 50 chlorhydrate as a white solid (360 mg; 1.87 mmol; 97%).

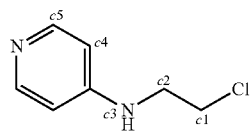

$^1$H NMR (DMSO) δ 8.22 (brs, 1H, FINE), 8.11 (d, J=6.8 Hz, 2H, Hc5), 6.81 (d, J=6.8 Hz, 2H, Hc4), 3.76 (t, J=6.0 Hz, 2H, Hc1), 3.58 (q, J=5.6 Hz, 2H, Hc2).

$^{13}$C NMR (DMSO) δ : 156.6 (Cc3), 143.9 (Cc5), 107.8 (Cc4), 44.1 (Cc1), 43.5 (Cc2).

HRMS-ESI(m/z) calculated for $C_7H_{10}N_2Cl$ [M+H]$^+$: 157.0527. found: 157.0541.

4-(3-phenylpropylamino)-7-((1-(2-(pyridin-4-ylamino)ethyl)piperidin-4-yl)methoxy)quinazoline (Compound J)

To a solution of 45 (10 mg; 27 μmol), $K_2CO_3$ (15 mg; 109 μmol) and a catalytic amount of KI in DMF (0.5 mL) was added 50 (13 mg, 68 μmol). The mixture was stirred at 65° C. overnight. The mixture was diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.01% of TEA (0→80% CH$_3$CN) to afford Compound J (9.2 mg, 19 μmol, 69%) as a white powder.

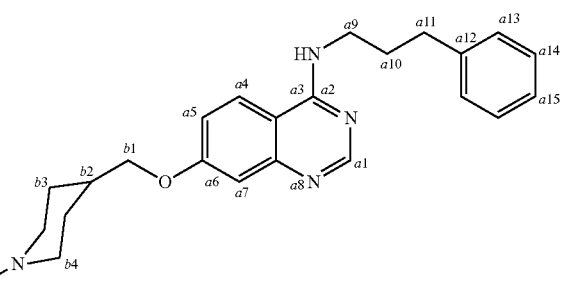

$^1$H NMR (500 MHz; CDCl$_3$) δ 8.57 (s, 1H, Ha1), 8.18 (dd, J=1.5, 4.8 Hz, 2H, Hc5), 7.32-7.28 (m, 3H, Ha4 and Ha13), 7.25-7.20 (m, 3H, Ha15 and Ha14), 7.12 (d, J=2.5 Hz, 1H, Ha7), 7.00 (dd, J=2.5, 9.0 Hz, 1H, Ha5), 6.44 (dd, J=1.5, 4.8 Hz, 2H, Hc4), 5.96 (brt, J=5.2, 1H, HNHa), 4.85 (brt, J=5.1 Hz, 1H, HNHc), 3.94 (d, J=6.0 Hz, 2H, Hb1), 3.70 (q, J=6.8 Hz, 2H, Ha9), 3.19 (q, J=5.5 Hz, 2H, Hc2), 2.95 (brd, J=11.4 Hz, 2H, Hb4eq), 2.79 (t, J=7.3 Hz, 2H, Ha11), 2.62 (t, J=6.2 Hz, 2H, Hc1), 2.09 (quint, J=6.8 Hz, 2H, Ha10), 2.05 (dt, J=2.1, 9.8 Hz, 2H, Hb4ax), 1.90 (m, 1H, Hb2), 1.87 (d, J=12.2 Hz, 2H, Hb3eq), 1.44 (dq, J=2.9-12.2 Hz, 2H, Hb3ax).

$^{13}$C NMR (125 MHz, CDCl$_3$) δ 162.2 (Ca6), 159.0 (Ca2), 155.9 (Ca1), 153.3 (Cc5), 151.5 (Ca8), 150.5 (Cc4), 149.9 (Cc3), 141.5 (Ca12), 128.6 (Ca13), 128.4 (Ca14), 126.1 (Ca15), 121.8 (Ca4), 117.9 (Ca5), 109.0 (Ca3), 107.8 (Ca7), 107.6 (Cc4), 72.7 (Cb1), 56.3 (Cc1), 53.0 (Cb4), 41.1 (Ca9), 38.9 (Cc2), 35.6 (Cb2), 33.6 (Ca11), 30.7 (Ca10), 29.0 (Cb3).

HRMS-ESI (m/z) calculated for $C_{30}H_{37}N_7O$ [M+H]$^+$: 497.3023. found: 497.3025.

Example 12: Compound M

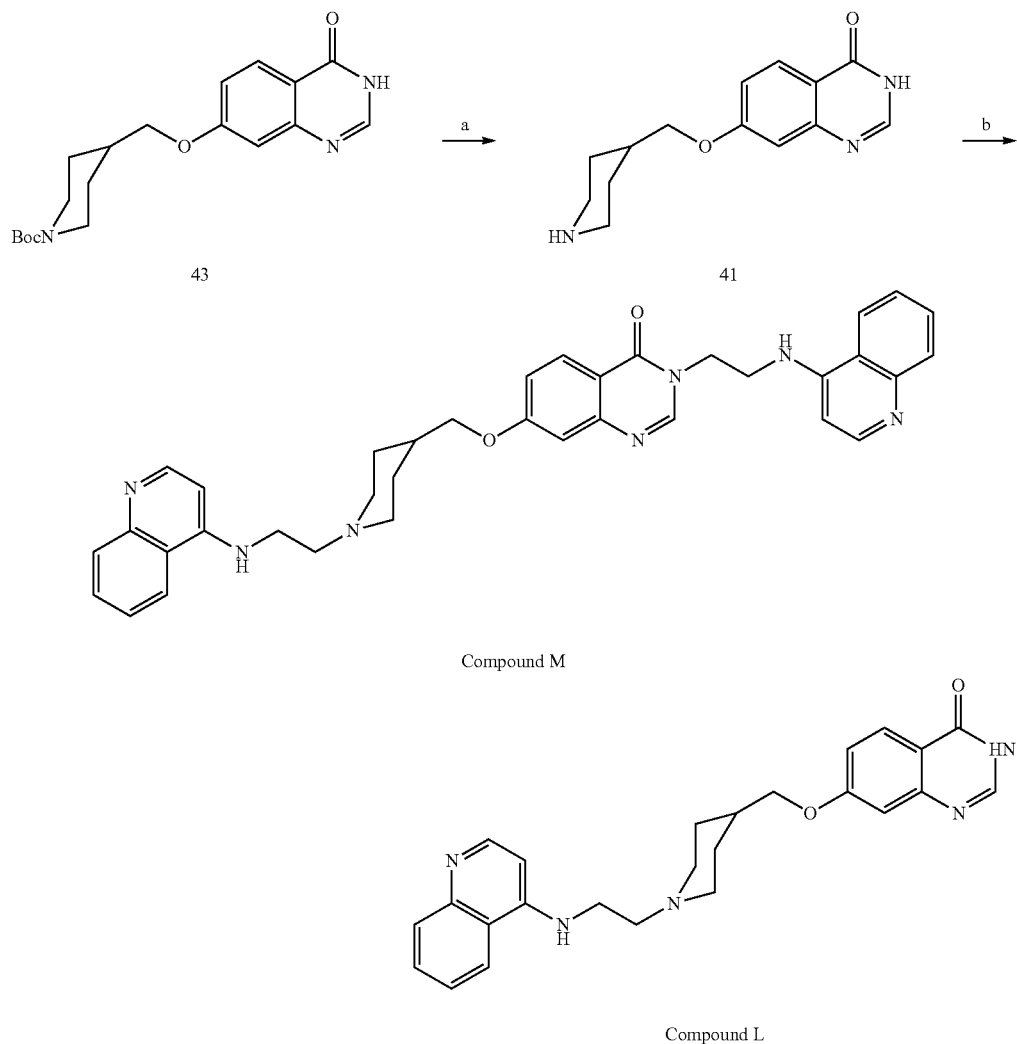

a) TFA, RT, 2 h, quantitative yield. b) 26, K₂CO₃, KI, DMF, 24 h, 69%.

7-O-(piperidin-4-ylmethoxy)quinazolinone (51)

A mixture of 43 (220 mg; 0.46 mmol) in TFA was stirred for 1 h at room temperature. TFA was removed. The residue was diluted with dichloromethane and the organic phase was washed with saturated Na₂CO₃. The solvent was removed and 51 was obtained as pale blue foam (155 mg; 0.43 mmol; 94%).

3-(2-(quinolin-4-ylamino)ethyl)-7-((1-(2-(quinolin-4-ylamino)ethyl)piperidin-4-yl)methoxy)quinazolinone (Compound M)

To a solution of 51 (100 mg; 0.39 mmol), K₂CO₃ (160 mg; 1.16 mmol) and a catalytic amount of KI in DMF (5 mL) was added 26 (187 mg; 0.77 mmol). The mixture was stirred at 65° C. overnight and 90° C. for 7 hours. The resulting mixture was filtered and the residue was purified by silica gel flash chromatography using a linear gradient of ammonia 1N in methanol (0→10% MeOH/NH₃) in dichloromethane to afford Compound M as a white powder (92 mg; 154 µmol; 40%) and Compound L as a white solid (17 mg; 39 µmol; 11%).

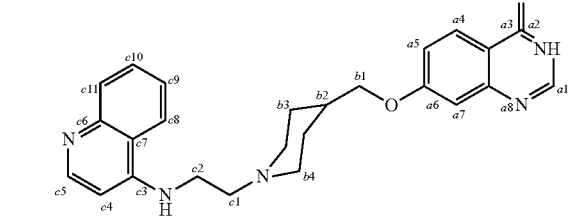

L $^1$H NMR (500 MHz; CDCl₃) δ 8.56 (d, J=5.5 Hz, 1H, Hc5), 8.19 (d, J=8.8 Hz, 1H, Ha4), 8.08 (s, 1H, Ha1), 8.03 (d, J=8.5 Hz, 2H, Hc8), 7.78 (d, J=8.5Hzs, 1H, Hc11), 7.65 (ddd, J=1.2, 6.7 Hz, 1H, Hc10), 7.47 (ddd, J=1.2, 6.7 Hz, 1H, Hc9), 7.13-7.06 (m, J=2.4, 8.3 Hz, 1H, Ha5 and Ha7), 6.40 (d, J=5.4 Hz, 1H, Hc4), 7.05 (brs, 1H, HNH), 3.97 (d, J=2.2 Hz, 2H, Hb1), 3.37 (q, J=6.5 Hz, 2H, Hc2), 3.02 (brd, J=11.1 Hz, 2H, Hb4eq), 2.80 (t, J=5.6 Hz, 2H, Hc1), 2.15 (brt, J=11.5 Hz, 2H, Hb4ax), 2.00-1.87 (m, 3H, Hb2 and Hb3eq), 1.54-1.41 (m, 2H, Hb3ax).

$^{13}$C NMR (125 MHz, CDCl$_3$) δ 164.3 (Ca6), 162.4 (Ca2), 151.2 (Ca8), 150.4 (Ca3), 150.0 (Cc5), 147.1 (Cc6), 144.3 (Ca1), 129.6 (Cc11), 128.8 (Cc10), 127.9 (Ca4), 125.0 (Cc9), 120.0 (Cc8), 118.6 (Cc7), 117.6 (Ca5), 115.9 (Ca3), 109.0 (Ca7), 98.8 (Cc4), 72.8 (Cb1), 58.4 (Cc1), 55.8 (Cb4), 52.9 (Cc2), 39.2 (Cb2), 29.1 (Cb3).

HRMS-ESI (m/z) calculated for C$_{25}$H$_{27}$N$_5$O$_2$ [M+H]$^+$: 430.5216. Found: 430.5223.

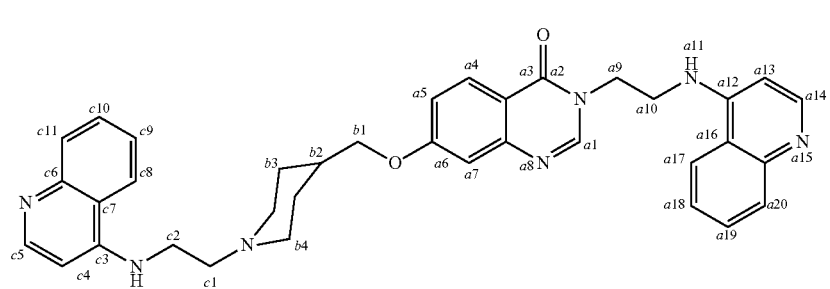

M $^1$H NMR (500 MHz; DMSO) δ 8.40 (d, J=5.3 Hz, 2H, Hc5 and Ha14), 8.15 (d, J=8.2 Hz, 1H, Ha4), 8.14 (s, 1H, Ha1), 8.16 (d, J=8.8 Hz, 2H, Hc8 and Ha17), 7.79 (m, 2H, Hc11 and Ha20), 7.61 (m, 2H, Hc10 and Ha19), 7.42 (m, 2H, Hc9 and Ha18), 7.37 (brt, J=6.2 Hz, HNH), 7.14 (dd, J=2.4, 8.3 Hz, 1H, Ha5), 7.07 (d, J=7.07 Hz, 1H, Ha7), 7.05 (brt, J=5.5 Hz, 1H, HNH), 6.66 (d, J=5.3 Hz, 1H, Ha13), 6.47 (d, J=5.3 Hz, 1H, Hc4), 4.22 (t, J=6.0 Hz, 2H, Ha9), 3.99 (d, J=2.0 Hz, 2H, Hb1), 3.69 (q, J=5.8 Hz, 2H, Ha10), 3.41 (q, J=6.3 Hz, 2H, Hc2), 3.00 (brd, J=11.3 Hz, 2H, Hb4eq), 2.68-2.60 (m, 3H, Hc1), 2.07 (t, J=11.0 Hz, 2H, Hb4ax), 1.85-1.72 (m, 3H, Hb2 and Hb3eq), 1.37 (m, 2H, Hb3ax).

$^{13}$C NMR (125 MHz, DMSO) δ 163.8 (Ca6), 160.6 (Ca2), 151.2 (Cc5 and Ca14), 150.7 (Ca8), 150.2 (Cc3), 149.9 (Ca12), 149.0 (Ca1), 148.8 (Cc6), 148.7 (Ca15), 129.6 (Cc11), 129.5 (Ca20), 129.2 (Cc10), 129.1 (Ca19), 128.1 (Ca4), 124.5 (Ca18), 124.3 (Cc9), 121.8 (Cc8), 121.8 (Ca17), 119.3 (Ca16), 119.2 (Cc7), 117.2 (Ca5), 115.4 (Ca3), 109.2 (Ca7), 98.8 (Ca13), 98.7 (Cc4), 72.9 (Cb1), 56.6 (Cc1), 53.4 (Cb4), 44.8 (Ca9), 41.1 (Cc2), 40.6 (Ca10), 35.7 (Cb2), 28.9 (Cb3).

HRMS-ESI (m/z) calculated for C$_{34}$H$_{38}$N$_5$O$_2$ [M+H]$^+$: 600.3080. Found: 600.3076.

Example 13: Compound S

42 $\xrightarrow{a}$

-continued

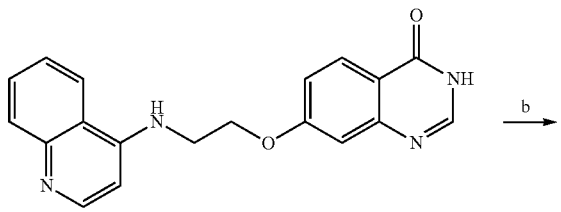

56

-continued

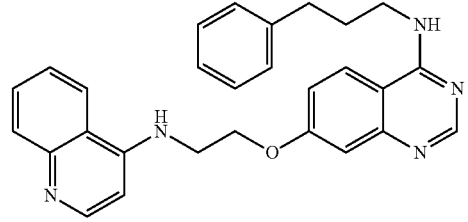

Compound S a) 25, NaH, DMF, 110° C., 4 h, 54%. b) i) POCl$_3$, triazole, TEA, MeCN, RT, 18 h. ii) 3-Phenylpropylamine, TEA, DMF, RT, 2 h, 45 %.

7-(2-(quinolin-4-ylamino)ethoxy)quinazolinone (56)

To a mixture of 25 (143 mg; 760 μmol) in DMF (3 mL) at 0° C. under argon was added sodium hydride (91 mg; 3.81 mmol). The mixture was stirred for 10 min at 0° C. then 42 (250 mg. 1.52 mmol) was added. The mixture was stirred at 110° C. for 4 h. The reaction mixture was diluted with ethyl acetate and washed with water. The aqueous phase was filtered and the precipitate was dried to afford 56 as a white powder (136 mg; 409 μmol; 54%).

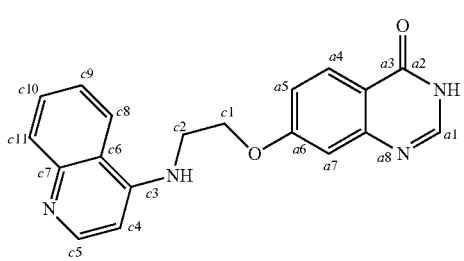

56

$^1$H NMR (500 MHz; DMSO) δ 8.43 (d, J=5.3 Hz, 1H, Hc5), 8.24 (dd, J=0.7, 8.5 Hz, 1H, Hc8), 8.06 (s, 1H, Ha1), 8.03 (d, J=8.7 Hz, 1H, Ha4), 7.79 (dd, J=0.7, 8.5 Hz, 1H, Hc11), 7.61 (ddd, J=1.2, 6.7, 8.1 Hz, 1H, Hc10), 7.43 (ddd, J=1.2, 6.7, 8.2 Hz, 1H, Hc9), 7.37 (brt, J=6.0 Hz, 1H, HNHc), 7.15 (d, J=2.6 Hz, 1H, Ha7), 7.13 (dd, J=2.4, 8.9 Hz, 1H, Ha5), 6.61 (d, J=5.4 Hz, 1H, Hc4), 4.42 (t, J=5.5 Hz, 2H, Hc1), 3.75 (q, J=5.5 Hz, 2H, Hc2).

$^{13}$C NMR (125 MHz, DMSO) δ 163.5 (Ca6), 160.7 (Ca2), 151.4 (Ca8), 151.2 (Cc5), 150.2 (Cc3), 148.8 (Cc6), 146.5 (Ca1), 129.5 (Cc11), 129.2 (Cc10), 128.0 (Ca4), 124.3 (Cc9), 122.1 (Cc8), 119.2 (Cc7), 116.9 (Ca5), 116.5 (Ca3), 109.5 (Ca7), 98.9 (Cc4), 66.6 (Cc1), 42.2 (Cc2).

HRMS-ESI (m/z) calculated for $C_{19}H_{17}N_4O_2$ [M+H]$^+$: 333.1346. Found: 333.1350.

4-(3-phenylpropylamino)-7-(2-(quinolin-4-ylamino)ethoxy)quinazoline (Compound S)

To a solution of 56 (50 mg; 13 μmol), TEA (26 mg; 26 μmol) in DMF (1 mL) was added 3-phenylpropylamine (35 mg; 26 μmol). The mixture was stirred at room temperature overnight. The solvent was removed and the residue was purified by reversed phase HPLC using a linear acetonitrile gradient with 0.01% of TEA (0→80% $CH_3CN$) to afford Compound S as a white powder (25 mg; 56 μmol; 45%).

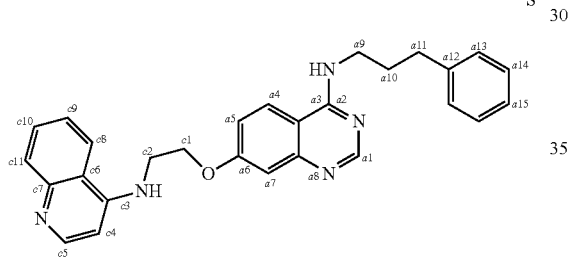

S $^1$H NMR (500 MHz; DMSO) δ 8.44 (d, J=5.3 Hz, 1H, Hc5), 8.39 (s, 1H, Ha1), 8.25 (dd, J=0.9, 8.3 Hz, 1H, Hc8), 8.15 (m, 1H, Ha4), 8.10 (brt, J=5.3 Hz, 1H, HNH), 7.79 (dd, J=0.9, 8.5 Hz, 1H, Hc11), 7.61 (ddd, J=1.2, 6.9, 8.0 Hz, 1H, Hc10), 7.43 (ddd, J=1.2, 6.9, 8.0 Hz, 1H, Hc9), 7.36 (brt, J=5.2 Hz, 1H, HNHc), 7.32-7.22 (m, 4H, Ha14 and Ha13), 7.17 (m, 1H, Ha15), 7.15-7.10 (m, 2H, Ha7 and Ha5), 6.62 (d, J=5.4 Hz, 1H, Hc4), 4.41 (t, J=5.6 Hz, 2H, Hc1), 3.75 (q, J=5.4 Hz, 2H, Hc2), 3.52 (q, J=5.9 Hz, 2H, Ha9), 2.67 (t, J=7.8 Hz, 2H, Ha11), 1.95 (quint, J=7.8 Hz, 2H, Ha10).

$^{13}$C NMR (125 MHz, DMSO) δ 161.9 (Ca6), 159.5 (Ca2), 156.1 (Ca1), 151.8 (Ca8), 151.2 (Cc5), 150.3 (Cc3), 148.8 (Cc6), 140.9 (Ca12), 129.5 (Cc8), 129.2 (Cc10), 128.8 (Ca13), 128.7 (Ca14), 126.2 (Ca15), 124.3 (Cc9), 122.1 (Ca4), 118.8 (Cc11), 119.2 (Cc7), 117.1 (Ca5), 109.7 (Ca3), 108.0 (Ca7), 98.9 (Cc4), 66.4 (Cc1), 42.3 (Cc2), 40.5 (Ca9), 33.1 (Ca11), 30.8 (Ca10).

HRMS-ESI (m/z) calculated for $C_{28}H_{28}N_5O$ [M+H]$^+$: 450.2288. Found: 450.2287.

Example 14: Compound R

43 $\xrightarrow{a}$

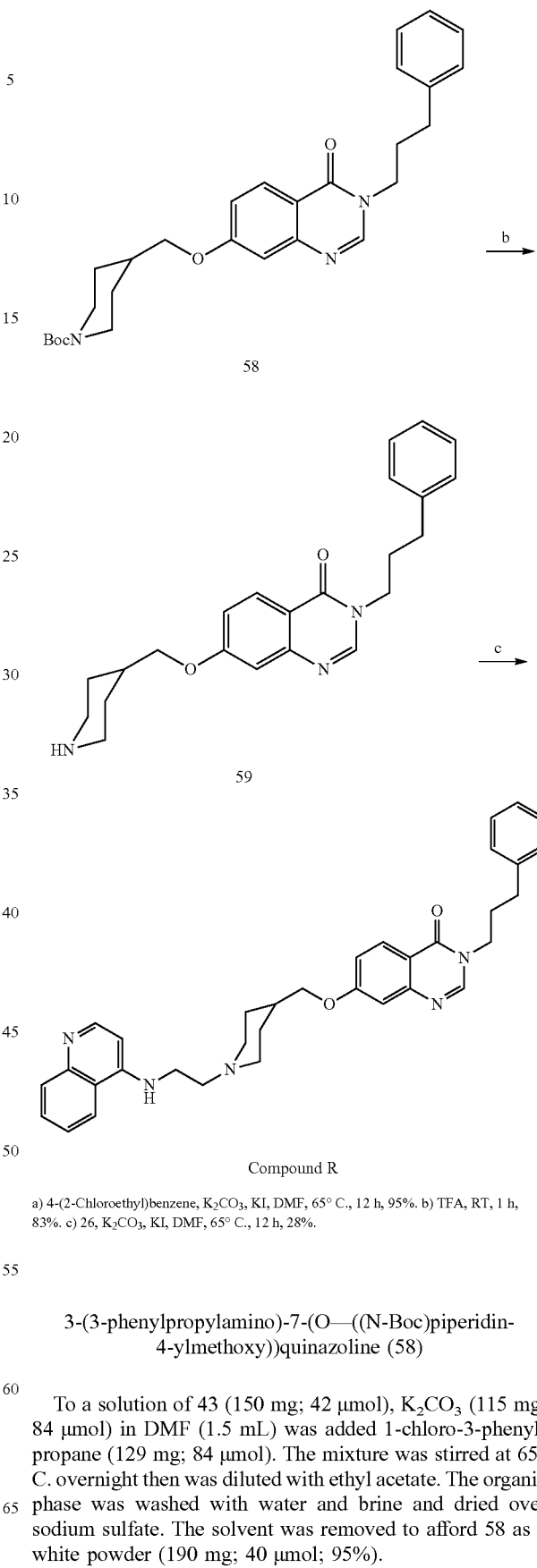

Compound R a) 4-(2-Chloroethyl)benzene, $K_2CO_3$, KI, DMF, 65° C., 12 h, 95%. b) TFA, RT, 1 h, 83%. c) 26, $K_2CO_3$, KI, DMF, 65° C., 12 h, 28%.

3-(3-phenylpropylamino)-7-(O—((N-Boc)piperidin-4-ylmethoxy))quinazoline (58)

To a solution of 43 (150 mg; 42 μmol), $K_2CO_3$ (115 mg; 84 μmol) in DMF (1.5 mL) was added 1-chloro-3-phenylpropane (129 mg; 84 μmol). The mixture was stirred at 65° C. overnight then was diluted with ethyl acetate. The organic phase was washed with water and brine and dried over sodium sulfate. The solvent was removed to afford 58 as a white powder (190 mg; 40 μmol; 95%).

58

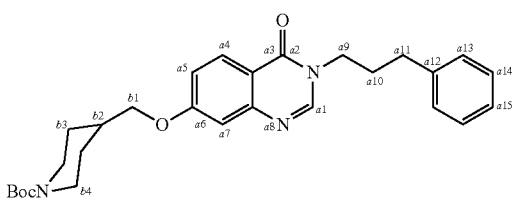

¹H NMR (500 MHz; DMSO) δ 8.31 (s, 1H, Ha1), 8.05 (d, J=8.4 Hz, 1H, Ha4), 7.31-7.25 (m, 2H Ha13), 7.25-7.20 (m, 2H, Ha14), 7.17 (m, 1H, Ha15), 7.14-7.08 (m, 2H, Ha7 and Ha5), 4.08-3.92 (m, 5H, HNH and Hb1 and Ha9), 2.78 (m, 2H, Hb4ax), 2.74 (t, J=8.5 Hz, 2H, Ha11), 2.07-1.95 (m, 3H, Hb2 and Ha10), 2.10-2.00 (brd, J=11 Hz, 2H, Hb3eq), 1.40 (s, 9H, HBoc), 1.26-1.13 (m, 2H, Hb3ax).

¹³C NMR (125 MHz, DMSO) δ 163.7 (Ca6), 160.2 (Ca2), 154.3 (CBoc), 150.6 (Ca8), 149.0 (Ca1), 1421.4 (CBoc), 128.8 (Ca13), 128.6 (Ca14), 128.1 (Ca4), 126.3 (Ca15), 117.2 (Ca5), 115.4 (Ca3), 109.2 (Ca7), 78.9 (CBoc), 72.6 (Cb1), 46.1 (Ca9), 45.1 (Cb4), 35.6 (Cb2), 32.6 (Ca11), 30.7 (Ca10), 28.6 (Cb3), 28.5 5 (CBoc).

HRMS-ESI (m/z) calculated for $C_{28}H_{35}N_3NaO_4$ [M+Na]⁺: 500.2520. Found: 500.2516.

3-(3-phenylpropyl)-7-(piperidin-4-ylmethoxy)quinazolinone (59)

A mixture of 58 (190 mg, 40 μmol) in TFA was stirred for 1 h30 at room temperature. TFA was removed. The solvent was removed and the residue was purified by reversed phase HPLC using a linear acetonitrile gradient with 0.01% of TEA (0→80% CH₃CN) to afford 59 as a white powder (124 mg, 33 μmol, 83%).

59

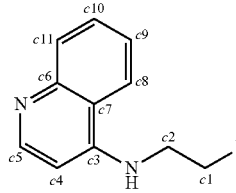

¹H NMR (500 MHz; CCl₃) δ 8.21 (d, J=8.4 Hz, 1H, Ha4), 7.93 (s, 1H, Ha1), 7.31-7.28 (m, 2H Ha13), 7.26-7.18 (m, 3H, Ha15 and Ha14), 7.08-7.00 (m, 2H, Ha7 and Ha5), 4.03-3.90 (m, 5H, HNH and Hb1 and Ha9), 3.56 (brd, J=9.6 Hz, 2H, Hb4eq), 2.96 (m, 2H, Hb4ax), 2.74 (t, J=7.5 Hz, 2H, Ha11), 2.22-2.10 (m, 3H, Hb2 and Ha10), 2.10-2.00 (m, 2H, Hb3eq), 1.95-1.72 (m, 2H, Hb3ax).

¹³C NMR (125 MHz, CCl₃) δ 163.2 (Ca6), 160.6 (Ca2), 150.2 (Ca8), 147.3 (Ca1), 128.6 (Ca13), 128.4 (Ca4), 128.3 (Ca14), 126.2 (Ca15), 117.2 (Ca5), 115.9 (Ca3), 108.7 (Ca7), 71.6 (Cb1), 46.5 (Ca9), 43.6 (Cb4), 34.1 (Cb2), 32.7 (Ca11), 30.5 (Ca10), 25.6 (Cb3).

HRMS-ESI (m/z) calculated for $C_{23}H_{28}N_3O_2$ [M+H]⁺: 378.2176. Found: 378.2173.

3-(3-phenylpropyl)-7-((1-(2-(quinolin-4-ylamino)ethyl)piperidin-4-yl)methoxy)quinazolinone (Compound R)

To a solution of 59 (124 mg; 0.33 mmol), K₂CO₃ (91 mg; 0.66 mmol) and a catalytic amount of KI in DMF (1.5 mL) was added 26 (80 mg; 0.33 mmol). The mixture was stirred at 65° C. for 24 hours. The solvent was removed and the residue was purified by reversed phase HPLC using a linear acetonitrile gradient with 0.01% of TEA (0→80% CH₃CN) to afford Compound R as a white powder (50 mg; 91 μmol, 28%).

R

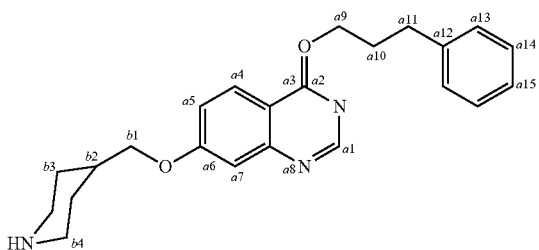

¹H NMR (500 MHz; DMSO) δ 8.40 (d, J=5.5 Hz, 1H, Hc5), 8.35 (s, 1H, Ha1), 8.16 (d, 8.4 Hz, 1H, Hc8), 8.05 (d, J=8.4 Hz, 1H, Ha4), 7.79 (dd, J=0.7, 8.5 Hz, 1H, Hc11), 7.61 (ddd, J=1.2, 6.8, 8.2 Hz, 1H, Hc10), 7.43 (ddd, J=1.2, 6.9, 8.2 Hz, 1H, Hc9), 7.31-7.25 (m, 2H, Ha13), 7.25-7.20 (m, 3H, Ha15 and Ha14), 7.14-7.08 (m, 2H, Ha7 and Ha5), 7.04 (brt, J=4.9 Hz, 1H, HNH), 6.47 (d, J=5.4 Hz, 1H, Hc4), 4.03-3.95 (m, 5H, HNH and Hb1 and Ha9), 3.40 (m, 2H, Hc2), 3.00 (brdd, J=11.0 Hz, 2H, Hb4eq), 2.68-2.60 (m, 4H, Ha11 and Hc1), 2.10-1.96 (m, 4H, Hb4ax and Ha10), 1.85-1.72 (m, 3H, Hb2 and Hb3eq), 1.37 (dq, J=2.6, 11.5 Hz, 2H, Hb3ax).

¹³C NMR (125 MHz, DMSO) δ 163.7 (Ca6), 160.2 (Ca2), 151.2 (Cc5), 150.7 (Ca8), 150.2 (Cc3), 149.0 (Ca1), 148.8 (Cc6), 141.5 (Ca12), 129.5 (Cc11), 129.1 (Cc10), 128.7 (Ca13), 128.6 (Ca14), 128.1 (Ca4), 126.3 (Ca15), 124.3 (Cc9), 121.8 (Cc8), 119.2 (Cc7), 117.2 (Ca5), 115.4 (Ca3), 109.2 (Ca7), 98.7 (Cc4), 72.9 (Cb1), 56.6 (Cc1), 53.4 (Cb4), 46.0 (Ca9), 40.5 (Cc2), 35.7 (Cb2), 32.6 (Ca11), 30.7 (Ca10), 29.2 (Cb3).

HRMS-ESI (m/z) calculated for $C_{34}H_{38}N_5O_2$ [M+H]⁺: 548.3020. Found: 548.3026.

Example 15: Compounds AA to AU

Compounds 60 to 71 were synthesized following the general procedure below from compound 43.

General Procedure for Compounds 60 to 71.

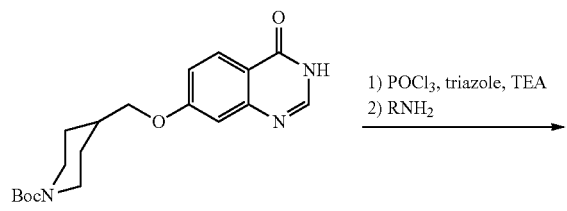

43

1) POCl₃, triazole, TEA
2) RNH₂
→

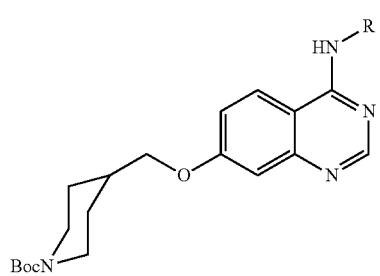

60 to 71

To a solution of triazole (0.93 mmol) and POCl₃ (0.32 mmol) in 0.7 mL of acetonitrile at 0° C. was added TEA (130 µL) dropwise. The reaction mixture was stirred at 0° C. for 40 min then 30 min at room temperature. 43 (0.14 mmol) was added and the mixture was vigorously stirred at room temperature overnight. The reaction was followed by TLC using ethyl acetate as eluent. The mixture was refluxed for 1 h to reach completion. After complete consumption of the starting material, the solvent was removed and the residue was taken off with ethyl acetate and washed with water and brine, and dried over sodium sulfate. The solvent was removed and the residue was solubilized in DMF (0.5 mL). The desired amine (0.23 mmol) and TEA (39 µL; 0.28 mmol) were added and the mixture was stirred for 3 h at room temperature. The mixture was diluted with ethyl acetate and washed with water, brine and dried over sodium sulfate. The solvent was removed and the residue was purified by silica gel flash chromatography using a linear gradient of ethyl acetate (0 to 100% AcOEt) in cyclohexane to afford 60 to 71.

| Amine used | Compound obtained |
|---|---|
| 3-chlorophenethylamine | 60 |
| 2-chlorophenethylamine | 61 |
| 4-chlorophenethylamine | 62 |
| 4-sulfamoylphenethylamine | 63 |
| 4-nitrophenethylamine | 64 |
| 4-isopropylphenethylamine | 65 |
| 4-methoxyphenethylamine | 66 |
| 4-aminophenethylamine | 67 |
| N-(quinolin-4-yl)ethylenediamine | 68 |
| N-(naphthalen-1-yl)ethylenediamine | 69 |
| N-phenylethylenediamine | 70 |
| 1-benzylpiperidin-4-amine | 71 |

4-(2-(3-chlorophenyl)ethylamino)-7-(O—((N-Boc)piperidin-4-ylmethoxy))quinazoline (60) (70 mg; 0.14 mmol, Quantitative)

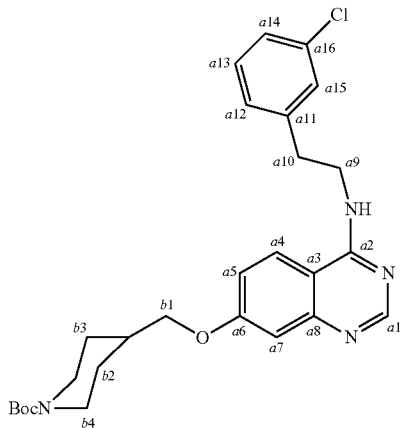 [SMILES: CC(C)(C)OC(=O)N1CCC(COc2ccc3c(NCCc4cccc(Cl)c4)ncnc3c2)CC1]

¹H NMR (500 MHz; DMSO) δ 8.41 (s, 1H, Ha1), 8.18 (brt, J=5.5 Hz, 1H, HNH), 8.10 (d, J=9.1 Hz, 1H, Ha4), 7.35-7.19 (m, 4H, Ha12, Ha13 et Ha14), 7.11 (dd, J=2.5, 9.1 Hz, 1H, Ha5), 7.06 (d, J=2.5 Hz, 1H, Ha7), 4.03-3.93 (m, 2H, Hb4eq), 3.99 (d, J=6.3 Hz, 2H, Hb1), 3.77-3.71 (m, 2H, Ha9), 2.97 (brt, J=7.0 Hz, 2H, Ha10), 2.85-2.68 (m, 2H, Hb4ax), 2.02-1.93 (m, 1H, Hb2), 1.81-1.74 (m, 2H, Hb3eq), 1.41 (s, 9H, HBoc), 1.20 (dq, J=4.9, 13.1 Hz, 2H, Hb3ax)

¹³C NMR (125 MHz; DMSO) δ 162.1 (Ca6), 159.4 (Ca2), 156.1 (Ca1), 154.3 (CBoc), 151.8 (Ca8), 142.7 (Ca11), 133.3 (Ca16), 130.5 (Ca15), 129.0 (Ca13), 127.9 (Ca12), 126.5 (Ca14), 124.61 (Ca4), 117.3 (Ca5), 109.5 (Ca3), 107.9 (Ca7), 78.9 (CBoc), 72.3 (Cb1), 42.02 (Ca9), 35.6 (Cb2), 34.5 (Ca10), 28.7 (Cb3), 28.6 (CBoc).

HRMS-ESI (m/z) calculated: 497.2319 [M+H]⁺. found: 497.2342.

4-(2-(2-chlorophenyl)ethylamino)-7-(O—((N-Boc)piperidin-4-ylmethoxy))quinazoline (61) (54 mg, 0.11 mmol, 88%)

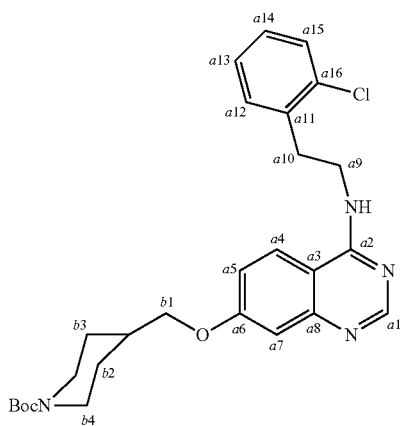 [SMILES: CC(C)(C)OC(=O)N1CCC(COc2ccc3c(NCCc4ccccc4Cl)ncnc3c2)CC1]

¹H NMR (500 MHz; DMSO) δ 8.41 (s, 1H, Ha1), 8.17 (brt, J=5.5 Hz, 1H, HNH), 8.09 (d, J=9.3 Hz, 1H, Ha4), 7.36-7.26 (m, 4H, Ha12, Ha13 et Ha14), 7.11 (dd, J=2.7, 9.12 Hz, 1H, Ha5), 7.06 (d, J=2.3 Hz, 1H, Ha7), 4.04-3.93 (m, 2H, Hb4eq), 3.99 (d, J=6.3 Hz, 2H, Hb1), 3.75-3.69 (m, 2H, Ha9), 2.95 (brt, J=7.3 Hz, 2H, Ha10), 2.83-2.68 (m, 2H, Hb4ax), 2.02-1.92 (m, 1H, Hb2), 1.81-1.73 (m, 2H, Hb3eq), 1.41 (s, 9H, HBoc), 1.20 (dq, J=3.8, 12.3 Hz, 2H, Hb3ax).

¹³C NMR (125 MHz; DMSO) δ 162.1 (Ca6), 159.4 (Ca2), 156.1 (Ca1), 154.3 (CBoc), 151.8 (Ca8), 139.1 (Ca11), 131.14 (Ca16), 131 (Ca15), 128.7 (Ca13), 128.7 (Ca14), 127.7 (Ca12), 124.6 (Ca4), 117.3 (Ca5), 109.5 (Ca3), 107.9 (Ca7), 78.9 (CBoc), 72.3 (Cb1), 43.3 (Cb4), 42.2 (Ca9), 35.6 (Cb2), 34.3 (Ca10), 28.7 (Cb3), 28.6 (CBoc).

HRMS-ESI (m/z) calculated: 497.2319 [M+H]⁺. found: 497.2325.

4-(2-(4-chlorophenyl)ethylamino)-7-(O—((N-Boc)piperidin-4-ylmethoxy))quinazoline (62) (93 mg, 0.14 mmol, Quantitatif)

¹H NMR (500 MHz; DMSO) δ 8.41 (s, 1H, Ha1), 8.21 (brt, J=5.74 Hz, 1H, HNH), 8.10 (d, J=9.20 Hz, 1H, Ha4), 7.47-7.31 (m, 4H, Ha12, Ha13 et Ha14), 7.11 (dd, J=2.47, 8.94 Hz, 1H, Ha5), 7.06 (d, J=2.65 Hz, 1H, Ha7), 4.03-3.94 (m, 2H, Hb4eq), 3.98 (d, J=6.41 Hz, 2H, Hb1), 3.80-3.71 (m, 2H, Ha9), 3.09 (brt, J=7.40 Hz, 2H, Ha10), 2.75-2.60 (m, 2H, Hb4ax), 2.02-1.92 (m, 1H, Hb2), 1.81-1.73 (m, 2H, Hb3eq), 1.41 (s, 9H, HBoc), 1.20 (dq, J=3.94, 12.45 Hz, 2H, Hb3ax).

¹³C NMR (125 MHz; DMSO) δ 162.1 (Ca6), 159.5 (Ca2), 156.1 (Ca1), 154.3 (CBoc), 151.8 (Ca8), 138.2 (Ca11), 131.6 (Ca14), 129.6 (Ca12), 127.7 (Ca13), 124.7 (Ca4), 117.3 (Ca5), 109.6 (Ca3), 107.9 (Ca7), 78.9 (CBoc), 72.3 (Cb1), 43.1 (Cb4), 42.4 (Ca9), 35.6 (Cb2), 32.8 (Ca10), 28.7 (Cb3), 28.6 (CBoc).

HRMS-ESI (m/z) calculated: 497.2319 [M+H]⁺. found: 497.2318.

4-(2-(4-sulfonamidophenyl)ethylamino)-7-(O—((N-Boc)piperidin-4-ylmethoxy))quinazoline (63) (53 mg, 98 μmol, 70%)

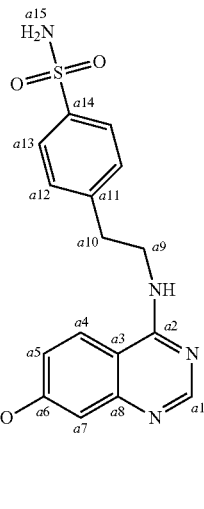

$^1$H NMR (500 MHz; DMSO) δ 8.42 (s, 1H, Ha1), 8.21 (brt, J=5.8 Hz, 1H, HNH), 8.10 (d, J=9.1 Hz, 1H, Ha4), 7.77-7.73 (m, 2H, Ha13), 7.47-7.43 (m, 2H, Ha12), 7.29 (brs, 2H, Ha15), 7.12 (dd, J=2.6, 9.1 Hz, 1H, Ha5), 7.07 (d, J=2.5 Hz, 1H, Ha7), 4.02-3.94 (m, 2H, Hb4eq), 3.99 (d, J=6.5 Hz, 2H, Hb1), 3.76 (q, J=6.5 Hz, 2H, Ha9), 3.04 (brt, J=7.4 Hz, 2H, Ha10), 2.84-2.68 (m, 2H, Hb4ax), 2.02-1.92 (m, 1H, Hb2), 1.81-1.74 (m, 2H, Hb3eq), 1.41 (s, 9H, HBoc), 1.26-1.13 (m, 2H, Hb3ax).

$^{13}$C NMR (125 MHz; DMSO) δ 162.1 (Ca6), 159.4 (Ca2), 156.1 (Ca1), 154.3 (CBoc), 151.8 (Ca8), 144.3 (Ca11), 142.6 (Ca14), 129.6 (Ca12), 126.2 (Ca13), 124.6 (Ca4), 117.3 (Ca5), 109.6 (Ca3), 107.9 (Ca7), 78.9 (CBoc), 72.3 (Cb1), 42 (Ca9), 35.6 (Cb2), 34.7 (Ca10), 28.7 (Cb3), 28.6 (CBoc).

HRMS-ESI (m/z) calculated: 542.2437 [M+H]$^+$. found: 542.2445.

4-(2-(4-nitrophenyl)ethylamino)-7-(O—((N-Boc)piperidin-4-ylmethoxy))quinazoline (64) (68 mg, 132 μmol, 93%)

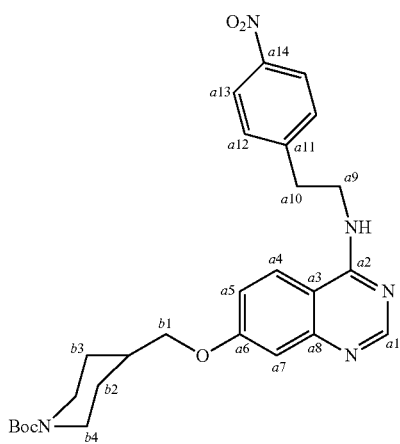 [SMILES: CC(C)(C)OC(=O)N1CCC(COc2ccc3c(NCCc4ccc([N+](=O)[O-])cc4)ncnc3c2)CC1]

$^1$H NMR (500 MHz; DMSO) δ 8.41 (s, 1H, Ha1), 8.20 (brt, J=5.6 Hz, 1H, HNH), 8.18-8.14 (m, 2H, Ha13), 8.12 (d, J=9.2 Hz, 1H, Ha4), 7.56-7.52 (m, 2H, Ha12), 7.11 (dd, J=2.5, 9.0 Hz, 1H, Ha5), 7.06 (d, J=2.5 Hz, 1H, Ha7), 4.06-3.96 (m, 2H, Hb4eq), 3.98 (d, J=6.3 Hz, 2H, Hb1), 3.74-3.67 (m, 2H, Ha9), 2.94-2.88 (m, 2H, Ha10), 2.88-2.72 (m, 2H, Hb4ax), 2.85 (q, J=6.69 Hz, 1H, Ha15) 2.02-1.94 (m, 1H, Hb2), 1.81-1.75 (m, 2H, Hb3eq), 1.41 (s, 9H, HBoc), 1.27-1.13 (m, 2H, Hb3ax).

$^{13}$C NMR (125 MHz; DMSO) δ 162.1 (Ca6), 159.4 (Ca2), 156.1 (Ca1), 154.3 (CBoc), 151.8 (Ca8), 146.5 (Ca11), 137.4 (Ca14), 130.6 (Ca12), 124.7 (Ca4), 123.8 (Ca13), 117.2 (Ca5), 109.6 (Ca3), 107.9 (Ca7), 78.9 (CBoc), 72.3 (Cb1), 43.2 (Cb4), 42.5 (Ca9), 35.6 (Cb2), 34.7 (Ca10), 28.8 (Cb3), 28.6 (CBoc).

HRMS-ESI (m/z) calculated: 508.2559 [M+H]$^+$. found: 508.2565.

4-(2-(4-isopropylphenyl)ethylamino)-7-(O—((N-Boc)piperidin-4-ylmethoxy))quinazoline (65) (44 mg, 87 μmol, 62%)

$^1$H NMR (500 MHz; DMSO) δ 8.41 (s, 1H, Ha1), 8.20 (brt, J=5.6 Hz, 1H, HNH), 8.10 (d, J=9.1 Hz, 1H, Ha4), 7.22-7.14 (m, 4H, Ha12, Ha13), 7.11 (dd, J=2.6, 9.1 Hz, 1H, Ha5), 7.06 (d, J=2.6 Hz, 1H, Ha7), 4.0-3.96 (m, 2H, Hb4eq), 3.98 (d, J=6.4 Hz, 2H, Hb1), 3.80 (q, J=5.9 Hz, 2H, Ha9), 3.11 (brt, J=7.2 Hz, 2H, Ha10), 2.85-2.67 (m, 2H, Hb4ax), 2.03-1.91 (m, 1H, Hb2), 1.81-1.73 (m, 2H, Hb3eq), 1.41 (s, 9H, HBoc), 1.26-1.13 (m, 8H, Hb3ax et Ha16).

$^{13}$C NMR (125 MHz; DMSO) δ 162.1 (Ca6), 159.4 (Ca2), 156.1 (Ca1), 154.3 (CBoc), 151.7 (Ca8), 146.5 (Ca14), 137.3 (Ca11), 129.6 (Ca12), 129 (Ca13), 124.7 (Ca4), 117.3 (Ca5), 109.5 (Ca3), 107.9 (Ca7), 78.9 (CBoc), 72.3 (Cb1), 43.2 (Cb4), 42.2 (Ca9), 35.6 (Cb2), 34.8 (Ca10), 33.5 (Ca15), 28.8 (Cb3), 28.6 (CBoc), 24.4 (Ca16).

HRMS-ESI (m/z) calculated: 505.3178 [M+H]$^+$. found: 505.3182.

4-(2-(4-methoxyphenyl)ethylamino)-7-(O—((N-Boc)piperidin-4-ylmethoxy))quinazoline (66) (49 mg, 101 μmol, 71%)

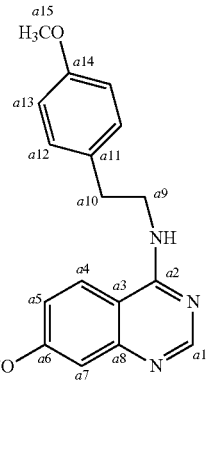

$^1$H NMR (500 MHz; DMSO) δ 8.42 (s, 1H, Ha1), 8.16 (brt, J=5.7 Hz, 1H, HNH), 8.10 (d, J=9.2 Hz, 1H, Ha4), 7.20-7.15 (m, 2H, Ha12), 6.88-6.83 (m, 2H, Ha13), 7.11 (dd, J=2.6, 9.1 Hz, 1H, Ha5), 7.06 (d, J=2.5 Hz, 1H, Ha7), 4.06-3.94 (m, 2H, Hb4eq), 3.99 (d, J=6.3 Hz, 2H, Hb1), 3.72 (s, 3H, Ha15), 3.71-3.64 (m, 2H, Ha9), 2.88 (brt, J=7.1 Hz, 2H, Ha10), 2.84-2.67 (m, 2H, Hb4ax), 2.04-1.93 (m, 1H, Hb2), 1.83-1.74 (m, 2H, Hb3eq), 1.41 (s, 9H, HBoc), 1.26-1.12 (m, 2H, Hb3ax).

$^{13}$C NMR (125 MHz; DMSO) δ 162.1 (Ca6), 159.4 (Ca2), 158.1 (Ca14), 156.1 (Ca1), 154.3 (CBoc), 151.8 (Ca8), 144.3 (Ca11), 130.2 (Ca12), 124.6 (Ca4), 117.2 (Ca5), 114.2 (Ca13), 109.6 (Ca3), 107.9 (Ca7), 78.9 (CBoc), 72.3 (Cb1), 55.4 (Ca15), 43.4 (Cb4), 42.7 (Ca9), 35.6 (Cb2), 34.2 (Ca10), 28.7 (Cb3), 28.6 (CBoc).

HRMS-ESI (m/z) calculated: 493.2814 [M+H]$^+$. found: 493.2825.

4-(2-(4-aminophenyl)ethylamino)-7-(O—((N-Boc)piperidin-4-ylmethoxy))quinazoline (67) (67 mg, 0.14 mmol, Quantitative)

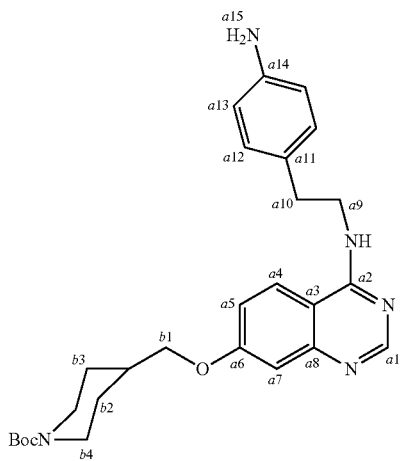 [SMILES: COc1ccc(CCNc2ncnc3cc(OCC4CCN(C(=O)OC(C)(C)C)CC4)ccc23)cc1]

$^1$H NMR (500 MHz; DMSO) δ 8.40 (s, 1H, Ha1), 8.14 (brt, J=5.5 Hz, 1H, HNH), 8.12 (d, J=9.3 Hz, 1H, Ha4), 7.10 (dd, J=2.6, 9.6 Hz, 1H, Ha5), 7.05 (d, J=2.5 Hz, 1H, Ha7), 6.93-6.88 (m, 2H, Ha12), 6.52-6.47 (m, 2H, Ha13) 4.85 (s, 2H, Ha15), 4.06-3.92 (m, 2H, Hb4eq), 3.99 (d, J=6.5 Hz, 2H, Hb1), 3.67-3.57 (m, 2H, Ha9), 2.75 (brt, J=7.5 Hz, 2H, Ha10), 2.84-2.68 (m, 2H, Hb4ax), 2.03-1.92 (m, 1H, Hb2), 1.82-1.73 (m, 2H, Hb3eq), 1.41 (s, 9H, HBoc), 1.26-1.14 (m, 2H, Hb3ax).

$^{13}$C NMR (125 MHz; DMSO) δ 162 (Ca6), 159.4 (Ca2), 156.1 (Ca1), 154.3 (CBoc), 151.8 (Ca8), 147.2 (Ca14), 129.6 (Ca12), 129.3 (Ca11), 114.4 (Ca13), 124.7 (Ca4), 117.1 (Ca5), 109.6 (Ca3), 107.9 (Ca7), 78.9 (CBoc), 72.3 (Cb1), 43.1 (Cb4), 42.9 (Ca9), 35.6 (Cb2), 34.4 (Ca10), 28.7 (Cb3), 28.6 (CBoc).

HRMS-ESI (m/z) calculated: 478.2818 [M+H]$^+$. found: 478.2831.

4-(2-(quinolinylamino)ethylamino)-7-(O—((N-Boc)piperidin-4-ylmethoxy))quinazoline (68) (52 mg, 98 μmol, 70%)

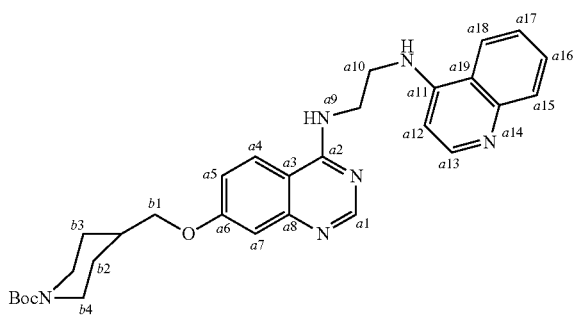

$^1$H NMR (500 MHz; DMSO) δ 8.50 (s, 1H, Ha1), 8.42 (d, J=5.3 Hz, 1H, Ha13), 8.16 (dd, J=0.7, 8.2 Hz, 1H, Ha18), 8.10 (d, J=9.2 Hz, 1H, Ha4), 7.79 (dd, J=0.9, 8.5 Hz, 1H, Ha15), 7.61 (ddd, J=0.9, 6.9, 9.3 Hz, 1H, Ha16), 7.45-7.38 (m, 2H, Ha17 and HNH), 7.14 (dd, J=2.5, 9.2 Hz, 1H, Ha5), 7.09 (d, J=2.6 Hz, 1H, Ha7), 6.69 (d, J=5.5 Hz, 1H, Ha12), 4.01-3.94 (m, 4H, Hb1 and Hb4eq), 3.81 (q, J=6.3 Hz, 2H, Ha9), 3.58 (q, J=6.2 Hz, 2H, Ha10), 2.03-1.93 (m, 1H, Hb2), 1.83-1.73 (m, 2H, Hb3eq), 1.41 (s, 9H, HBoc), 1.26-1.15 (m, 2H, Hb3ax).

$^{13}$C NMR (125 MHz; DMSO) δ 162.2 (Ca6), 159.7 (Ca2), 156.0 (Ca1), 154.3 (CBoc), 151.8 (Ca8), 151.2 (Ca13), 150.3 (Ca11), 148.9 (Ca14), 129.5 (Ca15), 129.1 (Ca16), 124.7 (Ca4), 124.4 (Ca17), 121.9 (Ca18), 119.3 (Ca19), 117.4 (Ca5), 109.6 (Ca3), 108.0 (Ca7), 80.0 (CBoc), 72.4 (Cb1), 42.1 (Ca10), 39.3 (Ca9), 35.6 (Cb2), 28.7 (Cb3), 28.6 (CBoc).

HRMS-ESI (m/z) calculated: 529.2922 [M+H]$^+$. found: 529.2928.

4-(2-(naphtylamino)ethylamino)-7-(O—((N-Boc) piperidin-4-ylmethoxy))quinazoline (69) (59 mg, 112 μmol, 79%)

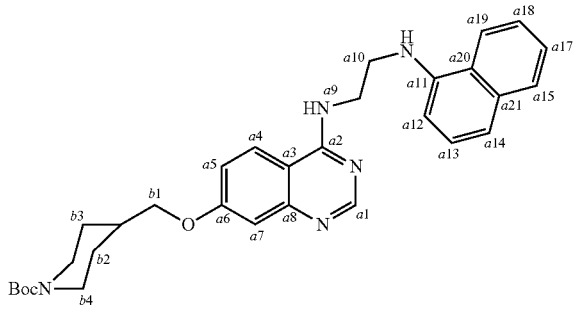 [SMILES: CC(C)(C)OC(=O)N1CCC(COc2ccc3c(NCCNc4ccnc5ccccc45)ncnc3c2)CC1]

$^1$H NMR (500 MHz; DMSO) δ 8.51 (s, 1H, Ha1), 8.42 (brt, J=5.1 Hz, 1H, HNH), 8.14 (d, J=9.2 Hz, 1H, Ha19), 8.09 (d, J=7.8 Hz, 1H, Ha4), 7.76 (dd, J=1.8, 6.9 Hz, 1H, Ha15), 7.46-7.35 (m, 2H, Ha17 and Ha18), 7.31 (t, J=7.9 Hz, 1H, Ha13), 7.15 (dd, J=2.5, 9.1 Hz, 1H, Ha5), 7.11 (d, J=8.1 Hz, 1H, Ha14), 7.08 (d, J=2.6 Hz, 1H, Ha7), 6.71 (d, J=7.5 Hz, 1H, Ha12), 6.45 (brt, J=5.1 Hz, HNH), 4.05-3.91 (m, 4H, Hb1 and Hb4eq), 3.85 (q, J=6.3 Hz, 2H, Ha9), 3.51 (brt, J=6.1 Hz, 2H, Ha10), 2.87-2.67 (m, 2H, Hb4ax), 1.98-1.92 (m, 1H, Hb2), 1.81-1.72 (m, 2H, Hb3eq), 1.25-1.15 (m, 2H, Hb3ax).

$^{13}$C NMR (125 MHz; DMSO) δ 162.2 (Ca6), 159.8 (Ca2), 155.9 (Ca1), 154.3 (Ca8), 151.5 (Ca11), 144.3 (Ca11), 134.5 (Ca21), 128.4 (Ca15), 127.6 (Ca13), 126.1 (Ca17), 124.8 (Ca19), 124.7 (Ca4), 124.5 (Ca18), 123.3 (Ca20), 121.8 (Ca4), 117.4 (Ca5), 115.8 (Ca14), 109.5 (Ca3), 107.8 (Ca7), 103.3 (Ca12), 79.0 (CBoc), 72.1 (Cb1), 46.2 (Cb4), 43.2 (Ca10), 39.4 (Ca9), 35.6 (Cb2), 28.7 (Cb3), 28.6 (CBoc).

HRMS-ESI (m/z) calculated: 528.2969 [M+H]$^+$. found: 528.3002.

4-(2-(phenylamino)ethylamino)-7-(O—((N-Boc) piperidin-4-ylmethoxy))quinazoline (70) (50 mg, 105 μmol, 75%)

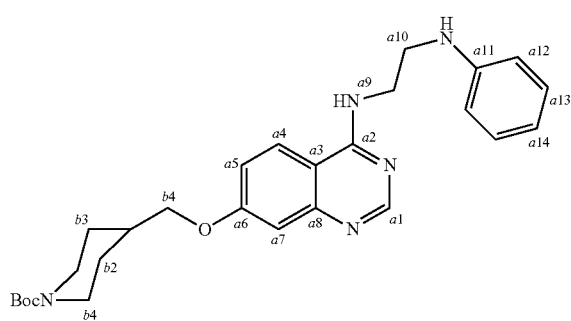 [SMILES: CC(C)(C)OC(=O)N1CCC(COc2ccc3c(NCCNc4ccccc4)ncnc3c2)CC1]

$^1$H NMR (500 MHz; DMSO) δ 8.42 (s, 1H, Ha1), 8.21 (brt, J=5.6 Hz, 1H, HNH), 8.09 (d, J=9.0 Hz, 1H, Ha4), 7.15 (dd, J=2.7, 9.1 Hz, 1H, Ha5), 7.11-7.05 (m, 3H, Ha7 and Ha13), 6.64 (dd, J=0.9, 8.6 Hz, 2H, Ha12), 6.53 (dt, J=0.9, 7.3 Hz, 2H, Ha14), 5.78 (brt, J=5.9 Hz, HNH), 4.06-3.91 (m, 4H, Hb1 and Hb4eq), 3.67 (q, J=6.5 Hz, 2H, Ha9), 3.30 (brt, J=6.51 Hz, 2H, Ha10), 2.85-2.67 (m, 2H, Hb4ax), 2.03-1.93 (m, 1H, Hb2), 1.82-1.75 (m, 2H, Hb3eq), 1.41 (s, 9H, HBoc), 1.26-1.15 (m, 2H, Hb3ax).

$^{13}$C NMR (125 MHz; DMSO) δ 162.1 (Ca6), 159.6 (Ca2), 156.0 (Ca1), 154.3 (CBoc), 151.8 (Ca8), 149.1 (Ca11), 129.4 (Ca13), 124.7 (Ca4), 117.3 (Ca5), 116.0 (Ca14), 112.4 (Ca12), 109.6 (Ca3), 108.0 (Ca7), 79.0 (CBoc), 72.3 (Cb1), 42.3 (Ca10), 40.2 (Ca9), 35.6 (Cb2), 28.7 (Cb3), 28.56 (CBoc).

HRMS-ESI (m/z) calculated: 478.2813 [M+H]$^+$. found: 478.2819.

4-((N-(1-benzylpiperidin-4-yl))amino)-7-(O—((N-Boc) piperidin-4-ylmethoxy))quinazoline (71) (60 mg, 113 μmol, 81%)

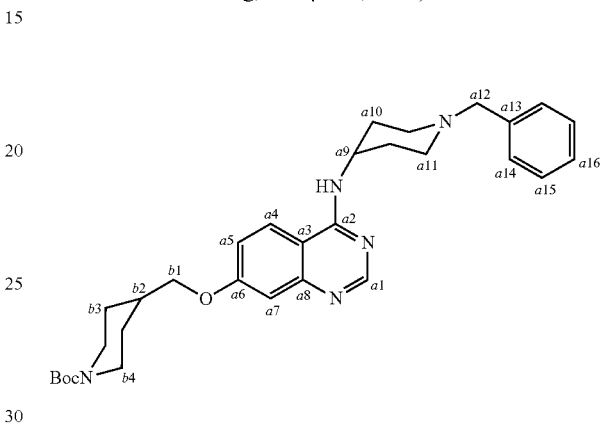

$^1$H NMR (500 MHz; DMSO) δ 8.36 (s, 1H, Ha1), 8.28 (brs, 1H, HNH), 8.21 (d, J=9.2 Hz, 1H, Ha4), 7.73 (d, J=7.6 Hz, 1H, Ha7), 7.37-7.22 (m, 5H, Ha14, Ha15 and Ha16), 7.10 (dd, J=2.6, 9.0 Hz, 1H, Ha5), 7.04 (d, J=2.7 Hz, 1H, Ha7), 4.16-4.10 (m, 1H, Ha9), 4.06-3.86 (m, 3H, Hb1 and Hb4eq), 3.49 (s, 2H, Ha12), 2.86 (brd, J=11.8 Hz, 2H, Ha11eq), 2.81-2.67 (m, 2H, Hb4ax), 2.06 (dd, J=1.7, 11.8 Hz, 2H, Ha11ax), 2.02-1.92 (m, 1H, Hb2), 1.90 (brd, J=12.4 Hz, 2H, Ha10eq), 1.78 (brd, J=13.4 Hz, 2H, Hb3eq), 1.64 (dd, J=3.6, 12.4 Hz, 2H, Ha10ax), 1.41 (s, 9H, HBoc), 1.19 (dd, J=4.6, 13.4 Hz, 2H, Hb3ax)

$^{13}$C NMR (125 MHz; DMSO) δ 162.1 (Ca6), 158.8 (Ca2), 156.0 (Ca1), 154.3 (CBoc), 151.9 (Ca8), 139.2 (Ca13), 129.1 (Ca14), 128.6 (Ca15), 127.3 (Ca15), 124.97 (Ca4), 117.4 (Ca5), 109.5 (Ca3), 107.9 (Ca7), 78.9 (CBoc), 72.3 (Cb1), 62.6 (Ca12), 52.8 (Ca11), 48.2 (Ca9), 35.7 (Cb2), 31.7 (Ca10), 28.7 (Cb3), 28.5 (CBoc).

HRMS-ESI (m/z) calculated: 532.3282 [M+H]$^+$. found: 532.3296.

Compounds 72 to 83 were synthesized following the general procedure below from compounds 60 to 71 respectively.

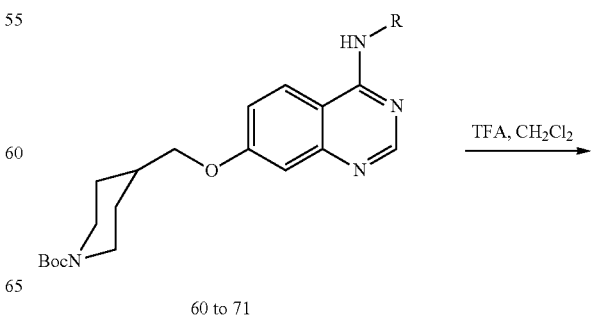

60 to 71

-continued

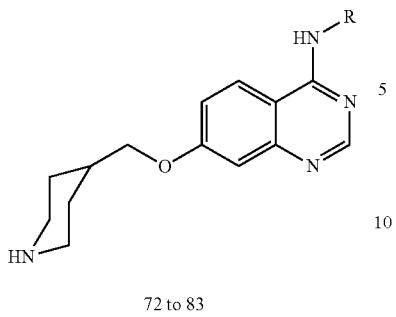

72 to 83

A mixture of the desired compound 60 to 71 in TFA was stirred for 1 h at room temperature. TFA was removed. The residue was diluted with dichloromethane and the organic phase was washed with saturated $Na_2CO_3$. The solvent was removed and gave respectively compound 72 to 83.

4-(2-(3-chlorophenyl)ethylamino)-7-O-(piperidin-4-ylmethoxy)quinazoline (72) (56 mg, 0.14 mmol, Quantitative) from 60 (0.14 mmol)

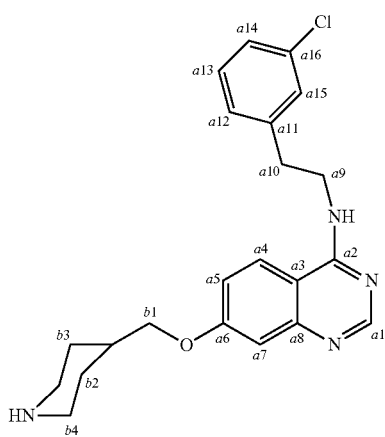 [SMILES: Clc1cccc(CCNc2ncnc3cc(OCC4CCNCC4)ccc23)c1]

$^1$H NMR (500 MHz; DMSO) δ 8.41 (s, 1H, Ha1), 8.21 (brt, J=5.3 Hz, 1H, HNH), 8.12 (d, J=9.1 Hz, 1H, Ha4), 7.35-7.20 (m, 4H, Ha12, Ha13 et Ha14), 7.11 (dd, J=2.6, 9.0 Hz, 1H, Ha5), 7.07 (d, J=2.54 Hz, 1H, Ha7), 3.96 (d, J=6.4 Hz, 2H, Hb1), 3.77-3.71 (m, 2H, Ha9), 3.11-3.06 (m, 2H, Hb4eq) 2.97 (brt, J=7.1 Hz, 2H, Ha10), 2.68-2.60 (m, 2H, Hb4ax), 2.00-1.89 (m, 1H, Hb2), 1.83-1.74 (m, 2H, Hb3eq), 1.30 (dq, J=2.9, 12.2 Hz, 2H, Hb3ax).

$^{13}$C NMR (125 MHz; DMSO) δ 162.1 (Ca6), 159.4 (Ca2), 156.1 (Ca1), 151.8 (Ca8), 142.7 (Ca11), 133.3 (Ca16), 130.6 (Ca15), 129.0 (Ca13), 127.9 (Ca12), 126.6 (Ca14) 124.7 (Ca4), 117.2 (Ca5), 109.6 (Ca3), 108 (Ca7), 72.7 (Cb1), 45.1 (Cb4), 42 (Ca9), 34.9 (Cb2), 34.5 (Ca10), 28.5 (cb3).

HRMS-ESI (m/z) calculated: 397.1795 [M+H]$^+$. found: 397.1799.

4-(2-(2-chlorophenyl)ethylamino)-7-O-(piperidin-4-ylmethoxy)quinazoline (73) (52 mg, 0.13 mmol, 93%) from 61 (0.11 mmol)

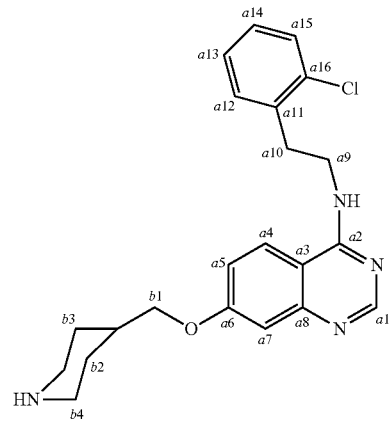 [SMILES: Clc1ccccc1CCNc1ncnc2cc(OCC3CCNCC3)ccc12]

$^1$H NMR (500 MHz; DMSO) δ 8.41 (s, 1H, Ha1), 8.19 (brt, J=5.6 Hz, 1H, HNH), 8.11 (d, J=9.1 Hz, 1H, Ha4), 7.37-7.22 (m, 4H, Ha12, Ha13 et Ha14), 7.10 (dd, J=2.7, 9.9 Hz, 1H, Ha5), 7.06 (d, J=2.5 Hz, 1H, Ha7), 3.95 (d, J=6.4 Hz, 2H, Hb1), 3.75-3.69 (m, 2H, Ha9), 3.07-3.01 (m, 2H, Hb4eq) 2.95 (brt, J=7.2 Hz, 2H, Ha10), 2.62-2.54 (m, 2H, Hb4ax), 1.97-1.87 (m, 1H, Hb2), 1.82-1.72 (m, 2H, Hb3eq), 1.32-1.20 (m, 2H, Hb3ax).

$^{13}$C NMR (125 MHz; DMSO) δ 162.1 (Ca6), 159.4 (Ca2), 156.1 (Ca1), 151.8 (Ca8), 139.1 (Ca11), 131.1 (Ca16), 131 (Ca15), 128.7 (Ca13), 128.7 (Ca14), 126.6 (Ca12) 126.6 (Ca4), 117.2 (Ca5), 109.5 (Ca3), 107.9 (Ca7), 72.9 (Cb1), 45.5 (Cb4), 42.2 (Ca9), 34.6 (Cb2), 34.3 (Ca10), 29.1 (cb3).

HRMS-ESI (m/z) calculated: 397.1795 [M+H]$^+$. found: 397.1791.

4-(2-(4-chlorophenyl)ethylamino)-7-O-(piperidin-4-ylmethoxy)quinazoline (74) (50 mg, 0.13 mmol, 93%) from 62 (0.14 mmol)

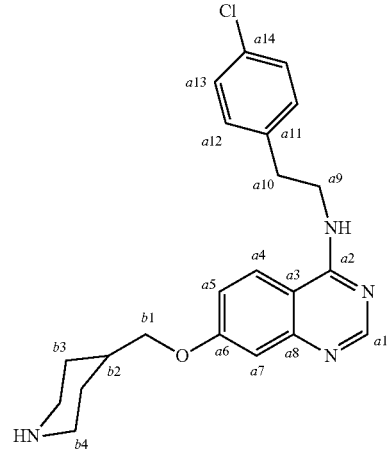 [SMILES: Clc1ccc(CCNc2ncnc3cc(OCC4CCNCC4)ccc23)cc1]

$^1$H NMR (500 MHz; DMSO) δ 8.41 (s, 1H, Ha1), 8.23 (m, 1H, HNH), 8.11 (d, J=9.12 Hz, 1H, Ha4), 7.37-7.22 (m,

4H, Ha12, Ha13 et Ha14), 7.13-7.08 (m, 1H, Ha5), 7.08-7.03 (m, 1H, Ha7), 3.95 (d, J=5.95 Hz, 2H, Hb1), 3.75-3.69 (m, 2H, Ha9), 3.07-3.01 (m, 2H, Hb4eq) 2.95 (brt, J=7.20 Hz, 2H, Ha10), 2.62-2.54 (m, 2H, Hb4ax), 1.97-1.87 (m, 1H, Hb2), 1.82-1.72 (m, 2H, Hb3eq), 1.32-1.20 (m, 2H, Hb3ax).

$^{13}$C NMR (125 MHz; DMSO) δ 162.1 (Ca6), 159.4 (Ca2), 156.1 (Ca1), 151.8 (Ca8), 139.1 (Ca11), 131.1 (Ca16), 131 (Ca15), 128.7 (Ca13), 128.7 (Ca14), 126.6 (Ca12) 126.6 (Ca4), 117.2 (Ca5), 109.5 (Ca3), 107.9 (Ca7), 72.9 (Cb1), 45.5 (Cb4), 42.2 (Ca9), 34.6 (Cb2), 34.3 (Ca10), 29.1 (cb3)

HRMS-ESI (m/z) calculated: 397.1795 [M+H]$^+$. found: 397.1794.

4-(2-(4-sulfonamidophenyl)ethylamino)-7-O-(piperidin-4-ylmethoxy)quinazoline (75) (33 mg, 75 µmol, 77%) from 63 (98 µmol)

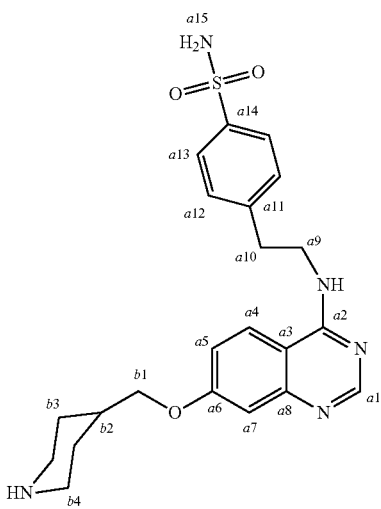 [SMILES: NS(=O)(=O)c1ccc(CCNc2ncnc3cc(OCC4CCNCC4)ccc23)cc1]

$^1$H NMR (500 MHz; DMSO) δ 8.42 (s, 1H, Ha1), 8.21 (brt, J=5.45 Hz, 1H, HNH), 8.10 (d, J=9.11 Hz, 1H, Ha4), 7.77-7.72 (m, 2H, Ha13), 7.47-7.42 (m, 2H, Ha12), 7.37-7.21 (brs, 2H, Ha15), 7.11 (dd, J=2.38, 9.03 Hz, 1H, Ha5), 7.05 (d, J=2.55 Hz, 1H, Ha7), 3.94 (d, J=6.47 Hz, 2H, Hb1), 3.79-3.72 (m, 2H, Ha9), 3.04 (brt, J=7.15 Hz, 2H, Ha10), 2.99-2.92 (m, 2H, Hb4eq), 2.63-2.52 (m, 2H, Hb4ax), 1.93-1.79 (m, 1H, Hb2), 1.76-1.66 (m, 2H, Hb3eq), 1.26-1.12 (m, 2H, Hb3ax).

$^{13}$C NMR (125 MHz; DMSO) δ 162.1 (Ca6), 159.4 (Ca2), 156.1 (Ca1), 151.8 (Ca8), 144.3 (Ca11), 142.6 (Ca14), 129.6 (Ca12), 126.2 (Ca13), 124.6 (Ca4), 117.3 (Ca5), 109.6 (Ca3), 107.9 (Ca7), 72.3 (Cb1), 43.2 (Cb4), 42 (Ca9), 35.6 (Cb2), 34.7 (Ca10), 28.7 (Cb3).

HRMS-ESI (m/z) calculated: 397.1795 [M+H]$^+$. found: 397.1794.

4-(2-(4-nitrophenyl)ethylamino)-7-O-(piperidin-4-ylmethoxy)quinazoline (76) (51 mg, 132 µmol, Quantitative) from 64 (132 µmol)

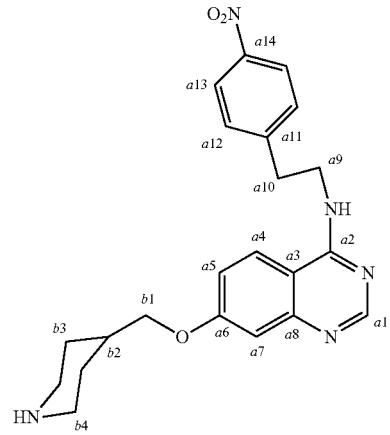 [SMILES: O=[N+]([O-])c1ccc(CCNc2ncnc3cc(OCC4CCNCC4)ccc23)cc1]

$^1$H NMR (500 MHz; DMSO) δ 8.41 (s, 1H, Ha1), 8.19 (brt, J=5.40 Hz, 1H, HNH), 8.18-8.14 (m, 2H, Ha13), 8.08 (d, J=9.18 Hz, 1H, Ha4), 7.57-7.52 (m, 2H, Ha12), 7.11 (dd, J=2.56, 9.09 Hz, 1H, Ha5), 7.06 (d, J=2.56 Hz, 1H, Ha7), 3.94 (d, J=6.44 Hz, 2H, Hb1), 3.83-3.76 (m, 2H, Ha9), 3.11 (brt, J=7.20 Hz, 2H, Ha10), 3.03-2.97 (m, 2H, Hb4eq), 2.61-2.53 (m, 2H, Hb4ax), 1.94-1.83 (m, 1H, Hb2), 1.77-1.69 (m, 2H, Hb3eq), 1.26-1.16 (m, 2H, Hb3ax).

$^{13}$C NMR (125 MHz; DMSO) δ 162.1 (Ca6), 159.4 (Ca2), 156.1 (Ca1), 151.8 (Ca8), 146.5 (Ca11), 137.4 (Ca14), 130.6 (Ca12), 124.7 (Ca4), 123.8 (Ca13), 117.2 (Ca5), 109.6 (Ca3), 107.9 (Ca7), 72.3 (Cb1), 43.2 (Cb4), 42.5 (Ca9), 35.6 (Cb2), 34.7 (Ca10), 28.8 (Cb3).

HRMS-ESI (m/z) calculated: 408.2035 [M+H]$^+$. found: 408.2024.

4-(2-(4-isopropylphenyl)ethylamino)-7-O-(piperidin-4-ylmethoxy)quinazoline (77) (34 mg, 80 µmol, 92%) from 65 (87 µmol)

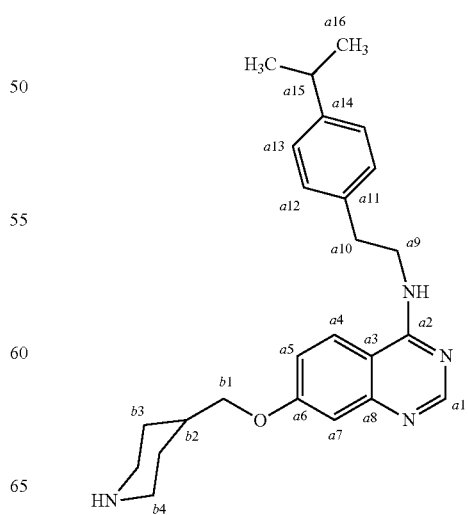

¹H NMR (500 MHz; DMSO) δ 8.41 (s, 1H, Ha1), 8.20 (brt, J=5.67 Hz, 1H, HNH), 8.12 (d, J=9.17 Hz, 1H, Ha4), 7.20-7.13 (m, 4H, Ha12, Ha13), 7.11 (dd, J=2.59, 9.03 Hz, 1H, Ha5), 7.06 (d, J=2.73, 1H, Ha7), 3.95 (d, J=6.39 Hz, 2H, Hb1), 3.73-3.66 (m, 2H, Ha9), 3.05-2.97 (m, 2H, Hb4eq), 2.91 (brt, J=7.21 Hz, 2H, Ha10), 2.58-2.53 (m, 2H, Hb4ax), 1.95-1.84 (m, 1H, Hb2), 1.78-1.70 (m, 2H, Hb3eq), 1.29-1.10 (m, 8H, Hb3ax et Ha16).

¹³C NMR (125 MHz; DMSO) δ 162.1 (Ca6), 159.4 (Ca2), 156.1 (Ca1), 151.7 (Ca8), 146.5 (Ca14), 137.3 (Ca11), 129.6 (Ca12), 129 (Ca13), 124.7 (Ca4), 117.3 (Ca5), 109.5 (Ca3), 107.9 (Ca7), 72.3 (Cb1), 43.2 (Cb4), 42.2 (Ca9), 35.6 (Cb2), 34.8 (Ca10), 33.5 (Ca15), 28.8 (Cb3), 24.4 (Ca16).

HRMS-ESI (m/z) calculated: 405.2654 [M+H]⁺. found: 405.2659.

4-(2-(4-aminophenyl)ethylamino)-7-O-(piperidin-4-ylmethoxy)quinazoline (78) (39.0 mg, 101 μmol, Quantitative) from 66 (101 μmol)

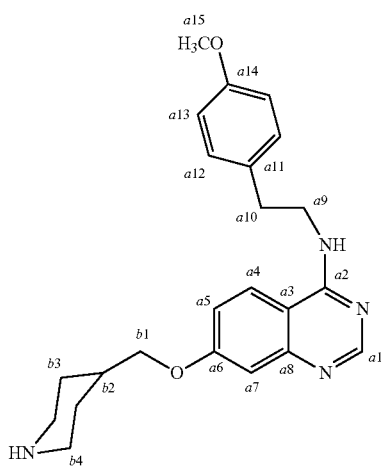 [SMILES: COc1ccc(CCNc2ncnc3cc(OCC4CCNCC4)ccc23)cc1]

¹H NMR (500 MHz; DMSO) δ 8.41 (s, 1H, Ha1), 8.16 (brt, J=5.40 Hz, 1H, HNH), 8.11 (d, J=9.20 Hz, 1H, Ha4), 7.20-7.15 (m, 2H, Ha12), 7.11 (dd, J=2.58, 9.12 Hz, 1H, Ha5), 7.05 (d, J=2.58, 1H, Ha7), 6.88-6.83 (m, 2H, Ha13), 3.94 (d, J=6.38 Hz, 2H, Hb1), 3.72 (s, 3H, Ha15) 3.71-3.65 (m, 2H, Ha9), 3.01-2.92 (m, 2H, Hb4eq), 2.88 (brt, J=7.30 Hz, 2H, Ha10), 2.57-2.52 (m, 2H, Hb4ax), 1.92-1.82 (m, 1H, Hb2), 1.76-1.68 (m, 2H, Hb3eq), 1.26-1.14 (m, 2H, Hb3ax).

¹³C NMR (125 MHz; DMSO) δ 162.1 (Ca6), 159.4 (Ca2), 158.1 (Ca14), 156.1 (Ca1), 151.8 (Ca8), 144.3 (Ca11), 130.2 (Ca12), 124.6 (Ca4), 117.2 (Ca5), 114.2 (Ca13), 109.6 (Ca3), 107.9 (Ca7), 72.3 (Cb1), 55.4 (Ca15), 42.7 (Ca9), 35.6 (Cb2), 34.2 (Ca10), 28.7 (Cb3).

HRMS-ESI (m/z) calculated: 393.2290 [M+H]⁺. found: 393.2297.

4-(2-(4-aminophenyl)ethylamino)-7-O-(piperidin-4-ylmethoxy)quinazoline (79) (34 mg, 90 mmol, 64%) from 67 (0.14 mmol)

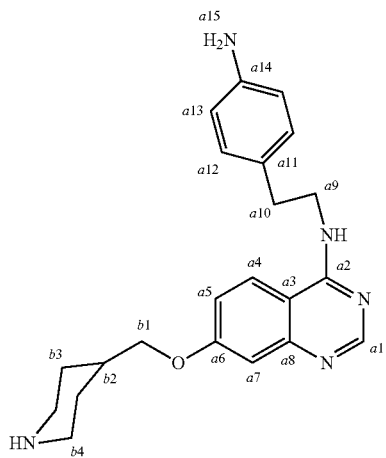 [SMILES: Nc1ccc(CCNc2ncnc3cc(OCC4CCNCC4)ccc23)cc1]

¹H NMR (500 MHz; DMSO) δ 8.40 (s, 1H, Ha1), 8.13 (brt, J=5.75 Hz, 1H, HNH), 8.11 (d, J=9.58 Hz, 1H, Ha4), 7.11 (dd, J=2.49, 9.10 Hz, 1H, Ha5), 7.04 (d, J=2.63, 1H, Ha7), 6.94-6.86 (m, 2H, Ha12), 6.52-6.46 (m, 2H, Ha13), 4.85 (s, 2H, Ha15), 3.94 (d, J=6.31 Hz, 2H, Hb1), 3.66-3.59 (m, 2H, Ha9), 3.02-2.94 (m, 2H, Hb4eq), 2.76 (brt, J=7.34 Hz, 2H, Ha10), 2.58-2.52 (m, 2H, Hb4ax), 1.94-1.83 (m, 1H, Hb2), 1.76-1.68 (m, 2H, Hb3eq), 1.26-1.15 (m, 2H, Hb3ax).

¹³C NMR (125 MHz; DMSO) δ 162 (Ca6), 159.4 (Ca2), 156.1 (Ca1), 151.8 (Ca8), 147.2 (Ca14), 129.6 (Ca12), 129.3 (Ca11), 114.4 (Ca13), 124.7 (Ca4), 117.1 (Ca5), 109.6 (Ca3), 107.9 (Ca7), 72.3 (Cb1), 43.1 (Cb4), 42.9 (Ca9), 35.6 (Cb2), 34.4 (Ca10), 28.7 (Cb3).

HRMS-ESI (m/z) calculated: 378.2293 [M+H]⁺. found: 378.2285.

4-(2-(phenylamino)ethylamino)-7-O-(piperidin-4-ylmethoxy)quinazoline (80) (3.2 mg, 5.3 μmol, 23%) from 68 (10 mg, 23.3 μmol)

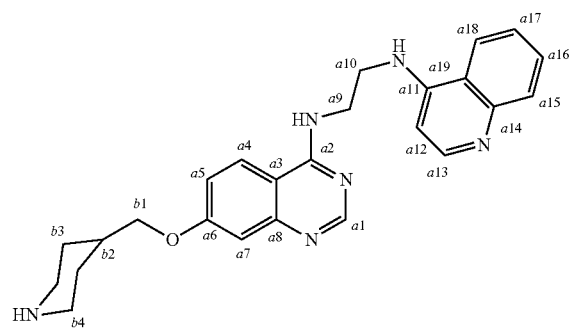 [SMILES: c1ccc2c(NCCNc3ncnc4cc(OCC5CCNCC5)ccc34)ccnc2c1]

¹H NMR (500 MHz; DMSO) δ 8.49 (s, 1H, Ha1), 8.43 (brt, J=5.7 Hz, 1H, HNH), 8.42 (d, J=5.3 Hz, 1H, Ha13), 8.17 (d, J=6.2 Hz, 1H, Ha18), 8.12 (d, J=9.2 Hz, 1H, Ha4), 7.78 (d, J=8.3 Hz, 1H, Ha15), 7.60 (t, J=7.2 Hz, 1H, Hc10), 7.42 (t, J=7.4 Hz, 1H, Ha17), 7.13 (dd, J=2.5, 9.0 Hz, 1H, Ha5), 7.09 (d, J=2.5 Hz, 1H, Ha7), 6.82 (brt, J=5.1 Hz, 1H, HNH), 6.70 (d, J=5.4 Hz, 1H, Ha12), 3.99 (d, J=5.7 Hz, 2H, Hb1), 3.82 (q, J=6.1 Hz, 2H, Ha9), 3.58 (q, J=6.2 Hz, 2H, Ha10), 3.00 (brd, 2H, Hb4eq), 2.06 (t, J=10.5 Hz, 2H, Hb4ax), 1.865-1.74 (m, 3H, Hb3eq and Hb2), 1.443-1.32 (m, 2H, Hb3ax).

$^{13}$C NMR (125 MHz; DMSO) δ 162.3 (Ca6), 159.8 (Ca2), 156.0 (Ca1), 151.8 (Ca8), 151.2 (Ca13), 150.3 (Ca11), 148.7 (Ca14), 129.5 (Ca15), 129.2 (Ca16), 124.7 (Ca4), 124.4 (Ca17), 127.3 (Ca13), 122.0 (Ca18), 121.8 (Ca4), 119.3 (Ca19), 117.5 (Ca5), 109.5 (Ca3), 108.0 (Ca7), 98.5 (Ca12), 72.7 (Cb1), 53.5 (Cb4), 42.1 (Ca10), 39.3 (Ca9), 35.7 (Cb2), 29.0 (Cb3).

HRMS-ESI (m/z) calculated: 429.2393 [M+H]$^+$. found: 429.2394.

4-(2-(naphtylamino)ethylamino)-7-O-(piperidin-4-ylmethoxy)quinazoline (81) (47 mg, 110 μmol, 91%) from 69 (121 μmol)

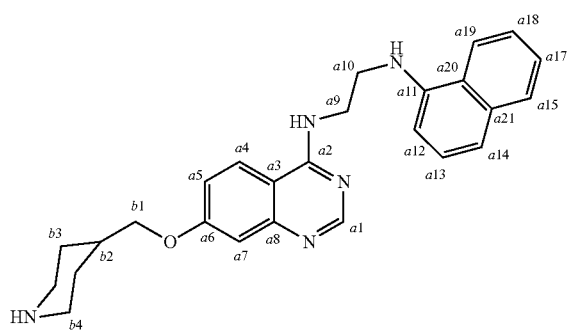 [SMILES: c1ccc2c(NCCNc3ncnc4cc(OCC5CCNCC5)ccc34)cccc2c1]

$^1$H NMR (500 MHz; DMSO) δ 8.50 (s, 1H, Ha1), 8.38 (brt, J=5.05 Hz, 1H, HNH), 8.12 (d, J=9.16 Hz, 1H, Ha19), 8.11 (d, J=7.6 Hz, 1H, Ha4), 7.76 (dd, J=1.6, 7.1 Hz, 1H, Ha15), 7.47-7.38 (m, 2H, Ha17 and Ha18), 7.31 (t, J=7.9 Hz, 1H, Ha13), 7.15 (dd, J=2.8, 9.1 Hz, 1H, Ha5), 7.11 (d, J=8.4 Hz, 1H, Ha14), 7.08 (d, J=2.5 Hz, 1H, Ha7), 6.71 (d, J=7.6 Hz, 1H, H12), 6.46 (brt, J=5.3 Hz, 1H, HNH), 3.96 (d, J=6.8 Hz, 2H, Hb1), 3.85 (q, J=6.8 Hz, 2H, Ha9), 3.51 (brt, J=6.8 Hz, 2H, Ha10), 3.07-3.00 (m, 2H, Hb4eq), 2.62-2.54 (m, 2H, Hb4ax), 1.97-1.96 (m, 1H, Hb2), 1.81-1.71 (m, 2H, Hb3eq), 1.31-1.20 (m, 2H, Hb3ax).

$^{13}$C NMR (125 MHz; DMSO) δ 162.3 (Ca6), 159.8 (Ca2), 156.0 (Ca1), 151.9 (Ca8), 151.8 (Ca11), 144.3 (Ca11), 134.5 (Ca21), 128.4 (Ca15), 127.3 (Ca13), 126.1 (Ca17), 124.7 (Ca19), 124.5 (Ca4), 124.4 (Ca18), 123.3 (Ca20), 121.9 (Ca4), 117.4 (Ca5), 115.8 (Ca14), 109.5 (Ca3), 108.0 (Ca7), 103.2 (Ca12), 72.9 (Cb1), 45.6 (Cb4), 43.2 (Ca10), 39.7 (Ca9), 35.8 (Cb2), 29.2 (Cb3).

HRMS-ESI (m/z) calculated: 428.2445 [M+H]$^+$. found: 428.2610.

4-(2-(phenylamino)ethylamino)-7-O-(piperidin-4-ylmethoxy)quinazoline (82) (38 mg, 101 μmol, 96%) from 70 (105 μmol)

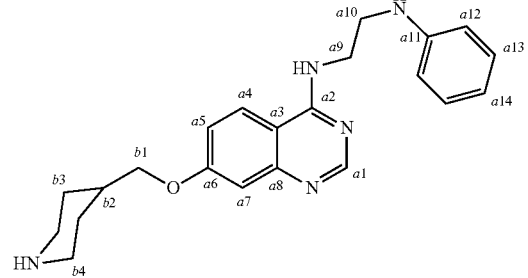

$^1$H NMR (500 MHz; DMSO) δ 8.43 (s, 1H, Ha1), 8.21 (brt, J=5.8 Hz, 1H, HNH), 8.11 (d, J=9.2 Hz, 1H, Ha4), 7.12 (dd, J=2.6, 9.2 Hz, 1H, Ha5), 7.11-7.05 (m, 3H, Ha7 and Ha13), 6.64 (dd, J=0.9, 8.6 Hz, 2H, Ha12), 6.53 (dt, J=0.9, 7.2 Hz, 2H, Ha14), 5.78 (brt, J=6.1 Hz, HNH), 3.96 (d, J=6.4 Hz 2H, Hb1), 3.68 (q, J=6.5 Hz, 2H, Ha9), 3.31 (brt, J=6.5 Hz, 2H, Ha10), 3.08-2.97 (m, 2H, Hb4eq), 2.62-2.547 (m, 2H, Hb4ax), 1.97-1.86 (m, 1H, Hb2), 1.81-1.72 (m, 2H, Hb3eq), 1.32-1.20 (m, 2H, Hb3ax).

$^{13}$C NMR (125 MHz; DMSO) δ 162.2 (Ca6), 159.6 (Ca2), 156.0 (Ca1), 151.8 (Ca8), 149.1 (Ca11), 129.4 (Ca13), 124.7 (Ca4), 117.3 (Ca5), 116.1 (Ca14), 112.4 (Ca12), 109.5 (Ca3), 108.0 (Ca7), 72.9 (Cb1), 45.6 (Cb4), 42.3 (Ca10), 40.1 (Ca9), 35.8 (Cb2), 29.2 (Cb3).

HRMS-ESI (m/z) calculated: 378.2289 [M+H]$^+$. found: 378.2280.

4-((N-(1-benzylpiperidin-4-yl))amino)-7-O-(piperidin-4-ylmethoxy)quinazoline (83) (42 mg, 97 μmol, 86%) from 71 (105 μmol)

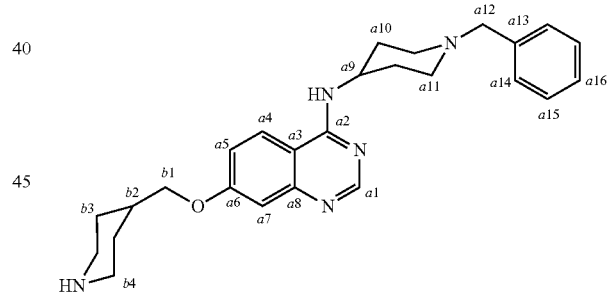

$^1$H NMR (500 MHz; DMSO) δ 8.37 (s, 1H, Ha1), 8.28 (brs, 1H, HNH), 8.22 (d, J=9.2 Hz, 1H, Ha4), 7.74 (d, J=7.6 Hz, 1H, Ha7), 7.37-7.24 (m, 4H, Ha14 and Ha15), 7.28-7.23 (m, 1H, Ha16), 7.09 (dd, J=2.6, 9.1 Hz, 1H, Ha5), 7.04 (d, J=2.6 Hz, 1H, Ha7), 4.20-4.10 (m, 1H, Ha9), 3.95 (d, J=6.4 Hz, 3H, Hb1), 3.49 (s, 2H, Ha12), 3.01 (brd, J=12.2 Hz, 2H, Hb4eq), 2.87 (brd, J=11.7 Hz, 2H, Ha11eq), 2.58 (m, 2H, Hb4ax), 2.06 (dt, J=1.5, 11.7 Hz, 2H, Ha11ax), 1.94-1.85 (m, 3H, Hb2 and Ha10eq), 1.78 (brd, J=10.5 Hz, 2H, Hb3eq), 1.65 (ddd, J=3.7, 11.7 Hz, 2H, Ha10ax), 1.23 (m, 2H, Hb3ax)

$^{13}$C NMR (125 MHz; DMSO) δ 162.1 (Ca6), 158.8 (Ca2), 156.0 (Ca1), 151.9 (Ca8), 139.2 (Ca13), 129.1 (Ca14), 128.6 (Ca15), 127.3 (Ca15), 124.9 (Ca4), 117.0 (Ca5), 109.4 (Ca3), 107.9 (Ca7), 72.9 (Cb1), 62.6 (Ca12), 52.8 (Ca11), 48.2 (Ca9), 45.7 (Cb4), 35.9 (Cb2), 31.7 (Ca10), 29.4 (Cb3).

HRMS-ESI (m/z) calculated: 432.2758 [M+H]$^+$. found: 432.2753.

Compounds AA to AL were synthesized following the general procedure below from compounds 72 to 83 respectively.

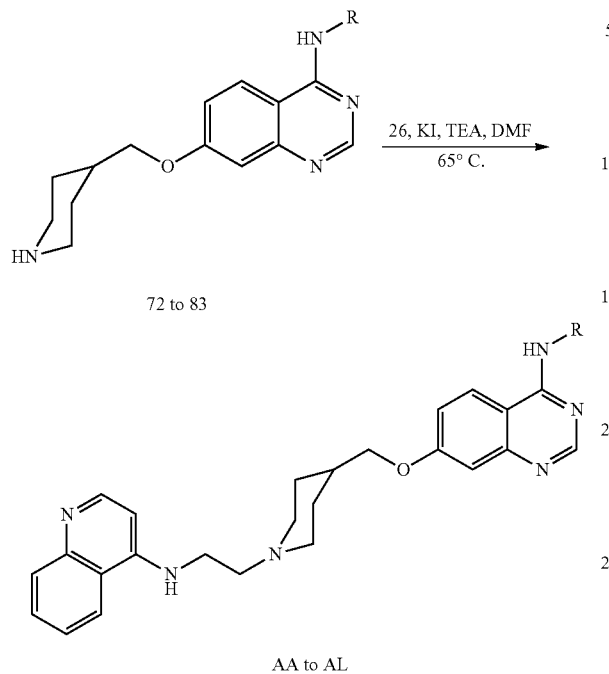

72 to 83

AA to AL

To a solution of 0.1 M of compound 72 to 83 K$_2$CO$_3$ (2eq) and a catalytic amount of KI in DMF was added 26 (2eq). The mixture was stirred at 65° C. overnight then was diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH$_3$) in dichloromethane or by reversed phase HPLC using a linear acetonitrile gradient with 0.01% of TEA (0→80% CH$_3$CN) to afford Compounds AA to AL.

4-(2-(3-chlorophenyl)ethylamino)-7-((1-(2-(quinolin-4-ylamino)ethyl)piperidin-4-yl)methoxy)quinazoline (AA) (5.0 mg, 8.8 μmol, 35%) from 72 (25 μmol)

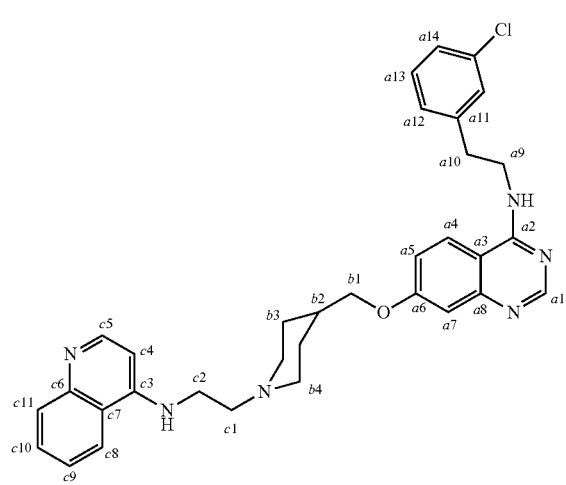 [SMILES: Clc1cccc(CCNc2ncnc3cc(OCC4CCN(CCNc5ccnc6ccccc56)CC4)ccc23)c1]

$^1$H NMR (500 MHz; DMSO) δ 8.41 (s, 1H, Ha1), 8.39 (d, J=5.37 Hz, 1H, Hc5) 8.18 (brt, J=5.35 Hz, 1H, HNH), 8.15 (d, J=8.40 Hz, 1H, Hc8), 8.10 (d, J=9.03 Hz, 1H, Ha4), 7.77 (dd, J=0.89, 8.40 Hz, 1H, Hc11), 7.60 (m, 1H, Hc10), 7.42 (m, 1H, Hc9), 7.36-7.18 (m, 4H, Ha12, Ha13 et Ha14), 7.11 (dd, J=2.6, 9.21 Hz, 1H, Ha5), 7.06 (d, J=2.53, 1H, Ha7), 7.03 (brt, J=5.42 Hz, 1H, HNH), 6.47 (d, J=5.35 Hz, 1H, Hc4), 3.98 (d, J=5.87 Hz, 2H, Hb1), 3.79-3.69 (m, 2H, Ha9), 3.44-3.36 (m, 2H, Hc2), 3.00 (m, 2H, Hb4eq), 2.97 (brt, J=7.13 Hz, 2H, Ha10), 2.63 (t, J=6.69 Hz, 2H, Hc1), 2.06 (m, 2H, Hb4ax), 1.85-1.72 (m, 3H, Hb2 et Hb3eq), 1.45-1.30 (m, 2H, Hb3ax).

$^{13}$C NMR (125 MHz; DMSO) δ 162.2 (Ca6), 159.4 (Ca2), 156.1 (Ca1), 151.8 (Ca8), 151.2 (Cc5), 150.2 (Cc7), 148.7 (Cc6), 142.7 (Ca11), 133.3 (Ca16), 130.6 (Ca15), 129.5 (Cc11), 129.1 (Cc10), 129.0 (Ca13), 127.9 (Ca12), 126.5 (Ca14), 124.6 (Ca4), 124.3 (Cc9), 121.9 (Cc8), 117.3 (Ca5), 109.5 (Ca3), 107.9 (Ca7), 98.7 (Cc4), 72.7 (Cb1), 56.6 (Cc1), 53.6 (Cb4), 42.1 (Ca9), 40.4 (Hc2), 34.5 (Cb2), 34.5 (Ca10), 29 (Cb3)

HRMS-ESI (m/z) calculated: 567.2639 [M+H]$^+$. found: 567.2644.

4-(2-(2-chlorophenyl)ethylamino)-7-((1-(2-(quinolin-4-ylamino)ethyl)piperidin-4-yl)methoxy)quinazoline (AB) (4.0 mg; 7.1 μmol, 29%) from 73 (25 μmol)

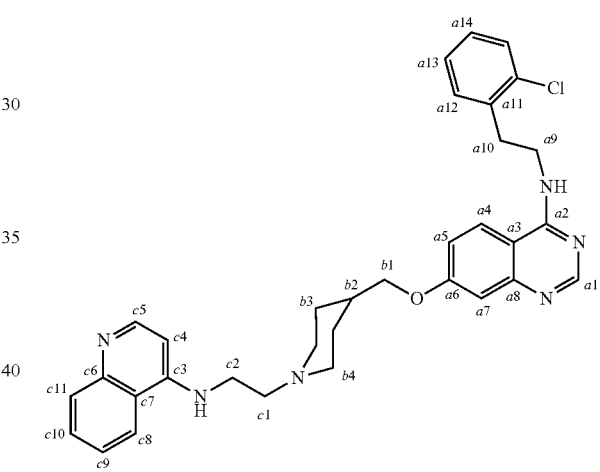

$^1$H NMR (500 MHz; DMSO) δ 8.40 (s, 1H, Ha1), 8.39 (d, J=5.8 Hz, 1H, Hc5) 8.16 (brt, J=5.06 Hz, 1H, HNH), 8.15 (d, J=8.1 Hz, 1H, Hc8), 8.10 (d, J=9.03 Hz, 1H, Ha4), 7.77 (dd, J=0.9, 8.3 Hz, 1H, Hc11), 7.60 (m, 1H, Hc10), 7.42 (m, 1H, Hc9), 7.36-7.24 (m, 4H, Ha12, Ha13 et Ha14), 7.11 (dd, J=2.47, 9.12 Hz, 1H, Ha5), 7.05 (d, J=2.61, 1H, Ha7), 7.03 (brt, J=5.1 Hz, 1H, HNH), 6.47 (d, J=5.3 Hz, 1H, Hc4), 3.98 (d, J=5.7 Hz, 2H, Hb1), 3.77-3.67 (m, 2H, Ha9), 3.44-3.36 (m, 2H, Hc2), 3.04-2.97 (m, 2H, Hb4eq), 2.94 (brt, J=7.1 Hz, 2H, Ha10), 2.63 (t, J=6.8 Hz, 2H, Hc1), 2.06 (m, 2H, Hb4ax), 1.84-1.74 (m, 3H, Hb2 et Hb3eq), 1.44-1.30 (m, 2H, Hb3ax).

$^{13}$C NMR (125 MHz; DMSO) δ 162.2 (Ca6), 159.4 (Ca2), 156.1 (Ca1), 151.8 (Ca8), 151.2 (Cc5), 150.2 (Cc7), 148.7 (Cc6), 139.1 (Ca11), 131.14 (Ca16), 131 (Ca15), 129.5 (Cc11), 129.1 (Cc10), 128.7 (Ca13), 128.7 (Ca14), 127.9 (Ca12), 124.6 (Ca4), 124.3 (Cc9), 121.9 (Cc8), 117.3 (Ca5), 109.5 (Ca3), 107.9 (Ca7), 98.7 (Cc4), 72.7 (Cb1), 56.6 (Cc1), 53.5 (Cb4), 42.2 (Ca9), 40.5 (Hc2), 35.7 (Cb2), 34.53 (Ca10), 29 (Cb3).

HRMS-ESI (m/z) calculated: 567.2639 [M+H]$^+$. found: 567.2641.

4-(2-(4-chlorophenyl)ethylamino)-7-((1-(2-(quinolin-4-ylamino)ethyl)piperidin-4-yl)methoxy)quinazoline (AC) (3.0 mg, 5.3 µmol, 21%) from 74 (25 µmol)

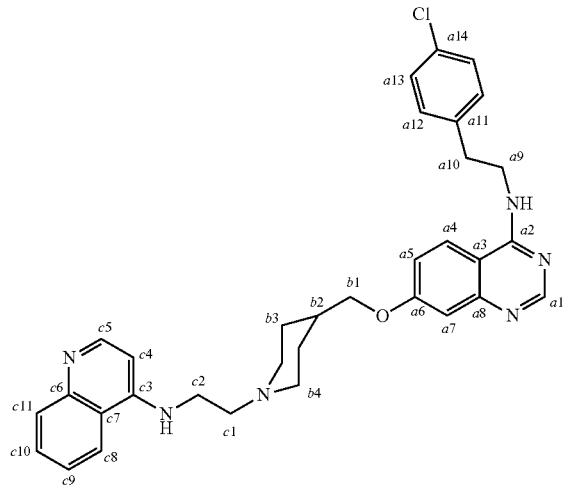 [SMILES: Clc1ccc(CCNc2ncnc3cc(OCC4CCN(CCNc5ccnc6ccccc56)CC4)ccc23)cc1]

$^1$H NMR (500 MHz; DMSO) δ 8.40 (s, 1H, Ha1), 8.40 (d, J=5.3 Hz, 1H, Hc5), 8.21 (brt, J=5.6 Hz, 1H, HNH), 8.16 (dd, J=0.9, 8.2 Hz, 1H, Hc8), 8.10 (d, J=9.3 Hz, 1H, Ha4), 7.78 (dd, J=1.1, 8.5 Hz, 1H, Hc11), 7.61 (m, 1H, Hc10), 7.46-7.22 (m, 5H, Hc9, Ha12 and Ha13), 7.11 (dd, J=2.6, 9.1 Hz, 1H, Ha5), 7.06 (d, J=2.5 Hz, 1H, Ha7), 7.03 (brt, J=5.3 Hz, 1H, HNH), 6.48 (d, J=5.5 Hz, 1H, Hc4), 3.99 (d, J=5.9 Hz, 2H, Hb1), 3.80-3.73 (m, 2H, Ha9), 3.41 (q, J=6.5 Hz, 2H, Hc2), 3.05-2.97 (m, 2H, Hb4eq), 3.09 (brt, J=6.9 Hz, 2H, Ha10), 2.64 (t, J=6.9 Hz, 2H, Hc1), 2.11-2.02 (m, 2H, Hb4ax), 1.85-1.76 (m, 3H, Hb2 et Hb3eq), 1.38 (dq, J=2.5, 12.2 Hz, 2H, Hb3ax).

$^{13}$C NMR (125 MHz; DMSO) δ 162.2 (Ca6), 159.5 (Ca2), 156.1 (Ca1), 151.8 (Ca8), 151.2 (Cc5), 150.2 (Cc7), 148.7 (Cc6), 137.5 (Ca11), 131.6 (Ca14), 129.6 (Ca12), 129.5 (Cc11), 129.1 (Cc10), 127.7 (Ca13), 124.7 (Ca4), 124.3 (Cc9), 121.9 (Cc8), 117.3 (Ca5), 109.5 (Ca3), 107.9 (Ca7), 98.7 (Cc4), 72.7 (Cb1), 56.6 (Cc1), 53.5 (Cb4), 46.1 (Ca9), 40.6 (Hc2), 35.7 (Cb2), 32.8 (Ca10), 29 (Cb3).

HRMS-ESI (m/z) calculated: 567.2639 [M+H]$^+$. found: 567.2635.

4-(2-(4-sulfonamidophenyl)ethylamino)-7-((1-(2-(quinolin-4-ylamino)ethyl)piperidin-4-yl)methoxy)quinazoline (AD) (11 mg, 18 µmol, 52%) from 75 (34 µmol)

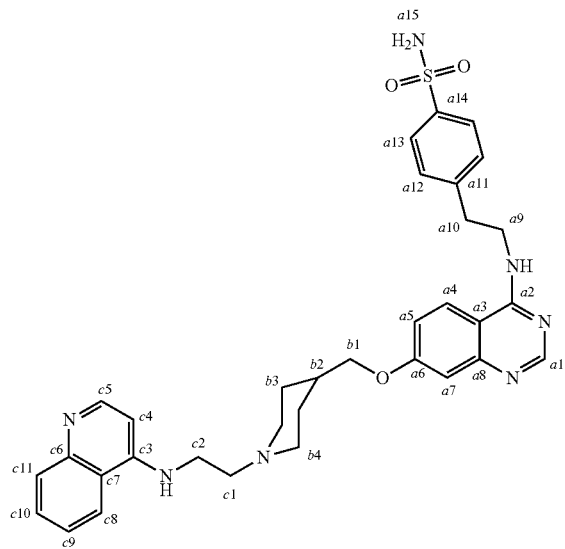 [SMILES: NS(=O)(=O)c1ccc(CCNc2ncnc3cc(OCC4CCN(CCNc5ccnc6ccccc56)CC4)ccc23)cc1]

$^1$H NMR (500 MHz; DMSO) δ 8.43 (s, 1H, Ha1), 8.40 (d, J=5.3 Hz, 1H, Hc5), 8.21 (brt, J=5.5 Hz, 1H, HNH), 8.16 (dd, J=0.8, 8.8 Hz, 1H, Hc8), 8.11 (d, J=9.1 Hz, 1H, Ha4), 7.78 (dd, J=1.1, 8.4 Hz, 1H, Hc11), 7.76-7.72 (m, 2H, Ha13), 7.61 (m, 1H, Hc10), 7.46-7.40 (m, 5H, Hc9, Ha12, Ha15), 7.12 (dd, J=2.6, 9.0 Hz, 1H, Ha5), 7.07 (d, J=2.6 Hz, 1H, Ha7), 7.04 (brt, J=5.5 Hz, 1H, HNH), 6.48 (d, J=5.46 Hz, 1H, Hc4), 3.99 (d, J=5.9 Hz, 2H, Hb1), 3.79-3.73 (m, 2H, Ha9), 3.41 (q, J=6.4 Hz, 2H, Hc2), 3.06-2.97 (m, 4H, Hb4eq, Ha10), 2.64 (t, J=7.2 Hz, 2H, Hc1), 2.10-2.02 (m, 2H, Hb4ax), 1.84-1.77 (m, 3H, Hb2 et Hb3eq), 1.38 (dq, J=2.6, 12.1 Hz, 2H, Hb3ax).

$^{13}$C NMR (125 MHz; DMSO) δ 162.2 (Ca6), 159.4 (Ca2), 156.1 (Ca1), 151.8 (Ca8), 151.2 (Cc5), 150.2 (Cc7), 148.7 (Cc6), 144.1 (Ca11), 142.9 (Ca14), 129.5 (Ca12), 129.5 (Cc11), 129.1 (Cc10), 126.1 (Ca13), 124.6 (Ca4), 124.3 (Cc9), 121.9 (Cc8), 117.3 (Ca5), 109.5 (Ca3), 107.9 (Ca7), 98.7 (Cc4), 72.7 (Cb1), 56.6 (Cc1), 53.5 (Cb4), 46.1 (Ca9), 40.6 (Cc2), 35.7 (Cb2), 34.7 (Ca10), 29 (Cb3).

HRMS-ESI (m/z) calculated: 612.2756 [M+H]$^+$. found: 612.2747.

4-(2-(4-nitrophenyl)ethylamino)-7-((1-(2-(quinolin-4-ylamino)ethyl)piperidin-4-yl)methoxy)quinazoline (AE) (7 mg, 12 µmol, 33%) from 76 (37 µmol)

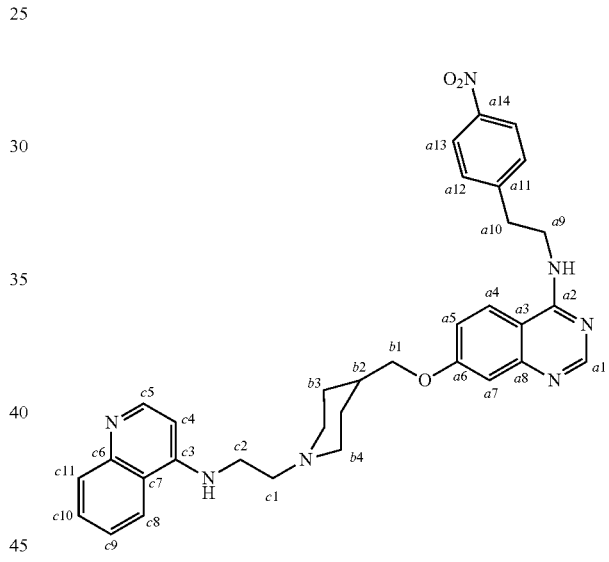

$^1$H NMR (500 MHz; DMSO) δ 8.41 (s, 1H, Ha1), 8.40 (d, J=5.3 Hz, 1H, Hc5), 8.21 (brt, J=5.5 Hz, 1H, HNH), 8.18-8.14 (m, 3H, Ha13 et Hc8), 8.09 (d, J=9.2 Hz, 1H, Ha4), 7.78 (dd, J=1.2, 8.4 Hz, 1H, Hc11), 7.61 (m, 1H, Hc10), 7.57-7.52 (m, 2H, Ha12), 7.43 (m, 1H, Hc9), 7.12 (dd, J=2.73, 9.25 Hz, 1H, Ha5), 7.06 (d, J=2.64 Hz, 1H, Ha7), 7.04 (brt, J=5.54 Hz, 1H, HNH), 6.48 (d, J=5.37 Hz, 1H, Hc4), 3.98 (d, J=5.9 Hz, 2H, Hb1), 3.83-3.77 (m, 2H, Ha9), 3.41 (q, J=8.44 Hz, 2H, Hc2), 3.12 (brt, J=6.9 Hz, 2H, Ha10), 3.04-2.97 (m, 2H, Hb4eq), 2.66-2.61 (m, 2H, Hc1), 2.10-2.02 (m, 2H, Hb4ax), 1.84-1.76 (m, 3H, Hb2 et Hb3eq), 1.44-1.31 (m, 2H, Hb3ax).

$^{13}$C NMR (125 MHz; DMSO) δ 162.2 (Ca6), 159.4 (Ca2), 156 (Ca1), 151.8 (Ca8), 151.2 (Cc5), 150.2 (Cc7), 148.7 (Cc6), 146.5 (Ca11), 137.7 (Ca14), 130.5 (Ca12), 129.5 (Cc11), 129.1 (Cc10), 123.8 (Ca13), 124.6 (Ca4), 124.3 (Cc9), 121.9 (Cc8), 117.4 (Ca5), 109.5 (Ca3), 107.9 (Ca7), 98.7 (Cc4), 72.7 (Cb1), 56.6 (Cc1), 53.5 (Cb4), 41.9 (Ca9), 40.6 (Cc2), 35.7 (Cb2), 34.8 (Ca10), 29 (Cb3).

HRMS-ESI (m/z) calculated: 578.2879 [M+H]$^+$. found: 578.2891.

4-(2-(4-isopropylphenyl)ethylamino)-7-((1-(2-(quinolin-4-ylamino)ethyl)piperidin-4-yl)methoxy)quinazoline (AF) (1.2 mg, 2.0 μmol, 6%) from 77 (37 μmol)

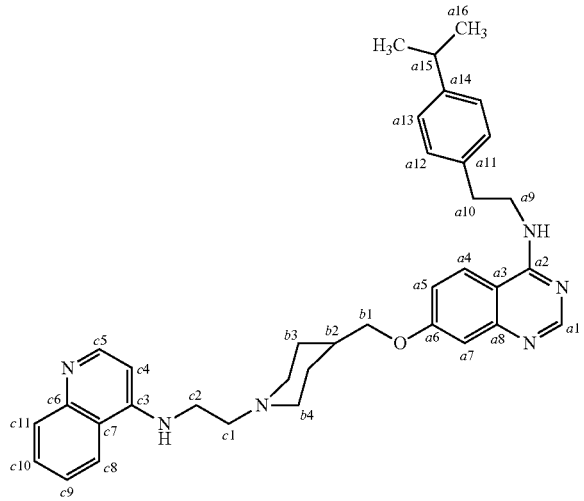 [SMILES: CC(C)c1ccc(CCNc2ncnc3cc(OCC4CCN(CCNc5ccnc6ccccc56)CC4)ccc23)cc1]

$^1$H NMR (500 MHz; DMSO) δ 8.41 (s, 1H, Ha1), 8.40 (d, J=5.2 Hz, 1H, Hc5), 8.22 (brt, J=5.9 Hz, 1H, HNH), 8.16 (m, 1H, Hc8), 8.10 (d, J=9.3 Hz, 1H, Ha4), 7.78 (dd, J=1.2, 8.4 Hz, 1H, Hc11), 7.61 (m, 1H, Hc10), 7.45-7.40 (m, 1H, Hc9), 7.20-7.09 (m, 4H, Ha12, Ha13), 7.12 (dd, J=2.56, 9.12 Hz, 1H, Ha5), 7.06 (d, J=2.2 Hz, 1H, Ha7), 7.04 (brt, J=5.3 Hz, 1H, HNH), 6.48 (d, J=5.4 Hz, 1H, Hc4), 3.99 (d, J=5.78 Hz, 2H, Hb1), 3.73-3.68 (m, 2H, Ha9), 3.44-3.38 (m, 2H, Hc2), 3.04-2.98 (m, 2H, Hb4eq), 2.88-2.82 (m, 2H, Ha10), 2.66-2.61 (m, 2H, Hc1), 2.10-2.02 (m, 2H, Hb4ax), 1.83-1.77 (m, 3H, Hb2 et Hb3eq), 1.26-1.16 (m, 8H, Hb3ax et Ha16).

$^{13}$C NMR (125 MHz; DMSO) δ 162.2 (Ca6), 159.4 (Ca2), 156.1 (Ca1), 151.8 (Ca8), 151.2 (Cc5), 150.2 (Cc7), 148.7 (Cc6), 146.5 (Ca14), 137.4 (Ca11), 129.5 (Ca12), 129.3 (Ca13), 129.1 (Cc11), 129.1 (Cc10), 124.6 (Ca4), 124.3 (Cc9), 121.9 (Cc8), 117.2 (Ca5), 109.6 (Ca3), 107.9 (Ca7), 98.7 (Cc4), 72.7 (Cb1), 56.6 (Cc1), 53.5 (Cb4), 42.5 (Ca9), 40.6 (Cc2), 35.7 (Cb2), 34.7 (Ca10), 29 (Cb3).

HRMS-ESI (m/z) calculated: 575.3498 [M+H]$^+$. found: 575.3496.

4-(2-(4-methoxyphenyl)ethylamino)-7-((1-(2-(quinolin-4-ylamino)ethyl)piperidin-4-yl)methoxy)quinazoline (AG) (15 mg, 27 μmol, 71%) from 78 (38 μmol)

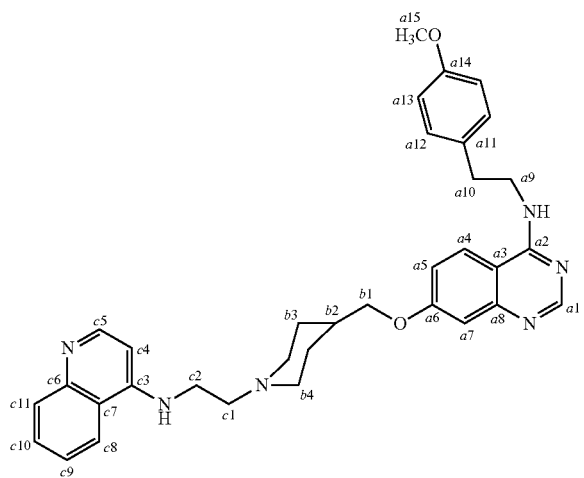 [SMILES: COc1ccc(CCNc2ncnc3cc(OCC4CCN(CCNc5ccnc6ccccc56)CC4)ccc23)cc1]

$^1$H NMR (500 MHz; DMSO) δ 8.41 (s, 1H, Ha1), 8.40 (d, J=5.37 Hz, 1H, Hc5), 8.18 (brt, J=5.40 Hz, 1H, HNH), 8.16 (m, 1H, Hc8), 8.12 (d, J=9.18 Hz, 1H, Ha4), 7.78 (dd, J=0.9, 8.3 Hz, 1H, Hc11), 7.61 (m, 1H, Hc10), 7.43 (m, 1H, Hc9), 7.20-7.15 (m, 2H, Ha12), 7.12 (dd, J=2.6, 9.1 Hz, 1H, Ha5), 7.06 (d, J=2.62, 1H, Ha7), 7.04 (brt, J=5.44 Hz, 1H, HNH), 6.88-6.82 (m, 2H, Ha13), 6.48 (d, J=5.4 Hz, 1H, Hc4), 3.98 (d, J=5.9 Hz, 2H, Hb1), 3.72 (s, 3H, Ha15), 3.73-3.64 (m, 2H, Ha9), 3.44-3.38 (m, 2H, Hc2), 3.04-2.96 (m, 2H, Hb4eq), 2.89 (brt, J=7.1 Hz 2H, Ha10), 2.63 (t, J=6.8 Hz, 2H, Hc1), 2.10-2.01 (m, 2H, Hb4ax), 1.84-1.74 (m, 3H, Hb2 et Hb3eq), 1.44-1.31 (m, 2H, Hb3ax).

$^{13}$C NMR (125 MHz; DMSO) δ 162.2 (Ca6), 159.4 (Ca2), 158.1 (Ca14), 156.1 (Ca1), 151.8 (Ca8), 151.2 (Cc5), 150.2 (Cc7), 148.7 (Cc6), 131.8 (Ca11), 130.1 (Ca12), 129.5 (Cc11), 129.1 (Cc10), 124.6 (Ca4), 124.3 (Cc9), 121.9 (Cc8), 117.2 (Ca5), 114.2 (Ca13), 109.6 (Ca3), 107.9 (Ca7), 98.7 (Cc4), 72.7 (Cb1), 56.6 (Cc1), 55.4 (Ca15), 53.5 (Cb4), 42.7 (Ca9), 40.6 (Cc2), 35.7 (Cb2), 34.2 (Ca10), 29 (Cb3).

HRMS-ESI (m/z) calculated: 563.3134 [M+H]$^+$. found: 563.3145.

4-(2-(4-aminophenyl)ethylamino)-7-((1-(2-(quinolin-4-ylamino)ethyl)piperidin-4-yl)methoxy)quinazoline (AH) (7 mg, 13 μmol, 33%) from 79 (40 μmol)

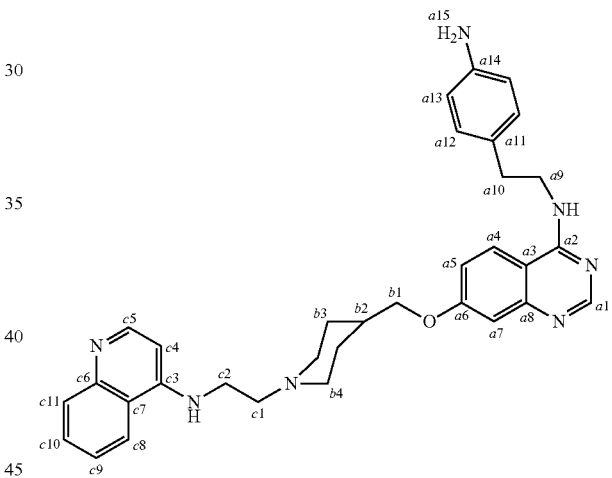

$^1$H NMR (500 MHz; DMSO) δ 8.42-8.36 (m, 2H, Ha1 et Hc5), 8.19-8.13 (m, 2H, HNH et Hc8), 8.12 (d, J=9.08 Hz, 1H, Ha4), 7.78 (dd, J=0.95, 8.45 Hz, 1H, Hc11), 7.61 (m, 1H, Hc10), 7.43 (m, 1H, Hc9), 7.11 (dd, J=2.5, 8.9 Hz, 1H, Ha5), 7.05 (d, J=2.46, 1H, Ha7), 7.04 (brt, J=5.28 Hz, 1H, HNH), 6.93-6.87 (m, 2H, Ha12), 6.52-6.48 (m, 2H, Ha13), 6.48 (d, J=5.4 Hz, 1H, Hc4), 4.86 (s, 2H, Ha15), 3.98 (d, J=5.9 Hz, 2H, Hb1), 3.67-3.58 (m, 2H, Ha9), 3.45-3.38 (m, 2H, Hc2), 3.05-2.97 (m, 2H, Hb4eq), 2.76 (brt, J=7.28 Hz 2H, Ha10), 2.63 (t, J=6.76 Hz, 2H, Hc1), 2.11-2.01 (m, 2H, Hb4ax), 1.84-1.75 (m, 3H, Hb2 et Hb3eq), 1.45-1.31 (m, 2H, Hb3ax).

$^{13}$C NMR (125 MHz; DMSO) δ 162.2 (Ca6), 159.4 (Ca2), 156.2 (Ca1), 151.8 (Ca8), 151.2 (Cc5), 150.2 (Cc7), 148.7 (Cc6), 147.2 (Ca14), 129.5 (Ca12), 129.5 (Ca11), 129.5 (Cc11), 128.4 (Cc10), 124.7 (Ca4), 124.3 (Cc9), 121.9 (Cc8), 117.2 (Ca5), 114.4 (Ca13), 109.6 (Ca3), 107.9 (Ca7), 98.7 (Cc4), 72.7 (Cb1), 56.6 (Cc1), 53.5 (Cb4), 42.9 (Ca9), 40.6 (Cc2), 35.7 (Cb2), 34.4 (Ca10), 29 (Cb3).

HRMS-ESI (m/z) calculated: 548.3137 [M+H]$^+$. found: 548.3142.

4-(2-(quinolin-4-yl)ethylamino)-7-((1-(2-(quinolin-4-ylamino)ethyl)piperidin-4-yl)methoxy)quinazoline (AI) (3.2 mg, 5.3 μmol, 23%) from 80 (23.3 μmol)

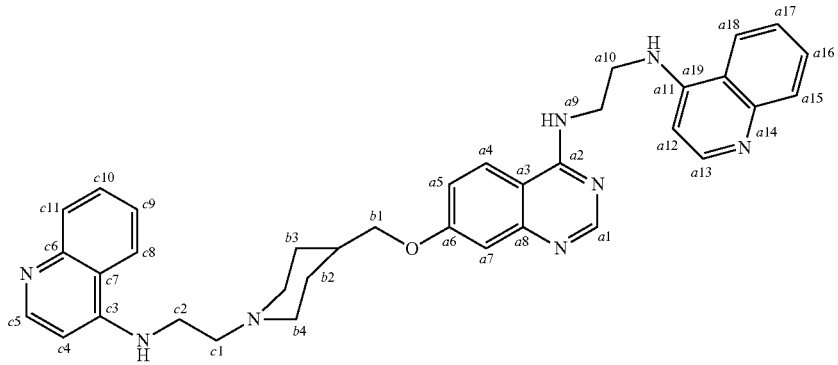 [SMILES: c1ccc2c(NCCNc3ncnc4cc(OCC5CCN(CCNc6ccnc7ccccc67)CC5)ccc34)ccnc2c1]

¹H NMR (500 MHz; DMSO) δ 8.49 (s, 1H, Ha1), 8.43 (brt, J=5.7 Hz, 1H, HNH), 8.42 (d, J=5.3 Hz, 1H, Ha13), 8.40 (d, J=5.3 Hz, 1H, Hc5), 8.17 (d, J=6.2 Hz, 1H, Ha18), 8.16 (d, J=5.6 Hz, 1H, Hc8), 8.12 (d, J=9.2 Hz, 1H, Ha4), 7.78 (d, J=8.4 Hz, 2H, Hc11 and Ha15), 7.61 (t, J=7.2 Hz, 2H, Hc10 and Ha16), 7.47 (t, J=5.5 Hz, 1H, HNH), 7.43 (t, J=7.6 Hz, 2H, Ha17 and Hc9), 7.14 (dd, J=2.5, 9.0 Hz, 1H, Ha5), 7.09 (d, J=2.5 Hz, 1H, Ha7), 7.06 (brt, J=5.1 Hz, 1H, HNH), 6.70 (d, J=5.4 Hz, 1H, Ha12), 6.48 (d, J=5.4 Hz, 1H, Hc4), 3.99 (d, J=5.7 Hz, 2H, Hb1), 3.82 (q, J=6.1 Hz, 2H, Ha9), 3.58 (q, J=6.2 Hz, 2H, Ha10), 3.41 (m, 2H, Hc2), 3.00 (brd, 2H, Hb4eq), 2.63 (t, J=7.0 Hz, 2H, Hc1), 2.06 (t, J=10.5 Hz, 2H, Hb4ax), 1.865-1.74 (m, 3H, Hb3eq and Hb2), 1.443-1.32 (m, 2H, Hb3ax).

¹³C NMR (125 MHz; DMSO) δ 162.3 (Ca6), 159.8 (Ca2), 156.0 (Ca1), 151.8 (Ca8), 151.2 (Cc5 and Ca13), 150.4 (Cc3), 150.3 (Ca11), 148.7 (Ca14), 148.6 (Cc6), 129.5 (Ce11 and Ca15), 129.2 (Cc10 and Ca16), 124.7 (Ca4), 124.4 (Ca17), 127.3 (Ca13), 122.0 (Cc9 and Ca18), 121.8 (Ca4), 119.3 (Ca19), 119.2 (Cc7), 117.5 (Ca5), 109.5 (Ca3), 108.0 (Ca7), 98.7 (Cc4), 98.6 (Ca12), 72.7 (Cb1), 56.6 (Cc1), 53.5 (Cb4), 42.1 (Ca10), 40.6 (Hc2), 39.3 (Ca9), 35.7 (Cb2), 29.0 (Cb3).

HRMS-ESI (m/z) calculated: 599.3242 [M+H]⁺. found: 599.3241.

4-(2-(naphthalen-1-yl)ethylamino)-7-((1-(2-(quinolin-4-ylamino)ethyl)piperidin-4-yl)methoxy)quinazoline (AJ) (13 mg, 22 μmol, 63%) from 81 (35 μmol)

¹H NMR (500 MHz; DMSO) δ 8.50 (s, 1H, Ha1), 8.40 (d, J=5.3 Hz, 1H, Hc5), 8.38 (brt, J=5.6 Hz, 1H, HNH), 8.16 (d, J=7.9 Hz, 1H, Hc8), 8.14 (d, J=9.4 Hz, 1H, Ha19), 8.11 (d, J=8.0 Hz, 1H, Ha4), 7.79 (d, J=8.4 Hz, 1H, He11), 7.75 (dd, J=1.8, 7.5 Hz, 1H, Ha15), 7.61 (ddd, J=0.8, 6.5, 7.7 Hz, 1H, Hc10), 7.45-7.38 (m, 3H, Ha17, Hc9 and Ha18), 7.31 (t, J=7.9 Hz, 1H, Ha13), 7.15 (dd, J=2.7, 9.3 Hz, 1H, Ha5), 7.11 (d, J=7.8 Hz, 1H, Ha14), 7.09 (d, J=2.6 Hz, 1H, Ha7), 7.04 (brt, J=5.2 Hz, 1H, HNH), 6.70 (d, J=7.8 Hz, 1H, Ha12), 6.48-45 (m, 2H, Hc4HNH), 3.99 (d, J=5.9 Hz, 2H, Hb1), 3.86 (q, J=6.0 Hz, 2H, Ha9), 3.51 (q, J=6.0 Hz, 2H, Ha10), 3.41 (q, J=6.3 Hz, 2H, Hc2), 3.05-2.97 (m, 2H, Hb4eq), 2.66-2.60 (m, 2H, Hc1), 2.10-2.02 (t, J=6.9 Hz, 2H, Hb4ax), 1.85-1.75 (m, 3H, Hb3eq and Hb2), 1.43-1.31 (m, 2H, Hb3ax).

¹³C NMR (125 MHz; DMSO) δ 162.3 (Ca6), 159.8 (Ca2), 156.0 (Ca1), 151.8 (Ca8), 151.2 (Cc5), 150.2 (Cc3), 148.7 (Cc6), 144.4 (Ca11), 134.5 (Ca21), 129.5 (Cc11), 129.1 (Cc10), 128.4 (Ca15), 127.3 (Ca13), 126.0 (Ca17), 124.7 (Ca19), 124.4 (Ca4), 124.3 (Ca18), 123.3 (Ca20), 121.9 (Ca4), 121.8 (Cc9), 119.2 (Cc7), 117.4 (Ca5), 115.8 (Ca14), 109.5 (Ca3), 108.0 (Ca7), 103.2 (Ca12), 98.7 (Cc4), 72.7 (Cb1), 56.6 (Cc1), 53.5 (Cb4), 43.2 (Ca10), 40.6 (Hc2), 39.7 (Ca9), 35.7 (Cb2), 29.0 (Cb3).

HRMS-ESI (m/z) calculated: 598.32893 [M+H]⁺. found: 598.3295.

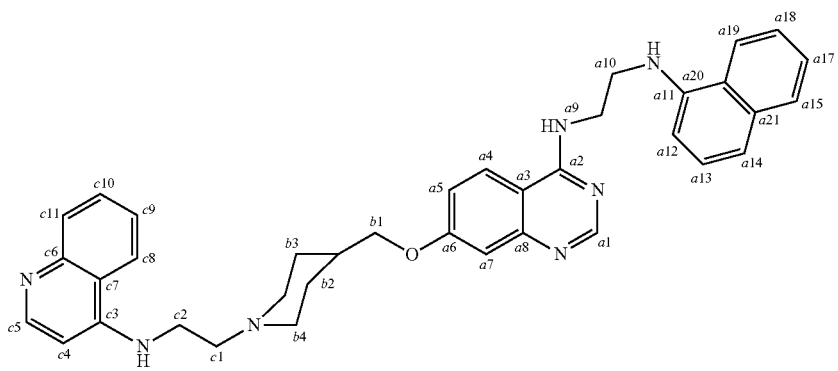 [SMILES: c1ccc2c(NCCNc3ncnc4cc(OCC5CCN(CCNc6ccnc7ccccc67)CC5)ccc34)cccc2c1]

4-(2-(phenylamino)ethylamino)-7-((1-(2-(quinolin-4-ylamino)ethyl)piperidin-4-yl)methoxy)quinazoline (AK) (11 mg, 20 µmol, 50%) from 82 (40 µmol)

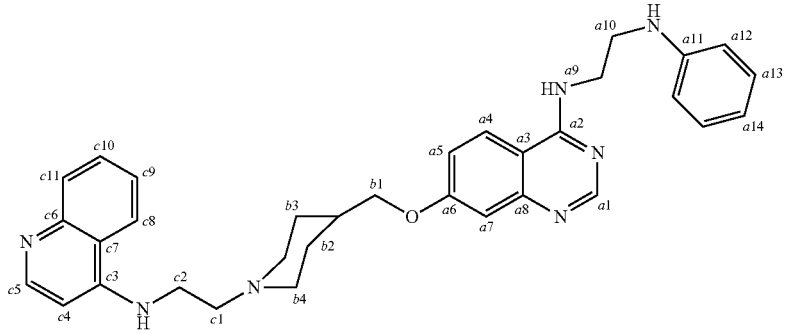 [SMILES: c1ccc(NCCNc2ncnc3cc(OCC4CCN(CCNc5ccnc6ccccc56)CC4)ccc23)cc1]

¹H NMR (500 MHz; DMSO) δ 8.42 (s, 1H, Ha1), 8.40 (d, J=5.2 Hz, 1H, Hc5), 8.26 (brt, J=5.5 Hz, 1H, HNH), 8.16 (d, J=7.9 Hz, 1H, Hc8), 8.13 (d, J=9.0 Hz, 1H, Ha4), 7.78 (dd, J=1.0, 8.3 Hz, 1H, Hc11), 7.61 (ddd, J=1.0, 6.8, 8.1 Hz, 1H, Hc10), 7.42 (ddd, j=1.0, 6.9, 7.9 Hz, 1H, Hc9), 7.13 (dd, J=2.5, 9.0 Hz, 1H, Ha5), 7.11-7.02 (m, 3H, Ha7 and Ha13), 6.64 (d, J=7.8 Hz, 2H, Ha12), 6.52 (t, J=7.3 Hz, 2H, Ha14), 6.48 (d, J=7.3 Hz, 1H, Hc4), 5.81 (brt, J=5.8 Hz, 1H, HNH), 3.99 (d, J=5.8 Hz, 2H, Hb1), 3.69 (q, J=6.4 Hz, 2H, Ha9), 3.41 (q, J=6.8 Hz, 2H, Hc2), 3.30 (q, J=6.40 Hz, 2H, Ha10), 3.05-2.97 (m, 2H, Hb4eq), 2.63 (t, J=6.8 Hz, 2H, Hc1), 2.05 (t, J=6.9 Hz, 2H, Hb4ax), 1.86-1.74 (m, 3H, Hb3eq and Hb2), 1.45-1.32 (m, 2H, Hb3ax).

¹³C NMR (125 MHz; DMSO) δ 162.2 (Ca6), 159.6 (Ca2), 156.0 (Ca1), 151.8 (Ca8), 151.1 (Cc5), 150.2 (Cc3), 149.1 (Ca11), 148.7 (Cc6), 129.5 (Cc11), 129.4 (Ca13), 129.1 (Cc10), 124.4 (Ca4), 124.3 (Cc9), 121.9 (Cc8), 119.2 (Cc7), 117.3 (Ca5), 116.0 (Ca14), 112.4 (Ca12), 109.6 (Ca3), 107.9 (Ca7), 98.7 (Cc4), 72.7 (Cb1), 56.6 (Cc1), 53.5 (Cb4), 42.4 (Ca10), 40.5 (Hc2), 40.2 (Ca9), 35.7 (Cb2), 29.0 (Cb3).

HRMS-ESI (m/z) calculated: 548.3133 [M+H]⁺. found: 548.3140.

4-((N-(1-benzylpiperidin-4-yl))amino)-7-((1-(2-(6,7-dimethoxyquinolin-4-ylamino)ethyl)piperidin-4-yl)methoxy)quinazoline (AL) (10 mg, 17 µmol, 48%) from 83 (34.7 µmol)

¹H NMR (500 MHz; DMSO) δ 8.40 (d, J=5.3 Hz, 1H, Hc5), 8.37 (s, 1H, Ha1), 8.22 (d, J=9.3 Hz, 1H, Ha4), 8.16 (dd, J=0.9, 7.8 Hz, 1H, Hc8), 7.78 (dd, J=1.0, 8.4 Hz, 1H, Hc11), 7.73 (d, J=7.6 Hz, 1H, Ha7), 7.60 (ddd, J=1.3, 7.3, 8.4 Hz, 1H, Hc10), 7.42 (ddd, j=1.3, 7.3, 8.4 Hz, 1H, Hc9), 7.36-7.29 (m, 4H, Ha14 and Ha15), 7.27-7.23 (m, 1H, Ha16), 7.13-7.05 (m, 3H, Ha5, Hc4 and Ha7), 7.10 (dd, J=2.6, 9.1 Hz, 1H, Ha5), 7.04 (d, J=2.6 Hz, 1H, Ha7), 7.02 (brt, J=5.3 Hz, 1H, HNH), 6.47 (d, J=5.4 Hz, 1H), 4.20-4.12 (m, 1H, Ha9), 3.97 (d, J=5.9 Hz, 3H, Hb1), 3.49 (s, 2H, Ha12), 3.41 (q, J=6.0, 13.0 Hz, 2H, Hc2), 3.01 (brd, J=11.2 Hz, 2H, Ha11eq), 2.87 (brd, J=11.7 Hz, 2H, Hb4eq), 2.64 (m, 2H, Hc1,), 2.06 (m, 4H, Ha1 lax and Hb4ax), 1.94-1.86 (m, 3H, Ha10eq), 1.86-1.74 (m, 2H, Hb2 and Hb3eq), 1.65 (ddd, J=3.3, 11.9 Hz, 2H, Ha10ax), 1.45-1.31 (m, 2H, Hb3ax).

¹³C NMR (125 MHz; DMSO) δ 162.1 (Ca6), 158.8 (Ca2), 156.0 (Ca1), 151.9 (Ca8), 151.1 (Cc5), 150.2 (Cc3), 148.7 (Cc6), 139.2 (Ca13), 129.5 (Cc11), 129.1 (Ca14), 129.1 (Cc10), 128.6 (Ca15), 127.3 (Ca15), 124.9 (Ca4), 124.3 (Cc9), 121.9 (Cc8), 119.2 (Cc7), 117.0 (Ca5), 109.5 (Ca3), 107.8 (Ca7), 98.7 (Cc4), 72.7 (Cb1), 62.6 (Ca12), 56.6 (Cc1), 53.6 (Ca11), 52.8 (Cb4), 48.2 (Ca9), 40.5 (Cc2), 35.7 (Cb2), 31.7 (Ca10), 29.0 (Cb3).

HRMS-ESI (m/z) calculated: 602.3602 [M+H]⁺. found: 602.3603.

Compound 84 was synthesized following the same procedure as for Compound 44 from compound 42.

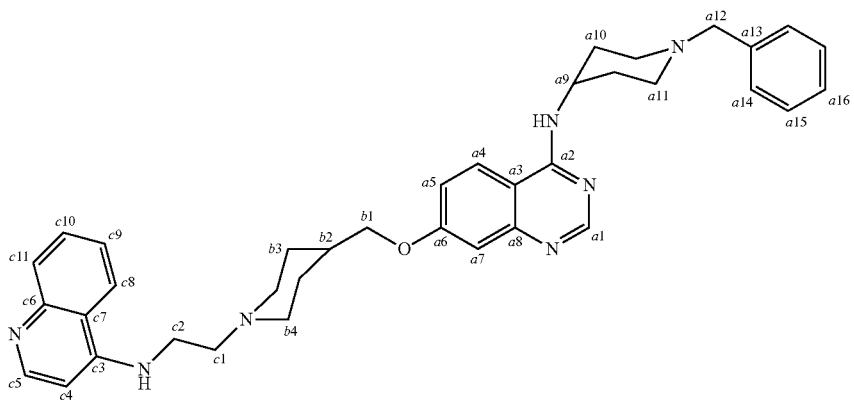 [SMILES: c1ccc(CN2CCC(Nc3ncnc4cc(OCC5CCN(CCNc6ccnc7ccccc67)CC5)ccc34)CC2)cc1]

4-((3-phenylpropyl)amino)-7-(O—((N-Boc)pyrrolidin-4-ylmethoxy))quinazoline (84)

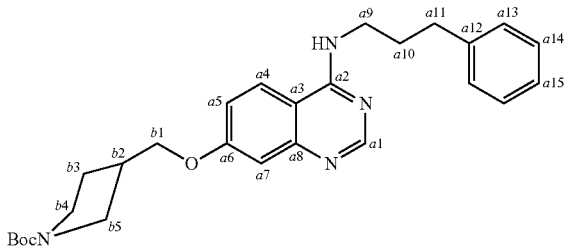 [SMILES: CC(C)(C)OC(=O)N1CCC(COc2ccc3c(NCCCc4ccccc4)ncnc3c2)C1]

$^1$H NMR (500 MHz; DMSO) δ 8.39 (s, 1H, Ha1), 8.17 (d, J=9.1 Hz, 1H, Ha4), 8.13 (brt, J=5.1 Hz, 1H, HNH), 7.32-7.22 (m, 4H, Ha13 and Ha14), 7.20-7.16 (m, 1H, Ha15), 7.11 (dd, J=2.4, 8.7 Hz, 1H, Ha5), 7.08 (d, J=2.5 Hz, 1H, Ha7), 4.16-4.05 (m, 2H, Hb1), 3.57-3.48 (m, 3H, Ha9 and Hb5), 3.44-3.24 (m, 2H, Hb4), 3.17-3.09 (m, 1H, Hb5), 2.75-2.60 (m, 3H, Ha11 and Hb2), 2.11-2.01 (m, 1H, Hb3), 1.96 (quint, J=7.3 Hz, 2H, Ha10), 1.80-1.69 (m, 1H, Hb3), 1.41 (s, 9H, HBoc).

$^{13}$C NMR (125 MHz; DMSO) δ 162.0 (Ca6), 159.5 (Ca2), 156.0 (Ca1), 154.0 (CBoc), 151.5 (Ca8), 142.2 (Ca12), 128.8 (Ca14), 128.7 (Ca13), 126.2 (Ca15), 124.8 (Ca4), 117.1 (Ca5), 109.6 (Ca3), 107.9 (Ca7), 78.6 and 78.4 (Cb1), 62.9 (CBoc), 49.0 and 48.7 (Cb5), 45.6 and 45.4 (Cb4), 40.5 (Ca9), 38.3 and 37.4 (Cb2), 33.1 (Ca11), 30.8 (Ca10), 28.6 (CBoc), 28.4 and 27.4 (Cb3).

HRMS-ESI (m/z) calculated: 463.2704 [M+H]$^+$. found: 463.2659.

4-((3-phenylpropyl)amino)-7-O-(pyrrolidin-3-ylmethoxy)quinazoline (85)

A mixture of 84 (100 mg; 216 µmol) in TFA was stirred for 1 h at room temperature. TFA was removed. The residue was diluted with dichloromethane and the organic phase was washed with saturated Na$_2$CO$_3$. The solvent was removed and 85 was obtained as pale blue foam (60 mg; 166 µmol, 76%).

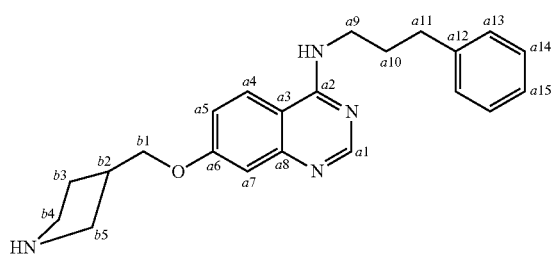 [SMILES: c1ccc(CCCNc2ncnc3cc(OCC4CCNC4)ccc23)cc1]

$^1$H NMR (500 MHz; DMSO) δ 8.38 (s, 1H, Ha1), 8.15 (d, J=9.5 Hz, 1H, Ha4), 8.09 (brt, J=5.7 Hz, 1H, HNH), 7.32-7.22 (m, 4H, Ha13 and Ha14), 7.18 (m, 1H, Ha15), 7.11 (dd, J=2.9, 9.5 Hz, 1H, Ha5) 7.07 (d, J=2.1 Hz, 1H, Ha7), 4.03-3.97 (m, 2H, Hb1), 3.56-3.49 (m, 2H, Ha9), 2.93-2.79 (m, 2H, Hb5 and Hb4), 2.76-2.60 (m, 4H, Hb5, Hb4 and Ha11), 2.49-2.41 (m, 1H, Hb2), 1.94 (quint, J=7.0 Hz, 2H, Ha10), 1.90-1.80 (m, 1H, Hb3), 1.50-1.39 (m, 1H, Hb3).

$^{13}$C NMR (125 MHz; DMSO) δ 162.2 (Ca6), 159.5 (Ca2), 156.1 (Ca1), 151.7 (Ca8), 142.2 (Ca12), 128.8 (Ca14), 128.7 (Ca13), 126.2 (Ca15), 124.7 (Ca4), 117.2 (Ca5), 109.5 (Ca3), 107.9 (Ca7), 71.2 (Cb1), 50.4 (Cb5), 46.7 (Cb4), 40.5 (Ca9), 38.7 (Cb2), 33.2 (Ca11), 31.7 (Ca10), 29.4 (Cb3).

HRMS-ESI (m/z) calculated: 363.2180 [M+H]$^+$. found: 363.2195.

4-((3-phenylpropyl)amino)-7-((1-(2-(quinolin-4-ylamino)ethyl)pyrrolidin-3-yl) methoxy)quinazoline (AM)

To a solution of 85 (15 mg; 41 µmol), K$_2$CO$_3$ (11 mg; 80 µmol) and a catalytic amount of KI in DMF (0.5 mL) was added 26 (16 mg; 80 µmol). The mixture was stirred at 65° C. overnight then was diluted with ethyl acetate. The organic phase was washed with water and brine and dried over sodium sulfate. The solvent was removed and the residue was purified by silica gel flash chromatography using a linear gradient of ammonia 1N in methanol (0 to 10% MeOH/NH$_3$) in dichloromethane or by reversed phase HPLC using a linear acetonitrile gradient with 0.01% of TEA (0 to 80% CH$_3$CN) to afford Compound AM as a white powder (7 mg; 13 µmol; 31%).

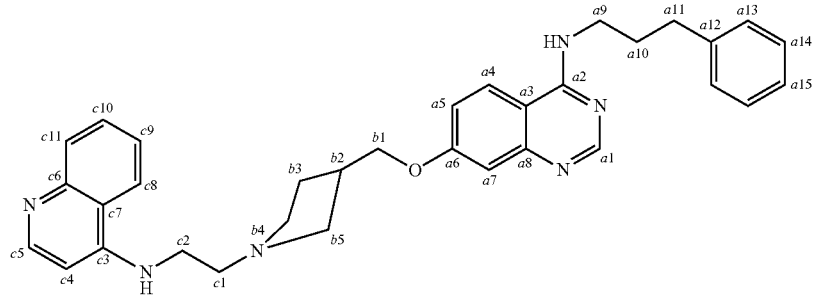 [SMILES: c1ccc(CCCNc2ncnc3cc(OCC4CCN(CCNc5ccnc6ccccc56)C4)ccc23)cc1]

$^1$H NMR (500 MHz; DMSO) δ 8.38 (s, 1H, Ha1), 8.37 (d, J=5.3 Hz, 1H, Hc5), 8.16 (d, J=7.8 Hz, 1H, Hc8), 8.15 (d, J=9.2 Hz, 1H, Ha4), 8.11 (brt, J=5.9 Hz, 1H, HNH), 7.77 (dd, J=1.0, 8.2 Hz, 1H, Hc11), 7.59 (ddd, J=1.0, 6.8, 8.2 Hz, 1H, Hc10), 7.41 (ddd, j=1.0, 6.8, 8.1 Hz, 1H, Hc9), 7.32-7.22 (m, 4H, Ha13 and Ha14), 7.18 (m, 1H, Ha15), 7.13-7.05 (m, 3H, Ha5, Hc4 and Ha7), 6.47 (d, J=5.4 Hz, 1H), 4.06-3.97 (m, 2H, Hb1), 3.46-3.39 (m, 2H, Hc2), 2.93 (q, J=6.1 Hz, 2H, Ha9), 2.82-2.72 (m, 3H, Hc1+Hb5), 2.72-2.57 (m, 6H, Hb4, Ha10, Hb2 and Ha11), 2.53-2.43 (m, 1H, Hb5), 1.99-1.86 (m, 1H, Hb3), 1.31-1.24 (m, 1H, Hb3).

$^{13}$C NMR (125 MHz; DMSO) δ 162.0 (Ca6), 159.5 (Ca2), 156.1 (Ca1), 151.7 (Ca8), 151.1 (Cc5), 150.2 (Cc3), 148.7 (Cc6), 142.2 (Ca12), 129.5 (Cc11), 129.1 (Cc10), 128.8

(Ca14), 128.7 (Ca13), 126.2 (Ca15), 124.7 (Ca4), 124.3 (Cc9), 121.9 (Cc8), 119.2 (Cc7), 117.1 (Ca5), 109.6 (Ca3), 108.0 (Ca7), 98.67 (Cc4), 71.6 (Cb1), 57.7 (Cc1), 53.8 (Cb4), 41.9 (Cc2), 40.4 (Ca9), 35.9 (Cb2), 33.7 (Ca11), 31.7 (Ca10), 30.8 (Cb3).

HRMS-ESI (m/z) calculated: 533.3024 [M+H]⁺. found: 533.3025.

Compound AN was synthesized following the general procedure above as for Compound G from 45.

To a solution of 45 (80 mg; 212 μmol), K₂CO₃ (59 mg; 424 μmol) and a catalytic amount of KI in DMF (1 mL) was added 26 (115 mg; 424 μmol). The mixture was stirred at 65° C. overnight then was diluted with ethyl acetate. The organic phase was washed 15 with water and brine and dried over sodium sulfate. The solvent was removed. The crude product was used without further purification and was solubilized in TFA. The reaction mixture was stirred at room temperature for 1 h. The solvent was removed and the residue was purified by silica gel flash chromatography using a linear gradient of ammonia 1N in methanol (0→10% MeOH/NH₃) in dichloromethane or by reversed phase HPLC using a linear acetonitrile gradient with 0.01% of TEA (0→80% CH₃CN) to afford Compound AN as a white powder (23 mg; 45 μmol; 21%).

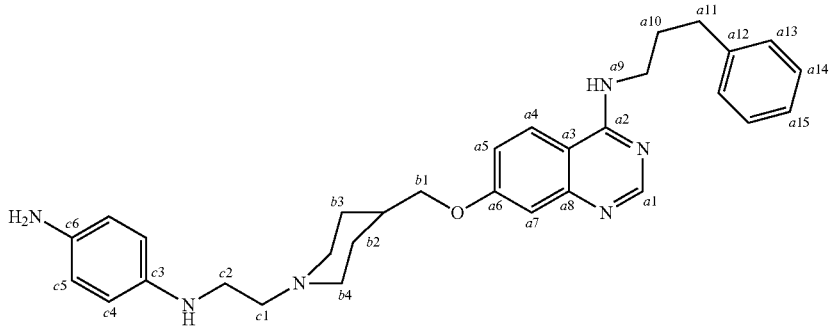 [SMILES: Nc1ccc(NCCN2CCC(COc3ccc4c(NCCCc5ccccc5)ncnc4c3)CC2)cc1]

¹H NMR (500 MHz; DMSO) δ 8.38 (s, 1H, Ha1), 8.15 (d, J=9.1 Hz, 1H, Ha4), 8.09 (brt, J=5.5 Hz, 1H, HNH), 7.32-7.21 (m, 4H, Ha13 and Ha14), 7.17 (t, J=7.0 Hz, 1H, Ha15), 7.11 (dd, J=2.9, 9.2 Hz, 1H, Ha5), 7.05 (d, J=2.4 Hz, 1H, Ha7), 6.45-6.36 (m, 4H, Hc4 and Hc5), 3.97 (d, J=5.9 Hz, 2H, Hb1), 3.53 (q, J=6.2 Hz, 2H, Ha9), 3.00 (t, J=6.6 Hz, 2H, Hc2), 2.97-2.85 (m, 2H, Hb4eq), 2.68 (t, J=8.0 Hz, 2H, Ha11), 2.47 (t, J=7.1 Hz, 2H, Hc1), 2.01-1.90 (m, 2H, Ha10 and Hb4ax), 1.83-1.73 (m, 3H, Hb3eq and Hb2), 1.42-1.29 (m, 2H, Hb3ax).

¹³C NMR (125 MHz; DMSO) δ 162.1 (Ca6), 159.5 (Ca2), 156.0 (Ca1), 151.7 (Ca8), 142.2 (Ca12), 140.7 (Cc3), 139.6 (Cc6), 128.8 (Cca14), 128.7 (Ca13), 126.2 (Ca15), 124.7 (Ca4), 117.2 (Ca5), 115.9 (Cc4), 114.2 (Cc5), 109.5 (Ca3), 107.9 (Ca7), 72.7 (Cb1), 57.8 (Cc1), 53.5 (Cb4), 42.1 (Cc2), 40.5 (Ca9), 35.8 (Cb2), 33.1 (Ca11), 30.8 (Ca10), 29.0 (Cb3).

HRMS-ESI (m/z) calculated: 511.3180 [M+H]⁺. found: 511.3180.

Compounds AO to AS were synthesized following the same procedure as for Compound G from 45.

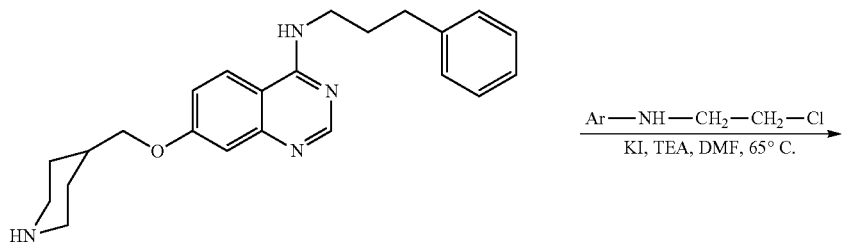

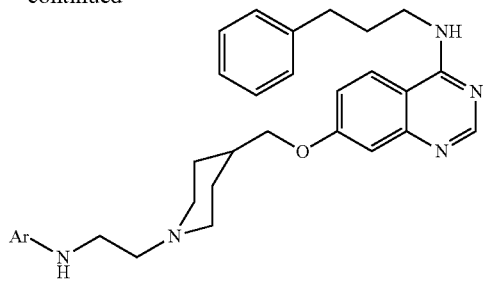

AO to AS

To a solution of 0.1 M of 45, K₂CO₃ (2eq) and a catalytic amount of KI in DMF was added the desired chloro-derivative (2eq). The mixture was stirred at 65° C. overnight then was diluted with ethyl acetate. The organic phase was washed with water and brine and dried over sodium sulfate. The solvent was removed and the residue was purified by silica gel flash chromatography using a linear gradient of ammonia 1N in methanol (0→10% MeOH/NH₃) in dichloromethane or by reversed phase HPLC using a linear acetonitrile gradient with 0.01% of TEA (0→80% CH₃CN) to afford Compounds AO to AS.

| Chloro-derivative | Compound obtained |
|---|---|
| (Cl-quinoline-NHCH₂CH₂Cl) | AO |
| (7-OMe-quinoline-NHCH₂CH₂Cl) | AP |
| (6,7-diOMe-quinoline-NHCH₂CH₂Cl) | AQ |
| (quinoline-N(CH₃)CH₂CH₂Cl) | AR |
| (6-quinolinyl-NHCH₂CH₂Cl) | AS |

4-((3-phenylpropyl)amino)-7-((1-(2-(7-chloroquinolin-4-ylamino)ethyl) piperidin-4-yl)methoxy)quinazoline (AO) (15 mg, 26 µmol, 97%) from 45 (27 µmol)

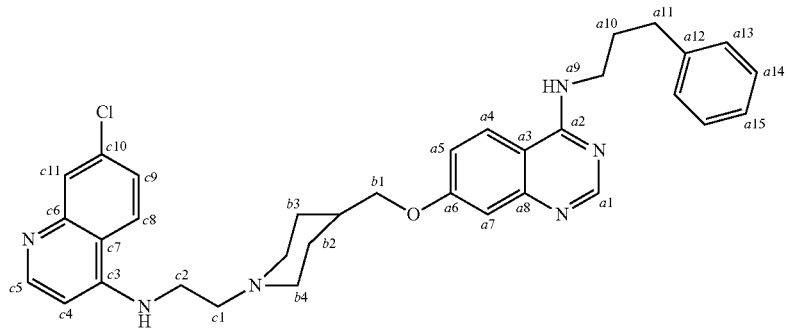 [SMILES: Clc1ccc2c(NCCN3CCC(COc4ccc5c(NCCCc6ccccc6)ncnc5c4)CC3)ccnc2c1]

¹H NMR (500 MHz; DMSO) δ 8.41 (d, J=5.3 Hz, 1H, Hc5), 8.38 (s, 1H, Ha1), 8.23 (d, J=9.1 Hz, 1H, Hc8), 8.15 (d, J=9.2 Hz, 1H, Ha4), 8.09 (brt, J=5.5 Hz, 1H, HNH), 7.79 (d, J=2.3 Hz, 1H, Hc11), 7.46 (dd, j=2.2, 7.3, 8.9 Hz, 1H, Hc9), 7.32-7.15 (m, 5H, Ha13, Ha14 and Ha15), 7.11 (dd, J=2.6, 9.1 Hz, 1H, Ha5), 7.05 (d, J=2.6 Hz, 1H, Ha7), 6.51 (d, J=5.4 Hz, 1H, Hc4), 3.98 (d, J=5.9 Hz, 2H, Hb1), 3.53 (q, J=6.1 Hz, 2H, Ha9), 3.41 (q, J=6.5 Hz, 2H, Hc2), 3.01 (brd, J=11.2 Hz, 2H, Ha4eq), 2.68 (t, J=7.5 Hz; 2H, Ha11,) 2.62 (t, J=7.1 Hz, 2H, Hc1,), 2.06 (t, J=11.1 Hz, 2H, Hb4ax), 1.95 (q, J=7.5 Hz, Ha10), 1.83-1.73 (m, 3H, Hb3eq and Hb2), 1.43-1.31 (m, 2H, Hb3ax).

¹³C NMR (125 MHz; DMSO) δ 162.1 (Ca6), 159.5 (Ca2), 156.1 (Ca1), 152.4 (Cc5), 151.8 (Ca8), 150.4 (Cc3), 149.5 (Cc6), 142.2 (Ca12), 133.8 (Cc10), 128.8 (Ca14), 128.7 (Ca13), 128.0 (Cc11), 126.2 (Ca15), 124.7 (Ca4), 124.5 (Cc9), 124.4 (Cc8), 117.9 (Cc7), 117.2 (Ca5), 109.5 (Ca3), 107.9 (Ca7), 99.2 (Cc4), 72.7 (Cb1), 56.6 (Cc1), 53.5 (Cb4), 40.7 (Ca9), 40.5 (Cc2), 35.7 (Cb2), 33.1 (Ca11), 30.8 (Ca10), 29.0 (Cb3).

HRMS-ESI (m/z) calculated: 581.2790 [M+H]⁺. found: 581.2791.

4-((3-phenylpropyl)amino)-7-((1-(2-(7-methoxyquinolin-4-ylamino)ethyl)piperidin-4-yl)methoxy)quinazoline (AP) (43 mg, 75 μmol, 71%) from 45 (106 μmol)

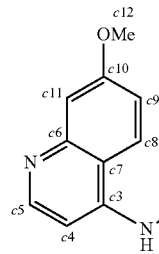
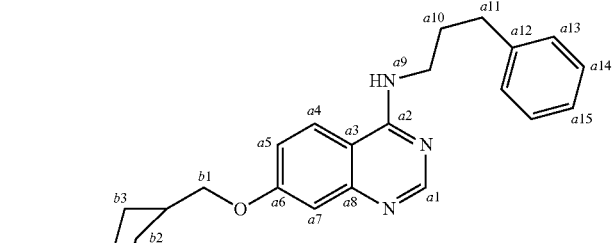

¹H NMR (500 MHz; DMSO) δ 8.38 (s, 1H, Ha1), 8.32 (d, J=5.3 Hz, 1H, Hc5), 8.15 (d, J=9.2 Hz, 1H, Ha4), 8.10 (brt, J=5.4 Hz, 1H, HNH), 8.06 (d, J=9.1 Hz, 1H, Hc8), 7.32-7.22 (m, 4H, Ha13 and Ha14) 7.21-7.15 (m, 2H, Ha15 and Hc11), 7.11 (dd, J=2.4, 9.1 Hz, 1H, Ha5), 7.08-7.03 (m, 2H, Ha7 and Hc9), 6.96 (brt, J=5.2 Hz, 1H, HNH), 6.36 (d, J=5.5 Hz, 1H, Hc4), 3.97 (d, J=5.7 Hz, 2H, Hb1), 3.87 (s, 3H, Hc12), 3.53 (q, J=6.4 Hz, 2H, Ha9), 3.41-3.36 (m, 2H, Hc2), 3.00 (brd, J=10.9 Hz, 2H, Ha4eq), 2.68 (t, J=7.7 Hz; 2H, Ha11) 2.61 (t, J=6.9 Hz, 2H, Hc1), 2.04 (t, J=11.1 Hz, 2H, Hb4ax), 1.95 (quint, J=7.4 Hz, Ha10), 1.85-1.73 (m, 3H, Hb3eq and Hb2), 1.44-1.31 (m, 2H, Hb3ax).

¹³C NMR (125 MHz; DMSO) δ 162.1 (Ca6), 160.0 (Cc3), 159.5 (Ca2), 156.1 (Ca1), 151.8 (Ca8), 151.5 (Cc5), 150.6 (Cc10), 150.3 (Cc6), 142.2 (Ca12), 128.8 (Ca14), 128.7 (Ca13), 126.2 (Ca15), 124.7 (Ca4), 123.3 (Cc8), 117.2 (Ca5), 116.0 (Cc9), 113.7 (Cc7), 109.5 (Ca3), 108.3 (Cc11), 107.9 (Ca7), 97.6 (Cc4), 72.7 (Cb1), 56.7 (Cc1), 55.6 (Cc12), 53.5 (Cb4), 40.6 (Cc2), 40.5 (Ca9), 35.7 (Cb2), 33.1 (Ca11), 30.8 (Ca10), 29.0 (Cb3).

HRMS-ESI (m/z) calculated: 577.3286 [M+H]⁺. found: 577.3296.

4-((3-phenylpropyl)amino)-7-((1-(2-(6,7-dimethoxyquinolin-4-ylamino)ethyl)piperidin-4-yl)methoxy)quinazoline (AQ) (9 mg, 15 μmol, 56%) from 45 (27 μmol)

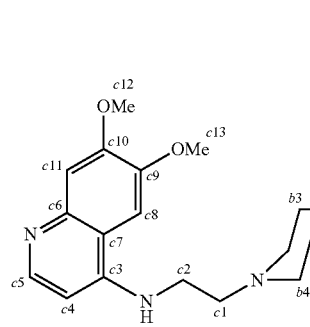

¹H NMR (500 MHz; DMSO) δ 8.37 (s, 1H, Ha1), 8.22 (d, J=5.3 Hz, 1H, Hc5), 8.15 (d, J=9.3 Hz, 1H, Ha4), 8.11 (brt, J=5.4 Hz, 1H, HNH), 7.45 (s, 1H, Hc8), 7.32-7.21 (m, 4H, Ha13 and Ha14), 7.21-7.15 (m, 2H, Ha15 and Hc11), 7.11 (dd, J=2.6, 9.1 Hz, 1H, Ha5), 7.05 (d, J=2.6 Hz, 2H, Ha7), 6.84 (brt, J=5.2 Hz, 1H, HNH), 6.37 (d, J=5.5 Hz, 1H, Hc4), 3.98 (d, J=5.9 Hz, 2H, Hb1), 3.89 (s, 3H, Hc13), 3.87 (s, 3H, Hc12), 3.56-3.49 (m, 2H, Ha9), 3.41-3.36 (m, 2H, Hc2), 3.00 (brd, J=10.8 Hz, 2H, Ha4eq), 2.68 (t, J=7.7 Hz; 2H, Ha11) 2.63 (t, J=6.9 Hz, 2H, Hc1), 2.06 (t, J=10.8 Hz, 2H, Hb4ax), 1.95 (quint, J=7.4 Hz, Ha10), 1.86-1.75 (m, 3H, Hb3eq and Hb2), 1.47-1.32 (m, 2H, Hb3ax).

¹³C NMR (125 MHz; DMSO) δ 162.1 (Ca6), 159.5 (Ca2), 156.1 (Ca1), 151.7 (Cc3), 151.5 (Ca8), 149.3 (Cc9), 148.9 (Cc5), 148.0 (Cc10), 145.4 (Cc6), 142.2 (Ca12), 128.8 (Ca14), 128.7 (Ca13), 126.2 (Ca15), 124.7 (Ca4), 117.2 (Ca5), 113.1 (Cc7), 109.5 (Ca3), 108.7 (Cc11), 107.9 (Ca7), 101.1 (Cc8), 97.9 (Cc4), 72.7 (Cb1), 56.9 (Cc1), 56.3 (Cc13), 55.8 (Cc12), 53.6 (Cb4), 40.7 (Cc2), 40.3 (Ca9), 35.7 (Cb2), 33.1 (Ca11), 30.8 (Ca10), 29.0 (Cb3).

HRMS-ESI (m/z) calculated: 607.3391 [M+H]⁺. found: 607.3391.

4-((3-phenylpropyl)amino)-7-((1-(2-(methyl(quinolin-4-yl)amino)ethyl)piperidin-4-yl)methoxy)quinazoline (AR) (13 mg, 23 μmol, 85%) from 45 (27 μmol)

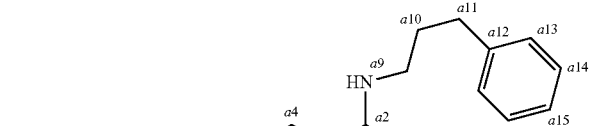
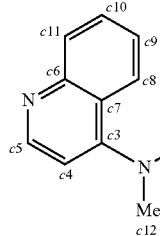

¹H NMR (500 MHz; DMSO) δ 8.61 (d, J=5.1 Hz, 1H, Hc5), 8.38 (s, 1H, Ha1), 8.21 (d, J=8.5 Hz, 1H, Hc8), 8.15 (d, J=9.2 Hz, 1H, Ha4), 8.09 (brt, J=5.4 Hz, 1H, HNH), 7.91 (dd, J=0.7, 8.3 Hz, 1H, Hc11), 7.66 (t, J=7.3 Hz, 1H, Hc9), 7.51 (t, J=7.3 Hz, 1H, Hc10), 7.32-7.22 (m, 4H, Ha13 and Ha14), 7.18 (t, J=7.3 Hz, 1H, Ha15), 7.10 (dd, J=2.5, 9.1 Hz, 1H, Ha5), 7.04 (d, J=2.6 Hz, 1H, Ha7), 6.93 (d, J=5.4 Hz, Hl, Hc4), 3.93 (d, J=5.9 Hz, 2H, Hb1), 3.53 (q, J=5.8 Hz, 2H, Ha9), 3.40 (t, J=6.3 Hz, 2H, Hc2), 2.97 (s, 3H, Hc12), 2.85 (brd, J=10.7 Hz, 2H, Ha4eq), 2.68 (t, J=7.7 Hz, 2H, Ha11), 2.64 (t, J=6.2 Hz, 2H, Hc1,), 2.02-1.88 (m, 4H, Hb4ax and Ha10), 1.79-1.63 (m, 3H, Hb3eq and Hb2), 1.29-1.15 (m, 2H, Hb3ax).

¹³C NMR (125 MHz; DMSO) δ 162.1 (Ca6), 159.5 (Ca2), 157.1 (Cc3), 156.1 (Ca1), 151.8 (Ca8), 150.8 (Cc5), 149.8 (Cc6), 142.2 (Ca12), 129.9 (Cc11), 129.1 (Cc10), 128.8 (Ca14), 128.7 (Ca13), 126.2 (Ca15), 124.9 (Cc9), 124.7 (Ca4), 124.6 (Cc8), 123.1 (Cc7), 117.1 (Ca5), 109.5 (Ca3), 108.8 (Cc4), 107.9 (Ca7), 72.6 (Cb1), 55.9 (Cc1), 54.2 (Cc2), 53.6 (Cb4), 40.5 (Ca9), 40.2 (Cc12), 35.6 (Cb2), 33.1 (Ca11), 30.8 (Ca10), 29.0 (Cb3).

HRMS-ESI (m/z) calculated: 561.3337 [M+H]⁺. found: 561.3339.

4-((3-phenylpropyl)amino)-7-((1-(2-(quinolin-6-ylamino)ethyl)piperidin-4-yl)methoxy)quinazoline (AS) (14 mg, 26 μmol, 96%) from 45 (27 μmol)

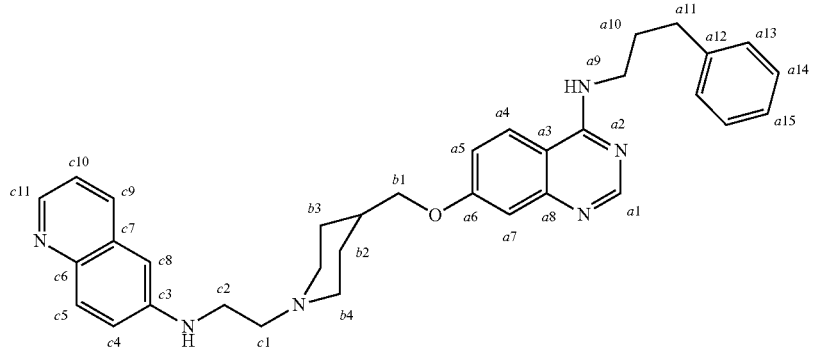 [SMILES: c1ccc(CCCNc2ncnc3cc(OCC4CCN(CCNc5ccc6ncccc6c5)CC4)ccc23)cc1]

$^1$H NMR (500 MHz; DMSO) δ 8.48 (dd, J=1.63, 4.18 Hz, 1H, Hc11), 8.38 (s, 1H, Ha1), 8.15 (d, J=9.2 Hz, 1H, Ha4), 8.09 (brt, J=5.5 Hz, 1H, HNH), 7.99 (dd, J=0.9, 7.4 Hz, 1H, Hc9), 7.70 (d, J=9.1 Hz, 1H, Hc4), 7.32-7.22 (m, 6H, Ha13, Ha14, Hc5 and Hc10), 7.18 (dt, J=1.4, 7.3 Hz, 1H, Ha15), 7.12 (dd, J=2.5, 9.1 Hz, 1H, Ha5), 7.06 (d, J=2.6 Hz, 1H, Ha7), 6.72 (d, J=5.4 Hz, Hl, Hc8), 5.99 (t, J=5.3 Hz, 1H, HNH), 3.98 (d, J=5.9 Hz, 2H, Hb1), 3.53 (q, J=6.0 Hz, 2H, Ha9), 3.24 (q, J=5.9 Hz, 2H, Hc2), 2.99 (brd, J=11.2 Hz, 2H, Ha4eq), 2.68 (t, J=7.7 Hz, 2H, Ha11), 2.59 (t, J=6.7 Hz, 2H, Hc1,), 2.03 (brt, j=10.8 Hz, 2H, Hb4ax), 1.94 (quint, J=7.4 Hz, 2H, Ha10), 1.85-1.75 (m, 3H, Hb3eq and Hb2), 1.45-1.35 (m, 2H, Hb3ax).

$^{13}$C NMR (125 MHz; DMSO) δ 162.1 (Ca6), 159.5 (Ca2), 156.1 (Ca1), 151.8 (Ca8), 174.3 (Cc3), 145.4 (Cc11), 142.7 (Cc6), 142.2 (Ca12), 133.6 (Cc9), 130.5 (Cc7), 129.8 (Cc4), 128.8 (Ca14), 128.7 (Ca13), 126.2 (Ca15), 124.7 (Ca4), 122.1 (Cc5), 121.7 (Cc10), 117.2 (Ca5), 109.5 (Ca3), 107.9 (Ca7), 101.6 (Cc8), 72.7 (Cb1), 57.3 (Cc1), 53.6 (Cb4), 41.1 (Cc2), 40.5 (Ca9), 35.7 (Cb2), 33.1 (Ca11), 30.8 (Ca10), 29.0 (Cb3).

HRMS-ESI (m/z) calculated: 547.3180 [M+H]$^+$. found: 547.3182.

II. Biological Tests of the Compounds According to the Invention

DNMT3A Assay.

DNMT3A enzyme inhibition was adapted from the restriction-based fluorescence assay protocol described in Ceccaldi et al. (*ChemBioChem* 2011, 12, 1337-45). Briefly, a 5'-labelled biotin oligonucleotide is hybridized to its complementary strand labelled with 6-carboxyfluorescein at the 3'-end into a 384 well microplate (black Optiplates; Perkin Elmer) pre-coated with avidin. The duplex contains a unique CpG site overlapping with a restriction site of a methylation sensitive restriction enzyme. The human C-terminal DNMT3A (a.a. 623-908), produced as described in Gros et al. (Nucleic Acids Research 2013 Aug. 25), was added in each well (200 ng/well) and mixed with the chemical compounds at desired concentrations and freshly prepared AdoMet (20 µM final concentration) to start the reaction in a total volume of 50 µL. After 1 hour incubation at 37° C. each well were washed three times with PBS, Tween-20 0.05%, NaCl (500 mM) and three more times with PBST. Specific fluorescent signals were detected with the methylation-sensitive restriction enzyme HpyCH4IV (NEB) as described and measured on a Perkin Elmer Envision detector. The percentage of inhibition is reported. The formula used to calculate the percentage of inhibition is [(X−Y)/X]×100, where X is the signal determined in the absence of the inhibitor and Y is the signal obtained in the presence of the inhibitor. The concentration at which 50% of efficacy of inhibition is observed (EC50) was determined by analysis of a concentration range of the tested compound in triplicates. The non-linear regression fittings with sigmoidal dose-response (variable slope) were performed with GraphPad Prism 4.03 (GraphPad Software).

DNMT1 Assay.

His-DNMT1 (182 kDa, human) was cloned, expressed and purified as described in Halby et al. (*ChemBioChem* 2012, 13, 157-65). The reaction was performed in a 10 µL total reaction volume in low volume NBS™ 384-well microplates (Corning), containing the tested compound (up to 1% DMSO), 1 µM of a SAM/[methyl-$^3$H] SAM (3 TBq/mmol, PerkinElmer) mix in a ratio of 3-to-1 (isotopic dilution 1*:3), 0.3 µM of biotinylated hemimethylated DNA duplex (5'-GATmCGCmCGATGmCGmCGAATmCGmC-GAT mCGATGmCGAT-3' and BIOT-5'-ATCGCATC-GATCGCGATTCGCGCATCGGCG ATC-3'), and 90 nM of DNMT1 in methylation buffer (20 mM HEPES pH 7.2, 1 mM EDTA, 50 mM KCl, 25 µg/mL BSA). The reaction was incubated at 37° C. for 2 hours. 8 µL are then transferred into a streptavidin 96-well scintillant coated Flashplate™ (PerkinElmer) containing 190 µL of 20 µM SAH in 50 mM Tris-HCl pH 7.4. The Flashplate™ was agitated at room temperature for 1 hour, washed three times with 200 µL of 0.05% Tween®-20 in 50 mM Tris-HCl pH 7.4, and read in 200 µL of 50 mM Tris-HCl pH 7.4 on TopCount NXT (PerkinElmer).

The results of these tests obtained with the compounds of the invention are indicated below:

| | DNMT1 (% of inhibition) | | | DNMT3A (% of inhibition) | | | |
|---|---|---|---|---|---|---|---|
| Compound | 100 µM | 32 µM | 10 µM | 32 µM | 20 µM | 10 µM | EC$_{50}$ µM |
| A | 97 | — | — | 85 | 76 | 60 | 10 |
| B | 86 | — | — | — | 67 | — | — |
| E | — | — | — | 51 | 27 | — | — |
| F | 90 | — | — | 87 | 76 | 59 | 10 |
| G | 91.2 | 24.5 | — | — | 97 | 81 | 2.4 |
| H | 94.9 | — | — | 69 | 44 | 28 | — |
| I | 99.3 | — | — | 68 | 32 | 16 | — |
| J | 33.7 | — | — | 72 | 65 | 47 | — |
| K | — | — | — | 44 | 40 | 10 | — |
| L | 45 | — | — | 26 | — | 10 | — |
| M | 100 | 100 | — | 91 | — | 89 | 1.1 |
| N | 69 | 24 | — | 83 | — | 86 | 1.1 |
| O | 98.4 | 38 | — | 99 | — | 80 | 4.9 |
| P | 22 | 26 | — | 81 | — | 43 | 13.1 |
| Q | 99.6 | 74 | — | 68 | — | 61 | 5.7 |
| R | 98.4 | 45 | — | 99 | — | 65 | — |
| S | 90 | — | — | 95 | — | 52 | |
| AA | 97 | — | — | 91 | — | 82 | 2.7 |
| AB | 97 | 42 | — | 100 | — | — | — |
| AC | 97 | 75 | — | 100 | — | 88 | 1.9 |
| AD | 100 | 59 | — | 93 | — | — | — |
| AE | 74 | 54 | — | 72 | — | 61 | 1.1 |
| AF | — | — | — | 83 | — | 53 | |
| AG | 59 | 77 | — | 100 | — | 82 | 3.4 |
| AH | 97 | 59 | — | 96 | — | 68 | — |
| AI | 99 | 99 | — | 99 | — | 86 | 1 |
| AJ | 94 | 94 | — | 90 | — | 91 | — |
| AK | 93 | 93 | — | 5 | — | 76 | — |
| AL | 81 | 81 | — | 93 | — | 72 | 8 |
| AM | 100 | — | — | 81 | — | — | — |
| AN | — | — | — | 65 | — | — | — |
| AO | 79 | — | — | 62 | — | 70 | — |
| AP | 90 | — | — | 80 | — | 70 | 2.6 |
| AQ | 100 | 61 | — | 95 | — | 95 | 1.4 |
| AR | — | — | — | 66 | — | 66 | 4.7 |
| AS | — | — | — | 60 | — | 60 | — |

Anti-Proliferative Activity.

On KG-1 and Karpas 299 Cells:

KG-1 and Karpas299 human leukemia cells were obtained from the ATCC (USA) and cultivated in RPMI 1640 medium (with HEPES and Glutamine, BE12-115F, Lonza, France) supplemented with, respectively, 20% and 15% foetal calf serum (Lonza, France), at 37° C. and under 5% CO$_2$. To measure the anti-proliferative properties of tested molecules, 2×10$^4$ cells were seeded at day 0 in a 96 wells plate. The compounds to be tested, stored at −20° C. as 10$^{-2}$ M stock solution in 100% DMSO, are freshly diluted on day 1 in RPMI 1640 medium, before adding a dose range of 3.2 nM to 10 µM to the cells. This treatment is repeated on day 2 and 3, and on day 4 cell viability is assessed using the ATPLite kit from Perkin (ATPlite 1 Step Luminescence Assay System, ref 3016739), following the provider instructions. The raw data are analyzed with GraphPad Prism software (v4.03) to generate $EC_{50}$ values corresponding to the compound concentrations giving 50% reduction in cell viability. The values presented are the mean results of at least two independent experiments. The 95% confidence intervals for these $EC_{50}$ values are also indicated.

On WM266.4, U87MG and PANC1 Cells:

The antiproliferative activity of compounds was measured in vitro using the ATP quantification method "ATPlite one step assay" (Perkin Elmer ref 6016739) according to the manufacturer conditions.

Briefly, WM266.4 cells (human melanoma cells) (5×104 cells per ml in RPMI1640 medium, 10% FBS, 2 mM glutamine, 50 U/mL penicillin/streptomycin and 1.25 μg/mL fungizone), PANC1 cells (human pancreatic carcinoma cells) (2×104 cells per ml in DMEM medium, 10% FBS, 2 mM glutamine, 50 U/mL penicillin/streptomycin and 1.25 μg/mL fungizone), and U87MG cells (human neuronal gliablastoma-astrocytoma-cells) (3×104 cells per ml in MEM medium, 10% FBS, 2 mM glutamine, 50 U/mL penicillin/streptomycin and 1.25 μg/mL fungizone) were seeded in 96-well plates, incubated for 24 h and treated with 8 increasing concentrations of test compounds diluted in cells respective mediums, or vehicle in triplicate.

Cells were then incubated for 72 h at 37° C. in humidified 5% $CO_2$ atmosphere.

At the end of the experiment, cell viability was evaluated by determining the level of ATP released by viable cells.

$EC_{50}$ values were determined with curve fitting analysis method (non linear regression model with a sigmoid dose response, variable Hill slope coefficient) provided by the Prism Software (GraphPad). Results were expressed as average $EC_{50}$ values (concentration of tested compound that inhibits 50% of the maximum effect for the considered compound).

The results of these tests obtained with the compounds of the invention are indicated below:

| Compound | $EC_{50}$ (μM) | | | | |
|---|---|---|---|---|---|
| | KG-1 | Karpas299 | WN226.4 | U87MG | PANC1 |
| G | 0.5 (0.4-0.6) | 1.8 (1.4-2.2) | 3.9 | 8.9 | 1.2. |
| M | 1.3 (1.0-1.6) | 0.7 (0.5-1.1) | | | |
| N | 0.4 (0.3-0.6) | | | | |

The invention claimed is:

1. A compound of the following formula (I-1c) or (I-1d):

(I-1c)

(I-1d)

or a pharmaceutically acceptable salt or solvate thereof, wherein:

n1 and n2 represent, independently of each other, an integer comprised between 0 and 8, Q represents a cycle of the following formula:

wherein:
$X_{11}$ represents $CR_{41}$,
$X_{12}$ represents $CR_{42}$,
$X_{13}$ represents N or C—$NR_{43a}R_{43b}$,
$X_{14}$ represents $CR_{44}$,
$X_{15}$ represents $CR_{45}$,
$R_{43a}$ and $R_{43b}$ each represent, independently of each other, H or $(C_1-C_6)$alkyl,
$R_{41}$, $R_{42}$, $R_{44}$ and $R_{45}$ each represent, independently of each other, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{17}R_{28}$, and $NR_{29}C(O)R_{30}$; or aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, and $NR_{39}C(O)R_{40}$; or
in the case of $R_{44}$ and $R_{45}$, $R_{44}$ and $R_{45}$ form together a chain of the following formula:

wherein:
$X_{16}$ represents $CR_{46}$,
$X_{17}$ represents $CR_{47}$,
$X_{18}$ represents $CR_{48}$,
$X_{19}$ represents $CR_{49}$, and
$R_{46}$, $R_{47}$, $R_{48}$ and $R_{49}$ each represent, independently of one another, hydrogen; halogen; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, and $NR_{29}C(O)R_{30}$; or aryl or aryl-$(C_1-C_6)$alkyl optionally substituted with one or several groups selected from halogen, $OR_{31}$, $NR_{32}R_{31}$, $C(O)R_{34}$, $CO_2R_{35}$, $OC(O)R_{36}$, $C(O)NR_{37}R_{38}$, and $NR_{39}C(O)R_{40}$;
W represents $NR_0$, a piperidinediyl, a piperazinediyl or a pyrrolidinediyl,
$X_1$ represents NH,
$X_2$ represents O,
$R_0$ represents H; CHO; $CO_2$—$((C_1-C_6)$alkyl); or a $(C_1-C_6)$alkyl optionally substituted with CHO, $CO_2H$ or $CO_2$—$((C_1-C_6)$alkyl),
$R_1$ and $R_2$ represent, independently of each other, H or a $(C_1-C_6)$alkyl,
$R_3$ and $R_4$ represent, independently of each other, H, $(C_1-C_6)$alkyl, aryl, heterocycle, —$((C_1-C_6)$alkyl)-$X_5$-aryl or —$((C_1-C_6)$alkyl)-$X_5$-heterocycle,
with $X_5$ representing a bond, O or $NR_6$ and each aryl or heterocycle moiety being optionally substituted, and
$R_5$ and $R_6$ represent, independently of each other, H or a $(C_1-C_6)$alkyl.

2. The compound according to claim 1, wherein it is a compound of the following formula (I-1c):

(I-1c)

or a pharmaceutically acceptable salt or solvate thereof.

3. The compound according to claim 1, wherein n1 and n2 represent, independently of each other, an integer comprised between 1 and 4.

4. The compound according to claim 1, wherein W represents $NR_0$,

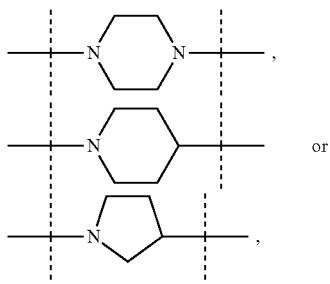

the nitrogen atom being linked to $(CH_2)_{n1}$.

5. The compound according to claim 1, wherein $R_3$ and $R_4$ represent, independently of each other, H, $(C_1-C_6)$alkyl, aryl, heterocycle, —$((C_1-C_6)$alkyl$)$-$X_5$-aryl or —$((C_1-C_6)$alkyl$)$-$X_5$-heterocycle, each aryl or heterocycle moiety being optionally substituted with one or several groups selected from halogen; oxo (=O); $NO_2$; $OR_{11}$; $NR_{12}R_{13}$; $C(O)R_{14}$; $CO_2R_{15}$; $OC(O)R_{16}$; $C(O)NR_{17}R_{18}$; $NR_{19}C(O)R_{20}$; $S(O)R_{50}$; $S(O)_2R_{51}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, $CO_2R_{25}$, $OC(O)R_{26}$, $C(O)NR_{27}R_{28}$, $NR_{29}C(O)R_{30}$, $S(O)R_{54}$, $S(O)_2R_{55}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, $CO_2R_{35}$, $OC(O)R_{36}$, $C(O)NR_{37}R_{38}$, $NR_{39}C(O)R_{40}$, $S(O)R_{58}$, $S(O)_2R_{59}$, and $S(O)_2NR_{60}R_{61}$, with $R_{11}$ to $R_{40}$ and $R_{50}$ to $R_{61}$ representing, independently of one another, H or $(C_1-C_6)$alkyl.

6. The compound according to claim 5, wherein $R_3$ and $R_4$ represent, independently of each other, H, $(C_1-C_6)$alkyl, aryl, heterocycle, aryl-$(C_1-C_6)$alkyl, heterocycle-$(C_1-C_6)$alkyl, —$((C_1-C_6)$alkyl$)$-NH-aryl or —$((C_1-C_6)$alkyl$)$-NH-heterocycle, each aryl or heterocycle moiety being optionally substituted with one or several groups selected from halogen; oxo (=O); $NO_2$; $OR_{11}$; $NR_{12}R_{13}$; $C(O)R_{14}$; $S(O)_2NR_{52}R_{53}$; $(C_1-C_6)$alkyl optionally substituted with one or several groups selected from halogen, $OR_{21}$, $NR_{22}R_{23}$, $C(O)R_{24}$, and $S(O)_2NR_{56}R_{57}$; and aryl or aryl-$(C_1-C_6)$alkyl optionally substituted with one or several groups selected from halogen, $OR_{31}$, $NR_{32}R_{33}$, $C(O)R_{34}$, and $S(O)_2NR_{60}R_{61}$.

7. A compound selected from the following compounds:

A

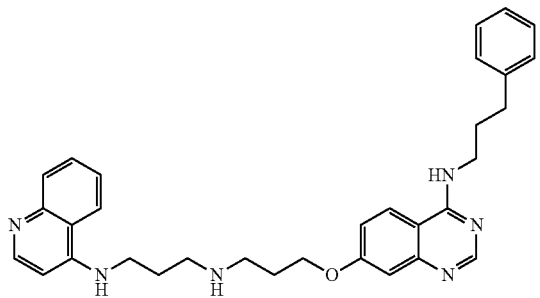

B

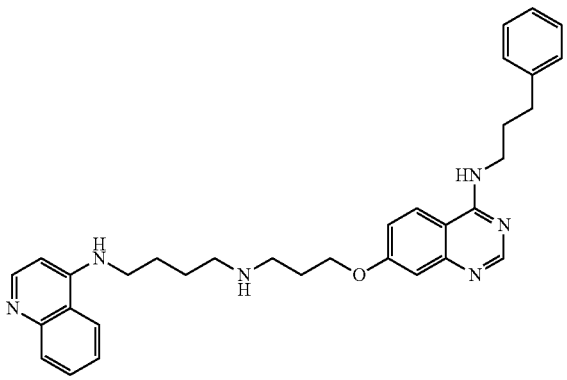

C

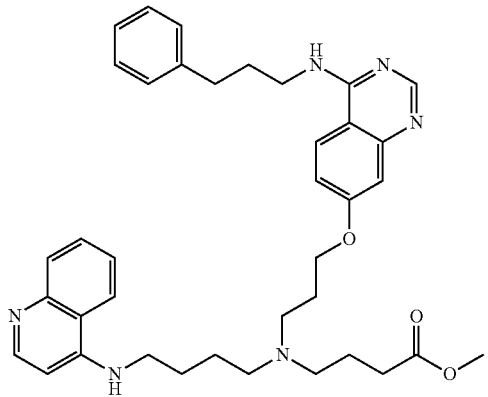

D

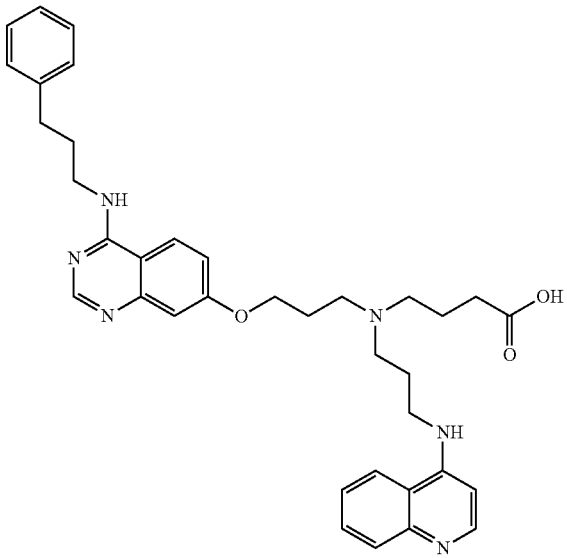

E
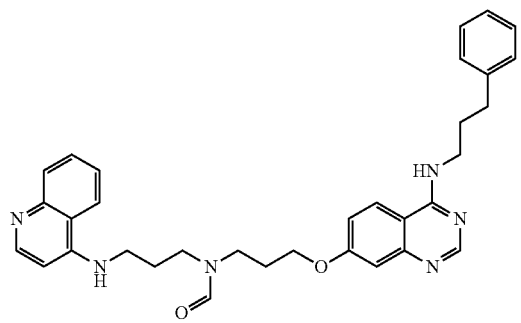
F
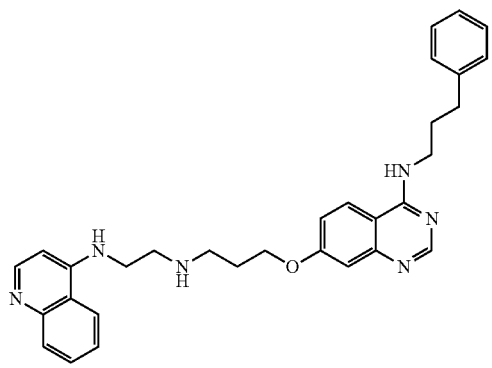
G
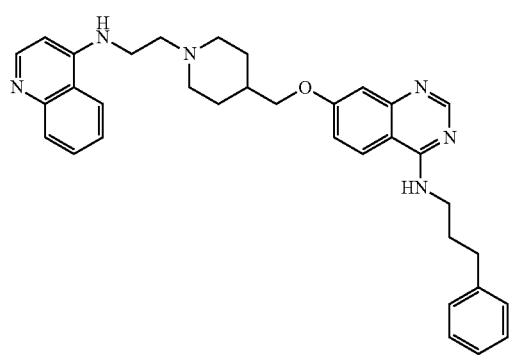
H
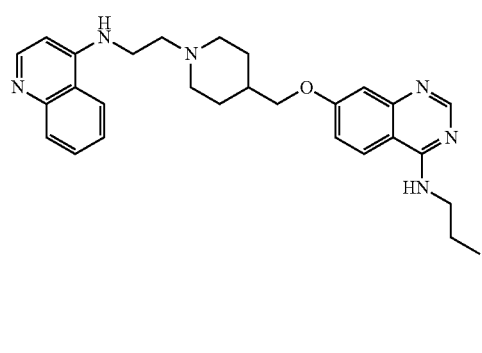
I
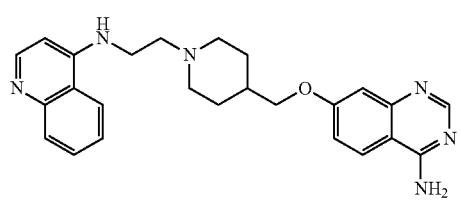
J
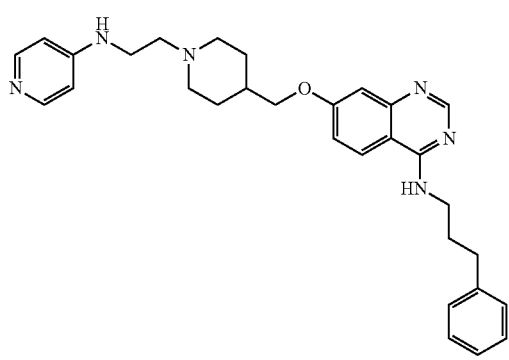
K
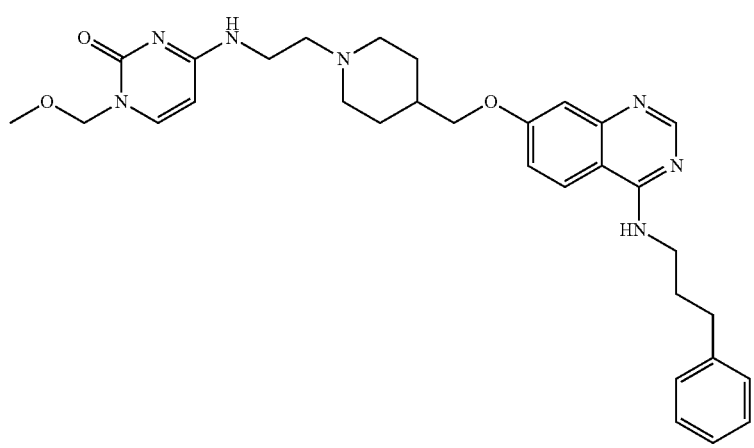

-continued
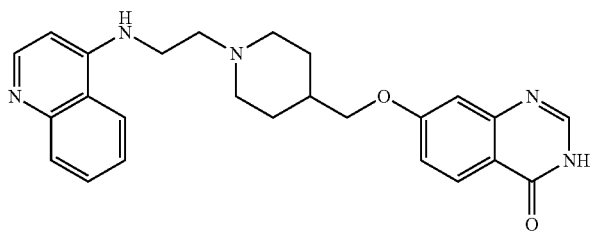
L
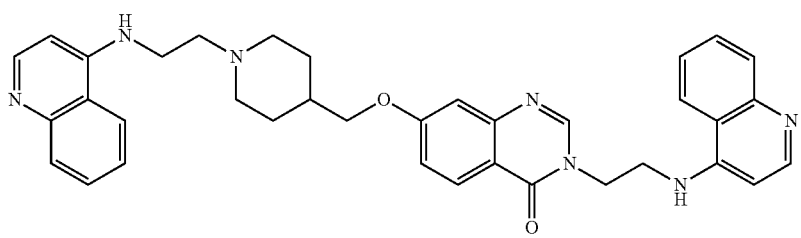
M
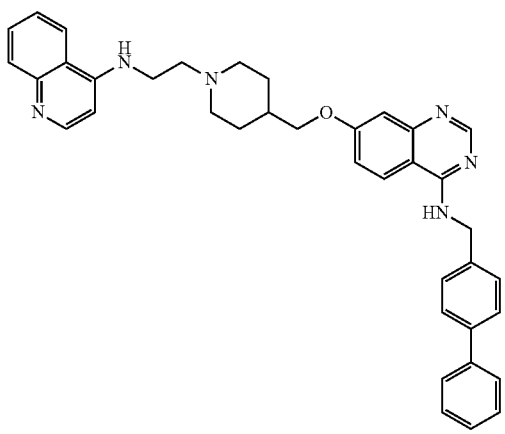
N
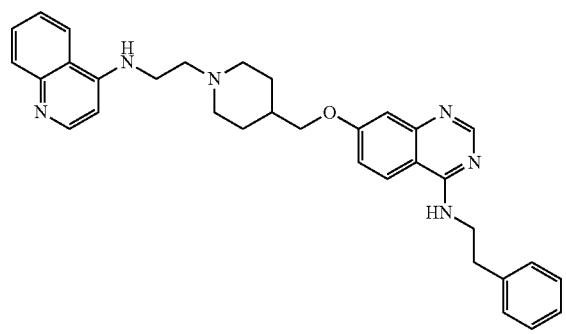
O
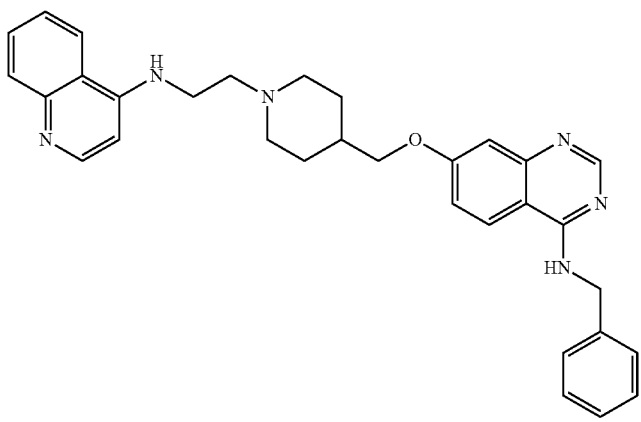
P -continued
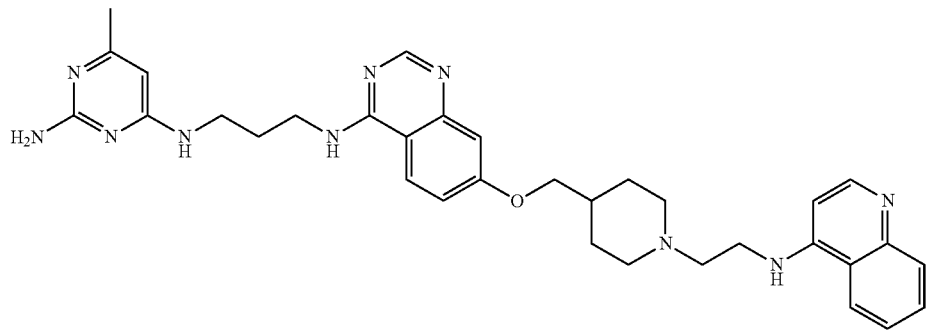
Q
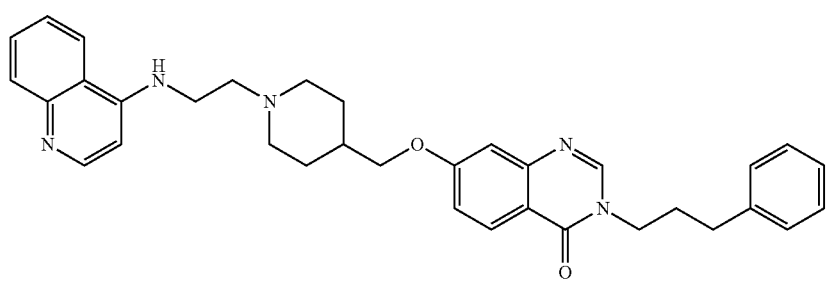
R
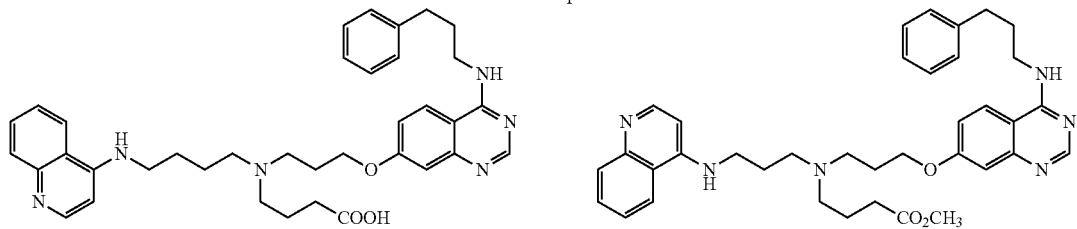
T     U
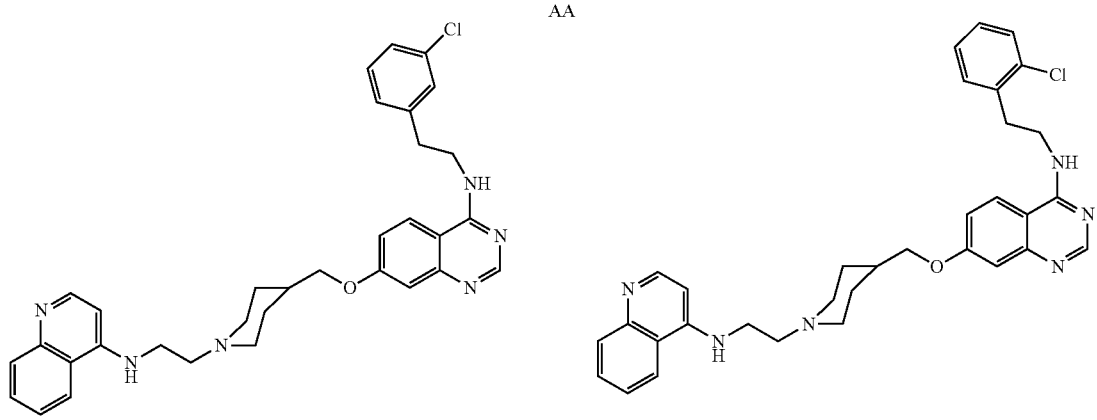
AA     AB -continued
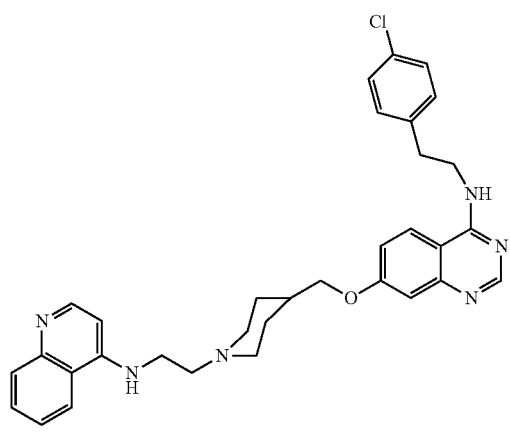
AC
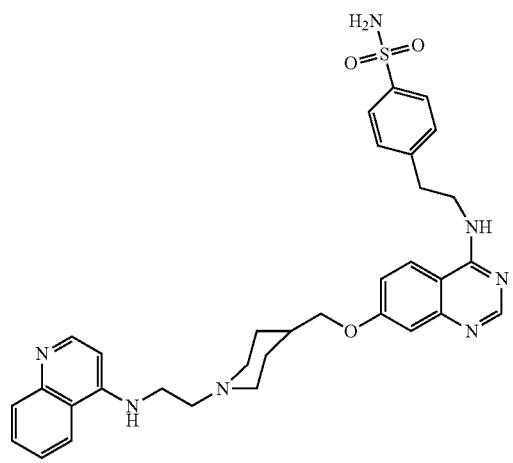
AD
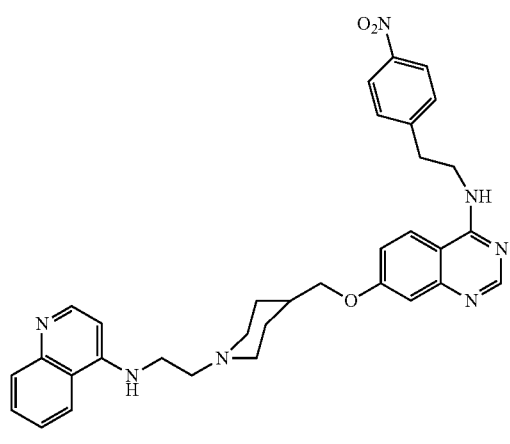
AE
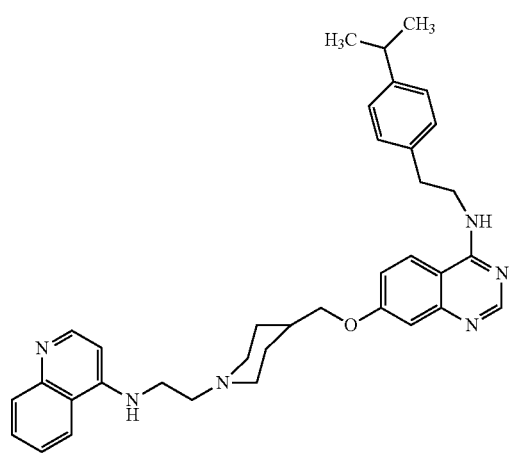
AF
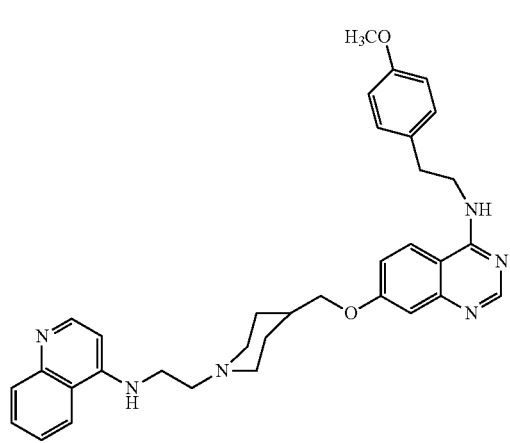
AG
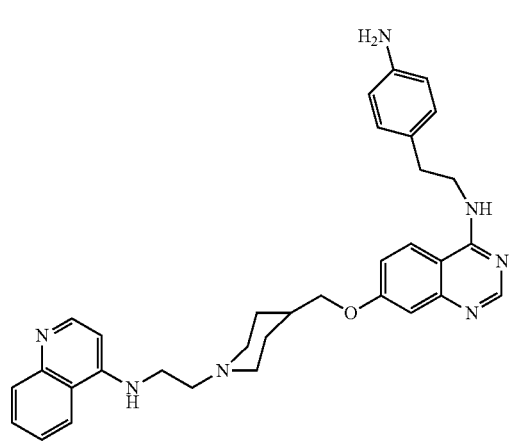
AH

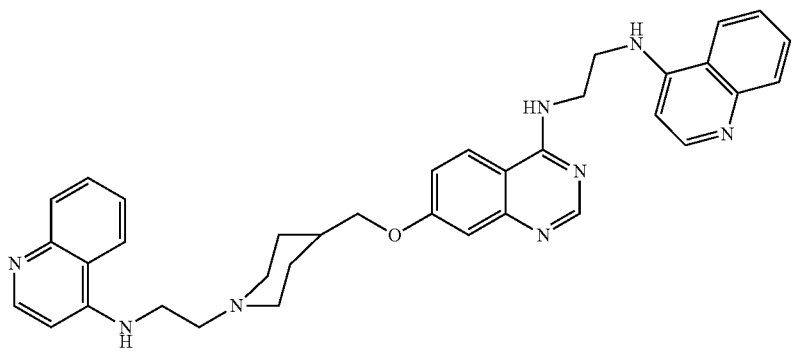
AI
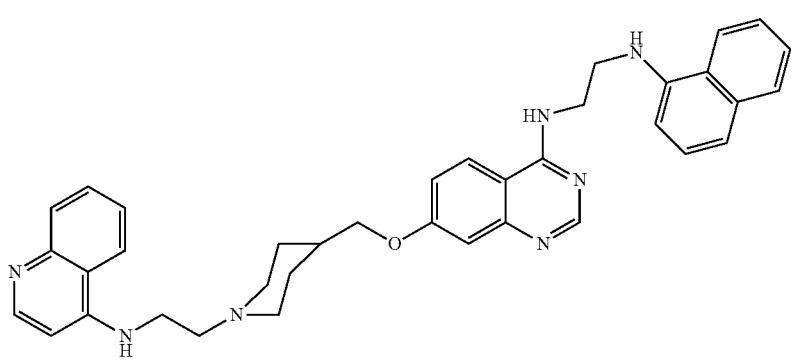
AJ
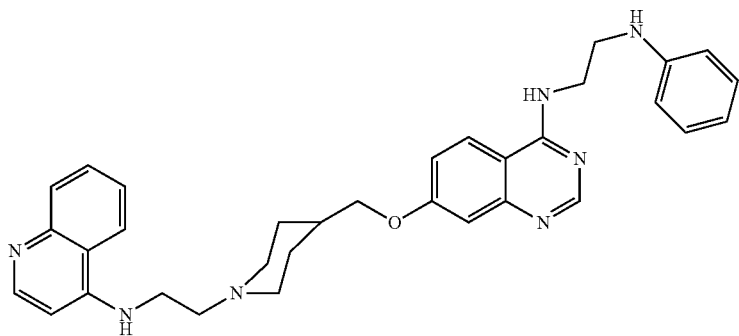
AK
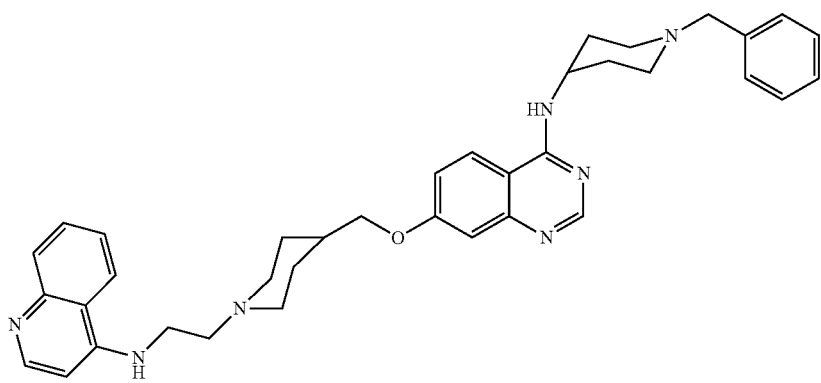
AL

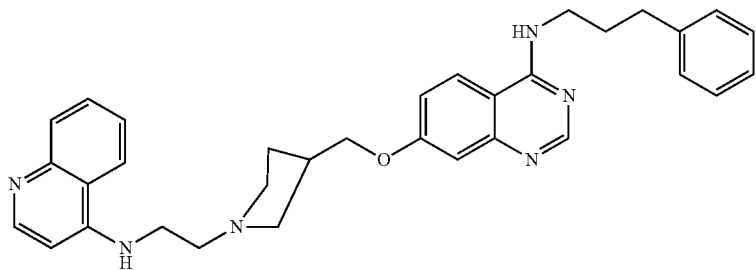
AM
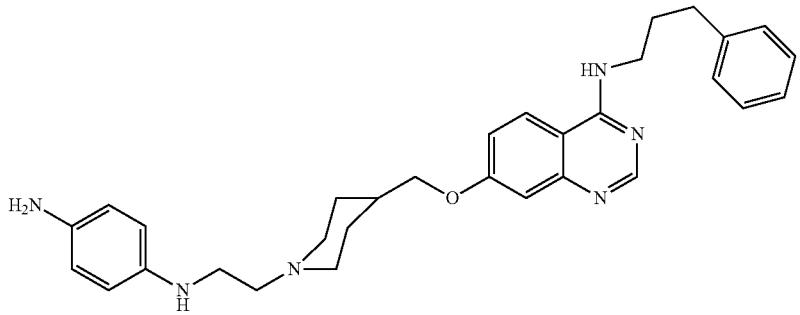
AN
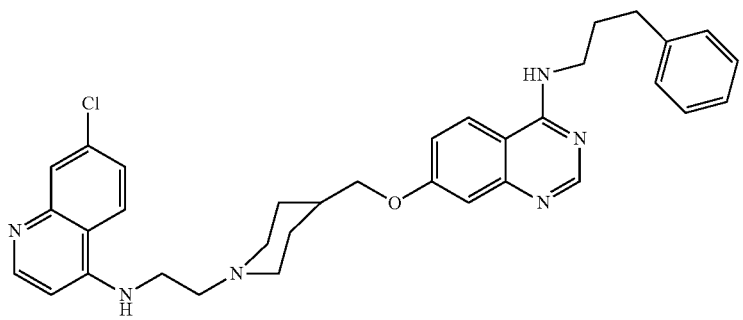
AO
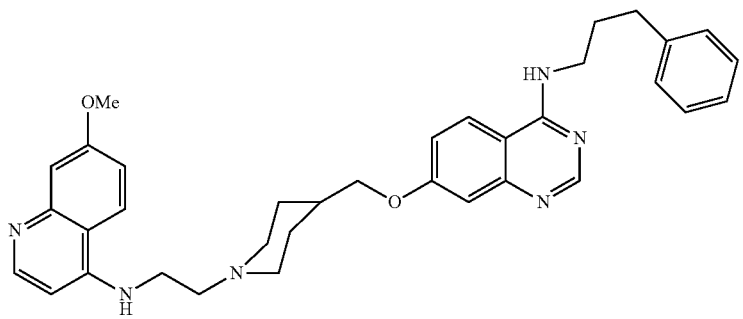
AP
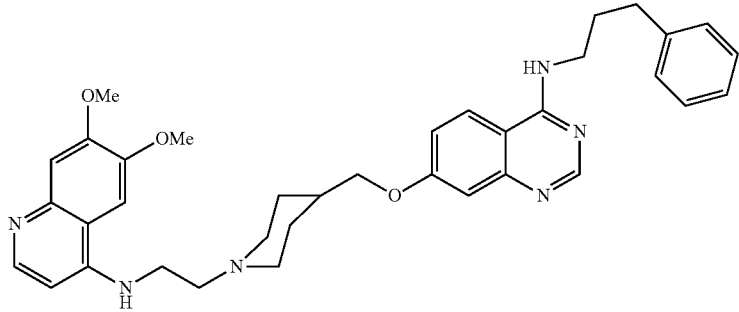
AQ

AR

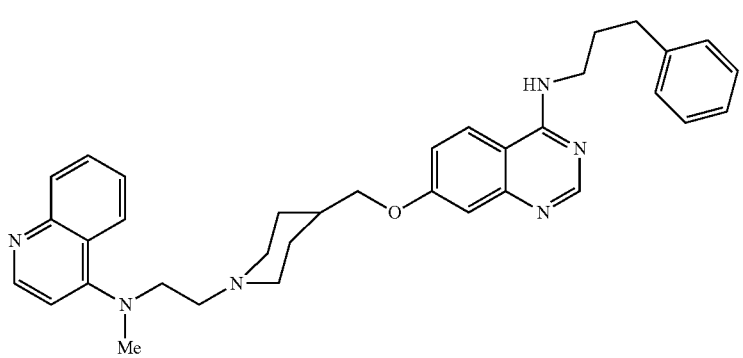

AS

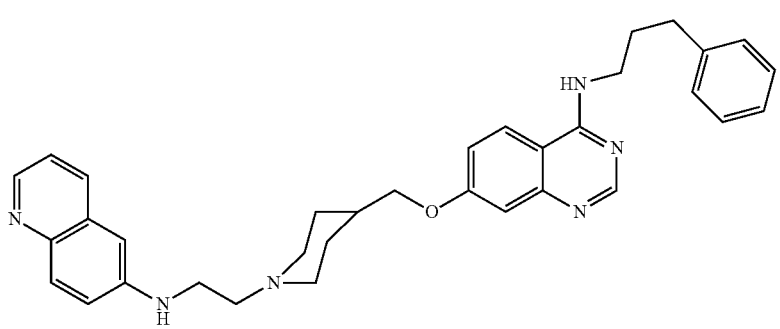

and the pharmaceutically acceptable salts and solvates thereof.

8. A pharmaceutical composition comprising at least one compound of formula (I-1c) or (I-1d) according to claim 1 and at least one pharmaceutically acceptable excipient.

9. A pharmaceutical composition comprising:
(i) at least one compound of formula (I-1c) or (I-1d) according to claim 1, and
(ii) at least one other active ingredient,
as a combination product for simultaneous, separate or sequential use.

10. A method to prepare a compound of formula (I-1c) or (I-1d) according to claim 1 or a pharmaceutically acceptable salt or solvate thereof, in which W=$NR_0$ with $R_0$ representing a ($C_1$-$C_6$)alkyl optionally substituted with CHO, $CO_2H$ or $CO_2$—(($C_1$-$C_6$)alkyl), comprising:
(a) reacting a compound of formula (I-1c) or (I-1d) according to claim 1 in which W=NH with:
a compound of formula $R_0$-LG where $R_0$ represents a ($C_1$-$C_6$)alkyl optionally substituted with CHO, $CO_2H$ or $CO_2$—(($C_1$-$C_6$)alkyl) and LG represents a leaving group to give a compound of formula (I-1c) or (I-1d) in which W=$NR_0$ with $R_0$ representing a ($C_1$-$C_6$)alkyl optionally substituted with CHO, $CO_2H$ or $CO_2$—(($C_1$-$C_6$)alkyl),
dimethylformamide (DMF) to give a compound of formula (I-1c) or (I-1d) in which W=$NR_0$ with $R_0$=CHO, or
a compound of formula $R_0$-$A_1$ where $R_0$ represents $CO_2$—(($C_1$-$C_6$)alkyl) and $A_1$ represents a ($C_1$-$C_6$) alkoxy group or a halogen atom to give a compound of formula (I-1c) or (I-1d) in which W=$NR_0$ with $R_0$ representing $CO_2$—(($C_1$-$C_6$)alkyl), and
(b) optionally salifying or solvating the compound obtained in step (a) to give a pharmaceutically acceptable salt or solvate of a compound of formula (I-1c) or (I-1d) according to claim 1 in which W=$NR_0$ with $R_0$ as defined above.

11. A method to prepare a compound of formula (I-1c) or (I-1 d) according to claim 1 or a pharmaceutically acceptable salt or solvate thereof, in which W represents $NR_0$,

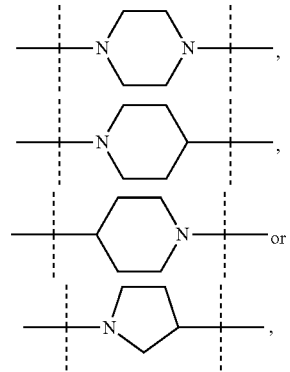

comprising:
(1) reacting a compound of the following formula (II):

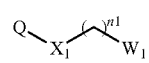
(II)

in which Q, $X_1$ and n1 are as defined in claim 1 and $W_1$ represents $LG_1$, $NHR_8$,

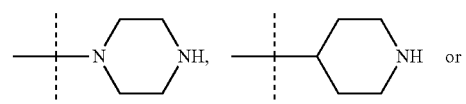

-continued

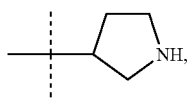

with a compound of the following formula (III-1c) or (III-1d):

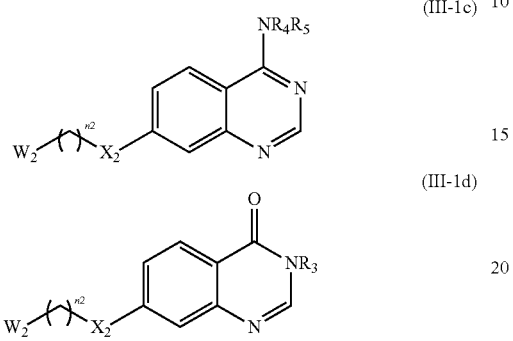

in which $R_3$, $R_4$, $R_5$, and n2 are as defined in claim 1 and $W_2$ represents $LG_2$, $NHR_8$,

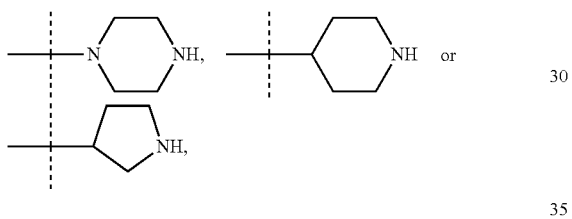

wherein $LG_1$ and $LG_2$ represent, independently of each other, a leaving group and $R_8$ represents $R_0$ as defined in claim 1 or a N-protecting group,
on the condition that:
when $W_1$ represents $LG_1$, then $W_2$ represents $NHR_8$,

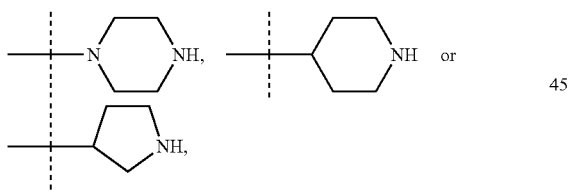

and
when $W_1$ represents $NHR_8$,

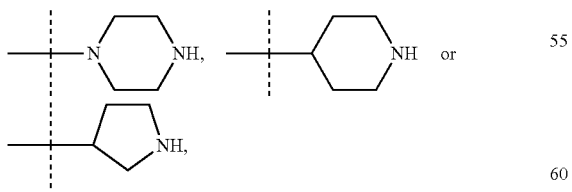

then $W_2$ represents $LG_2$,
and, when $W_1$ or $W_2$ represents $NHR_8$ with $R_8$ representing a N-protecting group, deprotecting the nitrogen atom bearing the N-protecting group,
to give a compound of formula (I-1c) or (I-1d) as defined in claim 1, and (2) optionally salifying or solvating the compound obtained in step (1) to give a pharmaceutically acceptable salt or solvate of a compound of formula (I-1c) or (I-1d) as defined in claim 1.

12. A method to prepare a compound of formula (I-1c) or (I-1d) according to claim 1 or a pharmaceutically acceptable salt or solvate thereof, comprising:
(A) reacting a compound of the following formula (VII):

$$Q\text{-}X_6 \qquad (VII)$$

in which Q is as defined in claim 1 and $X_6$ represents a halogen atom or $—X_1—(CH_2)_{n1}—W—(CH_2)_{n2}—X_2H$ with W, $X_1$, $X_2$, n1 and n2 as defined in claim 1,
with a compound of the following formula (VIII-1c) or (VIII-1d):

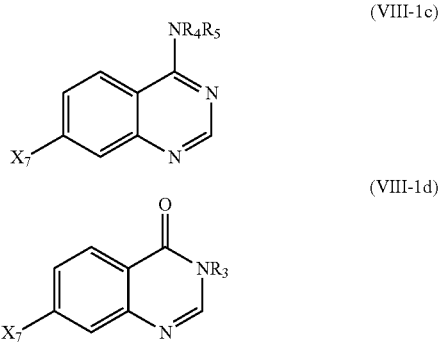

in which $R_3$, $R_4$, and $R_5$ are as defined in claim 1 and $X_7$ represents a halogen atom or $—X_2—(CH_2)_{n2}—W—(CH_2)_{n1}—X_1H$ with W, $X_1$, $X_2$, n1 and n2 as defined in claim 1,
on the condition that:
when $X_6$ represents a halogen atom, then $X_7$ represents $—X_2—(CH_2)_{n2}—W—(CH_2)_{n1}—X_1H$, and when $X_6$ represents $—X_1—(CH_2)_{n1}—W—(CH_2)_{n2}—X_2H$, then $X_7$ represents a halogen atom,
to give a compound of formula (I-1c) or (I-1d) as defined in claim 1, and
(B) optionally salifying or solvating the compound obtained in step (A) to give a pharmaceutically acceptable salt or solvate of a compound of formula (I-1c) or (I-1d) as defined in claim 1.

13. The compound according to claim 1, wherein:
$R_{43a}$ and $R_{43b}$ each represent H,
$R_{41}$, $R_{42}$, $R_{44}$ and $R_{45}$ each represent, independently of each other, hydrogen; halogen; $OR_{11}$; $NR_{12}R_{13}$; ($C_1$-$C_6$)alkyl optionally substituted with one or several groups selected from halogen, $OR_{21}$, and $NR_{22}R_{23}$; or aryl optionally substituted with one or several groups selected from halogen, $OR_{31}$, and $NR_{32}R_{33}$, or
in the case of $R_{44}$ and $R_{45}$, $R_{44}$ and $R_{45}$ form together a chain of the following formula:

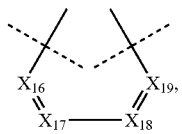

$R_{46}$, $R_{47}$, $R_{48}$ and $R_{49}$ each represent, independently of one another, hydrogen; halogen; $OR_{11}$; $NR_{12}R_{13}$; ($C_1$-$C_6$)alkyl optionally substituted with one or several groups selected from halogen, $OR_{21}$, and $NR_{22}R_{23}$; or aryl optionally substituted with one or several groups selected from halogen, $OR_{31}$, and $NR_{32}R_{33}$.

14. The compound according to claim 5, wherein the aryl is a phenyl or a naphtyl and the heterocycle is a saturated, unsaturated or aromatic hydrocarbon monocycle or bicycle, each cycle having 5 or 6 members and 1 to 4 carbon atoms having each been replaced with a nitrogen or oxygen atom.

15. A method for inhibiting DNA methylation comprising the administration to a person in need thereof of an effective dose of a compound according to claim 1.

16. The method according to claim 15, for inhibiting a DNA methyltransferase (DNMT).

* * * * *

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: DNA duplex
<220> FEATURE:
<221> NAME/KEY: modified_base
<222> LOCATION: (4)..(4)
<223> OTHER INFORMATION: methylCys
<220> FEATURE:
<221> NAME/KEY: modified_base
<222> LOCATION: (7)..(7)
<223> OTHER INFORMATION: methylCys
<220> FEATURE:
<221> NAME/KEY: modified_base
<222> LOCATION: (12)..(12)
<223> OTHER INFORMATION: methylCys
<220> FEATURE:
<221> NAME/KEY: modified_base
<222> LOCATION: (14)..(14)
<223> OTHER INFORMATION: methylCys
<220> FEATURE:
<221> NAME/KEY: modified_base
<222> LOCATION: (19)..(19)
<223> OTHER INFORMATION: methylCys
<220> FEATURE:
<221> NAME/KEY: modified_base
<222> LOCATION: (21)..(21)
<223> OTHER INFORMATION: methylCys
<220> FEATURE:
<221> NAME/KEY: modified_base
<222> LOCATION: (25)..(25)
<223> OTHER INFORMATION: methylCys
<220> FEATURE:
<221> NAME/KEY: modified_base
<222> LOCATION: (30)..(30)
<223> OTHER INFORMATION: methylCys

<400> SEQUENCE: 1
gatcgccgat gcgcgaatcg cgatcgatgc gat                                33
```

```
<210> SEQ ID NO 2
<211> LENGTH: 33
<212> TYPE: DNA
<213> ORGANISM: Artificial Sequence
<220> FEATURE:
<223> OTHER INFORMATION: DNA duplex
<220> FEATURE:
<221> NAME/KEY: misc_binding
<222> LOCATION: (1)..(1)
<223> OTHER INFORMATION: Biotinylation

<400> SEQUENCE: 2
atcgcatcga tcgcgattcg cgcatcggcg atc                           33
```